US008044061B2

(12) United States Patent
Müller et al.

(10) Patent No.: US 8,044,061 B2
(45) Date of Patent: Oct. 25, 2011

(54) 8-ALKYNYLXANTHINES AND DERIVATIVES

(75) Inventors: Christa E. Müller, Bonn (DE); Jörg Hockemeyer, Bonn (DE); Nikolay T. Tzvetkov, Bonn (DE); Joachim C. Burbiel, Alfter-Impekoven (DE)

(73) Assignee: UCB Pharma GmbH, Monheim (DE)

( * ) Notice: Subject to any disclaimer, the term of this patent is extended or adjusted under 35 U.S.C. 154(b) by 756 days.

(21) Appl. No.: 11/963,477

(22) Filed: Dec. 21, 2007

(65) Prior Publication Data

US 2008/0221134 A1 Sep. 11, 2008

Related U.S. Application Data

(60) Provisional application No. 60/945,248, filed on Jun. 20, 2007.

(30) Foreign Application Priority Data

Dec. 22, 2006 (EP) .................................... 06026739

(51) Int. Cl.

| | |
|---|---|
| ***C07D 473/06*** | (2006.01) |
| ***C07D 473/04*** | (2006.01) |
| ***A61K 31/522*** | (2006.01) |
| *A61P 25/26* | (2006.01) |
| *A61P 25/06* | (2006.01) |

(52) U.S. Cl. ........... 514/263.2; 514/263.23; 514/263.24; 514/263.34; 514/263.35; 514/263.36; 544/267; 544/268; 544/269; 544/270; 544/271; 544/272; 544/273

(58) Field of Classification Search .................. 544/267, 544/268, 269, 270, 271, 272, 273; 514/263.2, 514/263.23, 263.24, 263.34, 263.35, 263.36
See application file for complete search history.

(56) References Cited

U.S. PATENT DOCUMENTS

| | | | | |
|---|---|---|---|---|
| 5,484,920 | A | 1/1996 | Suzuki et al. | |
| 5,587,378 | A | 12/1996 | Suzuki et al. | |
| 5,703,085 | A | 12/1997 | Suzuki et al. | |
| 2006/0205711 | A1 * | 9/2006 | Himmelsbach et al. | 514/217.06 |

FOREIGN PATENT DOCUMENTS

| | | |
|---|---|---|
| EP | 1171442 | 7/2005 |
| WO | WO 02/064598 | 8/2002 |
| WO | WO 2004/014916 | 2/2004 |
| WO | WO/2004/092173 | 10/2004 |
| WO | WO/2004/092177 | 10/2004 |
| WO | WO/2005/097140 | 10/2005 |
| WO | WO 2006/091896 | 8/2006 |
| WO | WO 2006/091897 | 8/2006 |
| WO | WO 2006/091898 | 8/2006 |
| WO | WO 2006/091936 | 8/2006 |

OTHER PUBLICATIONS

Baraldi, et al., "Current Developments of A2A Adenosine Receptor Antagonists", Current Medicinal Chemistry, 2, pp. 707-722, 1995.

Burbiel et al., "Microwave-assisted ring closure reactions: Synthesis of 8-substituted xanthine derivatives and related pyrimido- and diazepinopurinediones", Beilstein J. Org. Chem., 2, pp. 20-25, 2006.

Cacciara et al., "Medicinal Chemistry of A2A adenosine receptor antagonists", Current Topics in Medicinal Chemistry, vol. 3, pp. 403-411, 2003.

Del Giudice et al., "(E)1-(Heterocyclyl or cyclohexyl)-2[1,3,7-trisubstituted (xanthin-8-yl)] ethenes as A2a adenosine receptor antagonists", Eur J Med Chem, 31, pp. 59-63, 1996.

Drabczynska et al., "N9-benzyl-substituted 1,3-dimethyl and 1,3-dipropyl-pyrimido[2,1-f]purinediones: syntehsis and structure-activity relationships at adenosine A1 and A2A receptors", Bioorg. Med. Chem., 15, pp. 5003-5017, 2007.

Drabczynska et al., "Phenylethyl-substituted pyrimido[2,1-f]purinediones and related compounds: Structure-activity relationships as adenosine A1 and A2A receptor ligands", Bioorg. Med. Chem., 15, pp. 6956-6974, 2007.

Hauser et al., "Randomized trial of the adenosine A2A receptor antagonist istradefylline in advanced PD", Neurology, 61, pp. 297-303, Aug. 2003.

Hockemeyer et al., "Multigram-Scale Syntheses, Stability, and Photoreactions of A2A Adenosine Receptor Antagonists with 8-Styrylxanthine Structure: Potential Drugs for Parkinson's Disease", J. Org. Chem., vol. 69, No. 10, pp. 308-318, 2004.

Jacobsen et al., "Adenosine Receptors: Pharmacology, Structure-Activity Relationships, and Therapeutic Potential", J. Med. Chem., vol. 35, No. 3, pp. 407-422, 1992.

Kiec-Konowicz et al., "New developments in A1 and A2 adenosine receptor antagonists", Pure Appl. Chem., vol. 73, No. 9, pp. 1411-1420, 2001.

Knutsen et al., "KW-6002", Curr. Opinion Invest Drugs, vol. 2, No. 5, pp. 668-673, 2001.

Müller et al., "1,8-Disubstituted xanthine derivatives: synthesis of potent A2B-selective adenosine receptor antagonists", J. Med. Chem., 45, pp. 1500-1510, 2002.

Müller et al., "A new versatile synthesis of xanthines with variable substituents in the 1-, 3-, 7-, and 8-positions", Synthesis, pp. 1295-1299, 1995.

(Continued)

*Primary Examiner* — Mark Berch

(74) *Attorney, Agent, or Firm* — Harness, Dickey & Pierce, P.L.C.; Leanne M. Rakers

(57) ABSTRACT

Disclosed are novel compounds of the general formula (Ia), and pharmaceutically acceptable salts, isomers, diastereomers or enantiomers thereof formula (Ia)

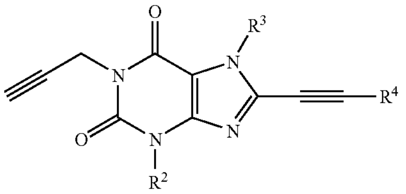

and their use as medicines, for example in the treatment of dopamine-related movement disorders.

10 Claims, 7 Drawing Sheets

OTHER PUBLICATIONS

Müller et al., "Adenosine receptors and their modulators", Pharm. Acta. Helv., 68, pp. 77-111, 1993.
Müller et al., "Aza-analogs of 8-styrylxanthines as A2A-adenosine receptor antagonists", Arch. Pharm. Pharm. Med. Chem., 330, pp. 181-189, 1997.
Müller et al., "Configurationally stable analogs of styrylxanthines as A2A adenosine receptor antagonists", Eur. J. Med. Chem., 32, pp. 709-719, 1997.
Müller et al., "Effect of trifluoromethyl- and other substituents on activity of xanthines at adenosine receptors", J. Med. Chem., 36, pp. 2639-2644, 1993.
Müller et al., "Pyrimidin-8-on[2,1-f]theophylline-9-alkylcarboxylic acids amides as A1 and A2A adenosine receptor ligands", Il Farmaco, 58, pp. 439-444, 2003.
Müller et al., "Syntheses of paraxanthine and isoparaxanthine analogs (1, 7- and 1, 9-Substituted Xanthine Derivatives)", Synthesis pp. 1428-1436, 1998.
Müller et al., "Synthesis and preliminary evaluation of new 1- and 3-[1-(2-hydroxy-3-phenoxypropyl)xanthines from 2-amino-2-oxazolines as potential A1 and A2A adenosine receptor antagonists", Bioorg. Med. Chem., 14, pp. 2697-2719, 2006.
Müller et al., "Synthesis and properties of a new water-soluble prodrug of the adenosine A2A receptor antagonist MSX-2", Molecules, 13, pp. 348-359, 2008.
Müller et al., "Synthesis and structure-activity relationships of deazaxanthanines—analogs of potent A1-and A2-adenosine receptor antagonists," J. Med. Chem., 37, pp. 1526-1534, 1994.
Müller et al., "Synthesis of paraxanthine analogs (1, 7-disubstituted xanthines) and other xanthines unsubstituted at the 3-position: structure-activity relationships at adenosine receptors", J. Med. Chem., 36, pp. 3341-3349, 1993.
Müller et al., "Synthesis and Structure-Activity Relationships of 3.7-Dimethyl-1-propargylxanthine Derivatives, A2A-Selective Adenosine Receptor Antagonists", J. Med. Chem., 40, pp. 4396-4405, 1997.
Müller, "A2A Adenosine receptor antagonists—future drugs for Parkinson's disease?", Drugs of the Future, 25, pp. 1043-1052, 2000.
Müller, "Synthesis and properties of 1-monosubstituted zanthines", Synthesis pp. 125-128, 1993.
Müller, et al., "A2A-Selective Adenosine Receptor Antagonists: Development of Water-Soluble Prodrugs and a New Tritiated Radioligand", Drug Development Research, Wiley-Liss, Inc., 45, pp. 190-197, 1998.
Müller, et al., "8(Sulfostyryl)xanthines: Water-soluble A2A-Selective Adenosine Receptor Antagonists", Biorg. Med. Chem., 6, pp. 707-719, 1998.
Müller, et al., "Adenosine Receptor Antagonists: Structures and Potential Therapeutic Applications", Current Pharmaceutical Design, 2, pp. 501-530, 1996.
Ongini et al., "Pharmacology of adensine A2A receptors", Elsevier Science Ltd.,(Trend Pharmacol. Sci.), vol. 17, pp. 364-372, 1996.
Ongini, "Selective adenosine A2A receptor antagonists", Il Farmaco, 56, pp. 87-90, 2001.
Sauer et al., "Water-Soluble Phosphate Prodrugs of 1-Propargyl-8-styrylxanthine Derivatives, A2A-Selective Adenosine Receptor Antagonists", J. Med. Chem, 43, pp. 440-448, 2000.
Shimada et al., "Adenosine A2A antagonists with potent anti-cataleptic activity", Bioorganic & Medicinal Chemistry Letters, vol. 7, No. 18, pp. 2349-2352, 1997.
Shimada et al., "(E)-1,3-Dialkyl-7-methyl-8-(3,4,5-trimethoxy-styryl)xanthines: Potent and Selective Adenosine A2 Antagonists", J. Med. Chem., 35, pp. 2342-2345, 1992.
Vu, "Recent advances in the design and optimization of adenosine A2A receptor antagonists", Current Opinion Drug Discovery & Development, vol. 8, No. 4, pp. 458-468, 2005.
Weiss, et al., "Discovery of nonxanthine adenosine A2A receptor antagonists for the treatment of Parkinson's disease", Neurology 61 (Suppl 6), pp. S101-S106, Dec. 2003.
Williams, "Purinergic Neurotransmission", Neuropsychopharmacology: The Fifth Generation of Progress, pp. 191-206, 2002.

* cited by examiner

8-ALKYNYLXANTHINES AND DERIVATIVES

CROSS-REFERENCE TO RELATED APPLICATIONS

This application claims the benefit of EP Application No. 06026739.0 filed Dec. 22, 2006 and U.S. Provisional Application No. 60/945,248 filed Jun. 20, 2007. The disclosures of the above applications are incorporated herein by reference.

INTRODUCTION

Adenosine receptors represent a subclass of the group of purine nucleotide and nucleoside G protein-coupled receptors known as purinoceptors; the main pharmacologically distinct adenosine receptor subtypes are known as $A_1$, $A_{2A}$, $A_{2B}$, and $A_3$. The dominant adenosine receptor subtypes in the brain are $A_1$ and $A_{2A}$. While the $A_1$ adenosine receptor subtype is found throughout the brain in high density, the distribution of the $A_{2A}$ receptor is more restricted; it is found in high density in the striatum (caudate-putamen, nucleus accumbens, olfactory tubercule), where it is co-localized with the dopamine D2 receptor on striatopallidal output neurons. The discrete localization of the $A_{2A}$ receptor within the striatum and its ability to functionally antagonize the actions of the D2 receptor has led to the suggestion of the potential utility of $A_{2A}$ receptor antagonists for the symptomatic treatment of Parkinson's disease (PD).

The first compounds that were identified as adenosine receptor antagonists were the naturally occurring xanthines, caffeine (1,3,7-trimethylxanthine) and theophylline (1,3-dimethylxanthine, Daly et al., Cell. Mol. Neurobiol., 1983, 3, 67). These xanthines have long been known to reverse motor deficits in a variety of PD models. However, they are non-selective and of moderate potency.

A variety of synthetic substitutions on the xanthine moiety led to the discovery that the introduction of the styryl group in the 8 position of xanthines was critical in achieving compounds endowed with selective $A_{2A}$ receptor antagonistic properties (Ongini et al., Trends Pharmacol. Sci., 1996, 17, 364; Shimada et al., J. Med. Chem., 1992, 36, 2343; Muller et al., Curr. Pharm. Des., 1996, 2, 501; Baraldi et al., Curr. Med. Chem., 1995, 2, 707). The results of this effort was the discovery of the structurally related compounds KF17837, (E)1, 3-dipropyl-8-(3,4-dimethoxystyryl)-7-methylxanthine, and its analog KW6002 (istradefylline), (E)1,3-diethyl-8-(3,4-dimethoxystyryl)-7-methylxanthine, whose pharmacological characteristics have been studied extensively. Despite having similar in vitro profiles, these two structurally similar xanthines appeared to have dramatically different in vivo potencies, as measured by the attenuation of haloperidol-induces catalepsy in mice, with KW6002 being clearly more potent. This divergence in in vivo activity may be due to differences in pharmacokinetics, pharmacodynamics, metabolism, and/or bioavailability (Kiec-Kononowicz et al., Pure and Appl. Chem., 2001, 73, 1411). KW6002 was chosen by Kyowa-Hakko as a drug development candidate and has shown potency in a recently completed Phase II clinical trial (now in Phase III trials) as a novel treatment for PD (Hauser et al., Neurology, 2003, 61, 297; Weiss et al., Neurology, 2003, 61, 101).

Further work on 8-substituted xanthines involved replacement of the styryl phenyl group with a heterocycle or replacement of the styryl double bond with its aza analogue (Del Giudice et al., Eur. J. Med. Chem., 1996, 31, 59). These compounds are also selective $A_{2A}$ receptor blockers.

Another approach used 3,7-dimethyl-1-propargylxanthine (DMPX) as a starting point for the development of $A_{2A}$ selective xanthines. In particular, 8-(m-bromostyryl)-DMPX was found to be very potent and highly selective for $A_{2A}$ adenosine receptors (Muller et al., J. Med. Chem., 1997, 40, 4396).

However, a drawback of the described $A_{2A}$ selective xanthine derivates is their high lipophilicity and low water solubility, which limits their use in in vivo studies. To increase water solubility, polar groups were introduced into the phenyl ring, as in p-sulfostyryl DMPX (Muller et al., Bioorg. Med. Chem., 1998, 6, 707). These modifications generally led to a drop in $A_{2A}$ receptor affinity of the compounds. An alternative approach was to prepare water-soluble prodrugs, which contained polar groups that would be split off after in vivo application (Muller et al., Drug Dev. Res., 1998, 45, 190; Sauer et al., J. Med. Chem., 2000, 43, 440). MSX-3 was developed as a phosphoric acid ester prodrug of MSX-2 (3-(3-hydroxypropyl)-8-(m-methoxystyryl)-1-propargylxanthine), which is a potent and selective $A_{2A}$ receptor antagonist soluble in water (Sauer et al., J. Med. Chem., 2000, 43, 440).

However, the presence of the double bonds on the 8-position makes all these compounds photosensitive (Muller et al., Curr. Pharm. Des., 1996, 2, 501; Ongini et al., Trends Pharmacol. Sci., 1996, 17, 364). For example, short exposure of dilute solutions to daylight produces an equilibrium mixture of the E/Z isomers, where only the E form (while possibly being present as the minor component in the stable mixture) possesses high $A_{2A}$ receptor affinity.

In addition, the compounds are not only unstable in solution, but also in the solid state, where they undergo light-induced dimerization forming cyclobutane derivatives that show largely reduced receptor affinity and selectivity (Hockemeyer et al., 2004, 69, 3308).

In order to avoid the complicating factor of isomerization, which is hard to prevent under normal laboratory conditions, configurationally stable analogs of 8-styrylxanthines were synthesized.

Thereby, 8-(phenylethynyl)-3,7-dimethylpropargylxanthine (DMPX) was found as configurationally stable $A_{2A}$ selective antagonist exhibiting a $K_i$ value at the $A_{2A}$ adenosine receptor of 300 nM and a more than 10-fold selectivity versus the $A_1$ adenosine receptor (Muller et al., Eur. J. Med. Chem., 1997, 32, 709).

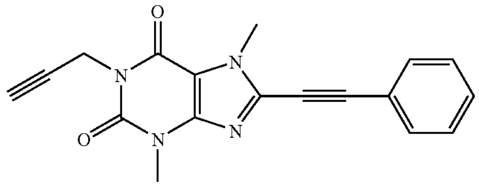

8-(phenylethynyl)-DPMX

However, in addition to the moderate affinity at the rat $A_{2A}$ receptor, 8-phenylethynyl)-3,7-dimethylpropargylxanthine (8-phenylethynyl-DMPX) also turned out to be only moderately affine towards the human receptor, having an $IC_{50}$ value of >300 nM and an Imax of only about 37% (unpublished results). Moreover, 8-(phenylethynyl)-DMPX seems not to be active in the Irwin Tests and in catalepsy in vivo models (such as e.g. reserpine, CGS-21680). Accordingly, configurationally stable compounds with a higher affinity towards the rat $A_{2A}$ receptor and/or at the human $A_{2A}$ receptor than 8-(phenylethynyl)-DMPX would be highly desirable. Particularly preferably, those compounds may be active in an in vivo model of Parkinson's disease such as, e.g. the reserpine-induced catalepsy model. There is a rather vague indication in Muller et al., 1997, supra, that the introduction of substituents in the phenyl ring "could perhaps yield more potent and selective $A_{2A}$-AR antagonists".

DETAILED DESCRIPTION

Figure 1:
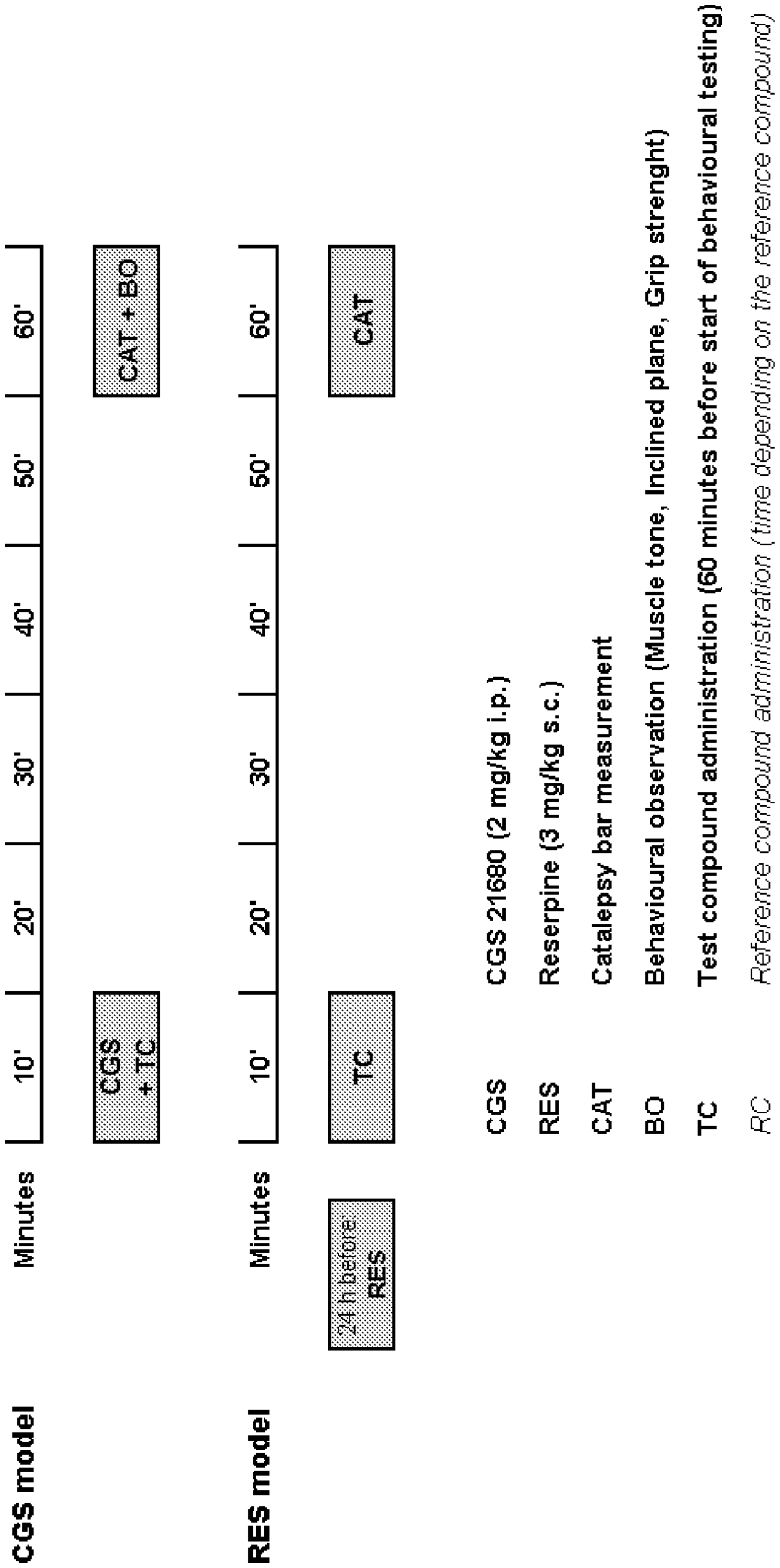
FIG. 1: Overview of the acute CGS-21680 induced catalepsy and acute Reserpine induced catalepsy tests (time schedule/application of compounds)

Surprisingly, derivatives of 8-(phenylethynyl)-DMPX carrying substitutions in the ortho position of the phenyl ring relative to the attachment position to the triple bond are more or less inactive (see table 2a). Also, derivatives with two meta substitutions did not show an improvement. However, rather unexpectedly, derivatives with a more potent binding at the rat(r)$A_{2A}$- and/or the human (h)$A_{2A}$ receptor can be obtained if the phenyl is substituted with certain residues in meta position. Additionally, some substituents in para position (relative to the triple bond) are also tolerated by the $A_{2A}$ acceptor (see tables 2a and 2b).

It has also been found, surprisingly, that while 8-(phenylethynyl)-DMPX was inactive in an acute in vivo reserpine induced catalepsy model as well as in a CGS model under the applied conditions (see biological part), two derivatives carrying two methoxy groups in ortho and para position of the phenyl, and an ethyl or hydroxypropyl substitution at the N3 position, respectively, showed significant effects both in the acute reserpin as well as in the CGS induced catalepsy model. ("test compound 1"=(3-Ethyl-8-(3,4-dimethoxyphenylethynyl)-7-methyl-1-prop-2-ynyl-3,7-dihydropurine-2,6 dione); "test compound 2"=(3-(3-Hydroxypropyl)-8-(3,4-dimethoxyphenylethynyl)-7-methyl-1-prop-2-ynyl-3,7-dihydropurine-2,6-dione). Moreover, test compound 1 also showed significant effects in a haloperidol induced model of Parkinson's Disease.

According to the present invention $A_{2A}$ receptor antagonists are thus 8-alkynylxanthines and derivatives, which are represented by the general formula (Ia), and pharmaceutically acceptable salts, isomers, diastereomers or enantiomers thereof formula (Ia)

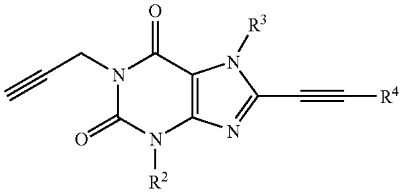

wherein, $R^2$ is hydrogen, methyl, $NR^6R^7$, or $R^2$ is $(C_2$-$C_4)$-alkyl, $(C_2$-$C_4)$-alkenyl, or $(C_2$-$C_4)$-alkynyl, or $R^2$ is methyl which is substituted with a residue selected from cyano, carboxy, $(C_3$-$C_5)$-cycloalkyl, $(C_1$-$C_2)$alkoxycarbonyl, $(C_1$-$C_2)$alkylcarbonyl, mono$(C_1$-$C_2)$alkylamino, di$(C_1$-$C_2)$alkylamino, heterocyclyl, preferably oxygen containing heterocyclyl, with 3 to 5 ring atoms and heteroaryl with 5 to 6 ring atoms, or $R^2$ is ethyl, which is substituted in one or more places, in the same way or differently with fluoro, chloro, bromo, cyano, carboxy, methylcarbonyl, methoxycarbonyl, mono$(C_1$-$C_2)$-alkylamino, di$(C_1$-$C_2)$-alkylamino, —$OR^8$, oxygen-containing heterocyclyl with 3 to 5 ring atoms, hydroxyl or a phosphate ester or an amino acid ester of said hydroxyl group, or $R^2$ is propyl or butyl, which is substituted in one or more places, in the same way or differently with fluoro, chloro, bromo, cyano, carboxy, —$OR^8$, hydroxyl or a phosphate ester or an amino acid ester of said hydroxyl group, $R^3$ is methyl, propargyl, butynyl, or cyanomethyl;

$R^4$ is a heteroaryl with five ring atoms, preferably selected from imidazolyl, furan-3yl, or thien-3yl, and optionally substituted with one or more substituents selected from halogen, methyl and methoxy, or $R^4$ is a phenyl which is substituted in meta and/or in para position to its attachment position to the triple bond with one or two groups selected from halogen, amino, —$OR^5$, and methyl, or $R^4$ is a phenyl that is annelated in meta and para position to a second heterocyclic five or six-membered ring which contains one or more oxygen atoms thus forming a bicyclic ring system, which can be substituted with one or two residues selected from methoxy, methyl or hydroxyl;

$R^5$ is a hydrogen, $(C_1$-$C_4)$-alkyl, $(C_2$-$C_4)$-alkenyl, $(C_2$-$C_4)$-alkinyl, or $R^5$ is $(C_1$-$C_5)$-alkyl substituted in one or more places, in the same way or differently, with halogen, furan-3-yl, methoxy, ethoxy, carboxy, hydroxyl or a phosphate or amino acid ester thereof, or —$NR^6R^7$, $R^6$ and $R^7$ are independently hydrogen or $(C_1$-$C_3)$-alkyl, or form together with the nitrogen atom to which they are attached a five or six membered ring which may contain one or two additional ring forming heteroatoms selected from N and O, and which five or six membered ring may be unsubstituted or substituted with one or more residues selected from $(C_1$-$C_3)$-alkyl, hydroxyl$(C_1$-$C_3)$-alkyl, amino$(C_1$-$C_3)$-alkyl, $(C_1$-$C_3)$-alkoxyl$(C_1$-$C_3)$-alkyl, halo $(C_1$-$C_3)$-alkyl, mono$(C_1$-$C_2)$alkylamino$(C_1$-$C_3)$alkyl, and di$(C_1$-$C_2)$alkylamino$(C_1$-$C_3$-alkyl); and $R^8$ is $(C_1$-$C_3)$-alkyl or $(C_1$-$C_3)$-alkoxy-$(C_1$-$C_3)$-alkyl.

Another aspect of the present invention are novel 8-ethinylxanthines which in N3 position carry a group R2 comprising at least 2 carbon atoms. Compared to 8-(phenylethynyl)-DMPX and derivatives with a methyl group in N3 position, these compounds with a moderately extended chain lengthhs often show an improved human $A_{2A}$ binding (see tables 2b and 3). Moreover, the two representatives from this group of compounds which have been tested in in vivo models of Parkinson's Disease (test compounds 1 and 2, see further above and FIGS. 4-7) showed significant activity, whereas 8-(phenylethynyl)-DMPX did not.

Accordingly, one embodiment of the present invention relates to a compound of formula Ia and pharmaceutically acceptable salts, isomers, diastereomers or enantiomers thereof, wherein $R^2$ is $(C_2-C_4)$-alkyl, $(C_2-C_4)$-alkenyl, $(C_2-C_4)$-alkynyl, or $R^2$ is methyl, which is substituted with a residue selected from cyano, carboxy, methylcarbonyl, $(C_3-C_5)$-cycloalkyl, methoxycarbonyl, monomethylamino, dimethylamino, furanyl, thienyl, imidazolyl, oxazolyl, isoxazolyl, or a heterocyclyl with 3 to 5 ring atoms, or $R^2$ is ethyl, which is substituted in one or more places with fluoro, chloro, bromo, cyano, methylcarbonyl, monomethylamino, dimethylamino, an oxygen-containing heterocyclyl with 3 to 5, preferably with 3 ring atoms, —$OR^8$, hydroxyl or a phosphate ester of said hydroxyl group, $R^2$ is propyl, which is substituted in one or more places with fluoro, chloro, bromo, or cyano, methoxy, or hydroxyl or a phosphate ester of said hydroxyl group, $R^2$ is butyl, which is substituted in one or more places with fluoro, chloro, hydroxyl or a phosphate ester of said hydroxyl group $R^4$ is imidazol-2-yl, furan-3-yl, or thien-3-yl optionally substituted with one or more substituents selected from halogen, methyl, or methoxy, or $R^4$ is a phenyl which is at least substituted in meta position and is optionally substituted in para position to its attachment position to the triple bond with a residue selected from the group consisting of halogen, amino, —$OR^5$, and methyl, or $R^4$ is a phenyl that is annelated in meta and para position to a second heterocyclic 5 or 6-membered ring which contains one or more oxygen atoms, which can be substituted with a methyl, methoxy or hydroxyl group;

$R^5$ is hydrogen, $(C_1-C_3)$-alkyl, or $(C_2-C_3)$-alkenyl or $R^5$ is $(C_1-C_4)$-alkyl substituted in one or more places, in the same way or differently, with methoxy, carboxy, furan-3-yl, OH, a phosphate ester thereof, or —$NR^6R^7$, $R^6$ and $R^7$ are independently hydrogen or $(C_1-C_3)$-alkyl, or form together with the nitrogen atom to which they are attached a five or six membered ring which may contain one additional nitrogen atom, and which five or six membered ring may be unsubstituted or which may be substituted at said additional nitrogen atom with a residue selected from $(C_1-C_2)$-alkyl, hydroxyl$(C_1-C_3)$-alkyl, amino$(C_1-C_3)$-alkyl, $(C_1-C_2)$-alkoxyl$(C_1-C_2)$-alkyl, halo $(C_1-C_2)$-alkyl, mono$(C_1-C_2)$alkylamino$(C_1-C_2)$-alkyl, and di$(C_1-C_2)$-alkylamino$(C_1-C_2)$-alkyl; and $R^8$ is $(C_1-C_3)$-alkyl or methoxy$(C_1-C_2)$-alkyl.

Another aspect is a compound according to formula Ia and pharmaceutically acceptable salts, isomers, diastereomers or enantiomers thereof, wherein $R^2$ is an ethyl, n-propyl, allyl, 2-fluoroethyl, thien-2-ylmethyl, cyclopropylmethyl, methylcarbonylethyl, methoxycarbonylmethyl, cyanomethyl, 2-cyanoethyl, 3-cyanopropyl, dimethylaminoethyl, $(OH)_2$ OP(O)-propyl, hydroxyethyl, 2-hydroxypropyl, 3-hydroxypropyl, furan-2-ylmethyl, furan-3-ylmethyl, imidazol-4-ylmethyl, isoxazol-5-ylmethyl, methoxyethyl, oxiran-2-ylmethyl, oxiran-2-ylethyl, or a 2,3-dihydroxypropyl group; and $R^4$ is a phenyl which is substituted in meta position to its attachment position to the triple bond with a group selected from methoxy, dimethylaminopropyloxy, dimethylaminoethyloxy, furan-3yl-methyloxy, methyl, methoxyethyloxy, or ethoxy, and is optionally substituted in para position with methoxy, or $R^4$ is a phenyl that is annelated in meta and para position to its attachment position to form a methylenedioxyphenyl.

Another aspect is a compound according to formula Ia and pharmaceutically acceptable salts, isomers, diastereomers or enantiomers thereof, wherein $R^2$ is hydrogen or methyl;

$R^4$ is imidazol-2-yl or thien-3-yl optionally substituted with one or more substituents selected from halogen, methyl, or methoxy, or $R^4$ is a phenyl which is substituted in meta position to its attachment position to the triple bond with a residue selected from the group consisting of amino, —$OR^5$ and methyl and which in para position is unsubstituted or substituted with a halogen, amino, $OR^5$, or methyl, and preferably with methoxy methyl, fluoro, chloro or bromo;

or $R^4$ is a phenyl that is annelated in 3- and 4-position to a second heterocyclic 5 or 6-membered ring which contains one or more oxygen atoms thus forming a bicyclic ring system, which can be substituted with a methyl, methoxy or hydroxyl group;

$R^5$ is hydrogen or methyl, or $R^5$ is $(C_1-C_4)$-alkyl substituted in one or more places, in the same way or differently, with methoxy, carboxy, hydroxyl or a phosphate ester thereof, or with —$NR^6R^7$, and $R^6$ and $R^7$ are independently hydrogen, or $(C_1-C_3)$-alkyl, or $R^6$ and $R^7$ form together with the nitrogen atom to which they are attached a five or six membered ring which may contain one or two additional ring forming heteroatoms selected from N and O, and which five or six membered ring may be unsubstituted or substituted with one or more residues selected from $(C_1-C_3)$-alkyl, hydroxyl$(C_1-C_3)$-alkyl, amino$(C_1-C_3)$-alkyl, $(C_1-C_3)$-alkoxy$(C_1-C_3)$-alkyl, halo $(C_1-C_3)$-alkyl, mono$(C_1-C_2)$-alkylamino$(C_1-C_3)$-alkyl, and di$(C_1-C_2)$-alkylamino$(C_1-C_3)$-alkyl.

According to one embodiment of the present invention, if $R^4$ is a phenyl that is substituted in meta position to its attachment positon to the triple bond with a chloro, then the substituent in para position is not chloro, and in one embodiment is not halogen.

Another embodiment is a compound of formula Ia and pharmaceutically acceptable salts, isomers, diastereomers or enantiomers thereof, wherein $R^4$ is a phenyl which is substituted in meta and/or in para position to its attachment to the triple bond with chloro, methyl, or a group —$OR^5$, $R^5$ is methyl, ethyl, or $(C_1-C_4)$-alkyl which is substituted with OH, a phosphate ester thereof or —$NR^6R^7$; and $R^6$ and $R^7$ are independently hydrogen, methyl or ethyl.

One drawback often associated with high affinity ligands of the $A_{2A}$-receptor, and particularly of purine and xanthine-based $A_{2A}$ ligands such as 8-(phenylethynyl)-DMPX is the low solubility of the compounds. Increased polarity and solubility often leads to a decrease in affinity at the $A_{2A}$ receptor. One particular aspect of the present invention thus relates to compounds having improved solubility compared to 8-(phenylethynyl)-DMPX while maintaining an improved or at least comparable $A_{2A}$ affinity.

One aspect is thus a compound of formula Ia as disclosed and defined herein, wherein at least one of the group $R^2$ or the meta substituent of the phenyl ring ($R^4$) comprises a primary, secondary or tertiary amine, such as e.g. methylaminoethyl, or $NR^6R^7$ as further defined herein, or OH as well as phosphate or amino acid esters of a hydroxyl group.

According to one aspect, in the compounds of formula Ia R4 is a phenyl which is substituted in meta position to its attachment to the triple bond with the group di($C_1$-$C_2$)-alkylamino($C_2$-$C_4$)-alkoxy.

Another aspect of the present disclosure is a compound represented by formula Ia, wherein $R^4$ is a thien-3-yl, furan-3-yl or a imidazol-2-yl, each of which is optionally substituted at one of its ringforming carbon atoms with one or more substituents selected from halogen, methyl, methoxy and methylthio, or wherein the imidazolyl residue is substituted in its N1 position by a methyl or ethyl group.

Another embodiment of the present invention is having the general formula (IIIa)

formula (IIIa)

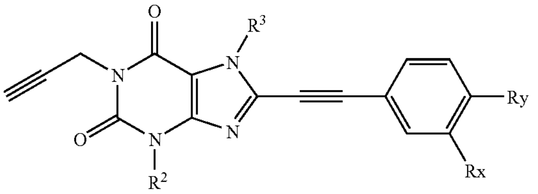

and salts thereof, wherein $R^2$ is hydrogen, methyl, $NR^6R^7$, or $R^2$ is ($C_2$-$C_4$)-alkyl, ($C_2$-$C_4$)-alkenyl, or ($C_2$-$C_4$)-alkynyl, or $R^2$ is methyl which is substituted with a residue selected from cyano, carboxy, ($C_3$-$C_5$)-cycloalkyl, ($C_1$-$C_2$)alkoxycarbonyl, ($C_1$-$C_2$)alkylcarbonyl, mono($C_1$-$C_2$)alkylamino, di($C_1$-$C_2$)alkylamino, heterocyclyl with 3 to 5 ring atoms and heteroaryl with 5 to 6 ring atoms, or $R^2$ is ethyl, which is substituted in one or more places, in the same way or differently with fluoro, chloro, bromo, cyano, methylcarbonyl, methoxycarbonyl, mono($C_1$-$C_2$)alkylamino, di($C_1$-$C_2$)alkylamino, oxiranyl, cyclopropyl, dioxolanyl, —$OR^8$, hydroxyl or a phosphate ester or an amino acid ester of said hydroxyl group, or $R^2$ is propyl or butyl, which is substituted in one or more places, in the same way or differently with fluoro, chloro, bromo, cyano, -carboxy, —$OCH_3$, hydroxyl or a phosphate ester or an amino acid ester of said hydroxyl group, $R^3$ is methyl, propargyl, butynyl, or cyanomethyl;

Rx and Ry are independently selected from halogen, amino, —$OR^5$, and methyl, and Ry may also be hydrogen, or Rx and Ry form together with the carbon atoms to which they are attached a second heterocyclic five or six-membered ring which contains one or more oxygen atoms thus forming a bicyclic ring system, which can be substituted with one or two residues selected from methoxy, methyl or hydroxyl;

$R^5$ is a hydrogen, ($C_1$-$C_4$)-alkyl, ($C_2$-$C_4$)-alkenyl, ($C_2$-$C_4$)-alkynyl, or $R^5$ is ($C_1$-$C_5$)-alkyl substituted in one or more places, in the same way or differently, with halogen, furan-3-yl, methoxy, ethoxy, carboxy, hydroxyl or a phosphate or amino acid ester thereof, or —$NR^6R^7$, $R^6$ and $R^7$ are independently hydrogen or ($C_1$-$C_3$)-alkyl, or form together with the nitrogen atom to which they are attached a five or six membered ring which may contain one or two additional ring forming heteroatoms selected from N and O, and which five or six membered ring may be unsubstituted or substituted with one or more residues selected from ($C_1$-$C_3$)-alkyl, hydroxyl($C_1$-$C_3$)-alkyl, amino($C_1$-$C_3$)-alkyl, ($C_1$-$C_3$)-alkoxyl($C_1$-$C_3$)-alkyl, halo ($C_1$-$C_3$)-alkyl, mono($C_1$-$C_2$)-alkylamino($C_1$-$C_3$)-alkyl, and di($C_1$-$C_2$)-alkylamino($C_1$-$C_3$)-alkyl; and $R^8$ is ($C_1$-$C_3$)-alkyl or ($C_1$-$C_3$)-alkoxy-($C_1$-$C_3$)-alkyl.

Another embodiment of the present disclosure is a compound of formula IIIa, wherein $R^2$ is ($C_2$-$C_4$)-alkyl, ($C_2$-$C_4$)-alkenyl, ($C_2$-$C_4$)-alkynyl, or $R^2$ is methyl, which is substituted with a residue selected from cyano, carboxy, methylcarbonyl, ($C_3$-$C_5$)-cycloalkyl, methoxycarbonyl, monomethylamino, dimethylamino, furanyl, thienyl, imidazolyl, oxazolyl, isoxazolyl, or a heterocyclyl with 3 to 5 ring atoms, or $R^2$ is ethyl, which is substituted in one or more places with fluoro, chloro, bromo, cyano, methylcarbonyl, monomethylamino, dimethylamino, —$OR^8$, oxiran-2yl, hydroxyl or a phosphate ester or an ester of an amino acid of said hydroxyl group, $R^2$ is propyl or butyl, which is substituted in one or more places with fluoro, chloro, bromo, or cyano, methoxy, hydroxyl or a phosphate ester or an ester of an amino acid of said hydroxyl group, Rx is selected from the group consisting of halogen, amino, methyl, or —$OR^5$;

Ry is selected from the group consisting of hydrogen, fluoro, chloro, bromo, methyl, or methoxy; or Rx and Ry form together with the C-Atoms to which they are attached a second heterocyclic 5 or 6-membered ring which contains one or more oxygen atoms thus forming a bicyclic ring system, which can be substituted with one or two residues selected from methoxy, methyl or hydroxyl;

$R^5$ is methyl or furanylmethyl, or $R^5$ is ($C_1$-$C_4$)-alkyl substituted in one or more places, in the same way or differently, with carboxy, hydroxyl or a phosphate ester thereof, or —$NR^6R^7$;

$R^6$ and $R^7$ are independently hydrogen, ($C_1$-$C_3$)-alkyl, or form together with the nitrogen atom to which they are attached a five or six membered ring which may contain one or two additional ring forming heteroatoms selected from N and O, and which five or six membered ring may be unsubstituted or may be substituted at the second ring forming nitrogen, if present, with one or more residues selected from ($C_1$-$C_3$)-alkyl, hydroxyl($C_1$-$C_3$)-alkyl, amino($C_1$-$C_3$)-alkyl, ($C_1$-$C_3$)-alkoxyl($C_1$-$C_3$)-alkyl, halo ($C_1$-$C_3$)-alkyl, mono($C_1$-$C_2$)-alkylamino($C_1$-$C_3$)alkyl, and di($C_1$-$C_2$)alkylamino($C_1$-$C_3$)-alkyl; and $R^8$ is methyl.

Another embodiment of the present invention is a compound of formula IIIa and pharmaceutically acceptable salts, isomers, diastereomers or enantiomers thereof, wherein $R^2$ is ($C_2$-$C_5$)-alkyl, ($C_2$-$C_4$)-alkenyl, ($C_2$-$C_4$)-alkynyl, or $R^2$ is methyl, which is substituted with cyano, carboxy, oxiran-2-yl, furan-2-yl, furan-3-yl, thien-2-yl, thien-3-yl, isoxazol-5-yl, imidazol-4-yl, cyclopropyl or methoxycarbonyl; or $R^2$ is ethyl, which is substituted in one or more places, in the same way or differently with fluoro, chloro, bromo, cyano, oxiran-2yl, mono($C_1$-$C_2$)-alkyl amino, di($C_1$-$C_2$)-alkyl amino, hydroxyl or a phosphate ester thereof or $R^2$ is propyl, which is substituted in one or more places, in the same way or differently with fluoro, chloro, bromo, cyano, hydroxyl or a phosphate ester thereof.

$R^2$ is butyl, which is substituted in one or more places with hydroxyl or a phosphate ester of said hydroxyl group; and Rx is selected from the group consisting of fluoro, chloro, bromo, methyl, methoxy, ethoxy, allyloxy, methoxyethoxy, hydroxyethoxy, mono($C_1$-$C_2$)-alkylaminopropoxy, mono($C_1$-$C_2$)-alkylaminoethyloxy, di($C_1$-$C_2$)-alkylaminopropoxy, di($C_1$-$C_2$)-alkylaminoethyloxy, furanylmethyloxy, or carboxymethyloxy;

Ry is selected from the group consisting of hydrogen, methoxy, ethoxy, fluoro, and chloro, or Rx and Ry form together with the carbon atoms to which they are attached a second heterocyclic five membered ring which contains one or two ring forming heteroatoms selected among O and N thus forming together with the phenyl ring a bicyclic ring system.

Another embodiment is a compound according to formula Ia or IIIa as described above, wherein $R^2$ is ethyl, propyl, butyl, allyl, butenyl, propargyl or butynyl, or $R^2$ is methyl, which is substituted with a residue selected from cyano, carboxy, methylcarbonyl, methoxylcarbonyl, cyclopropyl, furanyl, thienyl, imidazolyl, oxazolyl, isoxazolyl, or oxiranyl, or $R^2$ is ethyl, which is substituted in one or two places with fluoro, chloro, bromo, cyano, methylcarbonyl, monomethylamino, dimethylamino, methoxy, ethoxy, hydroxyl or a phosphate ester of said hydroxyl group, $R^2$ is propyl, which is substituted in one or two places with fluoro, chloro, bromo, cyano, methoxy, hydroxyl or a phosphate ester of said hydroxyl group, or $R^2$ is butyl, which is substituted in one or more places with hydroxyl or is substituted with a phosphate ester of a hydroxyl group Another embodiment relates to a compound of formula IIIa, wherein $R^2$ is a hydrophobic and Rx comprises a polar group. One example is a compound wherein (a)

$R^2$ is ($C_2$-$C_4$)-alkyl, ($C_3$-$C_4$)-alkenyl, ($C_3$-$C_4$)-alkynyl, or $R^2$ is methyl, which is substituted with cyano, oxiran-2-yl, furan-2-yl, furan-3-yl, thien-2-yl, thien-3-yl, isoxazol-5-yl, imidazol-4-yl, cyclopropyl, methylcarbonyl, methoxycarbonyl, or $R^2$ is ethyl which is substituted with halogen, cyano, methylcarbonyl, or oxiran-2-yl, or $R^2$ is propyl or butyl, which is substituted with halogen or cyano;

and (b)

Rx is amino or $OR^5$, and

Ry is selected from the group consisting of hydrogen, methoxy, and fluoro, $R^5$ is ($C_1$-$C_5$)-alkyl which is substituted with a hydroxyl group, a phosphate ester of a hydroxyl group, or with $NR^6R^7$ $R^6$ and $R^7$ are independently hydrogen, ($C_1$-$C_2$)-alkyl, or form together with the nitrogen atom to which they are attached a five membered ring which may contain one additional ring forming nitrogen atom which nitrogen atom may be further substituted with a residue selected from ($C_1$-$C_2$)-alkyl, hydroxyl($C_1$-$C_3$)-alkyl, amino($C_1$-$C_3$)-alkyl, ($C_1$-$C_2$)-alkoxyl($C_1$-$C_2$)-alkyl, halo($C_1$-$C_2$)-alkyl, mono($C_1$-$C_2$)-alkylamino($C_1$-$C_2$)-alkyl, and di($C_1$-$C_2$)-alkylamino($C_1$-$C_2$alkyl).

Another aspect is a compound of formula IIIa, wherein $R^2$ is a polar group. For examples, compounds in which $R^2$ is methyl, which is substituted with (i) methylamino, or (ii) di($C_1$-$C_2$)-alkylamino; or $R^2$ is ethyl, which is substituted with (iii) one or more —OH groups, (iv) a phosphate ester of a OH group (v) methylamino, or (vi) di($C_1$-$C_2$)-alkylamino; or $R^2$ is propyl or butyl, each of which is substituted with (i) one or more —OH groups or (ii) a phosphate ester of a OH group.

Another aspect of the present disclosure are compounds of formula IIIa, $R^2$ is ethyl, propyl, butyl; allyl, butenyl, propargyl, methylcarbonylmethyl, methylcarbonylethyl, methoxycarbonylmethyl, carboxy, cyanomethyl, 2-cyanoethyl, 3-cyanopropyl, 2,3-dihydroxypropyl and the phosphate esters thereof, furan-2-ylmethyl, furan-3-ylmethyl, thien-2-ylmethyl, thien-3-ylmethyl, isoxazol-5-ylmethyl, imidazol-4-ylmethyl, oxiran-2-yl-methyl, 2-methoxyethyl, 2-hydroxyethyl and the phosphate ester thereof, oxiran-2-yl-ethyl, 3-hydroxypropyl and the phosphate ester thereof, 2-hydroxypropyl and the phosphate ester thereof, 3-hydroxy-2-methylpropyl and the phosphate ester thereof, 2,2,2-trifluoroethyl, 3,3,3-trifluoropropyl, cyclopropylmethyl, 2-ethoxyethyl, 2-methoxyethyl, 2-fluoroethyl, 2-bromoethyl, 3-fluoropropyl, 4-fluorobutyl, 3-methoxypropyl, methylaminoethyl, or N,N-dimethylaminoethyl, A preferred embodiment of the present invention are compounds of formula IIIa, as described herein, wherein $R^2$ is methyl.

Another aspect are compounds wherein $R^2$ is ethyl, n-propyl or fluoro($C_2$-$C_4$)-alkyl.

In a one embodiment, if Rx is chloro then Ry is not halogen.

One aspect is a compound of formula IIIa as disclosed and defined herein, wherein at least one of the groups $R^2$ and Rx comprises a tertiary amine of the type $NR^6R^7$ as further defined herein, or a group OMe, or OH as well as phosphate or amino acid esters of a hydroxyl group.

In another preferred embodiment of the present disclosure, in the compounds of formula IIIa, $R^2$ is dimethylaminoethyl, carboxy($C_1$-$C_3$)-alkyl, or hydroxy($C_2$-$C_4$)-alkyl or a phosphate ester thereof, and/or wherein Rx is methoxy or a group N,N-di($C_1$-$C_2$)-alkylamino($C_2$-$C_4$)-alkoxy.

In another preferred embodiment of the present disclosure, in the compounds of formula IIIa, Rx and Ry are both methoxy.

In another specific embodiment, in the compounds of formula Ia or IIIa $R^2$ is $NR^6R^7$, wherein $R^6$ and $R^7$ maybe the same or different and are preferably selected from hydrogen, methyl, ethyl and propyl. Particular examples are compound wherein $R^2$ is amino or N,N-dimethylamino. Amino-containing $R^2$ groups generally tend to confer favourable solubility properties on the compounds.

Another aspect of the present invention relates to compounds which in addition to $A_{2A}$ binding properties also are MAO-B inhibitors. Such compounds hence show effects on two known targets of Antiparkinsonian drugs, and are particularly interesting candidates. In one embodiment, these compounds have the general formula IVa formula (IVa)

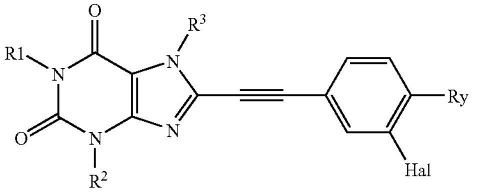

wherein Hal is chloro or bromo, and wherein $R^1$, $R^2$, $R^3$, and Ry are as defined as in the compounds of formula IIIa above. Two specific examples are 8-(3-chlorophenylethynyl)-3,7-dimethyl-1-prop-2-ynyl-3,7-dihydropurine-2,6-dione and 8-(3-bromophenylethynyl)-3,7-dimethyl-1-prop-2-ynyl-3,7-dihydropurine-2,6-dione which both showed Mao-B-inhibition values in the submicromolar range.

In one embodiment of formula (IVa), Ry is not halogen. In a more specific embodiment of formula (IVa), Ry is hydrogen.

Another embodiment is a compound according to formula (Va)

formula (Va)

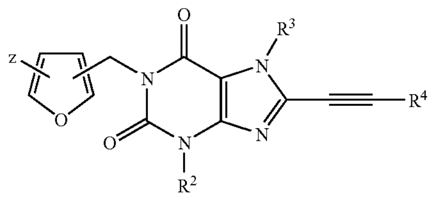

wherein $R^2$, $R^3$ and $R^4$ are as described in formula (Ia) above, and wherein z is selected from hydrogen, halogen, methyl, and methoxy.

Specific compounds according to the invention are for example but not only the compounds listed in table 1. Preferred compounds are those exhibiting a $K_i$ of less than 150 nM, less than 100 nM, less than 50 nM, or less than 20 nM with respect to the $rA_{2A}$ and/or the $hA_{2A}$ receptor as shown in tables 2a and 2b herein. Particularly preferred are those compounds having selectivity over the respective $A_1$ receptor of at least a factor 10, more preferably of a factor 30, and particularly preferably of a factor of at least 100.

Suitable salts of the compounds of the present invention, e.g. those of formula (Ia), (IIIa) and (IVa) usually have a pharmaceutically acceptable anion or cation. Suitable pharmaceutically acceptable acid addition salts of the compounds of the present invention, e.g. those of formula (Ia), (IIIa) and (IVa) are salts of inorganic acids such as hydrochloric acid, hydrobromic, phosphoric, metaphosphoric, nitric and sulfuric acid, and of organic acids such as, for example, acetic acid, benzenesulfonic, benzoic, citric, ethanesulfonic, fumaric, gluconic, glycolic, isethionic, lactic, lactobionic, maleic, malic, methanesulfonic, succinic, p-toluenesulfonic and tartaric acid. Suitable pharmaceutically acceptable basic salts are ammonium salts, alkali metal salts (such as sodium and potassium salts), alkaline earth metal salts (such as magnesium and calcium salts) and salts of trometamol (2-amino-2-hydroxymethyl-1,3-propanediol), diethanolamine, lysine or ethylenediamine.

Salts with a pharmaceutically unacceptable anion, such as, for example, trifluoroacetate, likewise belong within the framework of the invention as useful intermediates for the preparation or purification of pharmaceutically acceptable salts and/or for use in non-therapeutic, for example in vitro, applications.

When the compounds of the present invention, e.g. those of formula (Ia), (IIIa) and (IVa) are substituted with alkenyl groups, they exist in various embodiments in the form of their E-isomers, their Z-isomers, or in mixtures of E- and Z-isomers in equal amounts or wherein one of the isomers, is enriched.

Further, the compounds of the present invention, e.g. those of formula (Ia), (IIIa) and (IVa) may be in the form of their racemates, enantiomer-enriched mixtures, pure enantiomers, diastereomers and mixtures thereof in the case that the compound of the present invention, e.g. those of formula (Ia), (IIIa) and (IVa) comprises one or more centers of asymmetry.

The term “alkyl” (alone or in combination with another term(s)) means a straight or branched chain saturated hydrocarbyl substituent preferably containing from 1 to about 10 carbon atoms ($C_1$-$C_{10}$-alkyl), more preferably from 1 to 8 carbon atoms ($C_1$-$C_8$-alkyl), even more preferably from 1 to 6 carbon atoms ($C_1$-$C_6$-alkyl), even more preferably from 1 to 5 carbon atoms ($C_1$-$C_5$-alkyl), even more preferably from 1 to 4 carbon atoms ($C_1$-$C_4$-alkyl), or 2 to 5 carbon atoms ($C_2$-$C_5$-alkyl), even more preferably from 2 to 4 carbon atoms ($C_2$-$C_4$-alkyl), from 2 to 3 carbon atoms ($C_2$-$C_3$-alkyl), or from 1 to 3 carbon atoms ($C_1$-$C_3$-alkyl). The alkyl groups include methyl, ethyl, propyl, isopropyl, butyl, isobutyl, tertiary butyl, amyl, hexyl, and the like. Further, alkyl groups are unsubstituted if not indicated otherwise, see for example haloalkyl or hydroxyalkyl.

The terms “alkenyl” and “alkynyl” include straight and branched chain radicals of up to 10 carbon atoms, preferably 2 to 8 carbon atoms, more preferably 2 to 6 carbon atoms, most preferably 2 to 5 carbon atoms, and even more preferably from 2 to 4, or even 2 to 3 carbon atoms wherein the hydrocarbon chain comprises at least one carbon to carbon double bond (in the case of “alkenyl”) or at least one carbon to carbon triple bond (in the case of “alkynyl”). Examples of “alkenyl” substituents include ethenyl (“vinyl”), 2-propenyl, 3-propenyl (“allyl”), 1,4-pentadienyl, 1,4-butadienyl, 1-butenyl, 2-butenyl, 3-butenyl, pentenyl, hexenyl, and octenyl. Examples of “alkynyl” substituents include ethynyl, 2-propynyl, 3-propynyl (“propargyl”), 1-butynyl, 2-butynyl, 3-butynyl, pentynyl, hexynyl, and octynyl.

The term “alkoxy” (alone or in combination with another term(s) refers to —O-alkyl and means a straight or branched chain alkoxy substituent preferably containing from 1 to 10 carbon atoms ($C_1$-$C_{10}$-alkoxy), more preferably from 1 to 6 carbon atoms ($C_1$-$C_6$-alkoxy), even more preferably from 1 to 5 carbon atoms ($C_1$-$C_5$-alkoxy), from 1 to 4 carbon atoms ($C_1$-$C_4$-alkoxy), or from 1 to about 3 carbon atoms ($C_1$-$C_3$-alkoxy), the alkoxy groups include methoxy, ethoxy, propoxy, butoxy, isobutoxy, tert-butoxy, pentoxy, hexoxy and the like.

The term “alkoxyalkoxy” refers to an “alkoxy” group as defined above, which is substituted with at least one another “alkoxy” group. In a preferred embodiment, “alkoxyalkoxy” is an “alkoxy” group which is substituted by one other “alkoxy” group.

The term “alkoxyalkyl” refers to an alkyl group as defined above, which is substituted with at least one alkoxy group as further defined above. In a preferred embodiment, “alkoxyalkyl” is an “alkyl” group which is substituted by one other “alkoxy” group.

The term “monoalkylamino” refers to the group —NHR wherein R is an “alkyl” as defined further above.

The term "dialkylamino" refers to the group —N—RR' wherein R and R' are "alkyl" groups as defined further above and which may be the same or different. For example the term di($C_1$-$C_2$)-alkylamino refers to the group —N—RR' wherein R and R' are independently selected from methyl and ethyl.

The term "monoalkylaminoalkyl" refers to the group —R—NHR' wherein R and R' are "alkyl" groups as defined further above which may be the same or different.

The term "dialkylaminoalkyl" refers to the group —R"—NRR' wherein R, R' and R" are alkyl (or alkylene) groups as defined further above, which may be the same or different. For example the term di($C_1$-$C_2$)-alkylamino($C_1$-$C_3$)-alkyl refers to the group NRR' which is bound to the group R", wherein R and R' are independently selected from methyl and ethyl, and wherein R" is methyl(en)e, ethyl(en)e or propyl (en)e. Non-limiting examples of such a group are N,N-dimethylaminopropyl, N,N-dimethylaminoethyl or N,N-methylethylaminopropyl.

The term "alkylcarbonyl" refers to the group —C(═O)-alkyl wherein "alkyl" is as defined further above.

The term "alkoxycarbonyl" refers to the group —C(═O)—O-alkyl wherein "alkyl" is as defined further above The term "amino" denotes a nitrogen moiety having two hydrogen substituents attached to the nitrogen atom.

The term "aminoalkyl" includes an "alkyl" residue as defined further above which is substituted one or more times with an amino group. Examples include but are not limited to 2-aminoethyl, 3-aminopropyl, or 3-amino-2-methyl-propyl. The term amino($C_1$-$C_3$)-alkyl refers to an alkyl with 1 to 3 carbon atoms at least one of which is substituted with an amino group. Preferably, an "aminoalkyl" is a mono-aminoalkyl, i.e. the alkyl is substituted with only one amino group.

The term "cycloalkyl" when used alone or in combination with another term(s) means a cyclic group where all the ring atoms are saturated carbon. In various embodiments, a cycloalkyl group contains from 3 to 18 ring carbon atoms ($C_3$-$C_{18}$-cycloalkyl), from 3 up to 10 ring carbon atoms ($C_3$-$C_{10}$-cycloalkyl), more preferably from 3 up to 6 ring atoms ($C_3$-$C_6$-cycloalkyl) and even more preferably from 3 up to 5 ring atoms ($C_3$-$C_5$-cycloalkyl). The cycloalkyl groups may be monocyclic, bicyclic, tri-cyclic, or polycyclic, and is preferably monocyclic. Examples of single-ring cycloalkyls include cyclopropyl, cyclobutyl, cyclopentyl, and cyclohexyl. A cycloalkyl alternatively may be a fused, bridged or spiro-cyclic ring system of 2 or 3 rings such as, for example, norbornyl, decalinyl, bicycloheptanyl, adamantyl, and norpinanyl, and the rings may be fused.

The term "halogen" includes fluoro, chloro, bromo, and iodo.

The term "haloalkyl" includes an "alkyl" residue as defined further above which is substituted one or more times with the same or different halogen atoms. Examples include but are not limited to —$CF_3$, —$CF_2Cl$, —$CH_2CH_2F$ etc. The term halo($C_1$-$C_3$)-alkyl refers to an alkyl with 1 to 3 carbon atoms at least one of which is substituted with a halogen.

The term "hydroxylalkyl" includes an "alkyl" residue as defined further above which is substituted one or more times with a hydroxyl group. Examples include but are not limited to 2-hydroxyethyl, 3-hydroxypropyl, 2,3-dihydroxypropyl, or 3-hydroxy-2-methyl-propyl. The term hydroxyl($C_1$-$C_3$)-alkyl refers to an alkyl with 1 to 3 carbon atoms at least one of which is substituted with a hydroxygroup.

"Heterocyclyl" is a heterocyclic group characterized by a cyclic structure in which at least one of the ring atoms is a heteroatom (i.e., other than carbon). Typical heterocyclyls have one, two, three or four heteroatoms. Most commonly and preferably at least one heteroatom is independently selected from sulfur, nitrogen and oxygen. Less common heteroatoms include, P, As, Sb, Sn, Ge, and Si. The heterocyclic groups include saturated and partially saturated heterocyclic groups, and they may be monocyclic, bicyclic, tricyclic or polycyclic and may be fused rings and are preferably monocyclic. The heterocyclics also include the so-called benzoheterocyclics. These have a benzene ring fused to a heterocyclic ring.

The bonding valence of a heterocyclyl is at a carbon atom or at a nitrogen atom and preferably at the carbon atom. In various embodiments, the heterocyclyl group comprises 3 to 18 ring atoms, preferably 3 to 10 ring atoms, more preferably 3 to 7 ring atoms. A heterocyclyl ring with 3 ring atoms is for example oxiranyl or aziridinyl. A heterocyclyl with 4 ring atoms is for example azetidinyl. Heterocyclyl with 5 ring atoms encompasses for example the rings: pyrrolidinyl, imidazolidinyl and pyrazolidinyl. Heterocyclyl rings with 6 ring atoms encompass for example the rings: piperidinyl, piperazinyl, morpholinyl and thiomorphinyl. Heterocyclyl rings with 7 ring atoms encompasses for example the rings: azepanyl, [1,3]-diazepanyl and [1,4]-diazepanyl. Preferred are heterocyclyl rings with 3 to 6 ring atoms, or 3 to 5 ring atoms.

The term "aryl", when used alone or in combination with other term(s), refers to an aromatic group. In various embodiments, the aryl contains from 6 up to 18 ring carbon atoms ($C_6$-$C_{18}$-aryl), or from 6 up to 10 ring carbon atoms ($C_6$-$C_{10}$-aryl), and includes polynuclear aromatics. The aryl groups may be monocyclic, bicyclic, tricyclic or polycyclic and may be fused rings. A polynuclear aromatic compound as used herein, is meant to encompass bicyclic and tri-cyclic fused aromatic ring systems containing from 10-18 ring carbon atoms. Aryl groups include phenyl and polynuclear aromatics e.g., naphthyl, anthracenyl, phenanthrenyl, azulenyl and the like. The aryl group also includes groups such as ferrocenyl. A preferred aryl group is phenyl.

The term "benzoyl" denotes an acyl group of the formula —CO—$C_6H_5$ wherein the phenyl ring.

The term "heteroaryl" is a heterocyclyl that is aromatic. In various embodiments, a heteroaryl is monocyclic or bicyclic containing 1 to 3, preferably 1 or 2, or 1 heteroatom, especially N and/or O and/or S. The heteroaryl group contains 5 to 18 ring atoms, preferably from 5 to 14 ring atoms, more preferably from 5 to 6 ring atoms. Preferably, the "heteroaryl" group is bound via a carbon ring atom but may be also bound via a nitrogen atom. Specific examples of heteroaryl substituents include 6-membered ring substituents such as pyridinyl, pyrazinyl, pyrimidinyl, pyridazinyl, and 1,3,5-, 1,2,4-, and 1,2,3-triazinyl; 5-membered ring substituents such as thienyl, imidazolyl, furanyl, pyrazolyl, oxazolyl, isoxazolyl, thiazolyl, 1,2,3-, 1,2,4-, 1,2,5-, or 1,3,4-oxadiazolyl, pyrrolyl, triazolyl, thiadiazolyl, tetrazolyl and isothiazolyl; 6/5-membered fused ring substituents such as benzothiofuranyl, isobenzothiofuranyl, benzisoxazolyl, benzoxazolyl, purinyl, and anthranilyl; and 6/6-membered fused rings such as quinolinyl, isoquinolinyl, cinnolinyl, and quinazolinyl.

In the compounds according to the present invention the term "($C_3$-$C_{18}$)-cycloalkyl-carbonyl" denotes a group R—C(═O)—, wherein R is an $C_3$-$C_{18}$cycloalkyl group as defined above. The term "arylcarbonyl" denotes a group R—C(═O)—, wherein R is an aryl group as defined above. Other carbonyl containing groups are defined analogously.

The term "carbohydrate" denotes the residue of a polyhydroxy aldehyde or polyhydroxy ketone of the formula $C_nH_{2n}O_n$ or $C_n(H_2O)_n$, wherein n≧3, preferably 5-6, and corresponding carbohydrate groups are, for example, described in Aspinal, The Polysaccharides, New York: Academic Press 1982, 1983. A preferred carbohydrate group in the compounds according to the present invention is a glucosyl, in particular a 1-β-D-glucopyranosyl group.

The term "amino acid residue" denotes the residue of a naturally occurring or synthetic amino acid. Particularly preferred naturally occurring amino acid residues are selected from the group consisting of glycyl, valyl, alanyl, isoleucyl, phenylalanyl, prolyl, seryl, threonyl, methionyl, hydroxyprolyl. The amino acid residue may be substituted by a suitable group. Examples are benzylglycyl and N-acetylglycyl.

Suitable ester moieties of inorganic acids may be derived from inorganic acids such as sulfuric acid and phosphoric acid.

In a more general aspect of the present invention $A_{2A}$ receptor antagonists are selected from 8-alkynylxanthines and derivatives, which are represented by the general formula (I), (I)

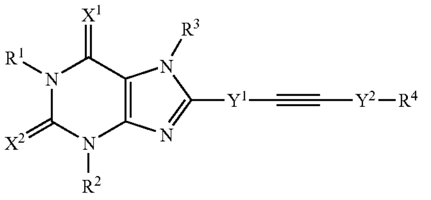

wherein, $X^1$, $X^2$ are independently S, O, $CH_2$, or Z, where Z is (Ak1)C(Ak2), where Ak1 and Ak2 are independently H or alkyl groups and the total number of carbon atoms in Z is 1-6, preferably 1-3, and preferably 1, $Y^1$, $Y^2$ are independently a direct bond or ($C_1$-$C_3$)-alkylene, $R^1$ and $R^3$ are independently hydrogen, optionally substituted heterocyclyl with 3 to 18 ring atoms, optionally substituted aryl, optionally substituted heteroaryl with 5 to 18 ring atoms, —C(O)$R^5$, —C(O)O$R^5$—O$R^5$, or —OC(O)$R^5$; or $R^1$ and $R^3$ are ($C_1$-$C_{10}$)-alkyl, ($C_2$-$C_{10}$)-alkenyl, ($C_2$-$C_{10}$)-alkynyl, or ($C_3$-$C_{18}$)-cycloalkyl, each of which can optionally be substituted in one or more places, in the same way or differently, with halogen, hydroxyl, cyano, amino, nitro, optionally substituted ($C_3$-$C_{18}$)-cycloalkyl, optionally substituted heterocyclyl with 3 to 18 ring atoms, optionally substituted aryl, optionally substituted heteroaryl with 5 to 18 ring atoms, —OC(O)$R^5$ or —C(O)$R^5$, or —O$R^5$;

$R^2$ is hydrogen, optionally substituted heterocyclyl with 3 to 18 ring atoms, optionally substituted aryl, optionally substituted heteroaryl with 5 to 18 ring atoms, —N$R^6R^7$, —O$R^8$, —C(O)$R^5$, or —C(O)O$R^8$; or $R^2$ is ($C_1$-$C_{10}$)-alkyl, ($C_2$-$C_{10}$)-alkenyl, ($C_2$-$C_{10}$)-alkynyl, or ($C_3$-$C_{18}$)-cycloalkyl, each of which can optionally be substituted in one or more places, in the same way or differently with halogen, hydroxyl, cyano, nitro, optionally substituted ($C_3$-$C_{18}$)-cycloalkyl, optionally substituted heterocyclyl with 3 to 18 ring atoms, optionally substituted aryl, optionally substituted heteroaryl with 5 to 18 ring atoms, —N$R^6R^7$, —O$R^8$, —C(O)$R^5$ or —C(O)O$R^8$;

$R^4$ is an optionally substituted heterocyclyl with 3 to 18 ring atoms, optionally substituted ($C_3$-$C_{18}$)-cycloalkyl, or optionally substituted heteroaryl with 5 to 18 ring atoms, or an aryl optionally substituted with one or more groups selected from the group consisting of halogen, amino, nitro, cyano, —O$R^9$, C(O)$R^9$, —OC(O)$R^8$, optionally substituted heterocyclyl with 3 to 18 ring atoms, optionally substituted ($C_3$-$C_{18}$)-cycloalkyl, optionally substituted aryl and optionally substituted heteroaryl with 5 to 18 ring atoms; or $R^4$ is an aryl optionally substituted with ($C_1$-$C_{10}$)-alkyl, ($C_2$-$C_{10}$)-alkenyl, ($C_2$-$C_{10}$)-alkynyl, or ($C_3$-$C_{18}$)-cycloalkyl, each of which can optionally be further substituted in one or more places, in the same way or differently with halogen, hydroxy, cyano, amino, nitro, ($C_1$-$C_8$)-alkyl, ($C_1$-$C_6$)-alkoxy, ($C_1$-$C_6$)-alkoxy-($C_1$-$C_6$)-alkoxy, heterocyclyl with 3 to 18 ring atoms, ($C_3$-$C_{18}$)-cycloalkyl, aryl, a heteroaryl with 5 to 18 ring atoms, —C(O)$R^5$, or —OC(O)$R^5$, with the proviso, that if the aryl is a phenyl, the phenyl is at least once substituted with a group other than hydrogen, $R^5$ is a hydrogen, ($C_1$-$C_6$)-alkyl, ($C_2$-$C_6$)-alkenyl, or ($C_2$-$C_6$)-alkynyl; or $R^5$ is a ($C_1$-$C_6$)-alkyl substituted in one or more places, in the same way or differently, with hydroxyl, ($C_1$-$C_6$)-alkoxy, aryl or —N$R^6R^7$;

$R^6$ and $R^7$ are independently hydrogen, ($C_1$-$C_6$)-alkyl, ($C_2$-$C_6$)-alkenyl or ($C_2$-$C_6$)-alkynyl;

$R^8$ is hydrogen, ($C_1$-$C_{10}$)-alkyl, ($C_2$-$C_{10}$)-alkenyl, or ($C_2$-$C_{10}$)-alkynyl; or $R^8$ is ($C_1$-$C_6$)-alkyl substituted in one or more places, in the same way or differently, with hydroxyl, ($C_1$-$C_6$)-alkoxy, aryl or —N$R^6R^7$; or $R^8$ is optionally substituted ($C_3$-$C_{18}$)-cycloalkyl, optionally substituted heterocyclyl with 3 to 18 ring atoms, optionally substituted aryl, optionally substituted heteroaryl with 5 to 18 ring atoms or carbohydrate; or $R^8$ is formyl, optionally substituted ($C_1$-$C_{10}$)-alkylcarbonyl, optionally substituted ($C_3$-$C_{18}$)-cycloalkylcarbonyl, optionally substituted arylcarbonyl, optionally substituted heteroarylcarbonyl in which the heteroaryl part has 5 to 18 ring atoms, optionally substituted heterocyclylcarbonyl in which the heterocyclyl part has 3 to 18 ring atoms, hydroxycarbonyl, hydroxyl-($C_1$-$C_6$)-alkylcarbonyl, ($C_1$-$C_{10}$)-alkoxycarbonyl, optionally substituted aryloxycarbonyl, benzoylacyl, benzoylglycyl, optionally substituted amino acid residue; or $R^8$ is selected from

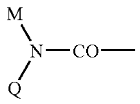

and

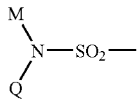

wherein M and Q independently represent hydrogen, ($C_1$-$C_{10}$)-alkyl, optionally substituted aryl, or phenoxy($C_1$-$C_6$)-alkyl and wherein M and Q may form a ring together with the amine nitrogen; or $R^8$ is an ester moiety of inorganic acids; or $R^8$ is an ester moiety of ascorbic acid; or $R^8$ is —Si$R_kR_jR_u$, wherein $R_k$, $R_j$, $R_u$ are independently selected from ($C_1$-$C_6$)-alkyl or aryl;

$R^9$ is hydrogen, ($C_1$-$C_{10}$)-alkyl, ($C_2$-$C_{10}$)-alkenyl, or ($C_2$-$C_{10}$)-alkynyl; or $R^9$ is ($C_1$-$C_6$)-alkyl substituted in one or more places, in the same way or differently, with hydroxyl, ($C_1$-$C_6$)-alkoxy or —N$R^6R^7$; or $R^9$ is optionally substituted ($C_3$-$C_{18}$)-cycloalkyl, optionally substituted heterocyclyl with 3 to 18 ring atoms or carbohydrate; or $R^9$ is formyl, optionally substituted ($C_1$-$C_{10}$)-alkylcarbonyl, optionally substituted ($C_3$-$C_{18}$)-cycloalkylcarbonyl, optionally substituted heterocyclylcarbonyl in which the heterocyclyl part has 3 to 18 ring atoms, hydroxycarbonyl, hydroxyl-($C_1$-$C_6$)-alkylcarbonyl, ($C_1$-$C_{10}$)-alkoxycarbonyl or an optionally substituted amino acid residue; or $R^9$ is selected from

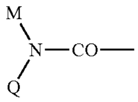

and, or

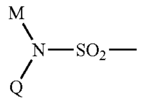

$R^9$ is an ester moiety of inorganic acids, or $R^9$ is an ester moiety of ascorbic acid, or $R^9$ is —$SiR_kR_jR_u$, wherein $R_k$, $R_j$, $R_u$ are independently selected from ($C_1$-$C_6$)-alkyl and aryl.

The antagonists include suitable salts of compounds of the above formula, as well as E- and Z-isomers, optical isomers, diastereomers, racemic mixtures, and the like (where applicable).

In various embodiments, $X^1$ and $X^2$ of general formula (I) are the same group. When $X^1$ and $X^2$ are O, the compounds are understood as substituted xanthines; when $X^1$ and $X^2$ are Z, the compounds can be understood as purine derivatives or substituted purines.

When $X^1$ and $X^2$ are S, the compounds are understood as thio derivatives of xanthines. Preferably, $X^1$ and $X^2$ are both O.

When $Y^1$ of general formula (I) is a direct bond, the compounds, salts, etc. of formula (I) are 8-ethynyl derivatives, which is a preferred embodiment. In various embodiments, both $Y^1$ and $Y^2$ are direct bonds, so the group $R^4$ is directly bonded to a triple bonded carbon. In various embodiments, $R^1$ is hydrogen; or is ($C_1$-$C_8$)-alkyl, ($C_2$-$C_8$)-alkenyl, ($C_2$-$C_8$)-alkynyl, or ($C_3$-$C_6$)-cycloalkyl, each of which can optionally be substituted in one or more places, in the same way or differently, with halogen, hydroxy, cyano, amino, nitro, ($C_3$-$C_6$)-cycloalkyl, heterocyclyl with 3 to 7 ring atoms, aryl, heteroaryl with 5 to 10 ring atoms, —$OC(O)R^6$ or —$C(O)R^6$.

In various embodiments, $R^1$ of general formula (I) stands for hydrogen, ($C_1$-$C_6$)-alkyl, allyl, propargyl, a ($C_1$-$C_6$)-alkyl substituted with one or more cyano or ($C_3$-$C_6$)-cycloalkyl groups, or a methyl group substituted with a 3 to 7-membered heterocyclic ring. Examples of the latter include furanylmethyl.

Illustratively, $R^1$ of general formula (I) is a ($C_1$-$C_4$)-alkyl, cyanomethyl, allyl, or a propargyl group. For example, $R^1$ is an ethyl, allyl or propargyl group; or a propargyl or methyl group. In various and preferred embodiments, $R^1$ is propargyl.

In another embodiment, $R^2$ of general formula (I) is H or is selected from allyl, propargyl, amino, ($C_1$-$C_4$)-alkyl-C(O)O—, or a ($C_1$-$C_6$)-alkyl, the latter optionally substituted with one or more groups selected from hydroxyl, halogen, cyano, —$NR^6R^7$, —C(O)OH, —C(O)H, ($C_1$-$C_3$)-alkoxy, ($C_1$-$C_3$)-alkoxy-($C_1$-$C_3$)-alkoxy, ($C_1$-$C_3$)-alkyl-C(O)O—, a heterocyclyl with 3 to 6 ring atoms, phosphate ester, or carbohydrate ester.

In another embodiment $R^2$ of general formula (I) is hydrogen or a methyl, ethyl, allyl, 2-bromoethyl, amino, cyano-($C_1$-$C_3$)-alkyl, propargyl, butyl-C(O)O—, butyl-C(O)O-methyl-, methyl-C(O)O-propyl-, $R^6R^7N$—($C_2$-$C_3$)-alkyl-, epoxide-ethyl, dioxolane-ethyl, $(OH)_2OP(O)$-propyl, H—C(O)-ethyl, HO—C(O)-ethyl, hydroxyl-($C_2$-$C_3$)-alkyl, dihydroxypropyl, glucosyl-O-propyl, methoxyethoxy-ethyl-, or a trihydroxypentyl-group.

In particular embodiments $R^2$ of general formula (I) stands for a hydrogen, methyl, ethyl, allyl, 2-bromoethyl, propargyl, hydroxyethyl, hydroxypropyl, dihydroxypropyl, $(CH_3)_2$—N-ethyl, $(OH)_2(O)PO$-propyl, or a dioxolane-ethyl group or methoxyethyl, oxiranylmethyl, 2,3-dihydroxypropyl, cyanomethyl, 2-cyanoethyl, 3-cyanopropyl, or is selected from the group consisting of hydrogen, methyl, ethyl, allyl, propargyl, hydroxyethyl, and hydroxypropyl, or $R^2$ is hydrogen, methyl, ethyl, or allyl.

$R^3$ of general formula (I) is selected from the same groups as $R^1$ noted above. In various embodiments, $R^3$ is a methyl, ethyl or propargyl group, or is furan-2-ylmethyl.

If $R^4$ of general formula (I) is a phenyl, the phenyl is at least once substituted with a group other than hydrogen.

In various embodiments, $R^4$ of general formula (I) is a heterocyclyl with 3 to 7 ring atoms; a heteroaryl with 5 to 10 ring atoms; or an aryl optionally substituted with one or more groups selected from the group consisting of halogen, amino, nitro, cyano, —OR5, —$C(O)R^6$, —$OC(O)R^6$, ($C_3$-$C_6$)-cycloalkyl, aryl, heterocyclyl with 3 to 7 ring atoms or a heteroaryl with 5 to 10 ring atoms. In addition, $R^4$ can be an aryl optionally substituted with ($C_1$-$C_8$)-alkyl, ($C_2$-$C_8$)-alkenyl, ($C_2$-$C_8$)-alkynyl, ($C_3$-$C_6$)-cycloalkyl each of which can optionally be further substituted in one or more places, in the same way or differently with halogen, hydroxy, cyano, amino, nitro, ($C_1$-$C_8$)-alkyl, ($C_1$-$C_6$)-alkoxy, ($C_1$-$C_6$)-alkoxy-($C_1$-$C_6$)-alkoxy, ($C_3$-$C_6$)-cycloalkyl, heterocyclyl with 3 to 7 ring atoms, aryl, —$C(O)R^6$, or —$OC(O)R^6$.

In various embodiments $R^4$ of general formula (I) stands for a heterocyclyl with 5 ring atoms selected from the group consisting of furyl, thienyl, pyrrolyl, pyrrolinyl, pyrrolidinyl, dioxolanyl, oxazolyl, thiazolyl, imidazolyl, imidazolinyl, pyrazolyl, pyrazolinyl, pyrazolidinyl, isoxazolyl, isothiazolyl, oxadiazolyl, triazolyl and thiadiazolyl, or a phenyl substituted with Ra and Rb, wherein Ra and Rb are connected to adjacent carbon atoms of the phenyl ring and form together a carbocyclic or heterocyclic ring with from 3 to 6 atoms, or an aryl optionally substituted with one or more groups selected from the group consisting of ($C_1$-$C_4$)-alkyl, halogenyl, nitro, amino, trifluoromethyl, —$OR^5$ and —$OC(O)R^6$. When $R^4$ is a 5-membered ring heterocycle, preferably Y1 and Y2 are direct bonds and the ring atom at the 3-position of the ring (measured from the point of attachment to the triply bonded carbon) is a heteroatom. The heterocyclic ring of $R^4$ of general formula (I) is optionally substituted with lower alkyl, such as methyl.

In various embodiments, $R^4$ of general formula (I) is a thiophene, furan, or benzodioxole, or a phenyl substituted with one or more groups selected from the group consisting of methyl-, halogen, nitro, amino, —$OC(O)CH_3$, methoxy, ethoxy, hydroxyethyl, hydroxypropyl, methoxyethyl, allyl, hydroxyethoxy, hydroxypropoxy, and Ra and Rb discussed above.

In a particular embodiment, $R^4$ of general formula (I) stands for a phenyl substituted with one or more groups discussed herein at the meta- and/or para-positions such as meta-methoxyphenyl, or 3,4-dimethoxyphenyl.

Preferably $R^5$ of general formula (I) stands for a hydrogen, ($C_1$-$C_4$)-alkyl, phenyl($C_1$-$C_3$)-alkyl, hydroxy($C_1$-$C_4$)-alkyl, $R^6R^7$—N—($C_1$-$C_4$)-alkyl, or allyl.

More preferably $R^5$ of general formula (I) stands for hydrogen, methyl, ethyl, hydroxy($C_2$-$C_3$)-alkyl, $(CH_3)2$-N—($C_2$-$C_3$)-alkyl, phenylmethyl or allyl.

In exemplary embodiments, $R^5$ of general formula (I) is a hydrogen, methyl, ethyl, allyl, hydroxy($C_2$-$C_3$)-alkyl or $(CH_3)2$-N—($C_2$-$C_3$)-alkyl.

For example, $R^5$ of general formula (I) is a methyl, ethyl, allyl, or hydroxyethyl.

Preferably $R^6$ and $R^7$ of general formula (I) stand independently from each other for hydrogen or a $(C_1-C_6)$-alkyl group or for H or a $(C_1-C_3)$-alkyl group;

Most preferably $R^6$ and $R^7$ of general formula (I) stand independently from each other for hydrogen or a methyl group.

In various embodiments, $R^8$ of general formula (I) stands for hydrogen, $(C_1-C_6)$-alkyl, $(C_1-C_6)$-alkoxy-$(C_1-C_6)$-alkyl, $(C_3-C_6)$-cycloalkyl, benzyl, allyl, carbohydrate, or formyl, $(C_1-C_6)$-alkylcarbonyl, $(C_3-C_6)$-cycloalkylcarbonyl, arylcarbonyl, hydroxycarbonyl, $(C_1-C_6)$-alkoxycarbonyl, aryloxycarbonyl, benzoylacyl, benzoylglycyl, amino acid residue, or is selected from the group

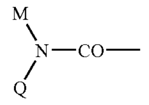

and

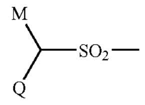

wherein M and Q independently represent hydrogen, $(C_1-C_6)$-alkyl, aryl, benzyl, or phenoxy$(C_1-C_6)$-alkyl and wherein M and Q may form a ring from 3 to 6 atoms together with the amine nitrogen, or an ester moiety of inorganic acids (e.g., sulfate or phosphate ester groups), or an ester moiety of ascorbic acid, or —$SiR_kR_jR_u$ wherein $R_k$, $R_j$, $R_u$ are independently selected from $(C_1-C_4)$-alkyl and aryl.

The various possibilities for $R^1$, $R^2$, $R^3$, $R^4$, $R^5$, and so on of general formula (I) can be combined to provide further embodiments of the compounds. In each of the embodiments $X^1$ and $X^2$ are O, S, or Z as discussed above, and in preferred embodiments, $X^1$ and $X^2$ are both O, and $Y^1$ and $Y^2$ are both direct bonds.

An example is compounds of Formula (I) where $R^1$ is hydrogen, $(C_1-C_6)$-alkyl, allyl, propargyl, or a $(C_1-C_6)$-alkyl substituted with one or more cycloalkyl groups, $R^2$ is a hydrogen or an allyl, propargyl, amino, $(C_1-C_4)$-alkyl-C(O)O—, or a $(C_1-C_6)$-alkyl-group optionally substituted with one or more groups selected from the group consisting of hydroxyl, halogen, cyano, —$NR^6R^7$, —C(O)OH, —C(O)H, $(C_1-C_3)$-alkoxy, $(C_1-C_3)$-alkoxy-$(C_1-C_3)$-alkoxy, $(C_1-C_3)$-alkyl-C(O)O—, a heterocyclyl with 3 to 6 ring atoms, phosphate ester, or carbohydrate ester, $R^3$ is a hydrogen, $(C_1-C_8)$-alkyl, propargyl, or a $(C_1-C_3)$-alkyl group substituted with one or more groups selected from the group consisting of hydroxyl, halogen, cyano, phenyl, $(C_3-C_6)$-cycloalkyl, —$OC(O)R^6$ and —$C(O)R^6$, $R^4$ is a heterocyclyl with 5 ring atoms selected from the group consisting of furyl, thienyl, pyrrolyl, pyrrolinyl, pyrrolidinyl, dioxolanyl, oxazolyl, thiazolyl, imidazolyl, imidazolinyl, pyrazolyl, pyrazolinyl, pyrazolidinyl, isoxazolyl, isothiazolyl, oxadiazolyl, triazolyl and thiadiazolyl, or a phenyl substituted with $R^a$ and $R^b$, wherein $R^a$ and $R^b$ are connected to adjacent carbon atoms of the phenyl ring and form together a carbocyclic or heterocyclic ring of from 3 to 6 atoms, or an aryl optionally substituted with one or more groups selected from the group consisting of $(C_1-C_4)$-alkyl, halogen, nitro, amino, trifluoromethyl, —$OR^5$ and —$OC(O)R^6$, $R^5$ is a hydrogen, $(C_1-C_4)$-alkyl, phenyl-$(C_1-C_3)$-alkyl, hydroxyl-$(C_1-C_4)$-alkyl, $R^6R^7$—N—$(C_1-C_4)$-alkyl, or allyl, and $R^6$ and $R^7$ are independently hydrogen or a $(C_1-C_3)$-alkyl group, or pharmaceutically acceptable salts, isomers, diastereomers or enantiomers thereof.

Another example is compounds of Formula (I) where

R is a $(C_1-C_4)$-alkyl, allyl, or a propargyl, $R^2$ is hydrogen or a methyl, amino, ethyl, allyl, bromoethyl, cyano-$(C_2-C_3)$-alkyl, propargyl, butyl-C(O)O—, butyl-C(O)O-methyl-, methyl-C(O)O-propyl-, $R^6R^7$N—$(C_2-C_3)$-alkyl-, epoxide-ethyl, 1,3-dioxo-1,3-dihydro-2H-isoindol-ethyl, dioxolane-propyl, morpholine-ethyl, $(OH)_2OP(O)$-propyl, H—C(O)-ethyl, HO—C(O)-ethyl, hydroxyl-$(C_2-C_3)$-alkyl, dihydroxypropyl, glucosyl-O-propyl, methoxyethoxy-ethyl-, or a trihydroxypentyl-group, $R^3$ is hydrogen or a $(C_1-C_5)$-alkyl, hydroxyethyl, propargyl, methyl-C(O)-methyl, phenyl-methyl, cyclobutylmethyl, or butyl-C(O)O-methyl-group, $R^4$ is a thiophene, furan, benzodioxole, or a phenyl substituted with one or more groups selected from the group consisting of methyl-, halogen, nitro, amino, trifluoromethyl-, —$OC(O)CH_3$ and —$OR^5$, $R^5$ is a hydrogen, methyl, ethyl, hydroxyl-$(C_2-C_3)$-alkyl, $(CH_3)_2$—N—$(C_2-C_3)$-alkyl, phenylmethyl or allyl, $R^6$ and $R^7$ are independently hydrogen or a methyl group, or pharmaceutically acceptable salts, isomers, diastereomers or enantiomers thereof.

Still further examples are laid out below.

Compounds of Formula (I) where:

$R^2$ is a hydrogen or an amino, methyl, ethyl, allyl, bromoethyl, cyanomethyl, propargyl, butyl-C(O)O—, butyl-C(O)O-methyl, methyl-C(O)O-propyl-, $(CH_3)_2$—N—$(C_2-C_3)$-alkyl, epoxide-ethyl, 3-dioxo-1,3-dihydro-2H-isoindol-ethyl, dioxolane-propyl, morpholine-ethyl, $(OH)_2$ $OP(O)$-propyl, H—C(O)-ethyl, HO—C(O)-ethyl, hydroxyethyl, hydroxypropyl, or a dihydroxypropyl group, and $R^4$ is a benzodioxole, or a phenyl substituted with one or more groups selected from the group consisting of methyl-, halogen, nitro, amino, trifluoromethyl, —$OC(O)CH_3$ and —$OR^5$, or pharmaceutically acceptable salts, isomers, diastereomers or enantiomers thereof.

Compounds of formula (I) where $R^1$ is a ethyl, allyl or propargyl group, $R^3$ is a methyl, ethyl or propargyl group, $R^4$ is phenyl substituted with one or more groups selected from the group consisting of methyl, halogen, —$OC(O)CH_3$ and —$OR^5$, and $R^5$ is a hydrogen, methyl, ethyl, allyl, hydroxyl-$(C_2-C_3)$-alkyl, or $(CH_3)_2$—N—$(C_2-C_3)$-alkyl, or pharmaceutically acceptable salts, isomers, diastereomers or enantiomers thereof.

Compounds of formula (I) where $R^1$ is a propargyl group, $R^2$ is a hydrogen, methyl, ethyl, allyl, propargyl, hydroxyethyl or hydroxypropyl group, $R^3$ is a methyl or propargyl group; and $R^5$ is a methyl, ethyl, allyl, or hydroxyethyl, or pharmaceutically acceptable salts, isomers, diastereomers or enantiomers thereof.

Compounds of general formula (I) wherein $R^1$ is a propargyl group, $R^2$ is a methyl, ethyl, furan-2-ylmethyl, furan-3-ylmethyl, or hydroxypropyl group, and $R^4$ is a phenyl substituted with one or more methoxy groups or a meta-methylphenyl group, or pharmaceutically acceptable salts, isomers, diastereomers or enantiomers thereof.

Compounds of general formula (I) wherein $R^1$ is a propargyl group, $R^3$ is a methyl group, and $R^4$ is phenyl substituted with one or more methoxy groups, or pharmaceutically acceptable salts thereof.

Compounds of general formula (I) wherein $R^1$ is a propargyl group, $R^2$ is an ethyl or hydroxypropyl group, and $R^4$ is phenyl substituted with two methoxy groups., including salts thereof.

In one embodiment the present invention relates to pharmaceutical compositions comprising compounds according to formula (I), wherein $R^1$, $R^2$, $R^3$ and $R^4$ have the meanings shown in table 1.

In another embodiment, compounds of Formula (II) are provided, as well as salts thereof and possible optical isomers, diastereomers, and configurational isomers (for example, E- and Z-configurations about double bonds). In one aspect, these are compounds like those of Formula I, wherein $Y^1$ and $Y^2$ are direct bonds and wherein $R^4$ is a substituted phenyl group or a heterocyclic. The substitution of the phenyl group is preferably at positions meta- and para- to the position of attachment to the alkynyl group. Suitable salts include those described above for Formula Ia.

(II)

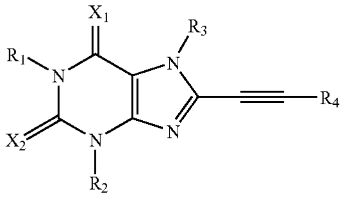

In Formula (II), the groups have the following meaning:

$X_1$ and $X_2$ are independently $CH_2$, O, or S;

$R_1$ is ($C_1$-$C_5$)-alkyl, ($C_2$-$C_4$)-alkyl, heteroarylmethyl, or ($C_3$-$C_4$)-alkynyl;

$R_2$ is —H, —$CH_3$, —$CH_2CH_3$, —$CH_2CN$, —$CH_2CH_2CN$, or —$CH_2CH_2CH_2CN$; in addition polar substituents are tolerated at $R_2$, for example those containing hydrogen bond acceptors;

In non-limiting embodiments:

$R_2$ is an aliphatic group A of 2 to 5 total carbon atoms, wherein the first two carbons are bonded to the ring in series and the second carbon from the ring is bonded to at least one of single bond O, OH, $OCH_3$, single bond N, triple bond N, ═CH, ═$CH_2$, —CH═O and acetals thereof, and halogen; or $R_2$ is an aliphatic group B of 3 to 5 total carbons, wherein the first three carbons are bonded to the ring in a chain, and the third carbon from the ring is bonded to single bond O or to OH; or $R_2$ is a methyl substituted with a 5-membered heterocyclic ring, preferably a heteroaromatic such as thiophene and furan;

$R_3$ is —H, methyl, ethyl, furan-2-ylmethyl, or propargyl;

$R_4$ is an optionally substituted heterocyclic ring of 5 to 7 ring atoms; in various embodiments $R_4$ is a 5- or -6-membered heterocycle, preferably an aromatic heterocycle. The ring is unsubstituted or preferably substituted with lower alkyl groups such as ($C_1$-$C_4$)-alkyl and especially methyl. Exemplary heterocycles include five membered aromatic heterocycles with O, S, or N as heteroatoms. Non-limiting examples include furan, thiophene, pyrrole, and imidazole. In various embodiments, R4 is bound to the triple bond of formula (I), (II), or (III) in such a way that a heteroatom occupies the 3-position, where the point of attachment to the triple bond is the 1-position; or $R_4$ is a group of Formula (IIa)

(IIa)

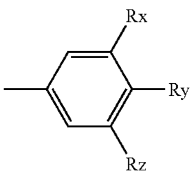

wherein optionally, any two adjacent Rx, Ry, and Rz together with the phenyl ring to which they are bonded form a 5- to 7-membered ring containing zero, one, or two ring oxygen atoms;

any of Rx, Ry, and Rz not forming a ring are independently selected from H, $CH_3$, halogen, and $OR^{17}$, wherein $R^{17}$ is ($C_1$-$C_4$)-alkylcarbonyl, ($C_1$-$C_4$)-alkyl, hydroxy($C_1$-$C_4$)-alkyl, ($C_1$-$C_4$)-alkoxy($C_1$-$C_4$)-alkyl, ($C_1$-$C_4$)-alkenyl, heterocyclyl($C_1$-$C_4$)-alkyl, or ($C_1$-$C_3$)-dialkylamino($C_1$-$C_4$)-alkyl; and at least one of Rx, Ry, and Rz is not —H.

In various embodiments of Formula II, $R_1$ is propargyl, $R_4$ is Formula IIa, and at least one of Rx, Ry, and Rz, is methoxy. In some embodiments, two of Rx, Ry, and Rz are methoxy. In various embodiments, at least one of Rx, Ry, and Rz is hydrogen. In various embodiments, $R_3$ is methyl. Additional suitable components of $R_4$ are given below and in the Examples.

When $R_1$ is propargyl and $X_1$ and $X_2$ are both O, compounds of Formula IIIa are obtained formula (IIIa)

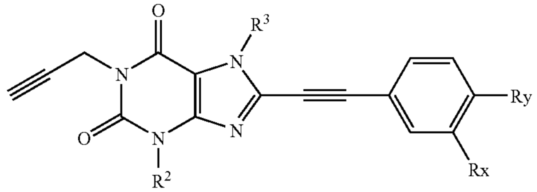

Salts of Formula IIIa compounds include those described above for Formula I and II. In a representative embodiment, Rx, Ry, and Rz are independently selected from hydrogen, halogen, methyl, methoxy, ethoxy, and ($C_1$-$C_3$)-dialkylamino-($C_1$-$C_4$)-alkyl. As with Formula II and illustrative embodiments of Formula I, preferably at least one of Rx, Ry, and Rz is other than hydrogen. In particular embodiments, one of Rx, Ry, and Rz is a methoxy and the others are hydrogen; or two of them are methoxy and the third is hydrogen. Optionally, any of the methoxy groups is further substituted with optionally substituted heterocycle. An example of the latter is furan-2-ylmethoxy or furan-3-ylmethoxy.

Illustratively in Formula II and IIIa, the group $R^2$ is selected from 2,3-dihydroxypropyl, cyanomethyl, 2-cyanoethyl, 3-cyanopropyl, furan-2-ylmethyl, furan-3-ylmethyl, allyl, glycidyl, 2-methoxyethyl, propargyl, 2-bromoethyl, 2-hydroxyethyl, glycidylmethyl, 3-hydroxypropyl and the phosphate ester thereof, 2-hydroxypropyl, 3-methoxypropyl, 2-(N,N-dimethylamino)ethyl, hydrogen, methyl, and ethyl. These groups are illustrated also in the compounds given below in Tables 1-6.

In various embodiments, the compounds of the present invention such as compounds of formula Ia, IIIa, II and III exhibit a high affinity for $A_{2A}$ receptors when measured in rats or in humans, and are generally useful as therapeutic agents for conditions mediated by the $A_{2A}$ receptor and its antagonists. In addition, these compounds often show a marked selectivity for the $A_{2A}$ over the $A_1$ receptor (as indicated by measured Ki values), with most showing a greater than 10 fold higher sensitivity for the former, as indicated by a Ki for $A_{2A}$ that is lower by at least a factor of 10 than the Ki for $A_1$. Inhibitor data for a representative group of these compounds is given in the Tables.

In various embodiments, the compounds of the present disclosure exhibit a binding equilibrium constant or $K_i$ of 180 nM or less with respect to the $A_{2A}$ receptor, measured either on human receptors or in a mouse model. By judicious choice of substituents within the Formulas given above, it is possible to provide inhibitors having even higher affinity. Thus in various embodiments, the compounds exhibit $K_i$ less than 150 nM, less than 100 nM, less than 50 nM, or less than 20 nM with respect to the $A_{2A}$ inhibitor. Compounds are provided that have a $K_i$ of as low as 5 nM with respect to the $A_{2A}$ receptor.

Provision of $A_{2A}$ antagonists of high affinity based on the current disclosure is based in part on the discovery that certain sizes of substituent groups on the xanthine ring, and certain patterns of substitution about the phenyl ring of Formula IIa lead to inhibitors of high affinity. For example, when $R_2$ is other than hydrogen, methyl, ethyl, cyanomethyl, cyanoethyl, or cyanopropyl, it is described that the second or third carbon atom from the ring nitrogen is bonded to certain functional groups or atoms in order to have high affinity for the receptors. The presence of these groups is indicative of corresponding structure on the receptors themselves. In one aspect, the inventors have probed that structure by identifying inhibitor molecules that bind tightly with the receptor binding site. Specifically, certain kinds and locations of dipoles are provided by the aliphatic groups A and B described above and exemplified in the Examples and Tables. In particular, in various embodiments such dipoles are provided at the 2- and 3-positions of the aliphatic groups A and B.

Preferred compounds in various aspects include 3-ethyl-8-(3,4-dimethoxyphenylethynyl)-7-methyl-1-prop-2-ynyl-3,7-dihydropurine-2,6-dione, which is given as test compound 1 in the Tables. This compound induces a potent hyperlocomotion in the Irwin Test. This compound also significantly reduced catalepsy time in acute CGS-21680 and reserpine-induced catalepsy models. These models are e.g. described by Ferré S. et al., Neurosci. Let., 1991, 130, 162; Ferré S. et al., Neuroscience, 1992, 51, 501; Kafka S. H. et al., Eur. J. Pharma col., 1996, 295, 147; Rimondini R. et al., Neuropsychopharmacology, 1997, 17, 82 and are herein incorporated by reference. The compound was also effective in a haloperidol model.

Another useful compound is 3-(3-hydroxypropyl)-8-(3,4-dimethoxyphenylethynyl)-7-methyl-1-prop-2-ynyl-3,7-dihydropurine-2,6-dione, shown as test compound 2. This compound induces a potent hyperlocomotion in the Irwin Test. This compound also reduced catalepsy time in acute CGS-21680 and reserpine-induced catalepsy models. Another preferred compound is 8-[(3,4-dimethoxyphenyl)ethynyl]-7-methyl-1-prop-2-ynyl-3,7-dihydro-1H-purine-2,6-dione.

Intermediate products used for the production of a compound according to general formula (I), (II), and (III) of the invention are those of general formula (IV), (IV)

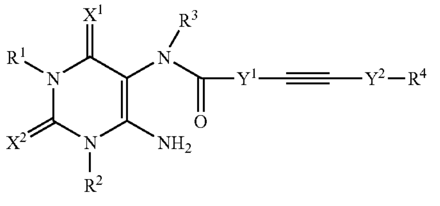

in which $X^1$, $X^2$, $Y^1$, $Y^2$, $R^1$, $R^2$, $R^3$ and $R^4$ have the meanings indicated in one of Formulas (Ia), (IIIa), (IVa), (Va), (I), (II), and (III). The intermediates include salts, optical isomers, and diastereomers of the Formula (IV) compounds. In various embodiments, one or more of $R^1$, $R^2$, and $R^3$ are hydrogen, and are subsequently alkylated according to the synthetic strategy, as described further below. Thus in one embodiment, $R^2$ or $R^3$ of general formula (IV) stands for a hydrogen. In another embodiment of the invention both $R^2$ and $R^3$ of general formula (IV) stand for hydrogen. As discussed further below, when $R^1$ in the ultimate product is propargyl, it is advantageous to start with a compound of Formula (IV) where $R^1$ is hydrogen and alkylate the position later with propargyl bromide, after ring closure.

When $R^1$ or $R^2$ is a hydrogen and $X^1$ and $X^2$ are O or S, the compounds can exist in tautomeric forms, either in the solid or in solution. Different tautomeric forms are illustrated by Formulas V or VI:

(V)

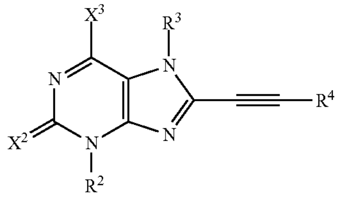

(VI)

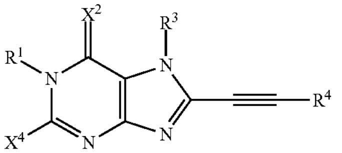

(illustrated for the case where $Y_1$ and $Y_2$ are direct bonds) where $X^1$ and $X^2$ are O or S; $X^3$ and $X^4$ are —OH or —SH; and $R^1$, $R^2$, $R^3$, and $R^4$ are as defined above.

A tautomeric form of formula (V) or (VI) can be produced according to the methods known to the skilled person in the art, such as e.g. by Muller et al., Synthesis, 1998, 1428. This document is herein incorporated by reference.

In various embodiments, the compounds of formula (Ia), (IIIa), (IVa), (Va), (I), (II), and (III) (hereafter the "compounds") can be used as pharmaceutical compounds based on their selective antagonistic activity relative to the $A_{2A}$ adenosine receptor. Where the compounds have ionizable groups (amino groups, carboxyl groups, and the like), suitable $A_{2A}$ antagonists are also selected from salts of the compounds, as well as from tautomeric forms.

In various embodiments, the compounds exhibit more than 3-fold, preferably a more than 5-fold, more preferably a more than 10-fold, even more preferably a more than 50-fold, most preferably a more than 100-fold selective affinity for $A_{2A}$ over $A_1$. Selective affinity is determined in the usual way by comparing the $K_i$ of an inhibitor or antagonist measured on a pair of receptors. If the $K_i$ of a compound for a first receptor is less than the $K_i$ for a second receptor, it is said that the compound has a higher affinity for the first receptor, or that it is selective for the first receptor. The degree of selectivity is indicated by the numeric ratio of the respective $K_i$'s. If for example $K_i$ on the first receptor is lower by a factor of ten than $K_i$ for the second, it is said that the affinity for the first receptor is ten times that for the second receptor. In some situations, selectivity versus the $A_1$ adenosine receptor is desirable e.g. due to potential negative effects on cardiac and kidney functions and in the central nervous system by compounds acting on the $A_1$ adenosine receptor.

Based on their profile of action, the compounds according to the invention are suitable for preventing or treating diseases such as Parkinson's disease (PD), catalepsy, dystonia, dyskinetic syndrome, restless legs syndrome, migraine, pain, dementia, neurodegenerative disorders, alcohol withdrawal and/or ischemic conditions such as e.g. stroke or cardiac ischemia. Preferably the compounds are used to treat PD and/or dyskinesia.

The term "treatment" of a given disease as used herein includes the elimination or the alleviating of one or more symptoms of the respective disease.

Subjects of this invention are also pharmaceutical compositions comprising a compound according to general formulas (Ia), (IIIa), (IVa), (Va), (I), (II), and (III). The pharmaceutical compositions are useful for preventing or treating the above-cited diseases. In a preferred embodiment of the invention, the pharmaceutical composition comprises additional suitable pharmaceutically acceptable carriers.

Suitable pharmaceutically acceptable carriers depend on the pharmaceutical form and are known by a person skilled in the art.

As used herein, "pharmaceutically acceptable carriers" includes any and all solvents and solvent mixtures, dispersion media, complexation agents, surface active excipients, solid carriers, coatings, antibacterial and antifungal agents, isotonic and absorption delaying agents for pharmaceutically active substances and mixtures thereof, as well known in the art.

Non-limiting examples for pharmaceutically acceptable carriers include those having components selected from gelatin, lactose, sugar alcohols, (e.g. mannitol, starch, corn starch, and the like), magnesium stearate, talc, vegetable oil, microcrystalline cellulose, carboxymethyl-cellulose, polysorbate, sodium lauryl sulphate, colloidal silicon oxide, copolyvidone, buffered aqueous solutions, ethanol, polyalkylene glycols, (preferably polyethylene glycols, e.g. PEG 400), propylene glycol, Tween® 80 (i.e. PEG (20) sorbitol monooleate), DMSO, mixtures of water and co-solvents, e.g. aqueous solutions comprising alcohols like ethanol and/or polyalkylene glycols like polyethylene glycol, complexation agents like cyclodextrins, e.g. α-cyclodextrin, (α-CD) or hydroxypropyl-β-cyclodextrin (HP-β-CD), surfactants like anionic, cationic, non-ionic and amphoteric surfactants, salts of bile acids or lipids, e.g. animal or vegetable phospholipids, esters of polyols like glycerol and/or poly-ethylene glycol with fatty acids, micelles forming agents, and oils like corn oil, or mixtures of two or more of the components mentioned before.

Further non-limiting examples of suitable pharmaceutically acceptable carriers as well as suitable additives useful in the compositions of the present invention are mentioned below.

In one embodiment the present invention relates to pharmaceutical compositions of the present invention forming in aqueous media lipid-based drug delivery systems (DDS). Said pharmaceutical compositions comprise at least one surfactant beside the at least one compound of formula (Ia), (IIIa), (IVa), (Va), (I), (II), and (III) or salt thereof. Non-limiting examples of suitable surfactants are mentioned above. In various embodiments, lipid-based drug delivery systems form the following structures:

- micelles, microemulsions, emulsions (i.e. simple self-assembly structures of lipids and surfactants)
- liposomes (i.e. dispersed closed bilayer assemblies of a lamellar phase in water), or
- nanoparticles of non-lamellar phases (e.g. cubic, hexagonal, sponge).

In some embodiments, the lipid-based drug delivery systems that form micelles, microemulsions or emulsions are preferred. The HLB-value (hydrophile-lipophile-balance) of suitable surfactants or surfactant mixtures for the formation of micelles, microemulsions or emulsions is in general about 8 to 18, about 10 to 18, or about 12 to about 16. The lipid-based drug delivery systems form an SEDDS (self-emulsifying drug delivery system) or an SMEDDS (self-microemulsifying drug delivery system). SEDDS and SMEDDS are mixtures, ideally isotropic, of oil(s) (i.e. lipid(s), e.g. a compound of formula (I) or salts thereof), at least one surfactant, optionally at least one co-surfactant and optionally at least one co-solvent, which emulsify spontaneously to produce fine oil-in-water emulsions when introduced into an aqueous phase under gentle agitation. The gentle agitation may be for example provided by gastric mobility.

The pharmaceutical compositions may comprise further excipients and/or additives. Suitable further excipients and/or additives are mentioned before and below.

The compounds or the pharmaceutical composition may be administered in a convenient manner, such as by oral, intravenous, intramuscular, intrathecal or subcutaneous routes. Enteral, parenteral or oral administration is preferred. Most preferred is oral administration.

The compounds can be orally administered, for example, with an inert diluent or with an assimilable edible carrier, enclosed in capsules, compressed into tablets, or be incorporated directly into the food of the diet. For oral therapeutic administration, the active compound in exemplary embodiments is incorporated with excipients and used in the form of ingestible tablets, buccal tablets, troches, capsules, elixirs, suspensions, syrups, wafers, pills, soft gel caps, powders, solutions, dispersions, liquids and the like. Such compositions and preparations contain a therapeutically effective amount of the active ingredient, which is normally present at a level of at least 1% by weight of the composition administered. In various embodiments, the compositions contain from 5 to about 80% by weight of the active compound.

In various embodiments, the tablets, troches, pills, capsules and the like contain one or more of the following: A binder such as gum tragacanth, acacia, corn starch or gelatine; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavouring agent such as peppermint, oil of wintergreen, or cherry flavouring. When the dosage unit form is a capsule, it may contain, in addition to materials of the above type, a liquid carrier.

Various other materials may be present as coatings or otherwise modify the physical form of the dosage unit. For instance, tablets, pills, or capsules may be coated with shellac, sugar or both. A syrup or elixir may contain the compound of formula (Ia), (IIIa), (IVa), (Va), (I), (II), and (III), sucrose as a sweetening agent, methyl and propylparabens as preservatives, a dye and flavouring such as cherry or orange flavour.

Of course, any material used in preparing any dosage unit form for human consumption should be pharmaceutically pure and substantially non-toxic in the amounts employed.

In one embodiment of the invention the compound of formula (Ia), (IIIa), (IVa), (Va), (I), (II), and (III) is included in a capsule. The capsule can be a hard or soft shell capsule. The capsule can be made from any suitable film forming material comprising e.g. gelatin, cellulose derivatives, pullulan or other glucans, polyvinyl alcohol, pectin, modified starches, such as starch ethers and oxidized starch, more particularly hydroxyethylated starch (HES) or hydroxypropylated starch (HPS)—alone or mixtures thereof and if appropriate in a mixture with a setting system or further components. The cellulose derivatives used for the manufacture of capsules include, but are not limited to, hydroxypropyl cellulose, hydroxyethyl cellulose, hydroxypropyl methyl cellulose, hydroxymethyl cellulose, methylcellulose, ethyl cellulose, cellulose acetate, cellulose acetate phthalate, cellulose acetate trimellitate, hydroxypropylmethyl cellulose phthalate, hydroxypropylmethyl cellulose succinate, carboxymethyl cellulose sodium, and mixtures thereof. Preferred cellulose derivatives are hydroxypropyl cellulose, hydroxyethyl cellulose, hydroxypropyl methyl cellulose, hydroxymethyl cellulose, methylcellulose, and ethyl cellulose.

In addition, the compounds may be incorporated into sustained-release preparations and formulations (retard compositions). For example, sustained release dosage forms are contemplated wherein the compounds are bound to an ion exchange resin that, optionally, can be coated with a diffusion barrier coating to modify the release properties of the resin.

The compounds may also be administered parenterally or intraperitoneally. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions (where water soluble) or dispersions and sterile powders for the extemporaneous preparation of sterile injectable solutions or dispersions. In all cases the form is preferably sterile and fluid to the extent that easy syringability exists, is must be stable under the conditions of manufacture and storage, and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersions, and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the compound of formula (Ia), (IIIa), (IVa), (Va), (I), (II), and (III) in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique.

It is especially advantageous to formulate the pharmaceutical compositions of the present invention in dosage unit form for ease of administration and uniformity of dosage. Dosage unit form as used herein refers to physically discrete units suited as unitary dosages for the mammalian subjects to be treated; each unit containing a predetermined quantity of the compound of formula (Ia), (IIIa), (IVa), (Va), (I), (II), and (III) calculated to produce the desired therapeutic effect in association with the required pharmaceutical carrier. The specifics for the novel dosage unit forms of the invention are dictated by and directly dependent on (a) the unique characteristics of the compound of formula (Ia), (IIIa), (IVa), (Va), (I), (II), and (III) and the particular therapeutic effect to be achieved, and (b) the limitations inherent in the art of compounding the compound of formula (Ia), (IIIa), (IVa), (Va), (I), (II), and (III) for the treatment of diseases in patients having a disease condition in which bodily health is impaired.

The compounds are compounded for convenient and effective administration in effective amounts with a suitable pharmaceutically acceptable carrier and optionally further suitable additives and excipients in dosage unit form as hereinbefore described. The dosage of the compound of formula (Ia), (IIIa), (IVa), (Va), (I), (II), and (III) varies depending on the route of administration, age and weight of the patient, nature and severity of the disease to be treated, and other factors. In various embodiments, the daily dosage is in general from 2 to 2000 mg/d, for example 50 to 500 mg/d. Within these ranges, in various embodiments subranges are chosen with a lower value of 2, 5, 10, 20, 25 50, 100, 200, 250, or 400 mg/d, and upper ranges of 50, 100, 200, 250, 500, 600, 750, 1000, 1500, and 2000 mg/d. The lower values and upper values can be combined to give a suitable dose range, which will depend on various factors such as those noted above. The daily dose may be administered in one single dosage unit per day or in two or more dosage units per day.

In various embodiments, compounds described herein are combined with other drugs to provided combination therapy for Parkinson's disease or other conditions. Compositions include at least one of the $A_{2A}$ inhibitors described herein and another therapeutic agent selected from L-dopa (optionally in combination with carboxylase inhibitors such as carbidopa and benserazide, COMT inhibitors such as tolcapone and entacapone, or with both a carboxylase inhibitor and an COMT inhibitor); a monoamine oxidase type B inhibitor such as selegiline and rasagiline; a glutamate antagonist such as amantadine; an anticholinergic such as trihexphenidyl, benztropine, orphenadrine, and procyclidine; and a dopamine agonist such as bromocriptine, cabergoline, pergolide, pramipexole, ropinirole, and rotigotine. In all cases the other therapeutic agent can be selected from the free base or neutral compound, or a pharmaceutically acceptable salt. In various embodiments, an $A_{2A}$ inhibitor described herein is combined into a unitary dose form with the other therapeutic agent or agents. In other embodiments, the $A_{2A}$ inhibitor and other agents are combined in kit form or otherwise provided for administration together.

Methods for treating Parkinson's disease or other indications described above include administering an $A_{2A}$ inhibitor described herein in combination therapy with one or more of L-dopa, a dopamine agonist, a MAO-B inhibitor, a glutamate antagonist, and an anticholinergic, where non-limiting examples of the co-therapeutic agents are listed above. The $A_{2A}$ inhibitor and other therapeutic agent are administered together as a single dose containing the two active ingredients, or separately in separate dosage forms, as appropriate. In non-limiting examples, one of the agents is administered in pill or tablet or other solid dosage form, while the other is administered in pill or tablet or other solid dosage form, in a transdermal patch, or as an injectable form.

Tables

Table 1: Overview of compounds of the present invention

Table 2a: Data of radioligand assay 1; data of rat receptors

Table 2b: Data of radioligand assay 1; data of human receptors

Table 3: Comparison of human $A_{2A}$ ligand data for different N3-substitutions Table 4: Data of radioligand assay 2 including the $A_{2B}$ adenosine receptor (and partly with other ligands)

Table 5: Data of the sodium chloride-shift-experiment

Table 6: Data of functional assay concerning inhibition of $A_1$- and $A_{2A}$-adenosine receptors Table 7: Methods and behavioural parameters of the functional observational battery (FOB)/modified Irwin test Table 8: Methods and behavioural parameters of the short animal check (SAC)/modified Irwin test Table 9: Methods and behavioural parameters of the follow-up observation (FU)/modified Irwin test Table 10: Compound data/modified Irwin test

Synthesis Scheme

The compounds according to formula (Ia), (IIIa), (IVa), (Va), (I), (II), and (III) of the present invention may be prepared by any process known by one skilled in the art. In preferred embodiments of the present invention the compounds according to formula (Ia), (IIIa), (IVa), (Va), (I), (II), and (III) are prepared according to six different general (methods A to F).

Method A

According to this method an amide bond is formed by the reaction of step (a), followed by selective substitution at the N1-atom (step (b)). Subsequently, the ring is closed with dehydrating reagents (step (c)) followed by substitution at the N7-atom (step (e)). This method (except step (c)) is described by Muller C. E. et al., Eur. J. Med. Chem. 1997, 32, 709-719 and is incorporated herein by reference.

The reaction is shown in the scheme below:

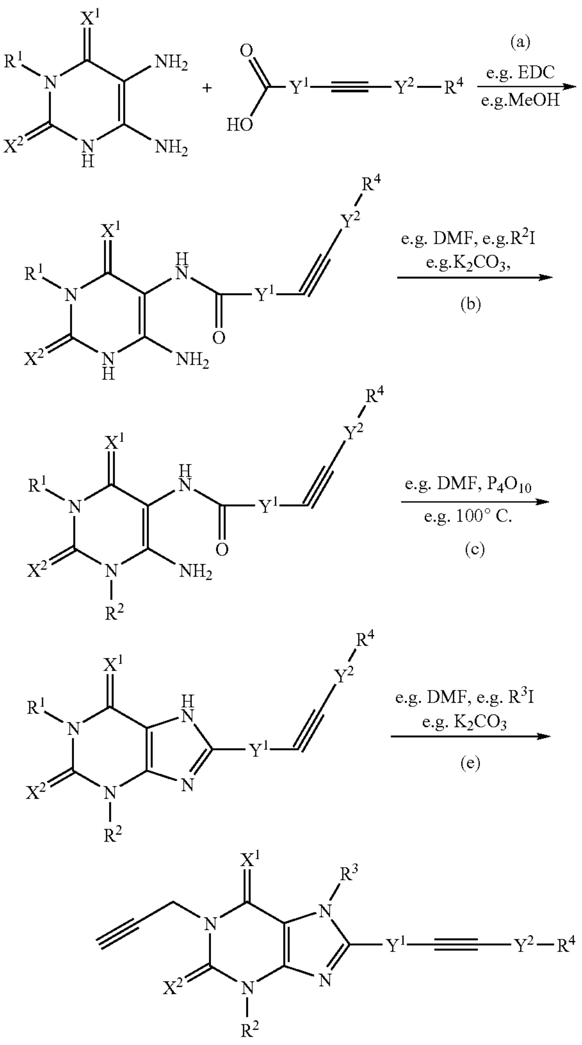

wherein $X^1$, $X^2$, $Y^1$, $Y^2$, $R^1$, $R^2$, $R^3$ and $R^4$ are defined as mentioned above.

Step (a): The reaction with the 5-amino group of the 5,6-diaminodihydropyrimidine derivatives with differently substituted carboxylic acids can be conducted similarly to the process described by Muller C. E. et al., Eur. J. Med. Chem. 1997, 32, 709-719. For this amide bond forming step methanol or another suitable solvent in the presence of a condensation agent such as e.g. (dimethylaminopropyl)ethylcarbodiimide×HCl (EDC), other carbodiimides, or other suitable amide coupling reagents and methods can be used. The step can be conducted at room temperature and takes seldom longer than 3 hours.

Step (b) An additional substituent (e.g. an alkyl group) is added at position N1 of the intermediate obtained through step (a). The intermediate can be suspended in DMF or another preferably polar solvent. The reaction can e.g. be conducted at room temperature (up to 60° C.) with $R^2$ substituted halogenides (e.g. iodide or bromide) in the presence of potassium carbonate or another suitable base. When using other less reactive e.g. alkylating agents higher temperatures may be required. The intermediates obtained through this step can for example be precipitated with water optionally in the presence of sodium chloride and dichloromethane.

Step (c). The intermediate obtained through step (b) is dissolved (e.g. in DMF). The ring forming step occurs at a temperature of between 70° C.-130° C., preferably at 100° C. with an excess of phosphorus pentoxide ($P_4O_{10}$) within a few minutes. Alternatively, other suitable conditions and/or dehydrating reagents can be used for the ring closure reaction.

Step (e). The addition of a substituent at position 7 of the intermediate obtained through step (c) is conducted in analogy to the reaction described under step (b). Further purification of the products may be conducted with column chromatography and/or crystalline transformation (e.g. with dichloromethane/petrol ether).

Method B

According to this method, the ring-closing step (a(1)) or alternatively (a(2)) directly follows the above described amide bond forming step (step (a) in method A). Substitution at position N3 and N7 can be done in one step (step (b)).

The reaction is shown in the scheme below:

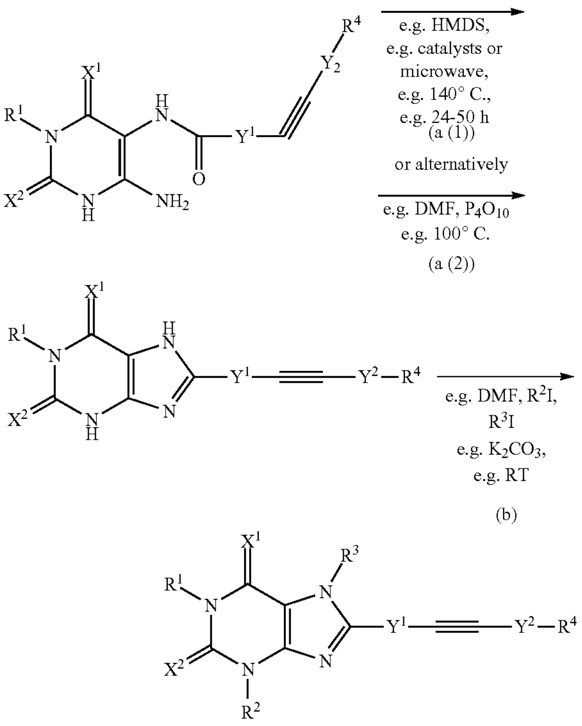

wherein $X^1$, $X^2$, $Y^1$, $Y^2$, $R^1$, $R^2$, $R^3$ and $R^4$ are defined as mentioned above.

Step (a (1)) The ring forming step can be conducted in analogy to described procedures using hexamethyldisilazane (HMDS) as condensing agent (Burbiel et al., 2006, Beilstein J. Org. Chem. 6, 1375). The intermediate obtained through step (b) is therefore suspended in HMDS or other silylating agents in the presence or absence of catalysts such as trimethylchlorosilane, p-toluenesulfonic acid, ammonium sulphate. The reaction takes place at various temperatures, preferably at 120° C.-160° C., more preferably at 140° C. within preferably 24-50 hours. The reaction can be accelerated by microwave heating. Other water detracting agents such as polyphosphoric acid trimethylsilyl ester (PPSE) or NaOH, dioxane/water can be used. However, decomposition of the reactant might occur or alternatively Step (a (2)) This step is similar to the Step (c) of method A. Step (b) This step is performed in analogy to the steps (b) and (e) of method A.

Method C

Step (a (1)) or step (a (2)) from method B are used to close the ring. Afterwards the N7 position is selectively substituted (step a) of method C). Optionally, the N7-substituted intermediate obtained through step a) can optionally be further purified by column chromatography. Step b) describes the substitution at N3.

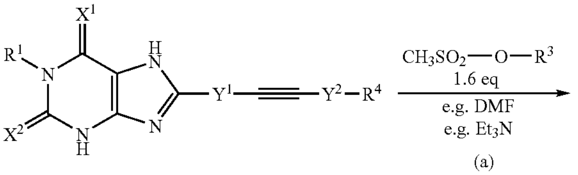

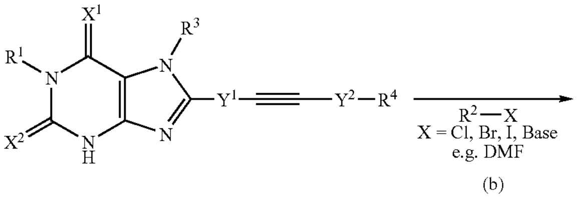

-continued

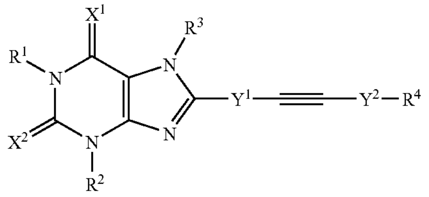

wherein $X^1$, $X^2$, $Y^1$, $Y^2$, $R^1$, $R^2$, $R^3$ and $R^4$ are defined as mentioned above.

Step (a) N7—selective addition of a substituent after the ring closing step described in method B (step (a (1)) or step (a (2))) occurs in the presence of 1.6 eq of substituted sulfonic acid methyl ester (e.g. methylmesylate), a solvent such as DMF and a base, preferably $Et_3N$, preferably at room temperature within 1 hour. The intermediate(s) obtained through this step can optionally be purified by column chromatography. Therefore, the intermediate reacts with an excess of pivaloyloxymethyl chloride, DMF, $K_2CO_3$ at room temperature for 1½ hours to different POM-substituted intermediates which can be easily separated by column chromatography (e.g. with petrol ether/acetic acid 7/3). Alternatively, other protecting groups can be introduced by suitable methods known to the skilled person in the art. The N3-POM group can then be cleaved off under basic conditions, e.g. with MeOH, THF, LiOH at room temperature within 3-4 hours. Step (b) A substituent is then introduced at N3 of the intermediate obtained through step (a) with substituted halogenides (or compound with another suitable leaving group) in the presence of a base and DMF or another suitable, preferably polar solvent, at room or elevated temperatures.

Preparation of 8-[(3,4-Dimethoxyphenyl)ethynyl]-7-methyl-1-prop-2-ynyl-3,7-dihydro-1H-purine-2,6-dione

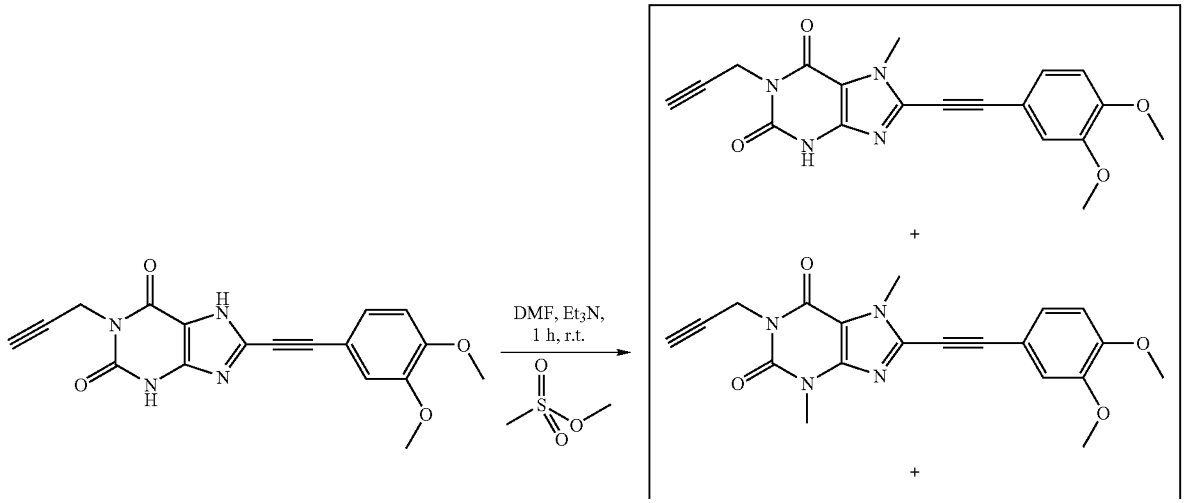

-continued

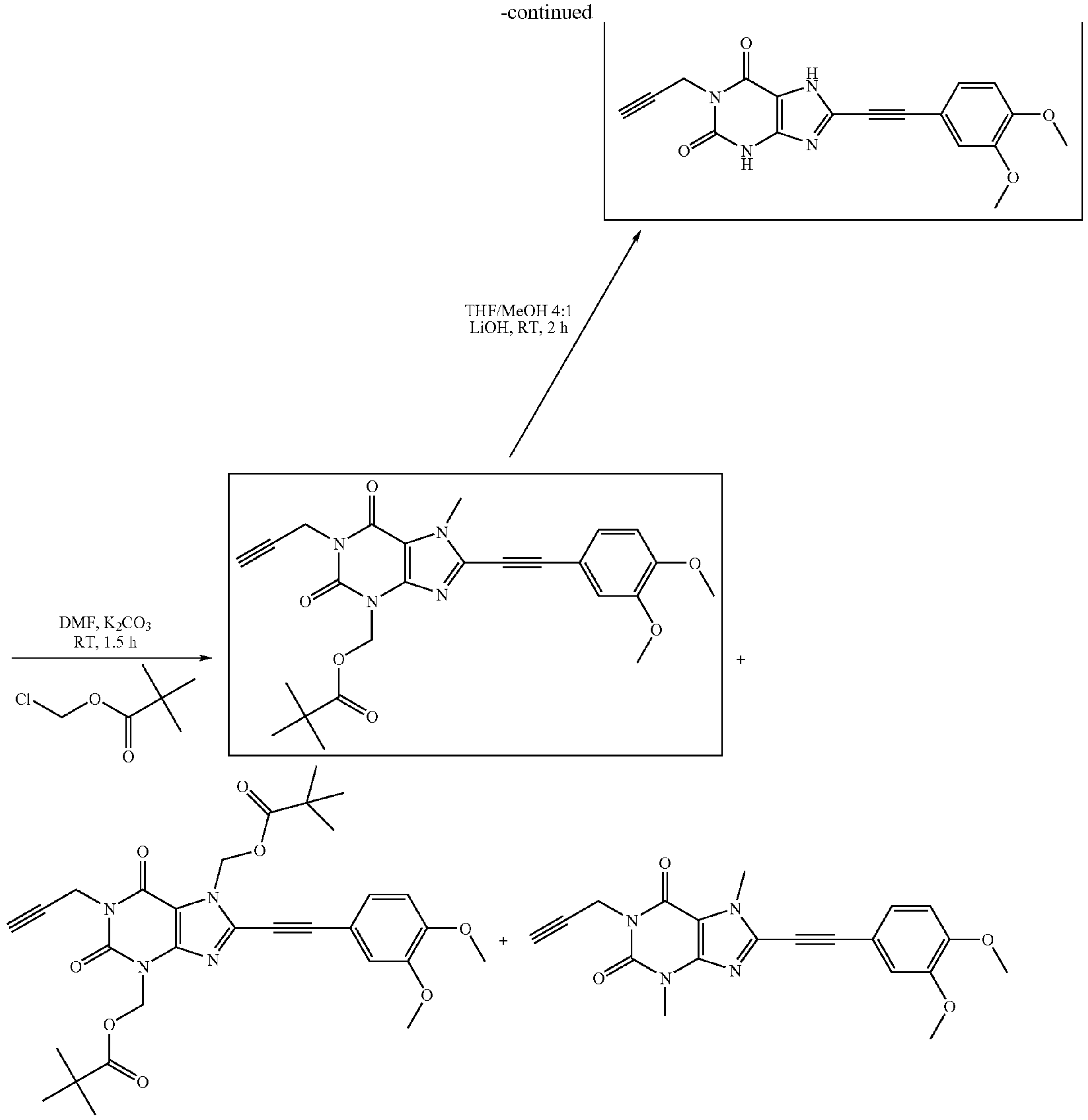

To a solution of 8-[(3,4-dimethoxyphenyl)ethynyl]-1-prop-2-ynyl-3,7-dihydro-1H-purine-2,6-dione (650 mg, 1.86 mmol) in DMF (10 mL) and triethylamine (0.4 mL, 3 mmol) was added methyl methanesulfonate (286 mg, 2.60 mmol). The solution was stirred at room temperature for 3 h (TLC-control: dichloromethane/methanol, 9.5:0.5), hydrolyzed with water (30 mL) and acidified with diluted hydrochloric acid. The precipitate was filtered under reduced pressure, washed with water and dried at 70° C.

The crude 8-[(3,4-dimethoxyphenyl)ethynyl]-7-methyl-1-prop-2-ynyl-3,7-dihydro-1H-purine-2,6-dione (ca. 452 mg, 1.24 mmol), contaminated with the starting material and with the dimethylated derivative (8-[(3,4-dimethoxyphenyl)ethynyl]-3,7-dimethyl-1-prop-2-ynyl-3,7-dihydro-1H-purine-2,6-dione), was suspended in dry DMF (7 mL). Subsequently dry potassium carbonate (514 mg, 3.72 mmol) and chloromethyl pivalate (654 mg, 4.34 mmol) was added. The mixture was stirred at room temperature for 3 h (TLC-control: dichloromethane/methanol, 9.5:0.5, $R_f$=0.60 for the main product) and the product was precipitated by adding water (30 mL), filtered under reduced pressure and dried at 70° C. The crude product was dissolved in a minimum of ethyl acetate (by slightly heating) and purified by column chromatography (eluent: petroleum ether/ethyl acetate, 1:1) affording 471 mg (79% yield over two steps) of {8-[(3,4-dimethoxyphenyl)ethynyl]-7-methyl-2,6-dioxo-1-prop-2-ynyl-1,2,6,7-tetrahydro-3H-purin-3-yl}methyl pivalate as a colorless solid.

To a solution of {8-[(3,4-dimethoxyphenyl)ethynyl]-7-methyl-2,6-dioxo-1-prop-2-ynyl-1,2,6,7-tetrahydro-3H-purin-3-yl}methyl pivalate (471 mg, 0.98 mmol) in a 4:1 mixture of dry tetrahydrofurane and methanol (20 mL) was added lithium hydroxide monohydrate (127 mg, 1.63 mmol). The mixture was stirred at room temperature for 3 h (TLC-control: dichloromethane/methanol, 9.5:0.5, $R_f$=0.40 for the product).

Subsequently the solvent was removed under reduced pressure, the remaining residue was dissolved in water (30 mL) and acidified with diluted hydrochloric acid. The precipitate was filtered under reduced pressure, washed with water and dried at 70° C., yielding 334 mg (93 yield for the deprotection reaction) of the title compound.

Method D

This method begins with a starting material 5,6-diaminodihydropyrimidine derivative that carries hydrogen on the 3-position (which will become the 1-position in the purine ring of the ultimate ethynylxanthine to be synthesized). The starting material also carries a non-hydrogen at the 1-position of the pyrimidine ring, which will be the 3-position of the purine ring of the ultimate product. In this method, the positions of the ultimate xanthine compound are alkylated in the order of first the 3-position, then the 7-position, then the 1-position. Thus in various embodiments, the method contemplates introduction of the N-1 propargyl group as a last step. An intermediate step is the preferential alkylation of N-7 over N-1, which proceeds with few side products because of the much higher nucleophilicity of N-7. This is illustrated in the dimethylsulfate alkylation step in the following scheme:

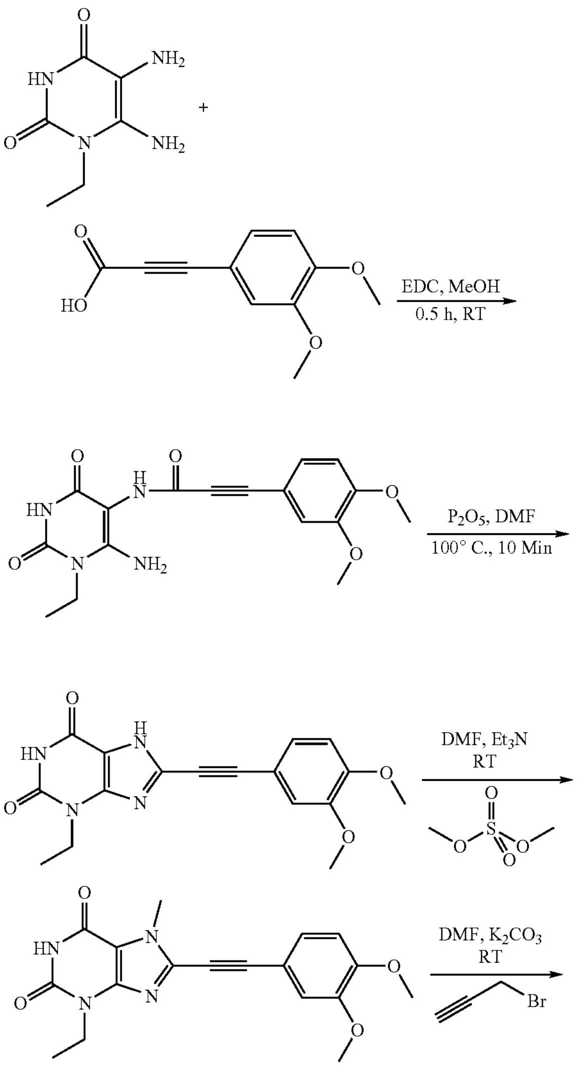

-continued

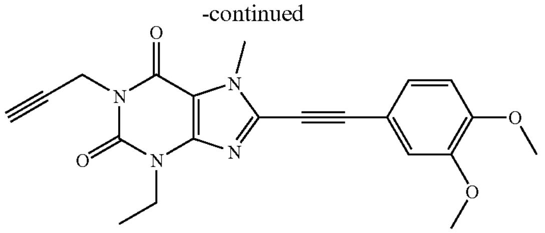

The scheme illustrates first the introduction (by incorporation into the starting material) of the group $R^2$ (ethyl in the illustration) at N-3 of the xanthine ring; then the introduction of $R^3$ (methyl in the illustration) at position N-7 by selective alkylation of the 7-position over the 1-position; and finally introduction of the $R^1$ group by alkylation of the N-1 position, using propargyl bromide in the illustration as the alkylating agent.

Preparation of 3-(3,4-Dimethoxyphenyl)propynoic acid (6-amino-1-ethyl-2,4-dioxo-1,2,3,4-tetrahydropyrimidin-5-yl)amide

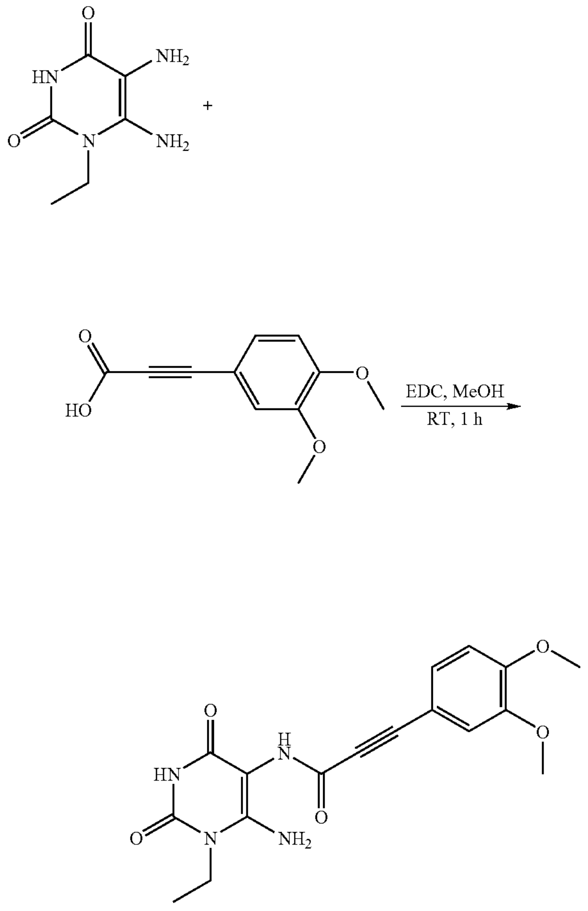

A mixture of the 5,6-diamino-1-ethyluracil (2.47 g, 14 mmol), 3,4-dimethoxyphenylacetylecic acid (3 g, 14 mmol) and EDC ((1-(3-dimethylaminopropyl)-3-ethyl-carbodiimid hydrochloride; 2.5 g, 13 mmol) was prepared in 150 ml of methanol and stirred at room temperature for 1 h. The precipitate was filtered under reduced pressure, washed with a little methanol and dried at 60° C. yielding 2.3 g (45%) of a yellowish solid.

Formation of 8-(3,4-Dimethoxyphenylethynyl)-3-ethyl-3,7-dihydropurine-2,6-dione

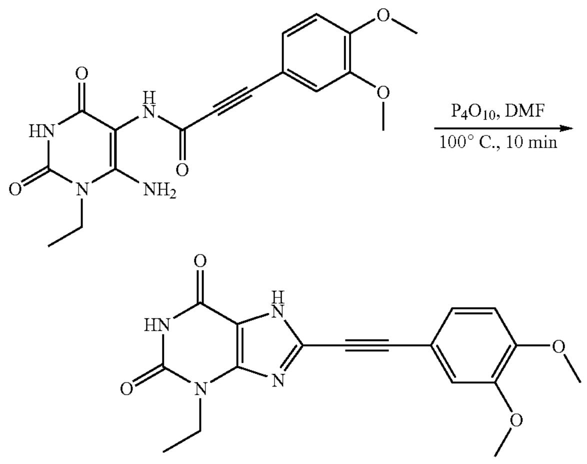

To a stirred solution of 3-(3,4-dimethoxyphenyl)propynoic acid (6-amino-1-ethyl-2,4-dioxo-1,2,3,4-tetrahydropyrimidin-5-yl) amide (2.27 g, 6.3 mmol) in 12 ml of dry dimethylformamide was added phosphorous pentaoxyde (5 g, 17 mmol). The mixture was stirred at 100° C. for 10 min and cooled to room temperature. The product was recipitated by adding water (100 ml), filtered under reduced pressure, washed thoroughly with water and dryed at 70° C., light yellow yielding 8-(3,4-dimethoxyphenylethynyl)-3-ethyl-3,7-dihydro-purine-2,6-dione (1.6 g, 74%).

Preparation of 8-(3,4-Dimethoxyphenylethynyl)-3-ethyl-7-methyl-3,7-dihydropurine-2,6-dione

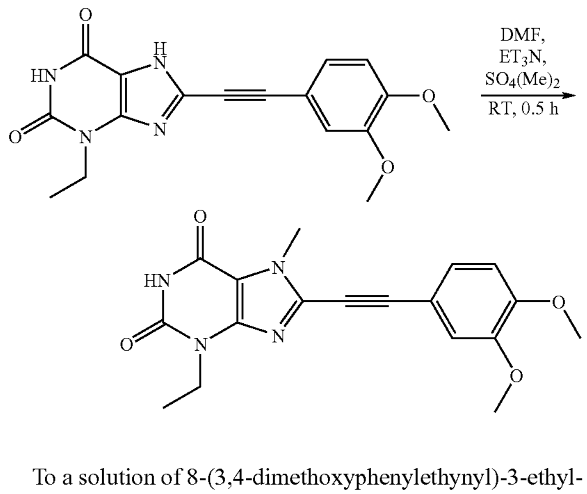

To a solution of 8-(3,4-dimethoxyphenylethynyl)-3-ethyl-3,7-dihydro-purine-2,6-dione (1.52 g, 4.4 mmol) in 10 ml of dimethylformamide (DMF) was added triethylamine (3 ml, 20 mmol) and dimethylsulfate (0.65 ml, 7 mmol). The mixture was stirred at room temperature for 0.5 h. The product was precipitated by addind water (40 ml), filtered under reduced pressure, washed with water and dried at 70° C. (310 mg, 20%).

Synthesis of 8-(3,4-dimethoxyphenylethynyl)-3-ethyl-7-methyl-1-prop-2-ynyl-3,7-dihydropurine-2,6-dione

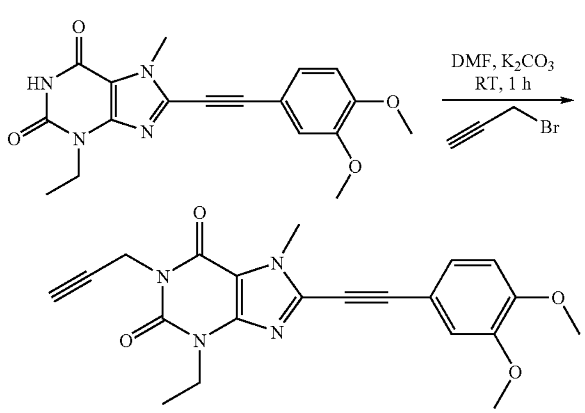

To a mixture of 40 mg (0.11 mmol) of 8-(3,4-dimethoxyphenylethynyl)-3-ethyl-7-methyl-3,7-dihydropurine-2,6-dione and potassium carbonate (75 mg, 0.5 mmol) in dimethylformamide (3 ml) were added propargyl bromide (0.4 mmol, 80% in toöuene). The solution was stirred at room temperature for 1 h (TLC-control: dichloromethane/methanol, 9.5:0.5). The product was precipitated by addition of water (30 ml), filtered under reduced pressure, was washed with water and dried at 70° C. Further purification was achieved by column chromatography on silica gel (eluent: $CH_2Cl_2$/methanol, 9.5:0.5) and subsequent crystallization from dichloromethane/petroleum ether.

Method E

The 8-ethynyl xanthines can also be made using Sonogashira coupling of a primary alkyne and a halogenated aryl group, as described in Firth et al., Tetrahedron Lett. 47, 2006, 3529-3533. According to this scheme, substitution groups are added to a xanthine skeleton at the 1-, 3-, 7-, and 8-positions in a strategic order to take advantage of the relative nucleophilicity of the positions. In a preferred embodiment, a 3-substituted xanthine is first brominated at the 8-position, followed by an alkylation at the 7-position to give a 3,7-disubstituted 8-bromoxanthine intermediate. The intermediate is reacted with an acetylene containing one active hydrogen and a protecting group PG at the position of the other acetylenic hydrogen. Following removal of the protecting group, this provides an 8-ethynyl intermediate. The 8-ethynyl intermediate undergoes Sonogashira coupling to provide an 8-arylethynyl intermediate, which can be subsequently alkylated at position 1 (for example, with propargyl bromide to introduce the 1-(2-propynyl) group) of the xanthine ring to provide the ethynylxanthines described herein. Method E is illustrated in the following scheme, where X is a suitable leaving group such as Br and OTf, and preferably I:

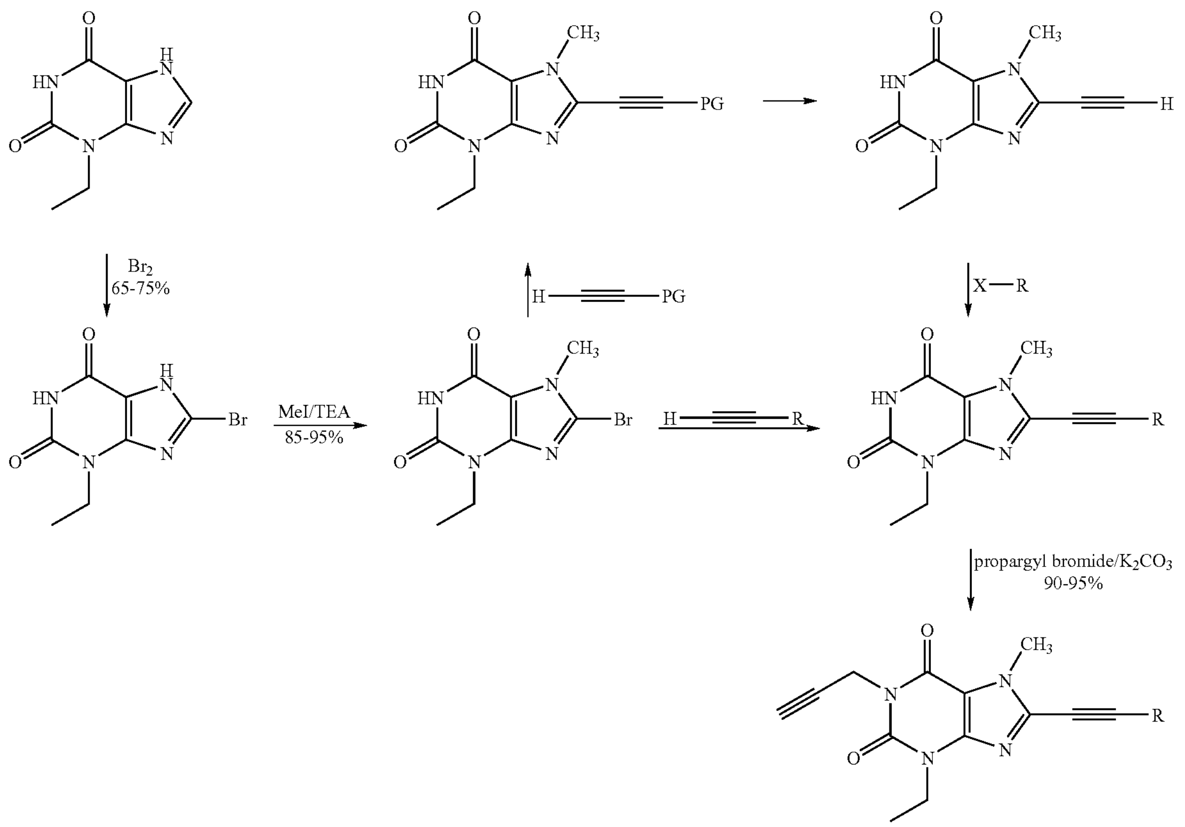

A suitable protecting group is an "acetone" group, as illustrated in the following scheme:

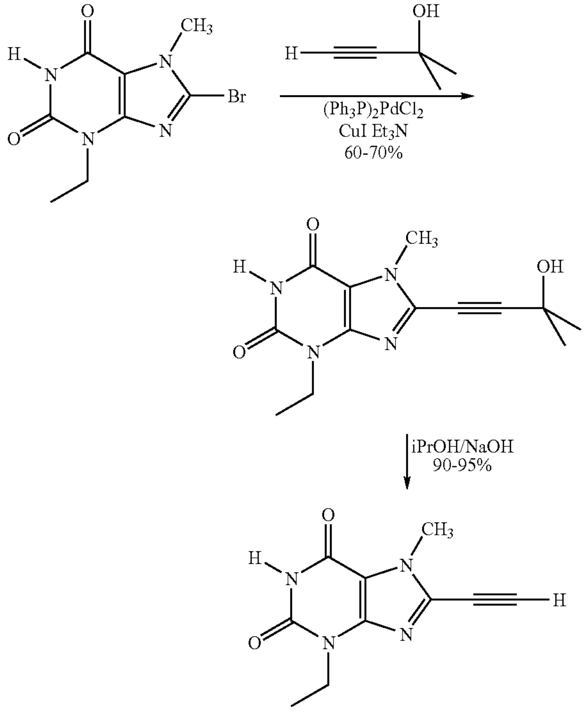

Method F

In method F, synthesis starts with a 1-substituted-6-aminouracil that is prepared by reaction of an N-substituted urea with cyanoacetic acid according to well known procedures. The substituent at the 1-position of the uracil will become the 3-position of the xanthine ring at the end of the synthesis. One example of a method F synthesis is given in FIG. 8, where the substituent is ethyl for illustration. In practice, the substituent can be any of the groups $R_2$ defined above that do not interfere with the protecting and synthetic reactions described herein.

The 6-amino group of the 1-substituted-6-amino uracil is then protected, for example using dimethylformamide dimethyl acetal (DMF DMA) as shown in FIG. 8. Then the protected uracil is alkylated at the 3-position. The 3-position of the uracil will become the 1-position of the xanthine. Suitable alkylating groups include those that result in incorporation of groups $R_1$ described above. In FIG. 8, in illustrative fashion, propargyl bromide is used to alkylate the amino-protected uracil to incorporate a 2-propynyl group at position 3 of the uracil.

Then the 6-amino group is deprotected, and an amino group is introduced at the 5-position of the uracil. In an embodiment illustrated in FIG. 8, the 6-amino is deprotected before adding an amino group at the 5-position, illustratively by nitrosation followed by reduction of the nitroso group to an amino group.

At this stage of the synthesis, a 5,6-diamino-1,3-disubstituted uracil has been formed, which is then subjected to further synthetic steps to form the 8-ethynyl xanthines. For example, the 5,6-diamino-1,3-disubstituted uracil is reacted with a 3-substituted propynoic acid according to

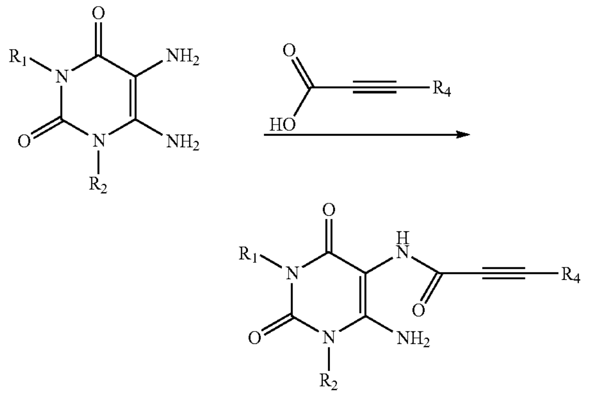

to make an open chain compound that is then ring closed to form the 8-ethylxnthines. In the scheme above, $R_4$ has the meaning given above; in FIG. 8, $R_4$ is illustrated as 3,4-dimethoxyphenyl so that the product of ring closure is compound 11 of the Tables. Further detail of the reactions in FIG. 8 is now provided.

Preparation of N'-(3-Ethyl-2,6-dioxo-1-prop-2-ynyl-1,2,3,6-tetrahydropyriminin-4-yl)-N,N-dimethylformamidine

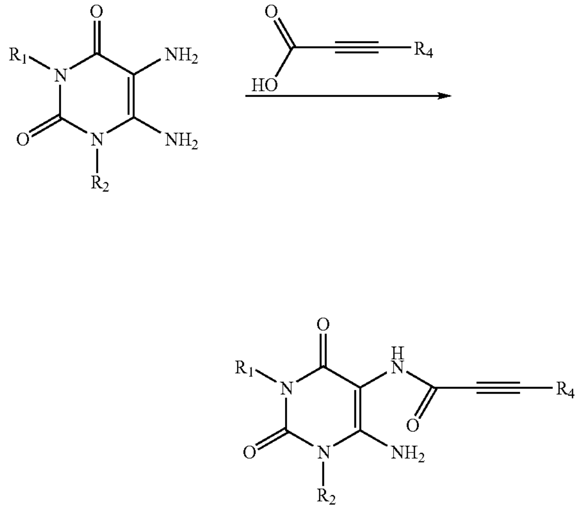

A mixture of 6-Amino-1-ethyluracil (6.6 g, 43 mmol) in dimethylformamide (DMF, 20 ml) and dimethylformamide dimethyl acetal (DMF DMA, 8.5 ml, 63 mmol) was heated at 40° C. for 2 h. After a complete conversion was indicated by TLC-control (dichloromethane/methanol 9:1) the excess of DMF DMA (b.p.: 104° C.) was evaporated under reduced pressure (70° C./150 mbar). Subsequently the residue was diluted with acetonitrile (50 ml) and $K_2CO_3$ (6.5 g, 47 mmol), 6 ml of propargyl bromide (80% in toluene, 54 mmol) as well as a catalytic amount of iodine (200 mg) were added. The mixture was heated at 80° C. for 4 h until a complete conversion could be observed by TLC (dichloromethane/methanol=9:1). Subsequently volatile components were removed under reduced pressure (70° C., 25 mbar). The product was precipitated by adding water, filtered under reduced pressure, washed with water and directly used for the next step.

Preparation of 6-Amino-1-ethyl-3-prop-2-ynyl-1H-pyrimidine-2,4-dione (6-Amino-1-ethyl-3-propargyluracil)

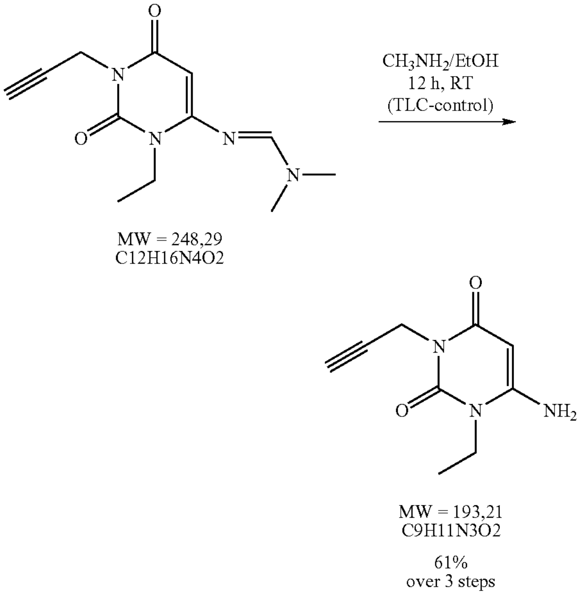

The crude N'-(3-ethyl-2,6-dioxo-1-prop-2-ynyl-1,2,3,6-tetrahydropyriminin-4-yl)-N,N-dimethylformamidine was suspended in 60 ml of a 33% solution of methylamine in ethanol and stirred at room temperature for approx. 12 h until a complete cleavage of the protecting group could be observed by TLC-control (dichloromethane/methanol=9:1). Subsequently methylamine and the solvent were evaporated under reduced pressure. The residue was treated with water and the product was filtered under reduced pressure and dried at 70° C. (yield: 5 g, 61% over 3 steps).

$^1$H NMR (500 MHz, DMSO-$d_6$): δ 1.10 (t, J=7 Hz, 3H, $CH_2CH_3$), 2.96 (t, J=2.5 Hz, 1H, ≡CH), 3.83 (q, J=7 Hz, 2H, $CH_2\underline{C}H_3$), 4.43 (d, J=2.5 Hz, 2H, ≡$CCH_2$), 4.68 (s, 1H, C5H), 6.91 (s, 2H, $NH_2$) ppm;

$^{13}$C NMR (125 MHz, DMSO-$d_6$): δ 13.2 ($CH_3$), 29.3 (≡C $CH_2$), 37.3 ($CH_2CH_3$), 72.3 (≡CH), 74.8 (≡$CCH_2$), 80.3 (C5), 150.7 (C6), 154.6 (C2), 160.2 (C4) ppm.

Preparation of 6-Amino-1-ethyl-5-nitroso-3-prop-2-ynyl-1H-pyrimidine-2,4-dione (6-Amino-1-ethyl-5-nitroso-3-propargyluracil)

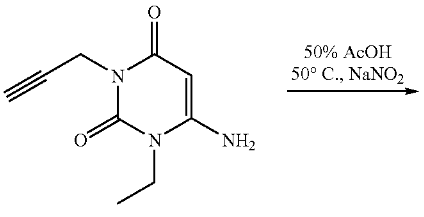

-continued

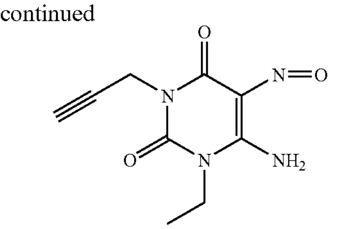

87%

A solution of 6-amino-1-ethyl-3-propargyluracil (5 g, 26 mmol) in 75 ml of 50% acetic acid was heated at 50-60° C. Subsequently sodium nitrite (2.5 g, 36 mmol) was added in small portions over a period of 5 min. The end of the reaction was indicated by the formation of brown nitric gases. The deep violet solution was highly concentrated under reduced pressure. The remaining violet crystals were was suspended in a minimum of water, cooled to 4° C., filtered under reduced pressure, washed with methanol and dried at 70° C. Yield: 5 g (87%).

$^1$H NMR (500 MHz, DMSO-$d_6$): δ 1.12 (t, J=7 Hz, 3H, $CH_2CH_3$), 3.15 (t, J=2.5 Hz, 1H, ≡CH), 3.89 (q, J=7 Hz, 2H, $CH_2CH_3$), 4.63 (d, J=2.5 Hz, 2H, ≡$CCH_2$), 9.21 (br s, 1H), 13.04 (s, 1H) ppm;

$^{13}$C NMR (125 MHz, DMSO-$d_6$): δ 12.1 ($CH_3$), 30.4 (≡C $CH_2$), 37.0 ($CH_2CH_3$), 73.5 (≡CH), 79.2 (≡$CCH_2$), 139.1 (C5), 145.4 (C6), 148.5 (C2), 159.4 (C4) ppm.

Formation of 5,6-Diamino-1-ethyl-3-prop-2-ynyl-1H-pyrimidine-2,4-dione (5,6-Diamino-1-ethyl-3-propargyluracil)

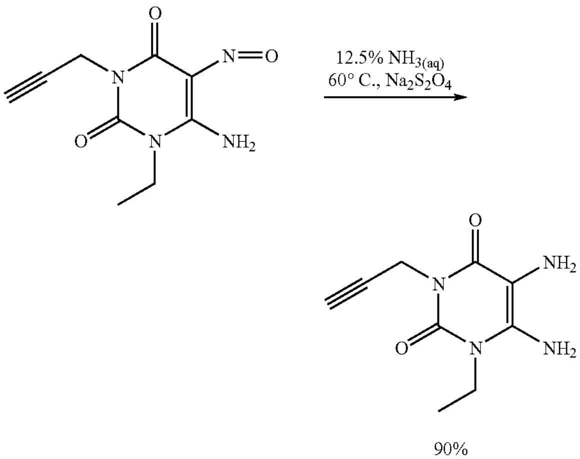

90%

A solution of 6-amino-1-ethyl-5-nitroso-3-propargyluracil (5 g, 23 mmol) in a mixture of 25 ml of 25% $NH_3$ solution and 25 ml of water was heated to 60° C. At this temperature, sodium dithionite (ca 7 g, 40 mmol) was added until the original red-violet color of the solution disappeared. The resulting yellowish solution was concentrated under reduced pressure, saturated with sodium chloride and extracted with dichloromethane (3 times with 75 ml each). The combined organic extracts were dried over $MgSO_4$, filtered and evaporated under reduced pressure affording 4.2 g of a colorless solid (yield: 90%). The resulting oxidation sensitive 5,6-diamino-1-ethyl-3-propargyluracil was used immediately for the next step.

Preparation of 3-(3,4-Dimethoxyphenyl)propynoic acid (6-amino-1-ethyl-3-prop-2-ynyl-2,4-dioxo-1,2,3,4-tetrahydropyrimidin-5-yl) amide

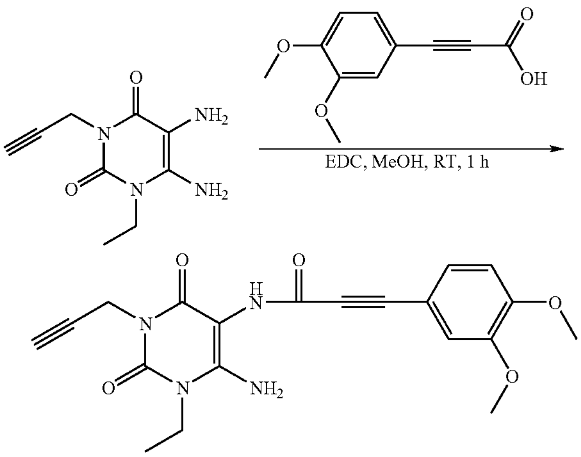

76%

A mixture of the 5,6-diamino-1-ethyl-3-propargyluracil (4.2 g, 20 mmol), 3,4-dimethoxyphenylacetylencarboxylic acid (4.2 g, 20 mmol) and EDC ((1-(3-dimethylaminopropyl)-3-ethyl-carbodiimid hydrochloride; 4.2 g, 22 mmol) in methanol (100 ml) was stirred at room temperature for 2 h. The colorless product was precipitated by adding water (ca. 150 ml), filtered under reduced pressure, washed thoroughly with ether (TLC-control indicated the purity of the product; eluent: dichloromethane/methanol 9:1) and dried at 60° C. Yield: 6 g (76%).

Formation of 8-(3,4-Dimethoxyphenylethynyl)-3-ethyl-1-prop-2-ynyl-3,7-dihydropurine-2,6-dione

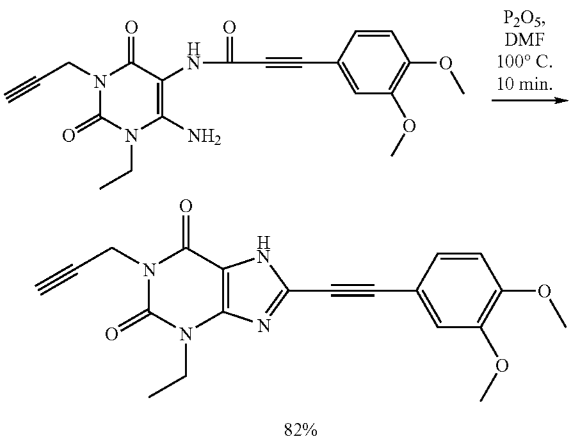

82%

To a solution of 3-(3,4-dimethoxyphenyl)propynoic acid (6-amino-1-ethyl-3-prop-2-ynyl-2,4-dioxo-1,2,3,4-tetrahydro-pyrimidin-5-yl)amide (3.2 g, 8.0 mmol) in 15 ml of dry dimethylformamide was added phosphorous pentoxide (6 g). The mixture was stirred at 100° C. for 10 min and subsequently cooled to room temperature. The product was precipitated by adding water (ca. 100 ml), filtered under reduced pressure, washed thoroughly with water and dried at 70° C., yielding light yellow 8-(3,4-dimethoxyphenylethynyl)-3-ethyl-1-prop-2-ynyl-3,7-dihydro-purine-2,6-dione (2.5 g, 82%).

Synthesis of 8-(3,4-dimethoxyphenylethynyl)-3-ethyl-7-methyl-1-prop-2-ynyl-3,7-dihydropurine-2,6-dione

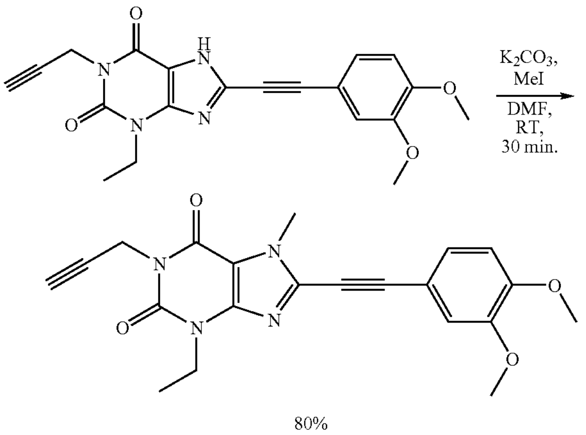

A mixture of 2.0 g (5.3 mmol) of 8-(3,4-dimethoxyphenylethynyl)-3-ethyl-1-prop-2-ynyl-3,7-dihydropurine-2,6-dione, potassium carbonate (0.83 g, 6 mmol) and methyl iodide (0.6 ml, 10 mmol) in dimethylformamide (20 ml) was stirred at room temperature for 0.5 h (TLC-control: dichloromethane/methanol, 9.5:0.5). The product was precipitated by addition of water (100 ml), filtered under reduced pressure, was washed with water and dried at 70° C. Further purification was achieved by column chromatography on silica gel (eluent: dichloromethane/methanol, 9.5:0.5) and subsequent crystallization from dichloromethane/petroleum ether. Yield: 1.76 g, 80% (crude product); m.p.: 221.5° C.

General Formation of 8-(Arylethynyl)-3-ethyl-7-methyl-1-prop-2-ynyl-3,7-dihydropurine-2,6-diones Further 8-(arylethynyl)-3-ethyl-7-methyl-1-prop-2-ynyl-3,7-dihydropurine-2,6-diones are synthesized analogously to the above described process using 5,6-diamino-1-ethyl-3-propargyluracil and the corresponding arylacetylenic acid as starting materials. See following sceeme:

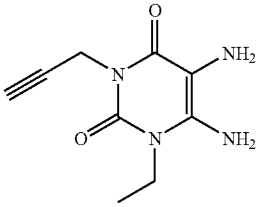

+

-continued

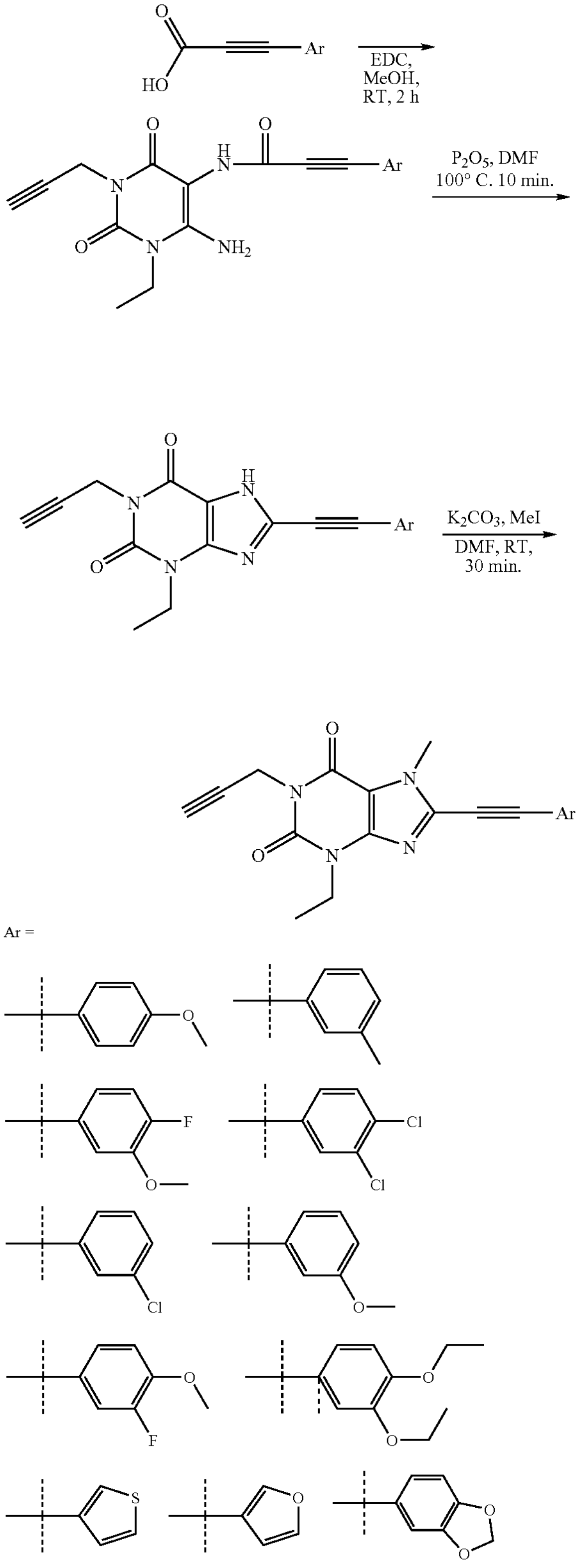

Starting Substances:

If the production of the starting compounds is not described, the latter are known or can be produced in a way that is similar to known compounds or processes that are described here.

5,6-Diaminodihydropyrimidine derivatives:

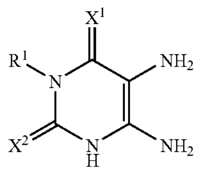

wherein $X^1$, $X^2$ and $R^1$ are defined as mentioned above—for example 5,6-diamino-3-propargyluracil—can be synthesized as described in the literature (Muller, Tetrahedron Lett., 1991, 32, 6539; Muller et al., J. Med. Chem., 1997, 40, 4396, herein incorporated by reference). 1,3-Disubstituted 5,6-diaminouracils are synthesized as previously described (e.g. Muller et al., J. Med. Chem. 1993, 36, 3341, herein incorporated by reference).

Another 5,6-diaminouracil is given by

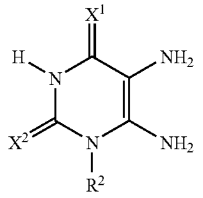

where $X^1$, $X^2$, and $R^2$ are defined herein. This starting material is preferred for synthetic method D described above.

Another starting material is substituted carboxylic acids:

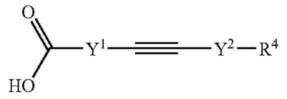

wherein $Y^1$, $Y^2$ and $R^4$ are defined as mentioned above.

The substituted carboxylic acids can for example be synthesized as described below (method 1, 2 and 3). In method 1 alkynes are treated with butyl lithium at low temperatures followed by quenching with $CO_2$. In method 2 carboxylic acids containing a double bond in the α-position are brominated followed by dehydrohalogenation leading to the formation of a triple bond. Method 3 uses a Wittig reaction starting from the aldehydes to yield the target acetylene carboxylic acids.

Phenylacetylenecarboxylic acid is commercially available. Other arylacetylenecarboxylic acids can e.g. synthesized as follows:

Method 1

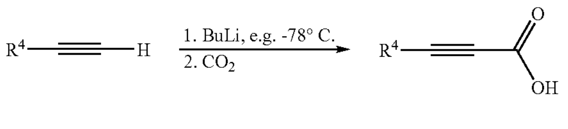

-continued

Method 2

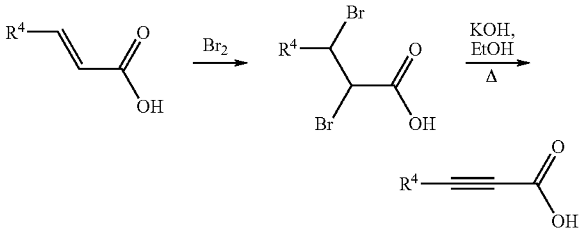

Method 3

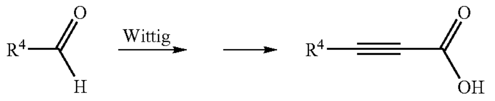

wherein $R^4$ is an optionally substituted aryl as mentioned above (see definition of $R^4$ for further explanation of the possible substituents).

Method 1): Starting material: arylacetylene. Lithiation of the arylacetylene at low temperatures and reaction of the intermediate with solid carbon dioxide.

Method 2) Starting material: cinnamic acid. Bromination of cinnamic acid and dehydrohalogenation with a strong base (e.g. potassium hydroxide).

Method 3) Starting material: aldehyde. Reaction with special Wittig-like reagents and subsequent catalysed elimination reaction with a base.

All three methods are known to the skilled person in the art. For the herein described compounds, method 1 and 2 were used.

Synthesis 1 of 3,4-dimethoxyphenylacetylenecarboxylic acid:

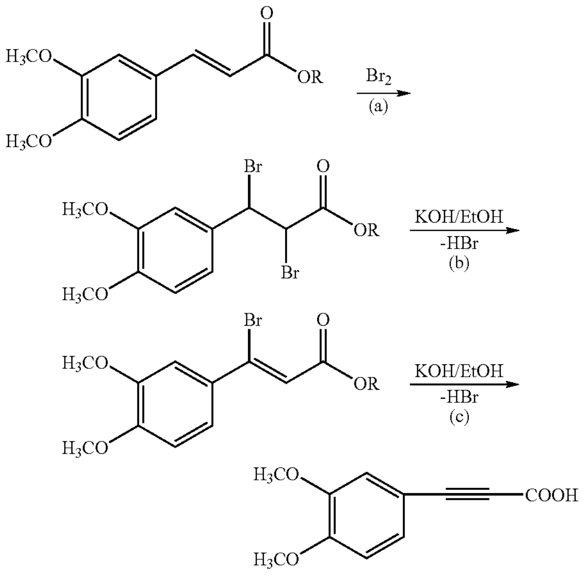

Synthesis 2 of 3,4-dimethoxyphenylacetylenecarboxylic acid:

1.

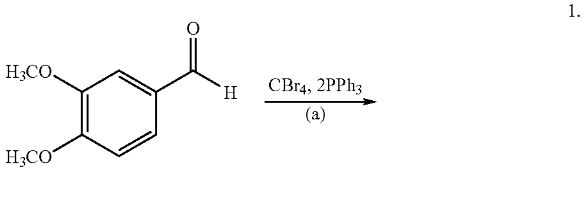

-continued

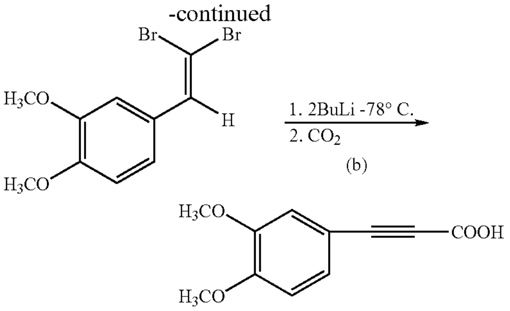

The present invention is illustrated by the following non-limiting examples.

EXAMPLES 5,6-Diamino-3-prop-2-ynyl-1H-pyrimidine-2,4-dione: were prepared as described in the literature (Muller, Tetrahedron Lett., 1991, 32, 6539; Muller et al., J. Med. Chem., 1997, 40, 4396, Hockemeyer et al., 2004, J. Org. Chem. 69, 3308). These documents are herein incorporated by reference.

3-Arylpropynoic acids: were prepared as described in the literature. In the synthetic schemes below, Ar stands for an aryl group, such as a substituted phenyl group.

Preparation of 3-Arylpropynoic acid 6-amino-2,4-dioxo-3-prop-2-ynyl-1,2,3,4-tetrahydropyrimidin-5-yl amides (according to method A)

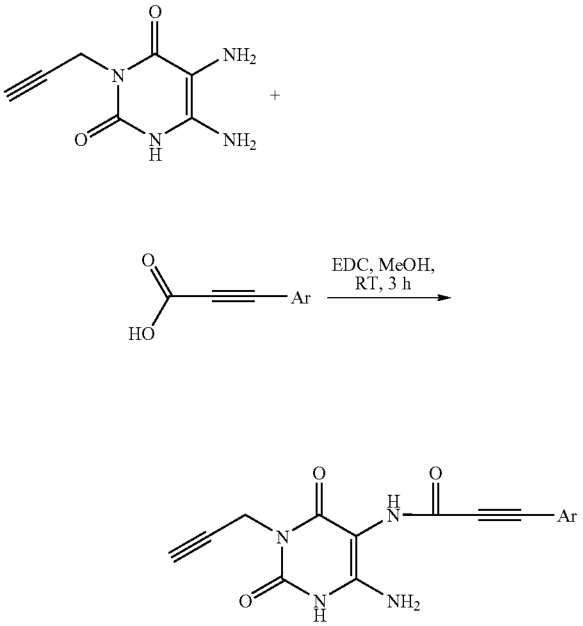

A mixture of 3 mmol of the corresponding 3-arylpropynoic acid, 3 mmol of freshly prepared 5,6-diamino-3-prop-2-ynyl-1H-pyrimidine-2,4-dione and 3.2 mmol of (3-dimethylaminopropyl)ethylcarbodiimide hydrochloride (EDC) in 40 mL of methanol was stirred for 5 h at room temperature. The precipitate was filtered under reduced pressure and washed with 40 mL of methanol and dried at 70° C. TLC analysis (eluent:$CH_2Cl_2$:methanol=5:1 or 7:1) of the products showed two spots indicating two stable tautomers which can also be observed in the NMR spectra.

Preparation of 3-arylpropynoic acid 6-amino-1-methyl-2,4-dioxo-3-prop-2-ynyl-1,2,3,4-tetrahydropyrimidin-5-yl amides (according to method A)

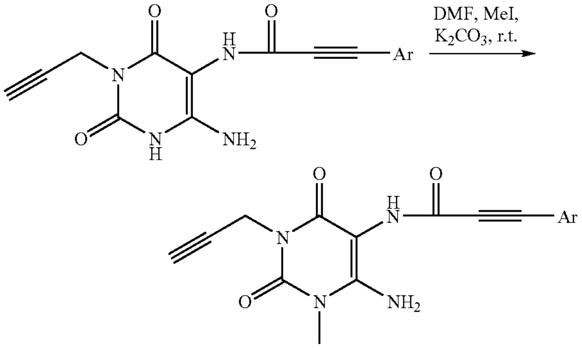

A solution of 1.5 mmol of the N1 unsubstituted 3-arylpropynoic acid 6-amino-2,4-dioxo-3-prop-2-ynyl-1,2,3,4-tetrahydropyrimidin-5-yl amide, 2 mmol of dry potassium carbonate and 5 mmol of methyl iodide in 5 mL of dry DMF was stirred at room temperature until no further starting material could be detected by TLC (eluent: $CH_2Cl_2$/methanol, 7:1). The TLC analysis showed two spots for the product tautomers. The product was precipitated by adding 40 mL of water, filtered under reduced pressure, washed with 50 mL of water and dried al 70° C.

Formation of 8-arylethynyl-1-prop-2-ynyl-3,7-dihydropurine-2,6-diones and 8-arylethynyl-3-methyl-1-prop-2-ynyl-3,7-dihydropurine-2,6-diones (according to method A)

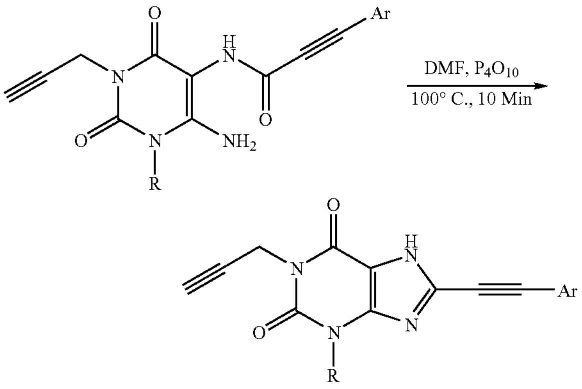

R = H or Me

To a solution of 1 mmol of the corresponding 3-arylpropynoic acid 6-amino-2,4-dioxo-3-prop-2-ynyl-1,2,3,4-tetrahydropyrimidin-5-yl amide or of the N1-methylated derivative in 5 mL of DMF was added phosphorous pentoxide (ca. 1.2 g, 8 mmol) under stirring. The stirred mixture was heated at 100° C. for 5 min and cooled to room temperature. The product was precipitated by adding water (30 mL), filtered under reduced pressure, washed thoroughly with water and dried at 70° C.

Methylation of 8-Arylethynyl-3-methyl-1-prop-2-ynyl-3,7-dihydropurine-2,6-diones to 8-Arylethynyl-3,7-dimethyl-1-prop-2-ynyl-3,7-dihydropurine-2,6-diones (according to method A)

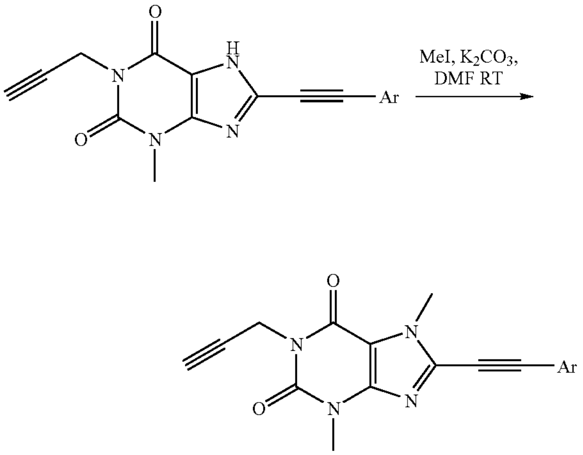

A suspension of 1 mmol of the corresponding 8-arylethynyl-3-methyl-1-prop-2-ynyl-3,7-dihydropurine-2,6-dione, $K_2CO_3$ (4 mmol) and 3 mmol of methyl iodide in DMF (20 mL) was stirred at room temperature for 0.5 h (TLC control: eluent $CH_2Cl_2$/methanol, 9.5:0.5). Subsequently the product was precipitated by adding water (50 mL), filtered off under reduced pressure, washed with water (150 mL) and dried at 70° C. Further purification was achieved by column chromatography on silica gel (eluent: $CH_2Cl_2$/methanol, 9.5:0.5) and/or recrystallization from dichloromethane/petroleum ether.

3,7-Dimethyl-8-(3-nitrophenylethynyl-1-prop-2-ynyl-3,7-dihydropurine-2,6-dione For purification (Method A) the crude product was entirely dissolved in chloroform, crystallized by adding ether, filtered under reduced pressure and washed with ether: light yellow crystals (yield 85%), m.p. 286-289° C. (dec).

Alkylation of 8-(3-Methoxyphenylethynyl)-3-methyl-1-prop-2-ynyl-3,7-dihydropurine-2,6-diones to 7-Alkyl-8-(3-methoxyphenylethynyl-3-methyl-1-prop-2-ynyl-3,7-dihydropurine-2,6-diones (according to method A)

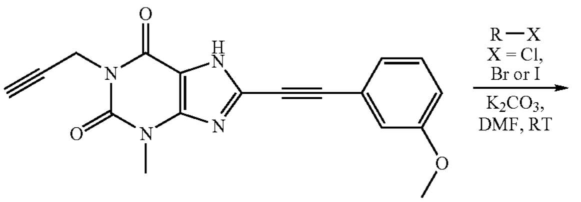

-continued

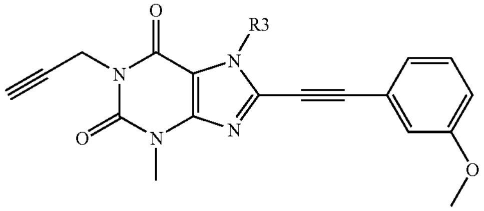

General procedure: To a suspension of 0.1 mmol of the corresponding 8-(3-Methoxyphenylethynyl)-3-methyl-1-prop-2-ynyl-3,7-dihydro-purine-2,6-dione and $K_2CO_3$ (0.5 mmol) in 3 mL of DMF were added 0.3 mmol of the corresponding alkyl halogenide. The mixture was stirred at room temperature until no further starting material could be observed by TLC analysis (eluent: dichloroethane/methanol, 9.5:0.5). Subsequently the product was precipitated by adding water (25 mL), filtered under reduced pressure and dried at 70° C. Further purification was achieved by column chromatography on silica gel (eluent: $CH_2Cl_2$/methanol, 9.5:0.5) and/or recrystallization from dichloromethane/petroleum ether. Examples: see following table.

| $R^3$ | $R^3$—X | Reaction Conditions |
|---|---|---|
| 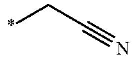 | $R^3$—I | 2 h, r.t. |
| 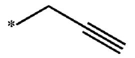 | $R^3$—Br (solution in toluene, 80%) | 0.5 h, r.t. |
| 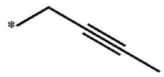 | $R^3$—Br | 1 h, r.t. |
| 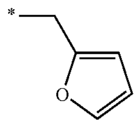 | $R^3$—Br (solution in DMF) | 1.5 h, r.t. |

Methylation of 8-Arylethynyl-1-prop-2-ynyl-3,7-dihydropurine-2,6-diones to 8-Arylethynyl-3,7-dimethyl-1-prop-2-ynyl-3,7-dihydropurine-2,6-diones (according to method B)

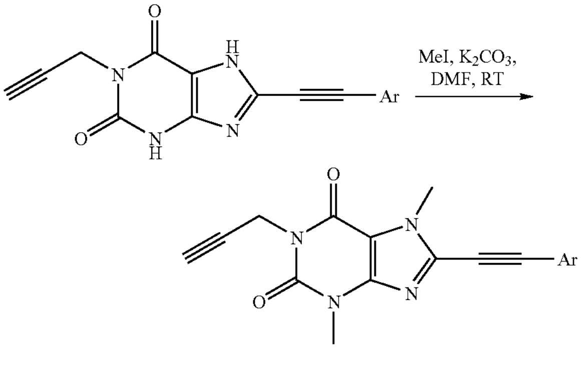

A suspension of 0.5 mmol of the corresponding 8-arylethynyl-1-prop-2-ynyl-3,7-dihydropurine-2,6-dione, $K_2CO_3$ (4 mmol) and 3 mmol of methyl iodide in DMF (15 mL) was stirred at room temperature for 0.5 h (TLC control: eluent $CH_2Cl_2$/methanol, 9.5:0.5). Subsequently the product was precipitated by adding water (50 mL), filtered under reduced pressure, washed with water (150 mL) and dried at 70° C. Further purification was achieved by column chromatography on silica gel (eluent $CH_2Cl_2$/methanol, 9.5:0.5) and subsequent recrystallization from dichloromethane/petroleum ether as described above.

Other 1-Alkyl-8-arylethynyl-3,7-dimethyl-3,7-dihydropurine-2,6-diones (according to the method described above)

Other 1-alkyl-8-arylethynyl-3,7-dimethyl-3,7-dihydropurine-2,6-diones bearing methyl, allyl, ethyl, propyl, butyl or cyclobutylmethyl substituents on the N1 position of the xanthine ring system were prepared analogously to the above mentioned procedures.

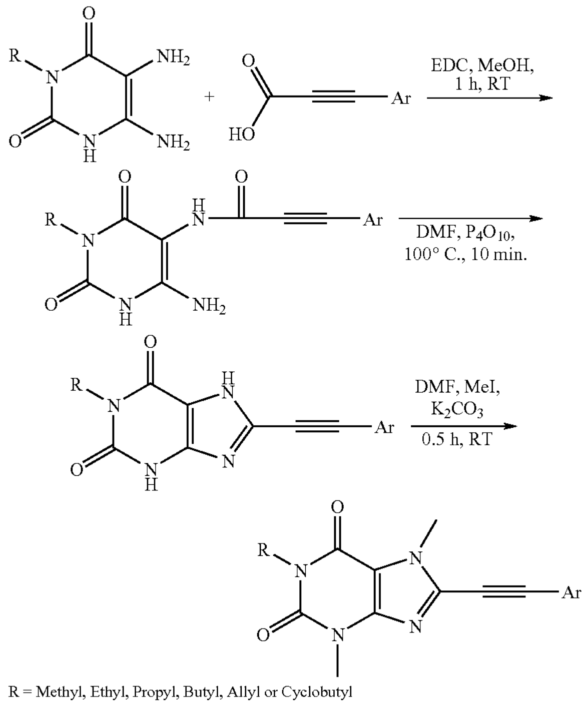

R = Methyl, Ethyl, Propyl, Butyl, Allyl or Cyclobutyl

Preparation of 8-(3-Hydroxyphenylethynyl)-3,7-dimethyl-1-prop-2-ynyl-3,7-dihydropurine-2,6-dione To a solution of 100 mg (0.28 mmol) 8-(3-methoxyphenylethynyl)-3,7-dimethyl-1-prop-2-ynyl-3,7-dihydropurine-2,6-dione in dichloromethane (25 mL) was added boron tribromide (0.5 mL, 5.3 mmol) at room temperature. After a few minutes precipitation of a yellow solid could be observed. The suspension was stirred for 0.5-1 h at room temperature until no starting material could be detected by TLC analyses (eluent: dichloromethane/methanol, 9.5:0.5). After hydrolysis with concentrated $NaHCO_3$ solution (50 mL) the dichloromethane was removed under reduced pressure. The precipitate was filtered under reduced pressure, washed with water, dried at 70° C. and purified by column chromatography on silica gel (eluent: dichloro-methane/methanol, 9.5:0.5 or 9:1): colorless crystals (yield: 76%), m.p. 271° C.

Alkylation of 8-(3-Hydroxyphenylethynyl)-3,7-dimethyl-1-prop-2-ynyl-3,7-dihydropurine-2,6-dione

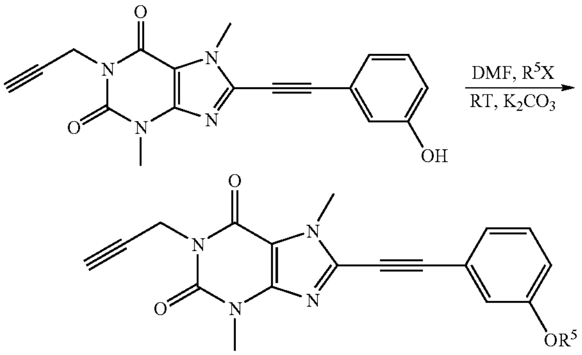

General procedure: To a suspension of 8-(3-hydroxyphenylethynyl)-3,7-dimethyl-1-prop-2-ynyl-3,7-dihydropurine-2,6-dione (0.1 mmol) and $K_2CO_3$ (0.5 mmol) in 3 mL of DMF were added 0.12-0.4 mmol of the corresponding alkyl halogenide. The mixture was stirred at room temperature until no further starting material could be observed by TLC analysis (eluent: dichloromethane/methanol, 9.5:0.5). Subsequently product was precipitated by adding water, filtered under reduced pressure and dried at 70° C. (unless otherwise noted, see following table). The crude product was purified by column chromatography on silica gel and subsequent recrystallization from dichloromethane/petroleum ether. Examples: see following table.

$R^5$=as mentioned above.

| $R^5$ | $R^5$—X (mmol) | Reaction Conditions, Purification (Eluent for Column Chromatography) |
|---|---|---|
| 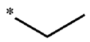 | $R^5$—I (0.4) | 1.5 h, r.t. ($CH_2Cl_2$:MeOH = 9.5:0.5) |
| 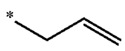 | $R^5$—I (0.3) | 45 min, r.t. ($CH_2Cl_2$:MeOH = 9.5:0.5) |
| 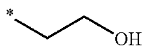 | $HOCH_2CH_2I$ (0.3) | 10 h, r.t.; $CH_2Cl_2$:MeOH = 9.5:0.5 |
| 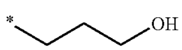 | $HOCH_2CH_2CH_2I$ (0.3) | 10 h, r.t.; $CH_2Cl_2$:MeOH = 9.5:0.5 |

-continued

| $R^5$ | $R^5$—X (mmol) | Reaction Conditions, Purification (Eluent for Column Chromatography) |
|---|---|---|
| 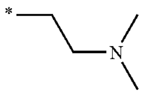 | $R^5$—Cl · HCl (0.12) | 1.5 h, 80° C., extraction with $CH_2Cl_2$, evaporation to dryness, column chromatography ($CH_2Cl_2$:MeOH = 3:1) |
| 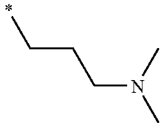 | $R^5$—Cl · HCl (0.12) | 1.5 h, 80° C., extraction with $CH_2Cl2$, evaporation to dryness, column chromatography ($CH_2Cl_2$:MeOH = 3:1) |
| 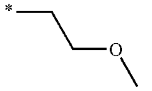 | $R^5$—Br (0.4) | 10 h, r.t., ($CH_2Cl_2$:MeOH = 9.5:0.5) |
| 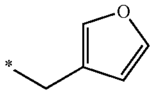 | $R^5$—Br in $Et_2O$ (ca. 0.3) | 1.5 h, r.t., ($CH_2Cl_2$:MeOH = 9.5:0.5) |

Acylation of 8-(3-Hydroxyphenylethynyl)-3,7-dimethyl-1-prop-2-ynyl-3,7-dihydropurine-2,6-dione

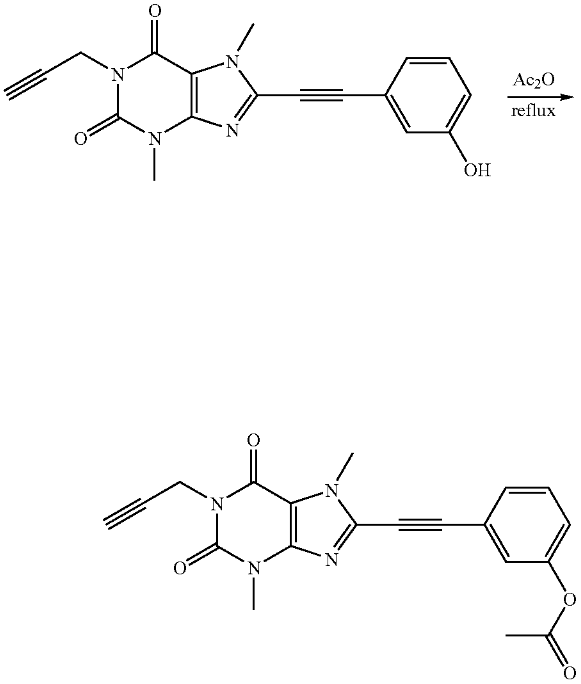

A mixture of 0.1 mmol of 8-(3-hydroxyphenylethynyl)-3,7-dimethyl-1-prop-2-ynyl-3,7-dihydropurine-2,6-dione and 0.5 mL acetic anhydride was heated under reflux for 15 min. Subsequently the mixture was hydrolyzed with concentrated $NaHCO_3$-solution (50 mL) and the product was extracted with dichloromethane. The organic extracts were dried over $MgSO_4$ and filtered and concentrated under vacuum. The crystalline residue was treated with ether and filtered under reduced pressure yielding 8-(3-acetoxyphenylethynyl)-3,7-dimethyl-1-prop-2-ynyl-3,7-dihydropurine-2,6-dione: colorless crystals (yield >95%), m.p. 238° C.

8-Arylethyny-3-(3-hydroxypropyl)-7-methyl-1-prop-2-ynyl-3,7-dihydropurine-2,6-diones

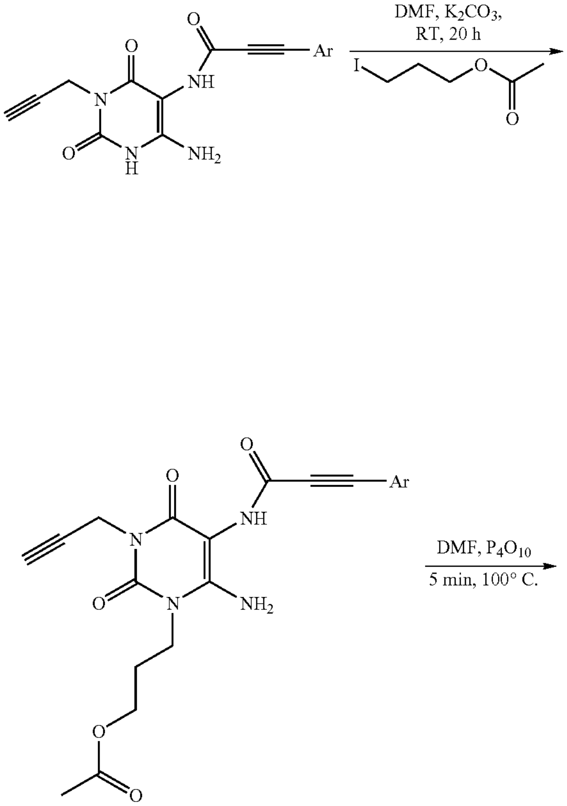

-continued

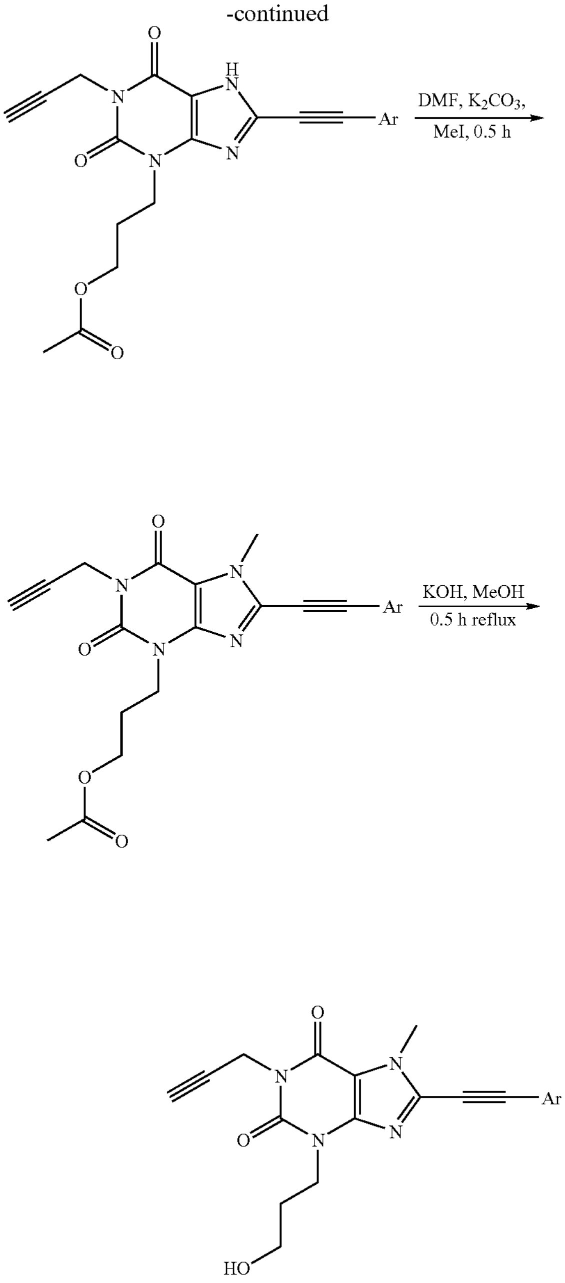

A mixture of the corresponding 3-arylpropynoic acid 6-amino-2,4-dioxo-3-prop-2-ynyl-1,2,3,4-tetrahydropyrimidin-5-yl amide (1 mmol), 250 mg $K_2CO_3$ (1.8 mmol), 4 mL of dry DMF and acetic acid-3-iodopropyl ester (0.8 g, 3.5 mmol) was stirred at room temperature until no starting material could be detected by TLC-analysis ($CH_2Cl_2$:MeOH=7:1).

After reaction times of ca. 16-20 h 30 mL of brine was added and the mixture was extracted five times with 50 mL of $CH_2Cl_2$ each. The combined organic extracts were dried over $MgSO_4$, filtered and concentrated under vacuum (the residue at least under 20 mbar at 60-70° C. in order to remove traces of water). The DMF containing oily residue was dissolved in additional 5 mL of DMF and treated with an excess of phosphorus pentoxide (ca. 1 g). The mixture was heated for 5 min under stirring at 100° C., cooled to room temperature and diluted with water (ca. 30 ml). In some cases the addition of diethyl ether (5-10 ml) was advantageous in order to dissolve unreacted alkyl iodide. The precipitate was filtered under vacuum, washed with water (ca. 150 ml) and dried at 70° C. or directly suspended in 8 mL of DMF and methylated with methyl iodide (0.5 ml) in the presence of $K_2CO_3$ (100 mg). After reaction times of less than 0.5 h (TLC-control, $CH_2Cl_2$:MeOH=9:1) the product was precipitated by adding water (ca. 30 ml), filtered under vacuum, and washed with water. The precipitate was directly dissolved in a mixture of methanol (10 ml) and KOH (0.5 g) and refluxed for 0.5 h. After cooling to room temperature, the product was precipitated by adding water (ca. 30 ml), filtered under reduced pressure, washed with water (ca. 100 ml) and dried at 70° C. Further purification was achieved by column chromatography on silica gel ($CH_2Cl_2$:MeOH=9:1) and subsequent recrystallization from $CH_2Cl_2$/petroleum ether.

Alkylation of 8-[(3,4-Dimethoxyphenyl)ethynyl]- and 8-[(3-Methoxyphenyl)ethynyl]-7-methyl-1-prop-2-ynyl-3,7-dihydropurine-2,6-dione Derivatives

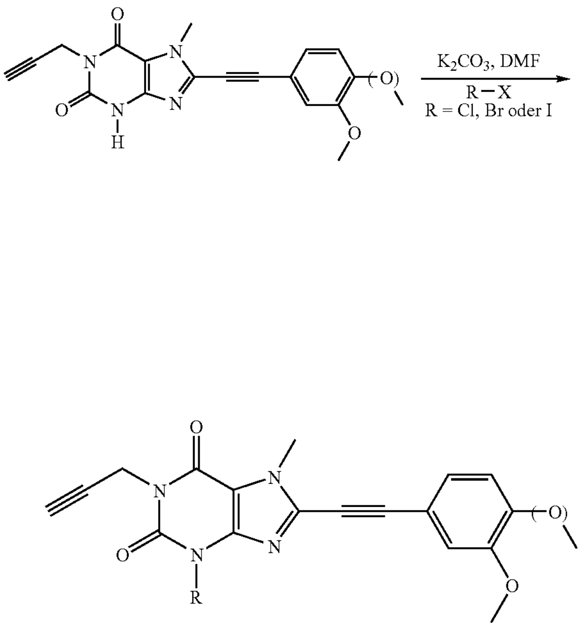

General Procedure:

To a mixture of the corresponding 8-(phenylethynyl)-7-methyl-1-prop-2-ynylxanthine derivative (0.1 mmol) and $K_2CO_3$ (0.5 mmol) in DMF (3.5 mL) 0.3 mmol of the alkylation reagent was added. The mixture was stirred at room temperature or heated until a complete conversion could be detected by TLC (TLC-control: dichloromethane/methanol, 9.5:0.5). Subsequently the product was precipitated by adding water (30 ml), filtered under reduced pressure, washed with water and dried at 70° C. Finally the products were crystallized from dichloromethane/petroleum ether, filtered under reduced pressure and washed with diethyl ether. A further purification was achieved by column chromatography on silica gel (eluent: dichloromethane/methanol, 9.5:0.5). Examples: see following tables.

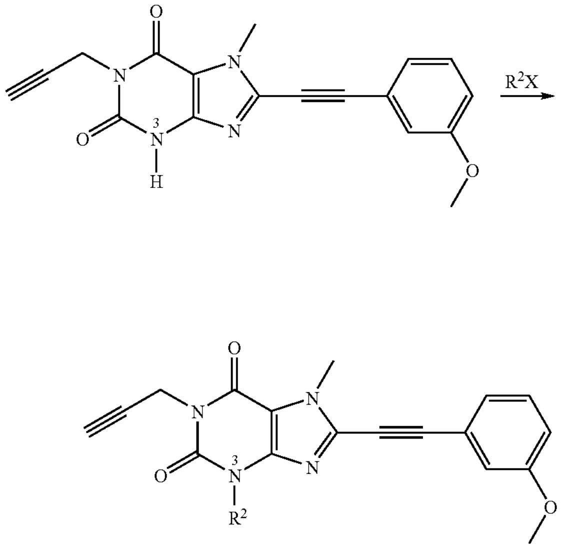

| $R^2$ | $R^2$—X | Reaction Conditions |
|---|---|---|
| 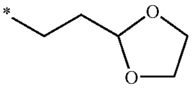 | $R^2$—Br | 3 h, 80° C. |
| 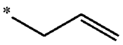 | $R^2$—I | 45 min., r.t. |
| 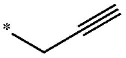 | $R^2$—Br (solution in toluene) | 1 h, r.t. |
| 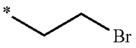 | $R^2$—Br | 3 h, r.t. |
| 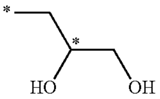 | $R^2$—Br | 8 h, 100° C. |
| 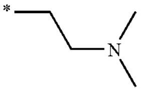 | $R^2$—Cl · HCl | 1.5 h, 80° C. or 16 h, r.t. |
| 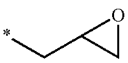 | $R^2$—Br | 2 h, 110° C. |
| 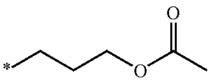 | $R^2$—I | 4 h, r.t. |
| 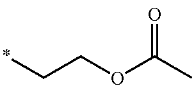 | $R^2$—I | 4 h, r.t. |

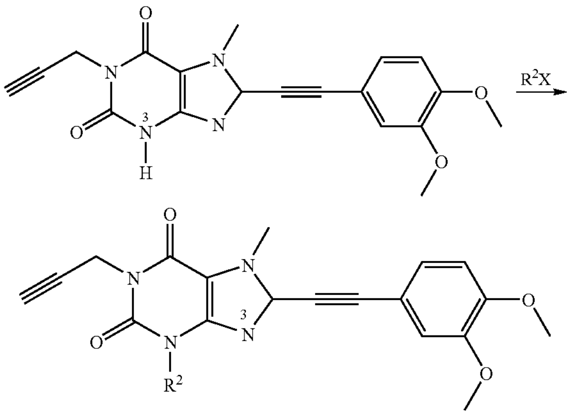

| $R^2$ | $R^2$—X | Reaction Conditions (Transformation Towards the Final Compound) |
|---|---|---|
| 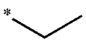 | $R^2$—I | 2 h, r.t.: |
| 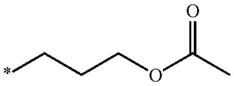 | R—I | 4 h, r.t. |
| 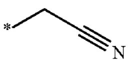 | $R^2$—I | 2 min, r.t. |
| 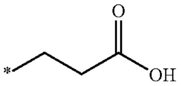 | $R^2$—I | 6 h, r.t. after the precipitation with water the mixture had to be acidified |
| 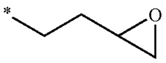 | $R^2$—Br | 1.5 h, 100° C. |
| 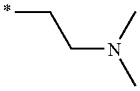 | $R^2$—Cl · HCl | 20 h, r.t. |
| 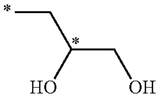 | $R^2$—Br | 16 h, r.t. |
| 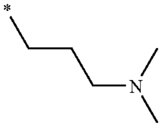 | $R^2$—Cl · HCl | 16 h, r.t. |
| 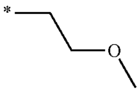 | $R^2$—Br | 12 h, r.t. |
| 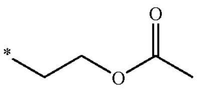 | $R^2$—I | 24 h, r.t. |
| 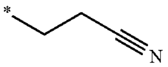 | $R^2$—Br | 20 h, r.t. |

-continued

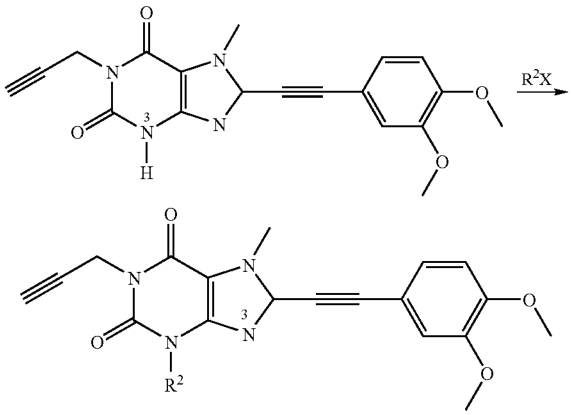

| $R^2$ | $R^2$—X | Reaction Conditions (Transformation Towards the Final Compound) |
|---|---|---|
| 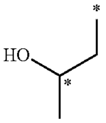 | $R^2$—Br | 24 h, r.r. |
| 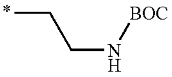 | $R^2$—Br | 18 h, r.t. |
| 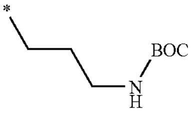 | $R^2$—Br | 4 h, r.t. |
| 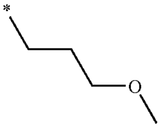 | $R^2$—Br | 4 h, r.t. |
| 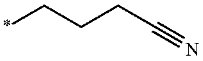 | $R^2$—Br | 4 h, r.t. |
| 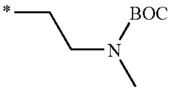 | $R^2$—Br | 7 d, 75° C. |
| 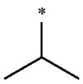 | $R^2$—I | 24 h, r.t. |
| 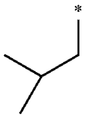 | $R^2$—I | 8 h, r.t. |
| 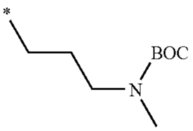 | $R^2$—Cl | 24 h, r.t. |

-continued

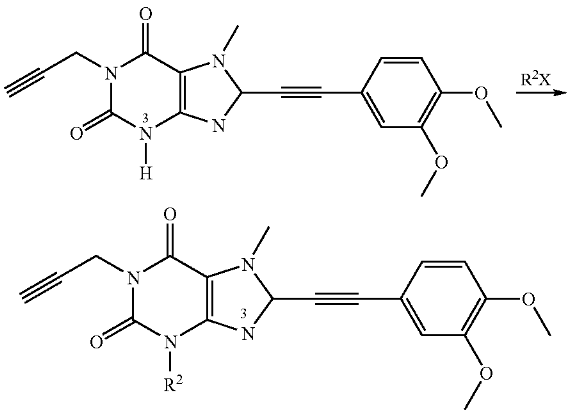

| $R^2$ | $R^2$—X | Reaction Conditions (Transformation Towards the Final Compound) |
|---|---|---|
| 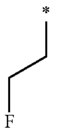 | $R^2$—Br | 5 h, r.t. |
| 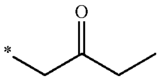 | $R^2$—Br | 2 h, r.t. |
| 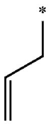 | $R^2$—I | 1 h, r.t. |
| 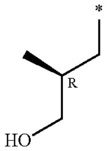 | $R^2$—Br | 24 h, r.t. |
| 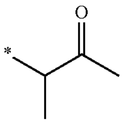 | $R^2$—Br | 1 h, r.t. |
| 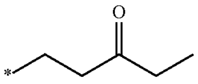 | $R^2$—Cl | 15 d, r.t. |
| 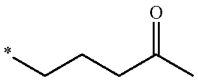 | $R^2$—Cl | 18 h, 75° C. |
| 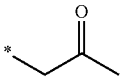 | $R^2$—I | 50 min, r.t. |
| 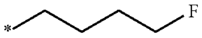 | $R^2$—Br | 4 h, r.t. |
| 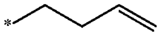 | $R^2$—Br | 3 h, r.t. |

-continued

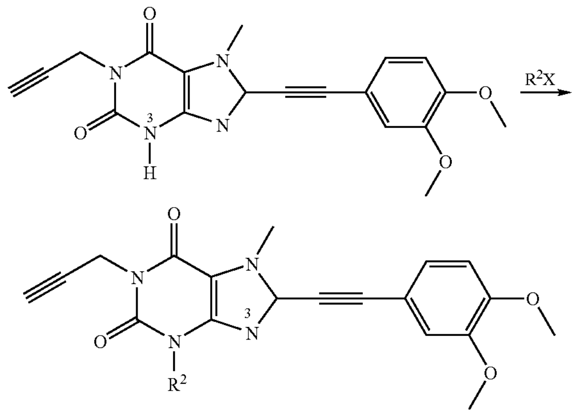

| $R^2$ | $R^2$—X | Reaction Conditions (Transformation Towards the Final Compound) |
| --- | --- | --- |
| 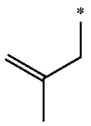 | $R^2$—Br | 1.5 h, r.t. |
| 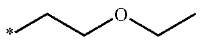 | $R^2$—Br | 18 h, r.t. |
| 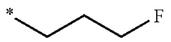 | $R^2$—Br | 18 h, r.t. |
| 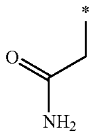 | $R^2$—Br | 4 h, r.t. |
| 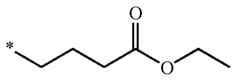 | $R^2$—Br | 16 h, r.t. |
| 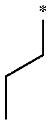 | $R^2$—I | 1 h, r.t. |
| 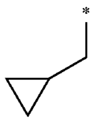 | $R^2$—Br | 2 h, r.t. |
| 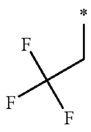 | $R^2$—I | 4 d, 50-60° C. |
| 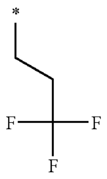 | $R^2$—Br | 2 h, r.t. |

-continued

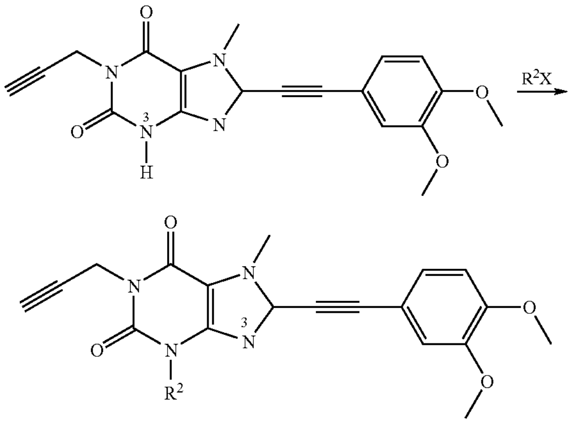

| $R^2$ | $R^2$—X | Reaction Conditions (Transformation Towards the Final Compound) |
| --- | --- | --- |
| 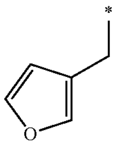 | $R^2$—Br (solution in $Et_2O$) | 1 h, r.t. |
| 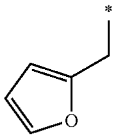 | $R^2$—Br (solution in DMF) | 1 h, r.t. |
| 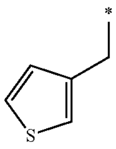 | $R^2$—Br | 1 h, r.t. |
| 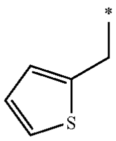 | $R^2$—Br | 1 h, r.t. |
| 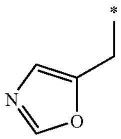 | $R^2$—Br | 2 h, r.t. |
| 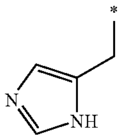 | $R^2$—Cl × HCl | 10 h, 80° C. |

Cleavage towards 3-(aminoalkyl)-8-[(3,4-dimethoxyphenyl)ethynyl)-7-methyl-1-prop-2-ynyl-3,7-dihydropurine-2,6-dione Derivatives

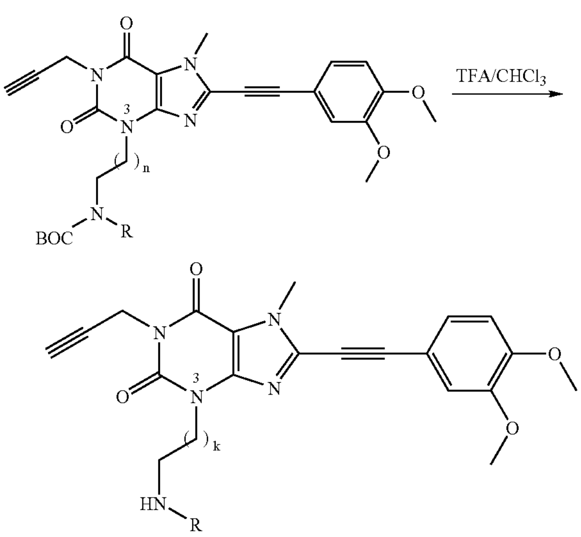

n = 1,2
R = H, Me

General Procedure:

The crude amino-protected derivatives (0.1 mmol) was dissolved in chloroform (7 mL) and treated with trifluoric acetic acid (TFA; 0.7 mL). The reaction mixture was stirred until a complete conversion could be detected by TLC (TLC-control: dichloromethane/methanol, 9.5:0.5). Subsequently the solvent was removed under reduced pressure and a mixture of methanol/triethylamine (8:2, 10 mL) was added. The product was precipitated by adding water (30 ml), filtered under reduced pressure, washed with water and dried at 70° C. Finally the products were crystallized from dichloromethane/petroleum ether, filtered under reduced pressure and washed with diethyl ether to yield the desired primary amino derivatives as white solids.

The compounds in table 1 are synthesized analogously to the above described processes.

Synthesis of 8-(3,4-Dimethoxyphenylethynyl)-3-dimethylamino-7-methyl-1-prop-2-ynyl-3,7-dihydropurine-2,6-dione This compound may be produced according to the following schemes (a) or (b)

(a)

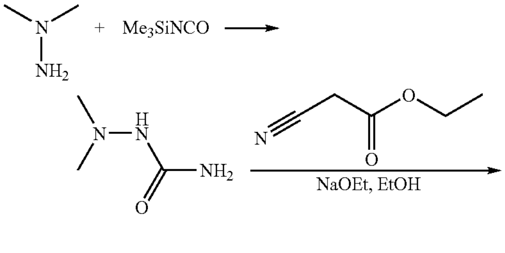

-continued

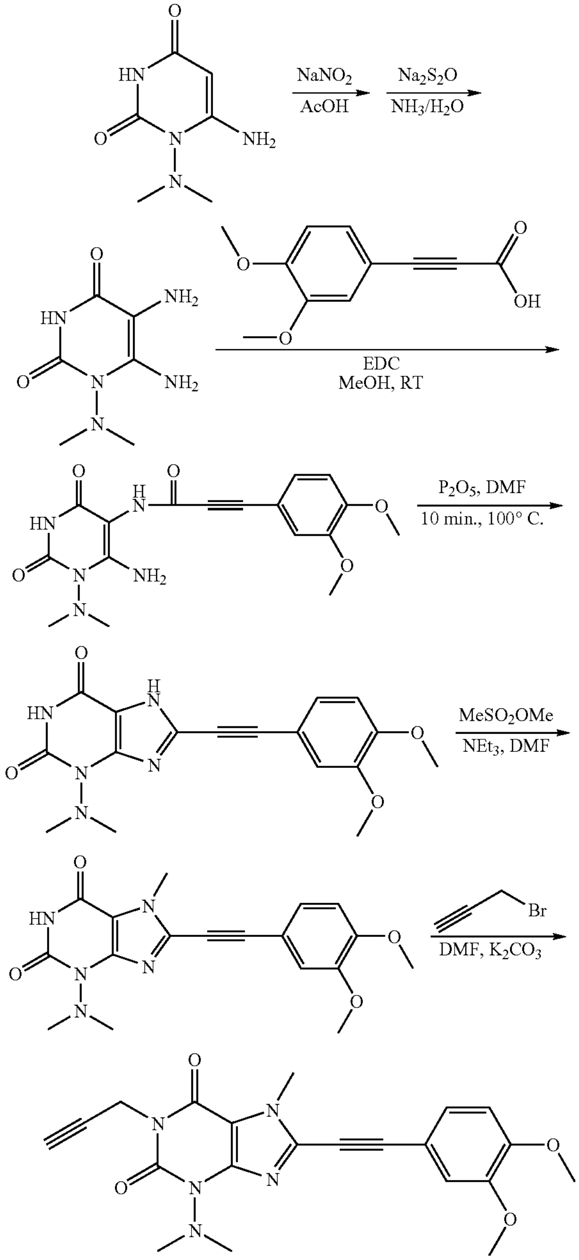

EDC = water soluble carbodiimide derivative (b)

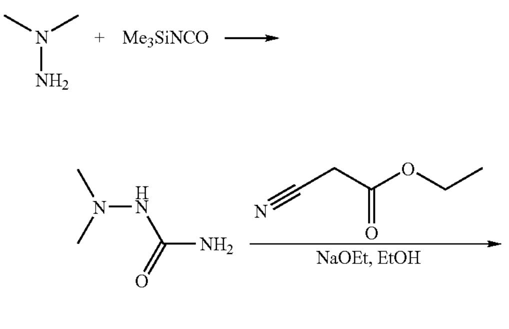

-continued
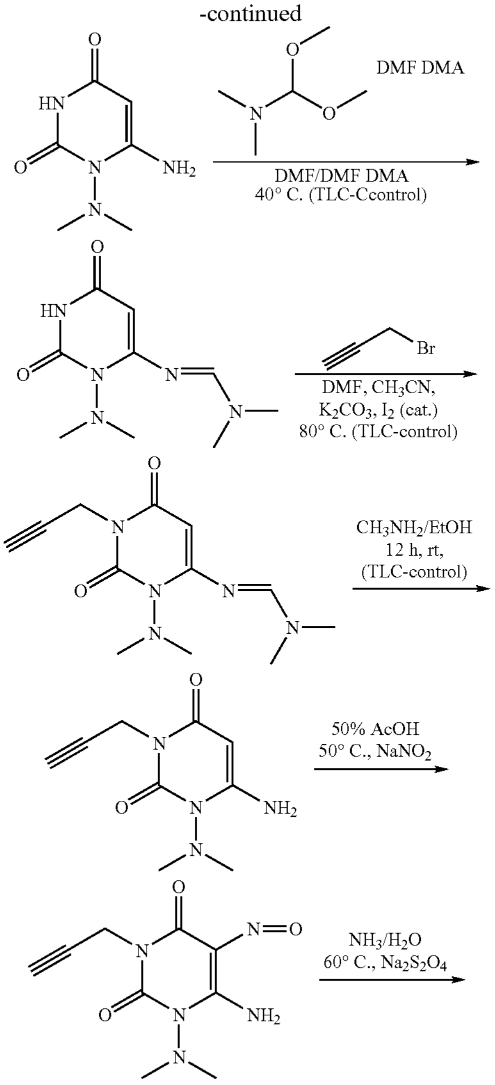
-continued
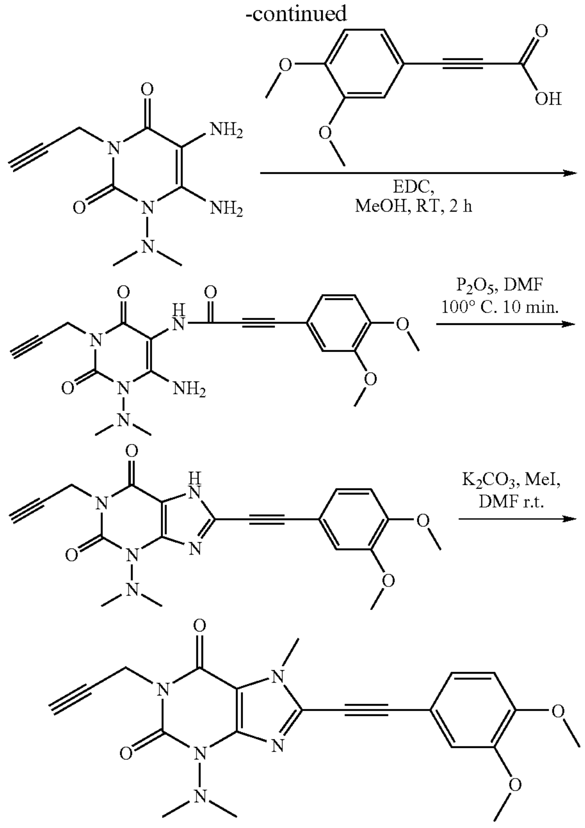
EDC = water soluble carbodiimide derivative
Synthesis of 3-Amino-8-(3,4-dimethoxyphenylethynyl)-7-methyl-1-prop-2-ynyl-3,7-dihydro-purine-2,6-dione
This compound can be produced according to the following scheme
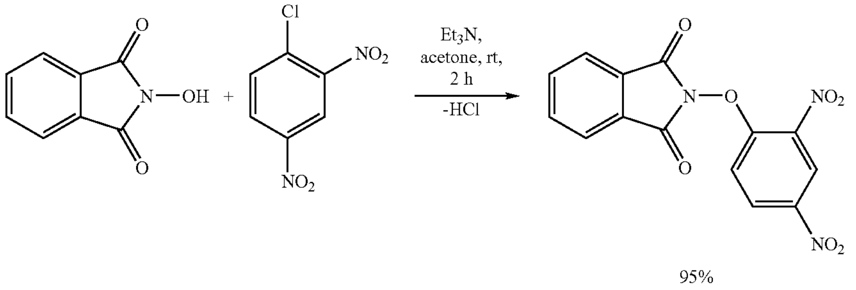
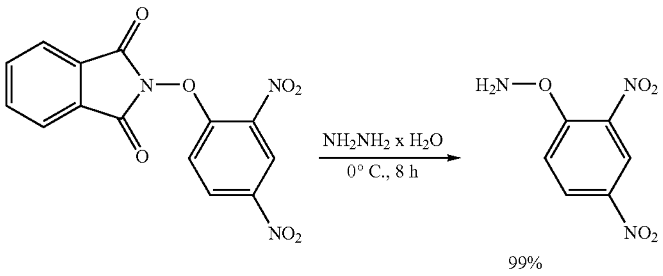

-continued

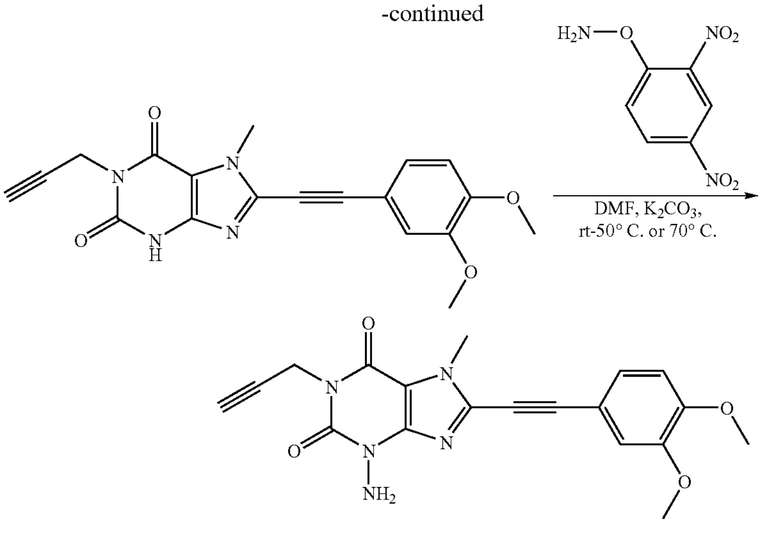

Biological Experiments

Radioligand Binding Assay 1:

Rat brain preparations were used for $A_1$- and $A_{2A}$ adenosine receptor (AR) and human recombinant cell samples for $A_1$-, $A_{2A}$- and $A_3$ adenosine receptor radioligand binding studies. Affinity and selectivity was tested in displacement experiments with following radioligands: [$^3$H]CCPA for $A_1$-adenosine receptors, [$^3$H]MSX-2 for $A_{2A}$-receptors and [$^3$H]PSB-11 for $A_3$-receptors. Results of these experiments are depicted in table 2b (human data) and table 2a (rat data). Radioligand binding test systems are e.g. generally described by Muller et al., Curr. Pharm. Des., 1996, 2, 501 and Weyler et al., ChemMedChem 2006, 1, 891 and references cited therein) These documents are incorporated herein by reference.

Radioligand and Binding Assay 2: Receptor Binding Profile of $A_{2A}$ Receptor Antagonists Including the $A_{2B}$ Adenosine Receptor:

The assays were performed under the conditions described below. The literature references are also provided for each assay:

| Adenosine $A_1$: | |
|---|---|
| Source: | Human recombinant CHO cells |
| Ligand: | 1 nM [$^3$H]CCPA |
| Incubation Time/Temp.: | 60 min/22° C. |
| Non-Specific Ligand: | CPA (10 μM) |
| Method of Detection: | Scintillation Counting |

The adenosine $A_1$ radioligand binding assay used is further described in Rivkees S. A. et al., J. Biol. Chem., 1995, 270, 20485 and is incorporated herein by reference.

| Adenosine $A_{2A}$: | |
|---|---|
| Source: | Human recombinant HEK-293 cells |
| Ligand: | 6 nM [$^3$H]CGS 21680 |
| Incubation Time/Temp.: | 120 min./22° C. |
| Non-Specific Ligand: | NECA (10 μM) |
| Method of Detection: | Scintillation Counting |

The adenosine $A_{2A}$ radioligand binding assay used is further described in Luthin D. R. et al., Mol. Pharmacol., 1995, 47 and is incorporated herein by reference.

| Adenosine $A_{2B}$: | |
|---|---|
| Source: | Human recombinant HEK-293 cells |
| Ligand: | 0.5 nM [$^3$H]MRS 1754 |
| Incubation Time/Temp.: | 120 min./22° C. |
| Non-Specific Ligand: | NECA |
| Method of Detection: | Scintillation Counting |

The adenosine $A_{2B}$ radioligand binding assay used is further described in Stehle J. H. et al., Mol. Endocrinol., 1992, 6, 384 and is incorporated herein by reference.

| Adenosine $A_3$: | |
|---|---|
| Source: | Human recombinant HEK-293 cells |
| Ligand: | 0.15 nM [$^{125}$I]AB-MECA |
| Incubation Time/Temp.: | 120 min./22° C. |
| Non-Specific Ligand: | IB-MECA (1 μM) |
| Method of Detection: | Scintillation Counting |

The adenosine $A_3$ radioligand binding assay used is further described in Salvatore C. A. et al., Proc. Natl. Acad. Sci. USA, 1993, 90, 10365 and is incorporated herein by reference.

The specific ligand binding to the receptors is defined as the difference between the total binding and the non-specific binding determined in the presence of an excess of unlabelled ligand. The results are expressed as a percent of control specific binding and as percent inhibition of control specific binding obtained in the presence of the test compounds. Results showing an inhibition higher than 50% are considered to represent significant effects of the test compounds.

The results of the binding assays are depicted in table 4 as the % inhibition of agonist binding at 1 μmol/l (≧50% inhibition of agonist binding is commonly regarded as a robust signal). As can be seen from table 4, all compounds bind specifically to the $A_{2A}$-receptor.

Sodium Chloride-Shift-Experiment:

The compounds were tested in a sodium chloride-shift experiment of whether they are functionally coupled to $A_{2A}$ adenosine receptors from rat striatum. In this experiment the $IC_{50}$-value is measured with and without sodium chloride present (100 mM). The presence of a relatively high concentration of sodium chloride should not influence the affinity of the antagonists. However, the affinity of $A_{2A}$ AR agonists should be attenuated and therefore lead to an elevated $IC_{50}$-value. As can be seen from table 5, the absence and presence of sodium chloride does not influence the $K_i$-value of the examined compounds. This confirms the $A_{2A}$-antagonistic function of the compounds. (Gao et al, Biochem. Pharmacol., 2000, 60, 669, herein incorporated by reference).

Functional Assay Concerning Inhibition of $A_1$- and $A_{2A}$-Adenosine Receptors:

The following experiment evaluated the compounds of the invention for their functional antagonistic activity on two cell lines expressing the human recombinant adenosine receptors $A_1$ or $A_{2A}$. CHO-DUKX cells expressing recombinant human adenosine $A_1$ or $A_{2A}$ (named CHO-DUKX-SRE-Luci-A1-44 and CHO-DUKX-CRE-$A_{2A}$-19, respectively) are prepared. These cell lines originated from CHO-DUKX (DSMZ: ACC 126) cells, and have the reporter-gene plasmid pSRE-Luci or pCRE-Luci (Biofrontera Pharmaceuticals Germany) stably integrated. CHO-DUKX-SRE-Luci-A1-44 and CHO-DUKX-CRE-$A_{2A}$-19 cells are cultivated in DMEM/F12-Mix (Invitrogen, San Diego, Calif., #31331-028) supplemented with 10% heat-inactivated FBS (PAA Laboratories, Germany, #A15-649), 0.2 mg/ml Hygromycin B (Invitrogen, San Diego, Calif., #1113347) and 0.4 mg/ml G418 (Invitrogen, San Diego, Calif., #10131-019). Cells are grown in a humidified chamber at 37° C., 5% $CO_2$. cDNA encoding the respective human receptors was cloned from human mRNA preparations by RT-PCR with sequence-specific primers covering the start and stop codons, respectively, using high-fidelity Taq polymerases (Pfu, Stratagen; Pfx, Invitrogen). cDNA inserts were directionally subcloned into the expression vector pCineo (Promega) and sequenced. The deduced amino acid sequences were in accordance with those published in GenBank. Expression plasmids were introduced into eukaryotic cells harboring the luciferase reporter-gene driven by a SRE-based (CHO-DUKX-SRE) promoter element or CRE-based (CHO-DUKX-CRE) promoter element as indicated in the name of the cell line.

The investigated receptor was shown to activate the respective reporter-gene in the selected cell line. Transfections were performed in 6-well plates using the Lipofectamine™ Plus reagent (Invitrogen, San Diego, Calif.) according to the instructions of the manufacturer. Two days after transfection cells were selected for G418 resistance (0.4 mg/ml) and grown for 10 days. Cells were seeded into 96-well plates in a limited dilution of 2 cells per well. Two weeks later single colonies were split into three wells and tested for agonist responsiveness. The clonal cell lines used for this study exhibited the most robust signals in terms of fold induction and absolute signal intensity in relative light units (RLUs) and have been pharmacologically characterized.

The luciferase reporter assay was then used to measure concentration response curves. Cells were seeded in white 96-well microtiter plates (Becton Dickinson, Heidelberg, Germany, #353296) at a density of approx. 30,000 cells per well in growth medium, supplemented with 0.2 mg/ml hygromycin (Invitrogen, San Diego, Calif.) and 0.4 mg/ml G418 (Invitrogen, San Diego, Calif.). After 24 h, the growth medium was removed, the cells washed and incubated further with 90 μl medium lacking supplements and serum. Cells were starved under these conditions for 15-20 h prior to stimulation by the antagonist. Test compounds (test stock solution: 10 mM in DMSO, stock solutions were kept frozen at minus 20° C. in aliquots until use) were added to the cells after dilution in PBS from DMSO-stocks. Test items were serially diluted from stock (with PBS (Invitrogen, San Diego, Calif., #14190-094, Lot #3091940) to the 10× final concentrations. Since the stock solutions were prepared in 100% DMSO, the final incubation medium contained DMSO at concentrations lower than 0.3%. DMSO concentrations below 4% did not influence the outcome of the experiment. With a multichannel pipette, 10 μl of a dilution of the test item was added to 90 μl of medium. Test items were tested in 14 different concentrations covering, after final dilution in the well, a concentration range from $10^{-13}$ M to $3\times10^{-5}$ M. After a 5-minute incubation, the cells were stimulated for 4 h at 37° C. with agonist at the respective calculated $EC_{50}$ concentrations (3.5 μM ADAC for the A1, 60 nM NECA for the $A_{2A}$ receptor), obtained from the concentration-response experiments of the receptor assays (data not shown). Subsequently, the medium was removed and the cells were lysed by the addition of 20 μl lysis buffer (25 mM Tris/HCl pH 7.8, 0.4 mM DTT, 0.4 mM CDTA, 2.5% Glycerol, 0.25% Triton X-100) and 30 μl of luciferase assay reagent (20 mM Tricine, 1.07 mM Mg(CO3)4×Mg(OH)2×5H2O, 2.67 mM MgSO4×7H2O, 0.1 mM EDTA, 33.3 mM DTT, 0.27 mM CoA×2H2O, 0.47 mM D-Luciferin, 0.53 mM ATP). After mixing, the luminescence of the solution was measured integrative for 3 s in an Fluoroskan™ Ascent FL (Labsystems, Helsinki, Finland). $IC_{50}$ values and the maximum antagonistic effect, Imax, were calculated from the concentration response curves of the compounds. The data were compared to the concentration response curves of CPX (8-Cyclopentyl 1,3-diprophylxanthine, Sigma, C-101), an $A_1$ receptor antagonist, and 5-Amino-7-(β-phenylethyl)-2-(8-furyl)pyrazolo(4,3-e)-1,2,4-triazolo(1,5-c)pyrimidine (Sigma, S-4568), an $A_{2A}$ receptor antagonist. Receptors were stimulated with 3.5 μM ADAC (adenosine amine congener, Sigma, A-111) for the $A_1$ and 60 nM NECA (5-(N-ethylcarboxamido)-adenosine, Sigma, E-2387) for the $A_{2A}$ receptor.

The background signal (background=mean of diluent values; PBS was used as diluent) was subtracted from each data point. Curve fitting was performed to determine $IC_{50}$, $I_{max}$ and p values using ORIGIN (Microcal Software, Northhampton, Mass., U.S.A.). The following model was applied:

$$y = \frac{[A1 - A2]}{1 + (x/x_0)^p} + A2$$

This model represents a four parametric logistic equation for the description of antagonist action. The parameters are initial value (A1), final value (A2), X at $Y_{50}$ ($X_0$), and power (p). To compare $I_{max}$ values of the test items with the $I_{max}$ of the corresponding antagonist $I_{max}$% values were calculated as $I_{max}$ in % of the corresponding antagonist. $K_i$ values were calculated using the equation: $K_i = IC_{50}/(1+\text{used concentration of agonist}/EC_{50})$. The results are depicted in table 6. The compounds proof to be full antagonists at $A_{2A}$ adenosine receptors.

Modified Irwin Test:

In this study the compounds of the present invention were screened for basal behavioural, autonomic, neurological and toxicological side-effects in rats. For this purpose, a functional observational battery (FOB) in form of an Irwin test (Irwin S., Psychopharmacologia, 1968, 13, 222; 1968; Warburton D. M. Psychopharmacology, 2002, 163, 4; Haggerty G. C. et al., J. Amer. Coll. Toxicol., 1991, 10, 677; Mattsson J. L. et al., J. Amer. Coll. Toxicol., 1996, 15, 239, all references are herein incorporated by reference) modified and validated by the Test Facility was used. Each test compound was tested at eight doses (0.01, 0.03, 0.1, 0.3, 1.0, 3.0, 10.0 and 30.0 mg/kg). All compounds were dissolved in DMSO (administration volume 1 ml/kg). Each dose group included three animals. Two vehicle groups (DMSO and Labrasol) served as negative controls.

At the first day of each test week all test compound solutions necessary for the test (1-2 weeks) were prepared by means of one dilution series starting with the highest concentration. All test compounds dissolved in DMSO were administered in a volume of 1 ml/kg. DMSO-containing solutions were stored at −18° C. All solutions were melted for administration at room temperature 16-20 hours before the start of the test.

Study design and time schedule:

4-7 days: Acclimatization and handling of the animals 1 day: Test day with (a) Four repeated functional observational battery (FOB): 30 min, 60 min, 120 min, 180 min following compound administration (b) Short animal check (SAC): 300 min following compound administration 1 day: Follow-up observation (FU): 24 h (1440 min) following compound administration.

In all experimental parts, an experienced ethologist used lists of predefined methods and behavioural parameters in order to rate the behaviour of the animal (see table 7 for functional observational battery (FOB), table 8 for short animal check (SAC) and table 9 for follow-up observation (FU).

A statistical evaluation of the data was performed that enabled an assessment of the compound's effects on each parameter. Dose-response relationships are not necessarily linear. It was not clear a priori whether the response would be dose-dependent or whether low, medium or high dose effects would occur. Therefore, the data were correlated against a set of different numeric models of theoretical dose-response curves. For this kind of evaluation the measurement times were not differentiated. An average value over all measurement times was calculated for each animal. This value was taken as one measurement within the observation vector. The complete set of parameters measured for the animal (each one averaged over time) formed the observation vector. Each dose was then represented by three observation vectors (3 animals per dose). The effects of all doses were compared with vehicle (DMSO) as the observation vectors for the zero dose. A common pool of 24 animals for the zero dose was used for all compounds to be tested. For each test compound the obtained values for each parameter together with values from the pool of vehicle-treated (DMSO) animals were then correlated with theoretical dose-response models (analysis profiles). Since 8 doses were be used, there were 8 models, each assuming that the maximum compound effect occurred at one of these doses. Effects of other doses were assumed to be attenuated with a linearly descending slope of the theoretical curve. Correlation values and statistical significance of regression were then calculated. An error probability of $p<0.05$ (two-tailed testing) was taken as significance level. Non-significant regressions were neglected. In consequence, each parameter was assessed as not affected or affected by the compound in a dose-response relationship according to type 1 (low dose effect) up to type 8 (high dose effect). Dose response is maximal for the effect with the greatest absolute correlation coefficient. The results were then summarized and visualized in a result matrix for each test compound. The outcome of this study is depicted in compressed form in table 10 (0.01-30 mg/kg). In summary, the compounds of the present invention induce a potent hyperlocomotion.

Acute CGS-21680 Induced Catalepsy and Acute Reserpine Induced Catalepsy Tests:

Animals were administered with Reserpine or CGS-21680 according to methods known to the skilled person in the art. These models and procedures are e.g. described by Ferré S. et al., Neurosci. Let., 1991, 130, 162; Ferré S. et al., Neuroscience, 1992, 51, 501; Kafka S. H. et al., Eur. J. Pharmacol., 1996, 295, 147; Rimondini R. et al., Neuropsychopharmacology, 1997, 17, 82 and are herein incorporated by reference. In the acute CGS-21680 induced catalepsy model (CGS model) the test compounds (TC, compounds according to the present invention) and CGS-21680 (i.p. 2 mg/kg) were administered 60 minutes before the start of the catalepsy bar measurement and behavioural testing described below (see also FIG. 1). In the acute Reserpine induced catalepsy model (RES model Resperine (subcutaneously, 3 mg/kg) was injected 24 h prior to the test compound application. Catalepsy bar measurement took place 60 minutes after test compound application (see FIG. 1). Test compounds were administered i.p. in DMSO in following doses (mg/kg): 0.1, 0.3, 1, 3, 10.

Dimethylsulfoxide (DMSO) was used as vehicle for the test compounds and Reserpine. Reserpine was dissolved in DMSO in a concentration of 3 mg/ml. A 10% (w/v) Cyclodextrin solution was used as vehicle for CGS-21680. CGS 21680 was dissolved in 10% (w/v) Cyclodextrine in a concentration of 2 mg/ml.

Caffeine was used as a reference compound in the CGS-21680 induced catalepsy model. A caffeine solution was prepared with water for injection purposes to a concentration of 30 mg/ml. The solution was administered intraperitoneally in a volume of 1 ml/kg (30 mg/kg) 30 minutes before the beginning of testing and after CGS-21680 pre-treatment (1 hour prior to testing).

Apomorphine was used as a reference compound in the Reserpine induced catalepsy model. Apomorphine injection solution was diluted with purified water to a concentration of 0.3 mg/ml. The solution was administered subcutaneously (s.c.) in a volume of 1 ml/kg (0.3 mg/kg) 20 minutes before the begin of testing after Reserpine pre-treatment (25 hours prior to testing).

The catalepsy bar after CGS-21680 administration was measured (CAT) as follows: The rat was placed with its forepaws on a log of wood. If it did not descend within 30 seconds, the trial ended and 30 seconds was taken as the time for that trial. If the animal descended faster than 1 second, the trial was regarded as invalid. If more than 20 trials were rated as invalid, the values of all uncompleted trials were noted as 0. The animal was tested until five trials had been completed and the time for each trial was noted. Only the values of the last three trials were used for the analysis. The following parameters were calculated: maximum time to descend(s) and median time to descend(s).

The catalepsy bar after Reserpine administration was measured (CAT) as follows: The rat was placed with its forepaws on a log of wood. If it did not descend within 30 seconds, the trial ended and 30 seconds was taken as the time for that trial. The animal was tested for three trials and the time for each trial was noted. The following parameters were calculated: maximum time to descend(s) and median time to descend(s).

Behavioural observation (BO) included the measurement of the body tone, inclined plane and grip strength.

Body Tone:

The rat is taken in the hand of the observer and the animal's body tone is rated as normal, soft or hard. The rating is performed immediately after taking the animal from its home cage before performance of catalepsy testing. The following parameters were calculated: mean occurrence of hard body tone and mean occurrence of soft body tone.

Inclined Plane:

The rat is horizontally placed to an inclined plane for a maximum time of 30 seconds. Time to reach bottom or top is measured. If the animal does not reach the bottom or top of the grid after 30 seconds inclined plane testing is stopped and 30 seconds are taken as result. The test is performed after catalepsy testing. Time to leave the inclined plane(s) was measured.

Grip Strength:

The rat is put on a grip and the observer pulls the animal back on his tail. The strength (fore paws and hind paws) by which it holds on the grid is scored as grasping and pulling, grasping without pulling or no grasping. The test is performed after the inclined plane test. The following parameters were calculated: mean score of fore paw grip strength and mean score of hind paw grip strength.

All statistical tests were performed two tailed with a value of $p<0.05$ considered as significant.

To assess the effects of CGS-21680 and Reserpine pretreatment compared to vehicle treated controls statistical comparisons between the test groups were performed using a U test statistic.

To assess the effects of test compounds on CGS-21680 and Reserpine pre-treated animals correlation analyses including animals from test groups and the respective test compound-treated groups were performed.

Additionally, parametric and non-parametric comparisons for the median catalepsy measure were performed to assess the reliability of the method. In case of parametric testing a GLM analyses was performed including animals from a control group (only vehicle treated animals) and the respective test compound-treated groups with dose as a categorical factor. In case of a significant result, a Dunnett's post hoc test was performed between the according test compound groups and a control group as reference group. In case of non-parametric testing a Kruskal-Wallis H-test was performed including animals from a control group and the respective test compound groups. In case of a significant result single U-test comparisons were performed between a control group and the groups treated with different doses of the test compound.

Figure 2:
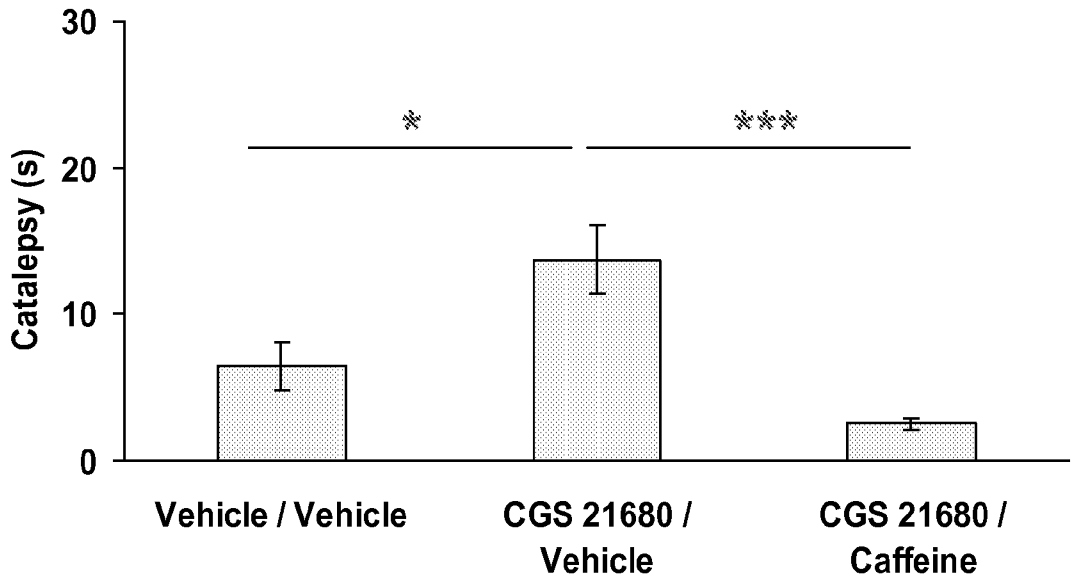
FIG. 2: CGS-21680 induced catalepsy time with control (vehicle/vehicle) and reference compound caffeine

FIG. 2 shows the CGS-21680 induced catalepsy time with control (vehicle/vehicle) and reference compound caffeine (mean±SEM. N=24). CGS-21680 compared to vehicle significantly increased rating of soft and decreased rating of hard body tone. Time leaving inclined plane and grip strength were unaffected. Compared to only CGS-21680-treated animals caffeine increased rating of hard and decreased rating of soft body tone almost to the level of only vehicle-treated animals. Caffeine significantly decreased median and maximum catalepsy values in CGS-21680 pre-treated animals to a level that was even lower than that of only vehicle-treated animals.

Figure 3:
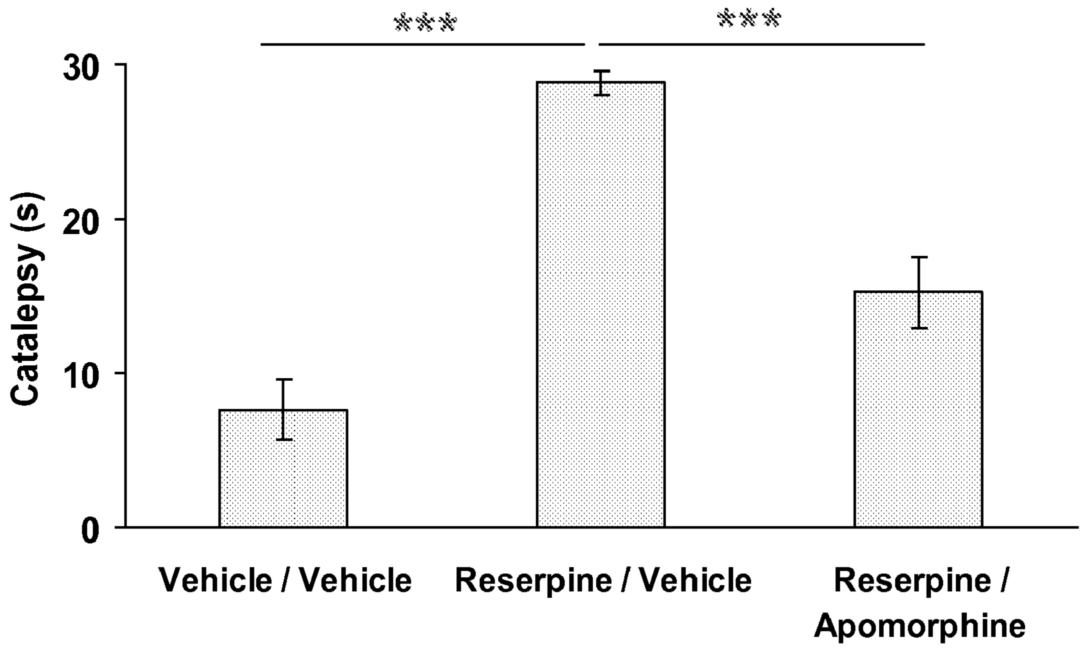
FIG. 3: Reserpine induced catalepsy time with control (vehicle/vehicle) and reference compound apomorphine

FIG. 3 shows the Reserpine induced catalepsy time with control (vehicle/vehicle) and reference compound apomorphine (mean±SEM. N=24). Reserpine compared to vehicle significantly increased median and maximum catalepsy values. Compared to only Reserpine-treated animals apomorphine decreased median and maximum catalepsy values to a level that was still higher than that of only vehicle-treated animals.

Figure 4A:
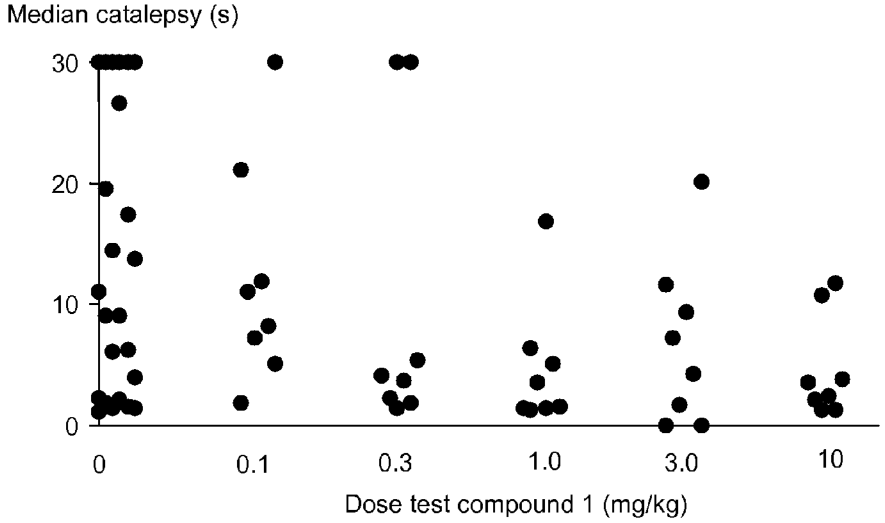
FIGS. 4*a* & 4*b*: Significant reduction of catalepsy time in acute CGS-21680 induced catalepsy model with test compound 1 (=3-Ethyl-8-(3,4-dimethoxyphenylethynyl)-7-methyl-1-prop-2-ynyl-3,7-dihydropurine-2,6 dione)
Figure 4B:
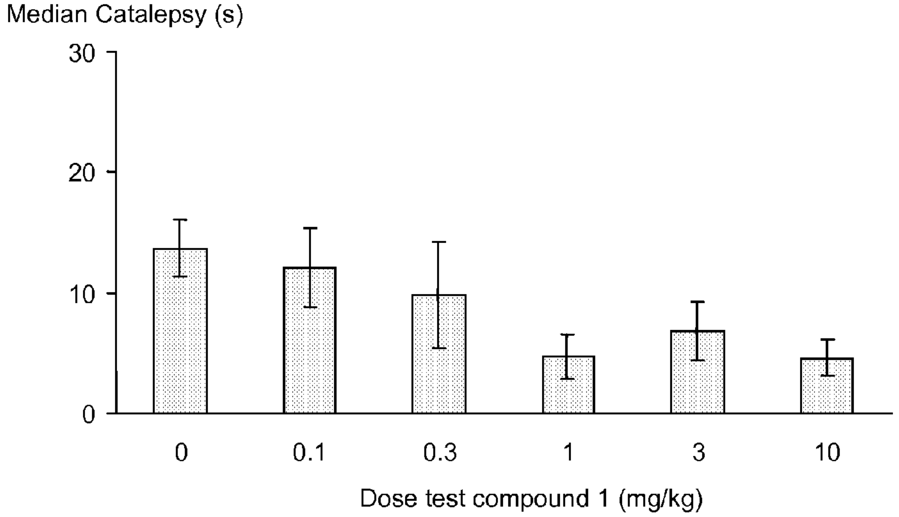

FIG. 4*a* and FIG. 4*b* show the significant reduction of catalepsy time in acute CGS-21680 induced catalepsy model with test compound 1 (=3-Ethyl-8-(3,4-dimethoxyphenylethynyl)-7-methyl-1-prop-2-ynyl-3,7-dihydropurine-2,6 dione).

Figure 5A:
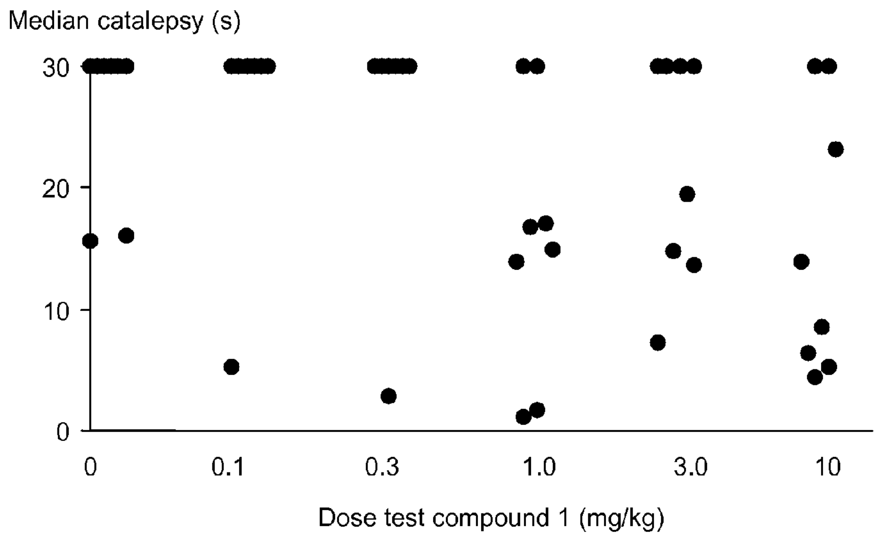
FIGS. 5*a* & 5*b*: Significant reduction of catalepsy time in acute Reserpine induced catalepsy model with test compound 1
Figure 5B:
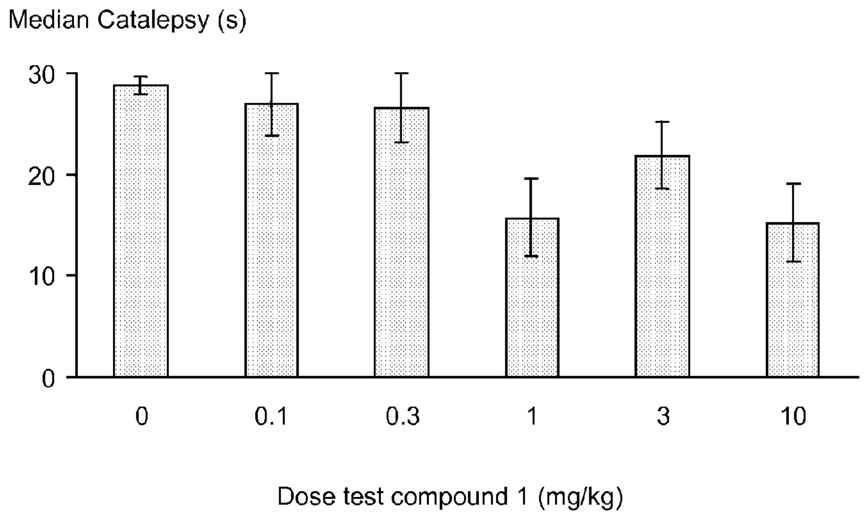

FIG. 5*a* and FIG. 5*b* show the significant reduction of catalepsy time in acute Reserpine induced catalepsy model with test compound 1 (=3-Ethyl-8-(3,4-dimethoxyphenylethynyl)-7-methyl-1-prop-2-ynyl-3,7-dihydropurine-2,6 dione).

Test compound 1 significantly increased hard body tone and decreased soft body tone, median and maximum catalepsy values after CGS-21680 treatment. Additionally test compound 1 led to a higher amount of grip strength. The effects were dose-dependent with a dose of 1 mg/kg and 10 mg/kg having the largest effects. Test compound 1 significantly reduced median catalepsy values after Reserpine treatment. The effects were dose-dependent with a dose of 1 mg/kg and 10 mg/kg having the strongest effects. Maximum catalepsy values were only weakly reduced by a dose of 1 mg/kg.

Figure 6A:
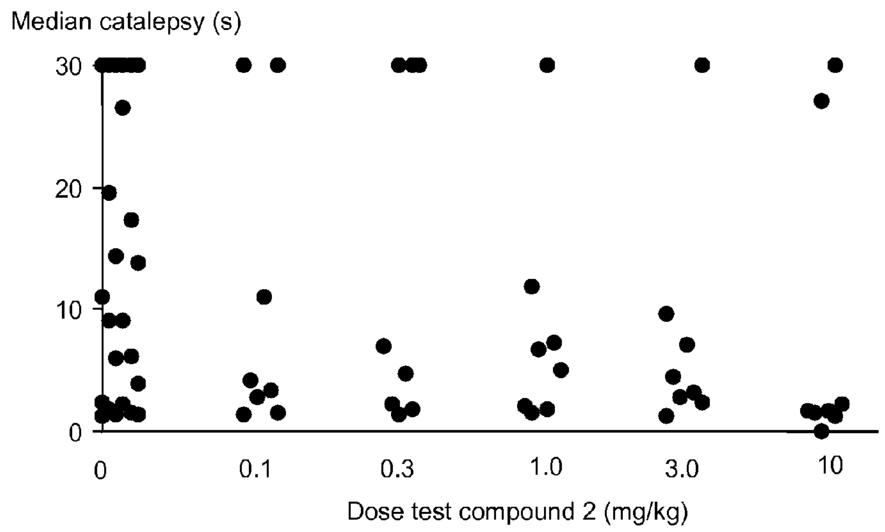
FIGS. 6*a* & 6*b*: Reduction of catalepsy time in acute CGS-21680 induced catalepsy model with test compound 2 (=3-(3-Hydroxypropyl)-8-(3,4-dimethoxyphenylethynyl)-7-methyl-1-prop-2-ynyl-3,7-dihydropurine-2,6-dione)
Figure 6B:
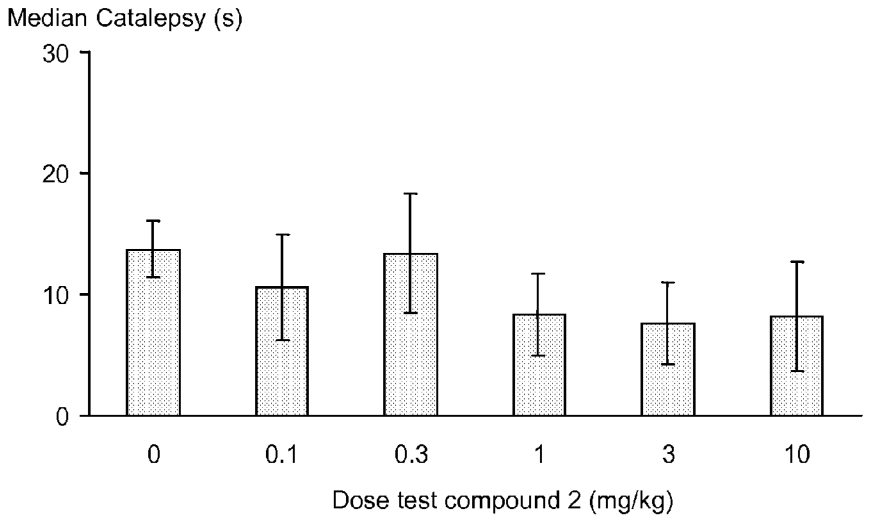

FIG. 6*a* and FIG. 6*b* show the reduction of catalepsy time in acute CGS-21680 induced catalepsy model with test compound 2 (=3-(3-Hydroxypropyl)-8-(3,4-dimethoxyphenylethynyl)-7-methyl-1-prop-2-ynyl-3,7-dihydropurine-2,6-dione.

Figure 7A:
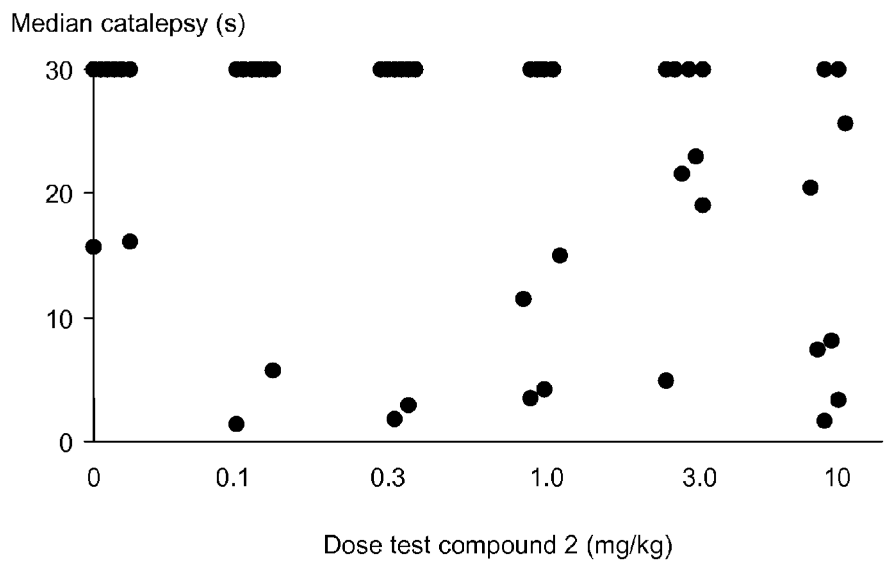
FIGS. 7*a* & 7*b*: Significant reduction of catalepsy time in acute Reserpine induced catalepsy model with test compound 2
Figure 7B:
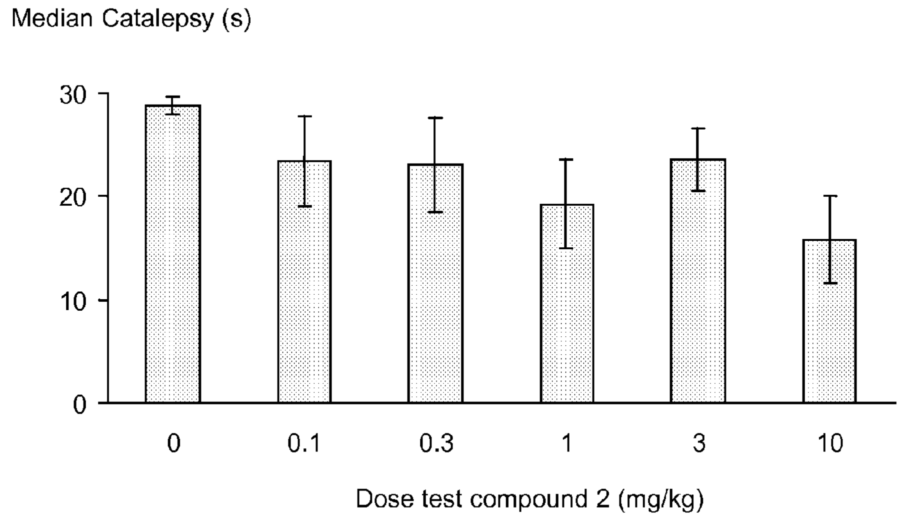

FIG. 7*a* and FIG. 7*b* show the significant reduction of catalepsy time in acute Reserpine induced catalepsy model with test compound 2 (=3-(3-Hydroxypropyl)-8-(3,4-dimethoxyphenylethynyl)-7-methyl-1-prop-2-ynyl-3,7-dihydropurine-2,6-dione.

Test compound 2 significantly increased hard body tone (strongest effect at 0.1 mg/kg) and decreased soft body tone (strongest effect at 10 mg/kg) after CGS-21680 treatment. There were no significant effects on any other parameter measured after CGS-21680 treatment. Test compound 2 significantly decreased medium and maximum catalepsy values after Reserpine treatment. The effects were dose dependent with the highest dose having the strongest effects. Mean±standard error of the mean (SEM) is indicated in FIGS. 2, 3, 4*b*, 5*b*, 6*b* and 7*b*.

TABLE 1

| $R^1$ | $R^2$ | $R^3$ | $R^4$ | Name | MW/m.p.,/NMR |
|---|---|---|---|---|---|
| 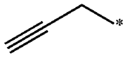 | $—CH_3$ | $—CH_3$ | 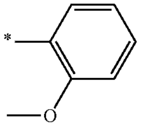 | 8-(2-Methoxyphenylethynyl)-3,7-dimethyl-1-prop-2-ynyl-3,7-dihydropurine-2,6-dione (Comparative Example 2) | M9W 348.4, colorless crystals, m.p. 282.3° C. $^1$H NMR($CDCl_3$): 2.17(s, 1 H), 3.59(s, 3 H), 3.91(s, 3 H), 4.09(s, 3 H), 4.78(s, 2 H), 6.91-6.6.97(m, 3 H), 7.38-7.41(m, 1 H), 7.52-7.54(m, 1 H) ppm. $^{13}$C NMR($CDCl_3$): 29.9, 30.5, 33.2, 55.8, 70.5, 78.6, 80.9, 94.6, 107.8, 109.7, 110.7, 120.7, 131.8, 133.7, 136.7, 148.3, 150.7, 153.8, 160.9 ppm. |
| 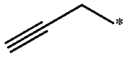 | $—CH_3$ | $—CH_3$ | 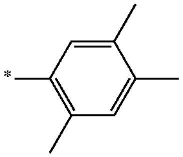 | 3,7-Dimethyl-8-(2,4,5-trimethylphenylethynyl)-1-prop-2-ynyl-3,7-dihydropurine-2,6-dione (Comparative Example 3) | MW 360.4, colorless crystals, m.p. 262.2° C. $^1$H NMR($CDCl_3$): 2.17 (t, J = 2.2 Hz, 1 H), 2.21(s, 3 H), 2.24(s, 3 H), 2.44(s, 3 H), 3.59(s, 3 H), 4.06(s, 3 H), 4.78(d, J = 2.2 Hz, 2 H), 7.02(s, 1 H), 7.33(s, 1 H) ppm. $^{13}$C NMR($CDCl_3$): 19.1, 19.9, 20.2, 29.9, 30.5, 33.2, 70.5, 78.6, 79.7, 97.3, 107.7, 117.3, 131.2, 133.5, 134.3, 136.7, 138.3, 139.6, 148.3, 150.7, 153.7 ppm. |
| 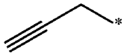 | $—CH_3$ | $—CH_3$ | 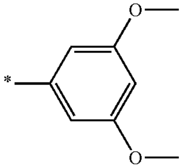 | 8-(3,5-Dimethoxyphenylethynyl)-3,7-dimethyl-1-prop-2-ynyl-3,7-dihydropurine-2,6-dione | MW 378.4, colorless crystals, m.p. 228° C. $^1$H NMR($CDCl_3$): 2.17(t, J = 2.5 Hz, 1 H), 3.59(s, 3 H), 3.79 (s, 6 H), 4.07(s, 3 H), 4.78(d, J = 2.5 Hz, 2 H), 6.53(t, J = 2.2 Hz, 1 H), 6.72(d, J = 2.2, 2 H) ppm. $^{13}$C NMR ($CDCl_3$): 29.9, 30.6, 33.3, 55.4, 70.6, 76.2, 78.5, 97.5, 103.6, 107.8, 109.9, 121.5, 136.1, 148.2, 150.7, 153.8, 160.7 ppm. |

TABLE 1-continued

| R¹ | R² | R³ | R⁴ | Name | MW/m.p./NMR |
|---|---|---|---|---|---|
| 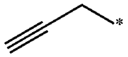 | 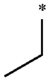 | —$CH_3$ | 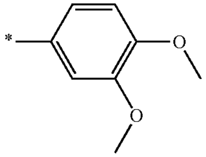 | 3-Ethyl-8-(3,4-dimethoxyphenylethynyl)-7-methyl-1-prop-2-ynyl-3,7-dihydropurine-2,6-dione (Test compound 1) | MW 392.4, colorless crystals, m.p. 221.5° C. $^1$H NMR($CDCl_3$): 1.35 (t, J = 7.25 Hz, 3H, $CH_3$), 2.17(t, J = 2.5 Hz, 1 H), 3.88(s, 3H, $OCH_3$), 3.90(s, 3H, $OCH_3$), 4.07(s, 3H, $NCH_3$), 4.18(q, J = 7.25 Hz, 2H, $CH_2$), 4.78(d, J = 2.5 Hz, 2 H), 6.85(d, J = 8.2 Hz, 1 H), 7.07(d, J = 1.9 Hz, 1 H), 7.22(dd, J = 8.2 and 1.9 Hz, 1 H) ppm. $^{13}$C NMR($CDCl_3$): 13.4, 30.5, 33.2, 38.8, 55.9, 56.0, 70.5, 75.8, 78.6, 97.9, 107.8, 111.1, 112.3, 114.4, 126.1, 136.5, 147.8, 148.9, 150.1, 151.1, 153.8 ppm. |
| 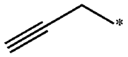 | —$CH_3$ | —$CH_3$ | 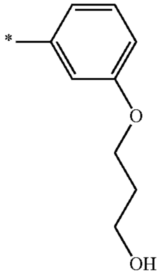 | 8-[3-(3-Hydroxypropoxy)phenylethynyl]-3,7-dimethyl-1-prop-2-ynyl-3,7dihydropurine-2,6-dione | MW 392.4, colorless crystals, m.p. 199.2° C. $^1$H NMR($CDCl_3$): 1.68 (t, J = 5.4 Hz, 1H, OH), 2.04(m, 2H, $CH_2$), 2.17(t, J = 2.2 Hz, 1 H), 3.59(s, 3H, N3$CH_3$), 3.85(m, 2H, $CH_2$), 4.07(s, 3H, N7$CH_3$), 4.12 (m, 2H, $CH_2$), 4.78(d, J = 2.2 Hz, 2 H $CH_2$), 6.97-6.99(m, 1 H), 7.11-7.12(m, 1 H), 7.17-7.19(m, 1 H), 7.27-7.30(m, 1 H) ppm. $^{13}$C NMR($CDCl_3$): 29.9, 30.6, 31.9, 33.2, 60.0, 65.7, 70.6, 76.6, 78.5, 97.3, 107.8, 117.3, 117.4, 121.3, 124.7, 129.8, 136.1, 148.2, 150.7, 153.8, 158.7 ppm. |
| 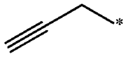 | —$CH_3$ | —$CH_3$ | 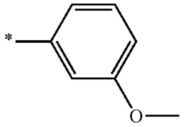 | 8-(3-Methoxyphenylethynyl)-3,7-dimethyl-1-prop-2-ynyl-3,7-dihydropurine-2,6-dione | MW 348.4, colorless crystals, m.p. 234.7° C. $^1$H NMR(500 MHz, $CDCl_3$): δ = 2.17(t, J = 2.52 Hz, 1H, CCH, 1 H), 3.59(s, 3H, $OCH_3$), 3.81(s, 3H, N3$CH_3$), 4.07(s, 3H, N7$CH_3$), 4.79(d, J = 2.52 Hz, 2H, $\underline{CH_2}$—CCH, 2 H), 6.98(ddd, J = 1.26/2.52 and 8.43 Hz, 1H, 5'H), 7.16 (dd, J = 1.26 and 2.52 Hz, 1H, 2'H), 7.19(dt, J = 1.26 and 7.56 Hz, 1H, 6'H), 7.29(dd, J = 7.57 and 8.36 Hz, 1H, 4'H) ppm. $^{13}$C NMR(125 MHz, $CDCl_3$): δ = 29.9, 30.6, 33.3, 55.4($OCH_3$), 70.6, 76.5, 78.5, 97.4, 107.8, 116.8, 116.9, 121.2, 124.6, 129.8, 136.1, 148.2, 150.7, 153.8, 159.5 ppm. |

TABLE 1-continued

| $R^1$ | $R^2$ | $R^3$ | $R^4$ | Name | MW/m.p./NMR |
|---|---|---|---|---|---|
| 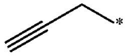 | $-CH_3$ | $-CH_3$ | 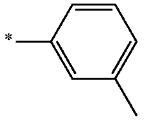 | 3,7-Dimethyl-8-(3-methylphenylethynyl)-1-prop-2-ynyl-3,7-dihydropurine-2,6-dione | MW 332.4, colorless crystals: m.p. 218.7° C.; $^1H$ NMR($CDCl_3$): 2.17 (t, J = 2.6 Hz, 1 H), 2.36(s, 3 H), 3.59(s, 3 H), 4.07(s, 3 H), 4.78(d, J = 2.6 Hz, 2 H), 7.23-7.29(m, 2 H), 7.39-7.42(m, 2 H) ppm. $^{13}C$ NMR($CDCl_3$): 21.2, 29.9, 30.5, 33.2, 70.5, 76.5, 78.6, 97.8, 107.8, 120.1, 128.6, 129.3, 131.2, 132.6, 136.3, 138.5, 148.3, 150.7, 153.7 ppm. |
| 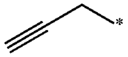 | $-CH_3$ | $-CH_3$ | 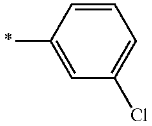 | 8-(3-Chlorophenylethynyl)-3,7-dimethyl-1-prop-2-ynyl-3,7-dihydropurine-2,6-dione | MW 352.8, colorless crystals: m.p. 216.6° C.; $^1H$ NMR($CDCl_3$): 2.17 (t, J = 2.3 Hz, 1 H), 3.59(s, 3 H), 4.07(s, 3 H), 4.78(d, J = 2.3 Hz, 2 H), 7.31-7.35(m, 1 H), 7.40-7.43 (m, 1 H), 7.46-7.49(m, 1 H), 7.57-7.58(m, 1 H) ppm. $^{13}C$ NMR($CDCl_3$): 29.9, 30.6, 33.3, 70.6, 77.7, 78.5, 95.6, 108.0, 122.0, 130.0, 130.2, 130.5, 131.9, 134.6, 135.6, 148.2, 150.6, 153.8 ppm. |
| 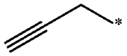 | $-CH_3$ | $-CH_3$ | 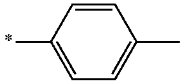 | 3,7-Dimethyl-8-(4-methylphenylethynyl)-1-prop-2-ynyl-3,7-dihydropurine-2,6-dione | MW 332.4, colorless crystals, m.p. 224.3° C. $^1H$ NMR($CDCl_3$): 2.17 (t, J = 2.5 Hz, 1 H), 2.38(s, 3 H), 3.59(s, 3 H), 4.06(s, 3 H), 4.78(d, J = 2.5 Hz, 2 H), 7.18-7.20(m, 2 H), 7.47-7.49(m, 2 H) ppm. $^{13}C$ NMR($CDCl_3$): 2.17, 29.9, 30.5, 33.2, 70.5, 76.3, 78.6, 97.9, 107.7, 117.2, 129.5, 132.1, 136.4, 140.9, 148.3, 150.7, 153.8 ppm. |
| 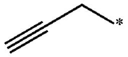 | $-CH_3$ | $-CH_3$ | 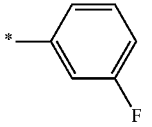 | 8-(3-Fluorophenylethynyl)-3,7-dimethyl-1-prop-2-ynyl-3,7-dihydropurine-2,6-dione | MW 336.3, colorless crystals: m.p. 220.6° C. $^1H$ NMR($CDCl_3$): 2.17 (t, J = 2.2 Hz, 1 H), 3.59(s, 3 H), 4.07(s, 3 H), 4.78(d, J = 2.2 Hz, 2 H), 7.13-7.17(m, 1 H), 7.27-7.30 (m, 1 H), 7.34-7.39(m, 2 H) ppm. $^{13}C$ NMR($CDCl_3$): 29.9, 30.6, 33.3, 70.6, 77.5, 78.5, 95.8(d), 108.0, 117.7(d), 118.8(d), 122.1 (d), 128.0(d), 130.4(d), 135.7, 148.2, 150.6, 153.8, 162.3(d) ppm. |

TABLE 1-continued

| $R^1$ | $R^2$ | $R^3$ | $R^4$ | Name | MW/m.p./NMR |
|---|---|---|---|---|---|
| 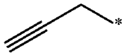 | —$CH_3$ | —$CH_3$ | 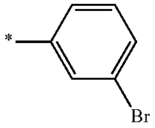 | 8-(3-Bromophenylethynyl)-3,7-dimethyl-1-prop-2-ynyl-3,7-dihydropurine-2,6-dione | MW 397.2, colorless crystals: m.p. 211.2° C.; $^{1}$H NMR($CDCl_3$): 2.17 (t, J = 2.2 Hz, 1 H), 3.59(s, 3 H), 4.07(s, 3 H), 4.78(d, J = 2.2 Hz, 2 H), 7.25-7.28(m, 1 H), 7.51-7.54 (m, 1 H), 7.56-7.58(m, 1 H), 7.73-7.74(m, 1 H) ppm. $^{13}$C NMR($CDCl_3$): 29.9, 30.6, 33.3, 70.6, 77.9, 78.5, 95.5, 108.0, 122.3, 122.5, 130.1, 130.6, 133.4, 134.7, 135.6, 148.2, 150.6, 153.8 ppm. |
| 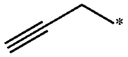 | —$CH_3$ | —$CH_3$ | 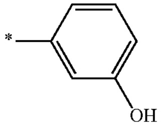 | 8-(3-Hydroxyphenylethynyl)-3,7-dimethyl-1-prop-2-ynyl-3,7-dihydropurine-2,6-dione | MW 334.3, colorless crystals, m.p. 271° C.; $^{1}$H NMR(DMSO-$d_6$): 3.08 (t, J = 2.2 Hz, 1 H), 3.42(s, 3 H), 3.98(s, 3 H), 4.60(d, J = 2.2 Hz, 2 H), 6.91-6.94(m, 1 H), 7.02-7.03 (m, 1 H), 7.10-7.12(m, 1 H), 7.26-7.29(m, 1 H), 9.85(d, 1H, OH) ppm. $^{13}$C NMR(DMSO-$d_6$): 29.6, 30.2, 33.2, 73.0, 76.9, 79.5, 96.6, 107.5, 118.2, 120.7, 122.9, 130.1, 130.4, 135.2, 147.7, 150.2, 153.2, 157.6 ppm. |
| 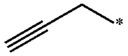 | —$CH_3$ | —$CH_3$ | 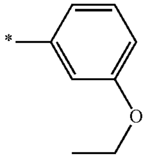 | 8-(3-Ethoxyphenylethynyl)-3,7-dimethyl-1-prop-2-ynyl-3,7-dihydropurine-2,6-dione | MW 362.4, colorless crystals(yield >95%), m.p. 204.2° C. $^{1}$H NMR (DMSO-$d_6$): ): 1.33(t, J = 6.9 Hz, 3 H), 3.09(t, J = 2.5 Hz, 1 H), 3.43 (s, 3 H), 4.00(s, 3 H), 4.07(q, J = 6.9 Hz, 2 H), 4.60(d, J = 2.5 Hz, 2 H), 7.07-7.09(m, 1 H), 7.23-7.26 (m, 2 H), 7.36-7.39(m, 1 H) ppm. $^{13}$C NMR(DMSO-$d_6$): 14.7, 29.6, 30.3, 33.2, 63.6, 73.1, 77.2, 79.5, 96.4, 107.5, 117.2, 117.6, 120.9, 124.4, 130.4, 135.1, 147.7, 150.2, 153.2, 158.7 ppm. |

TABLE 1-continued

| R[1] | R[2] | R[3] | R[4] | Name | MW/m.p./NMR |
|---|---|---|---|---|---|
| 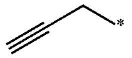 | $—CH_3$ | $—CH_3$ | 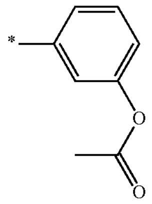 | 8-(3-Acetoxyphenylethynyl)-3,7-dimethyl-1-prop-2-ynyl-3,7-dihydropurine-2,6-dione | MW 376.4, off white crystals, m.p. 238° C. $^1$H NMR($CDCl_3$): ): 2.17 (t, J = 2.5 Hz, 1 H), 2.30(s, 3 H), 3.59(s, 3 H), 4.07(s, 3 H), 4.78(d, J = 2.5 Hz, 2 H), 7.16-7.18(m, 1 H), 7.33-7.34(m, 1 H), 7.38-7.41(m, 1 H), 7.45-7.47(m, 1 H) ppm. $^{13}$C NMR($CDCl_3$): 21.1, 29.9, 30.6, 33.3, 70.6, 77.4, 78.5, 96.2, 107.9, 121.6, 123.9, 125.2, 129.6, 129.8, 135.8, 148.2, 150.6, 150.7, 153.8, 169.0 ppm. |
| 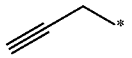 | $—CH_3$ | $—CH_3$ | 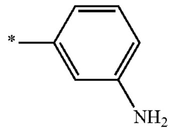 | 8-(3-Aminophenylethynyl)-3,7-dimethyl-1-prop-2-ynyl-3,7-dihydropurine-2,6-dione | MW 333.4, $^1$H NMR(DMSO-$d_6$): 3.05(t, J = 2.5 Hz), 3.43(s, 3 H), 3.97(s, 3 H), 4.60(d, J = 2.5 Hz, 2 H), 677-6.80(m, 1 H), 6.88-6.90 (m, 2 H), 7.13-7.17(m, 1 H) ppm. $^{13}$C NMR(DMSO-$d_6$): 29.6, 30.2, 33.1, 72.9, 76.4, 79.5, 97.3, 107.4, 117.3, 117.4, 120.1, 120.7, 135.3, 147.4, 147.7, 150.2, 153.1 ppm. |
| 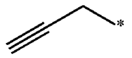 | $—CH_3$ | $—CH_3$ | 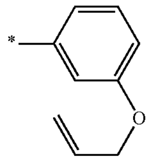 | 8-(3-Allyloxyphenylethynyl)-3,7-dimethyl-1-prop-2-ynyl-3,7-dihydropurine-2,6-dione | MW 374.4, colorless crystals(yield >95%), m.p. 189.2° C. $^1$H NMR ($CDCl_3$): 2.17(t, J = 2.2 Hz, 1 H), 3.59(s, 3 H), 4.07(s, 3 H), 4.54(m, 2 H), 4.78(d, J = 2.2 Hz, 2 H), 5.29 (m, 1 H), 5.40(m, 1 H), 6.03(m, 1 H), 6.99-7.01(m, 1 H), 7.11-7.12 (m, 1 H), 7.18-7.20(m, 1 H), 7.27-7.30(m, 1 H) ppm. $^{13}$C NMR($CDCl_3$): 29.9, 30.6, 33.3, 68.9, 70.6, 76.5, 78.5, 97.3, 107.8, 117.6, 117.7, 118.0, 121.3, 124.8, 129.8, 132.6, 136.1, 148.2, 150.7, 153.8, 158.5 ppm. |
| 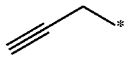 | 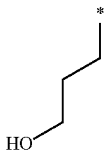 | $—CH_3$ | 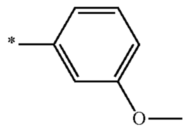 | 3-(3-Hydroxypropyl)-8-[3-methoxyphenylethynyl]-7-methyl-1-prop-2-ynyl-3,7-dihydropurine-2,6-dione | MW 392.4, colorless crystals, m.p. 177° C. $^1$H NMR($CDCl_3$): 1.97(m, 2H, $CH_2$), 2.18(t, J = 2.5 Hz, 1 H), 3.54(m, 2H, $CH_2$), 3.81(s, 3H, $CH_3$), 4.07(s, 3H, $CH_3$), 4.28(m, 2H, $CH_2$), 4.78(d, J = 2.5 Hz, 2 H), 6.98-6.99(m, 1 H), 7.00-7.09(m, 1 H), 7.10-7.19(m, 1 H), 7.28-7.31 (m, 1 H) ppm. $^{13}$C NMR($CDCl_3$): 30.6, 31.0, 33.3, 40.0, 55.4, 58.1, 70.7, 76.3, 78.3, 97.8, 107.8, 116.8, 117.1, 121.1, 124.7, 129.8, 136.2, 148.1, 150.9, 153.6, 159.5 ppm. |

TABLE 1-continued

| $R^1$ | $R^2$ | $R^3$ | $R^4$ | Name | MW/m.p./NMR |
|---|---|---|---|---|---|
| 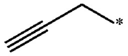 | 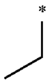 | —$CH_3$ | 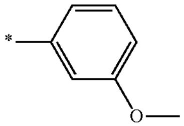 | 3-Ethyl-8-(3-methoxyphenylethynyl)-7-methyl-1-prop-2-ynyl-3,7-dihydropurine-2,6-dione | MW 362.4, colorless crystals, m.p. 174° C. $^1$H NMR($CDCl_3$): 1.35(t, J = 6.9 Hz, 3H, $CH_3$), 2.17(t, J = 2.5 Hz, 1 H), 3.81(s, 3H, $OCH_3$), 4.07 (s, 3H, $NCH_3$), 4.19(q, J = 6.9 Hz, 2H, $NCH_2$), 4.78(d, J = 2.5 Hz, 2 H), 6.97-6.99(m, 1 H), 7.10-7.11 (m, 1 H), 7.18-7.20(m, 1 H), 7.28-7.30(m, 1 H) ppm. $^{13}$C NMR($CDCl_3$): 13.5, 30.5, 33.2, 38.8, 55.4, 70.5, 76.6, 78.6, 97.3, 107.9, 116.8, 116.9, 121.3, 124.6, 129.8, 136.1, 147.8, 150.1, 153.9, 159.5 ppm. |
| 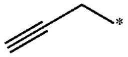 | 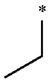 | —$CH_3$ | 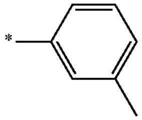 | 3-Ethyl-7-methyl-8-(3-methylphenylethynyl)-1-prop-2-ynyl-3,7-dihydropurine-2,6-dione | MW 346.4, colorless crystals, m.p. 211.7° C. $^1$H NMR($CDCl_3$): 1.35 (t, J = 6.95 Hz, 3H, $CH_3$), 2.17(t, J = 2.5 Hz, 1 H), 2.36(s, 3H, $CH_3$), 4.07(s, 3H, $NCH_3$), 4.18(q, J = 6.95 Hz, 2H, $NCH_2$), 4.77(d, J = 2.5 Hz, 2 H), 7.24-7.27(m, 2 H), 7.39-7.42(m, 2 H) ppm. $^{13}$C NMR($CDCl_3$): 13.4, 21.2, 30.5, 33.2, 38.8, 70.5, 76.6, 78.6, 97.7, 107.9, 120.2, 128.6, 129.2, 131.2, 132.6, 136.3, 138.5, 147.8, 150.1, 153.9 ppm. |
| 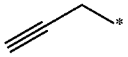 | 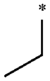 | —$CH_3$ | 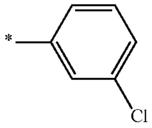 | 8-(3-Chlorophenylethynyl)-3-ethyl-7-methyl-1-prop-2-ynyl-3,7-dihydropurine-2,6-dione | MW 366.8, colorless crystals, m.p. 170.5° C. $^1$H NMR($CDCl_3$): 1.35 (t, J = 7.25 Hz, 3H, $CH_3$), 2.17(t, J = 2.5 Hz, 1 H), 4.08(s, 3H, $N7CH_3$), 4.18(q, J = 7.25 Hz, 2H, $NCH_2$), 4.78(d, J = 2.5 Hz, 2 H), 7.31-7.35(m, 1 H), 7.40-7.42(m, 1 H), 7.47-7.49(m, 1 H), 7.58-7.59 (m, 1 H) ppm. $^{13}$C NMR($CDCl_3$): 13.3, 30.5, 33.3, 38.8, 70.5, 77.8, 78.5, 95.6, 108.1, 122.1, 129.9, 130.2, 130.5, 131.9, 134.6, 135.7, 147.7, 150.1, 153.9 ppm. |

TABLE 1-continued

| $R^1$ | $R^2$ | $R^3$ | $R^4$ | Name | MW/m.p./NMR |
|---|---|---|---|---|---|
| 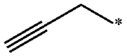 | —$CH_3$ | —$CH_3$ | 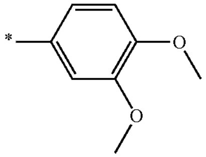 | 8-(3,4-Dimethoxyphenylethynyl)-3,7-dimethyl-1-prop-2-ynyl-3,7-dihydropurine-2,6-dione | MW 378.4, colorless crystals, m.p. 235.5° C. $^1H$ NMR(500 MHz, $CDCl_3$): δ = 2.17(t, J = 2.5 Hz, 1H, CCH), 3.60(s, 3H, N3$CH_3$), 3.89 (s, 3H, $OCH_3$), 3.91(s, 3H, $OCH_3$), 4.07(s, 3H, N7$CH_3$), 4.79(d, J = 2.5 Hz, 2H, $\underline{CH_2}$CCH), 6.86(d, J = 8.52 Hz, 1H, 6'H), 7.08(d, J = 1.89 Hz, 1H, 2'H), 7.22(dd, J = 1.89 and 8.20 Hz, 1H, 5'H) ppm. $^{13}C$ NMR(125 MHz, $CDCl_3$): δ = 29.7, 30.4, 32.2, 56.0($OCH_3$), 56.1 ($OCH_3$), 70.5, 75.7, 78.6, 98.0, 107.4, 111.1, 112.3, 114.4, 126.1, 136.6, 148.3, 148.9, 150.7, 151.2, 153.8 ppm. |
| 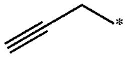 | 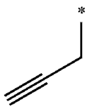 | —$CH_3$ | 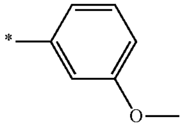 | 8-(3-Methoxyphenylethynyl)-7-methyl-1,3-diprop-2-ynyl-3,7-dihydropurine-2,6-dione | MW 372.4, colorless crystals, m.p. 217.4° C. $^1H$ NMR($CDCl_3$): 2.18 (t, J = 2.55 Hz, 1 H), 2.55(t, J = 2.55 Hz, 1 H), 3.81(s, 3H, $OCH_3$), 4.07(s, 3H, $NCH_3$), 4.78(d, J = 2.55 Hz, 2 H), 4.88(d, J = 2.55 Hz, 2 H), 6.97-7.00(m, 1 H), 7.10-7.11 (m, 1 H), 7.18-7.19(m, 1 H), 7.28-7.31(m, 1 H) ppm. $^{13}C$ NMR($CDCl_3$): 30.7, 32.7, 33.3, 55.4, 70.7, 72.2, 76.5, 77.3, 78.3, 97.6, 107.9, 116.8, 116.9, 121.2, 124.7, 129.8, 136.3, 146.9, 149.8, 153.6, 159.5 ppm. |
| 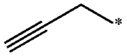 | —$CH_3$ | 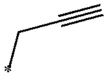 | 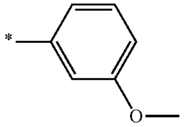 | 8-(3-Methoxyphenylethynyl)-3-methyl-1,7-diprop-2-ynyl-3,7-dihydropueine-2,6-dione | MW 372.4, colorless crystals, m.p. 227.1° C. $^1H$ NMR($CDCl_3$): 2.17 (t, J = 2.5 Hz, 1 H), 2.42(t, J = 2.5 Hz, 1 H), 3.60(s, 3H, $NCH_3$), 3.81 (s, 3H, $OCH_3$), 4.79(d, J = 2.5 Hz, 2 H), 5.28(d, J = 2.5 Hz, 2 H), 6.98-7.00(m, 1 H), 7.13-7.14(m, 1 H), 7.20-7.23(m, 1 H), 7.29-7.32(m, 1 H) ppm. $^{13}C$ NMR($CDCl_3$): 29.9, 30.6, 35.7, 55.4, 70.6, 74.2, 76.2, 77.2, 78.3, 98.4, 106.7, 116.9, 117.0, 121.1, 124.7, 129.8, 135.8, 148.3, 150.6, 153.4, 159.5 ppm. |

TABLE 1-continued

| R¹ | R² | R³ | R⁴ | Name | MW/m.p./NMR |
|---|---|---|---|---|---|
| 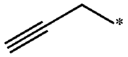 | 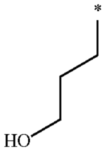 | —$CH_3$ | 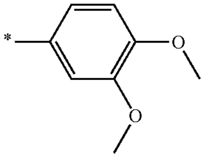 | 3-(3-Hydroxypropyl)-8-(3,4-dimethoxyphenylethynyl)-7-methyl-1-prop-2-ynyl-3,7-dihydropurine-2,6-dione ("Test compound 2") | MW 442.44, colorless crystals, m.p. 203.1° C. $^{1}$H NMR($CDCl_3$): 1.97(tt, J = 5.6/5.7 Hz, 2H, $CH_2$), 2.17(t, J = 2.5 Hz, 1 H), 3.54(t, J = 5.6 Hz, 2H, $CH_2$), 3.89(s, 3H, $OCH_3$), 3.90(s, 3H, $OCH_3$), 4.07 (s, 3H, N7$CH_3$), 4.27(t, J = 5.7 Hz, 2H, $CH_2$), 4.78(d, J = 2.5 Hz, 2 H), 6.85(d, J = 8.2 Hz, 1 H), 7.06(d, J = 1.6 Hz, 1 H), 7.22(dd, J = 8.2/1.6 Hz, 1 H) ppm. $^{13}$C NMR($CDCl_3$): 30.6, 31.0, 33.3, 40.0, 56.0, 56.1, 58.0, 70.7, 75.4, 78.3, 98.6, 107.5, 111.1, 112.0, 114.4, 126.2, 136.5, 148.0, 148.9, 150.9, 151.3, 153.6 ppm. |
| 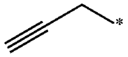 | 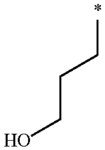 | —$CH_3$ | 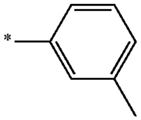 | 3-(3-Hydroxypropyl)-7-methyl-8-(3-methylphenylethynyl)-1-prop-2-ynyl-3,7-dihydropurine-2,6-dione | MW 376.42, colorless crystals, m.p. 184° C. $^{1}$H NMR($CDCl_3$): 1.97(m, 2H, $CH_2$), 2.17(t, J = 2.5 Hz, 1 H), 2.36(s, 3H, $CH_3$), 3.54(t, J = 5.4 Hz, 2H, $CH_2$), 4.07(s, 3H, $NCH_3$), 4.28(t, J = 6.0 Hz, 2H, $CH_2$), 4.78(d, J = 2.5 Hz, 2 H), 7.24-7.29(m, 2 H), 7.39-7.41(m, 2 H) ppm. $^{13}$C NMR($CDCl_3$): 21.2, 30.6, 31.0, 33.3, 40.0, 58.0, 70.7, 76.2, 78.3, 98.3, 107.7, 120.0, 128.6, 129.3, 131.3, 132.7, 136.3, 138.6, 148.0 ,150.9, 153.6 ppm. |
| 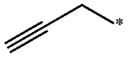 | —$CH_3$ | —$CH_3$ | 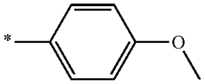 | 8-(4-Methoxyphenylethynyl)-3,7-dimethyl-1-prop-2-ynyl-3,7-dihydropurine-2,6-dione | MW 348.3 colorless crystals: m.p. 245° C.; $^{1}$H NMR($CDCl_3$): 2.17(t, J = 2.5 Hz, 1 H), 3.59(s, 3 H), 3.83 (s, 3 H), 4.06(s, 3 H), 4.78(d, J = 2.5 Hz, 2 H), 6.90(d, J = 8.8 Hz, 2 H), 7.53(d, J = 8.8 Hz, 2 H) ppm. $^{13}$C NMR($CDCl_3$): 29.8, 30.5, 33.2, 55.4, 70.5, 75.9, 78.6, 98.0, 107.6, 114.4, 133.9, 136.6, 148.3, 150.7, 153.7, 161.2 ppm. |

TABLE 1-continued

| R1 | R2 | R3 | R4 | Name | MW/m.p./NMR |
|---|---|---|---|---|---|
| 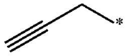 | 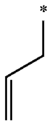 | —$CH_3$ | 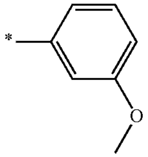 | 3-Allyl-8-(3-methoxyphenylethynyl)-7-methyl-1-prop-2-ynyl-3,7-dihydropurine-2,6-dione | MW 374.40, colorless crystals, m.p. 169.8° C. $^1$H NMR($CDCl_3$): 2.17(t, J = 2.2 Hz, 1 H), 3.81(s, 3H, $OCH_3$), 4.07(s, 3H, $N7CH_3$), 4.72(m, 2 H), 4.78(d, J = 2.2 Hz, 2 H), 5.22(m, 1 H), 5.28(m, 1 H), 5.98(m, 1 H), 6.97-6.99(m, 1 H), 7.10-7.11(m, 1 H), 7.18-7.20(m, 1 H), 7.27-7.31(m, 1 H) ppm. $^{13}$C NMR($CDCl_3$): 30.5, 33.2, 45.4, 55.4, 70.6, 76.6, 78.5, 97.4, 107.8, 116.8, 116.9, 118.4, 121.3, 124.6, 129.8, 131.2, 136.2, 147.8, 150.2, 153.8, 159.5 ppm. |
| 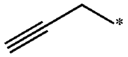 |  | —$CH_3$ | 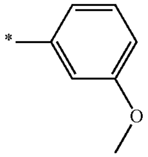 | 8-(3-Methoxyphenylethynyl)-7-methyl-1-prop-2-ynyl-3,7-dihydropurine-2,6-dione | MW 334.3, colorless crystals, m.p. 281° C. $^1$H NMR(DMSO-$d_6$): 3.07 (t, J = 2.5 Hz, 1 H), 3.80(s, 3H, $OCH_3$), 3.97(s, 3H, $N7CH_3$), 4.55 (d, J = 2.5 Hz, 2 H), 7.09-7.11(m, 1 H), 7.24-7.27(m, 2 H), 7.38-7.41 (m, 1 H), 12.13(s, 1H, N3H) ppm. $^{13}$C NMR($CDCl_3$): 29.5, 33.0, 55.6, 72.9, 77.4, 79.7, 96.0, 107.4, 116.7, 117.1, 121.0, 124.5, 130.6, 135.2, 147.0, 150.2, 153.9, 159.4 ppm. |
| 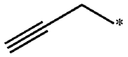 | —$CH_3$ | —$CH_3$ | 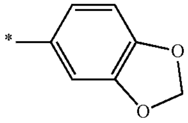 | 8-(3,4-Methylenedioxyphenylethynyl)-3,7-dimethyl-1-prop-2-ynyl-3,7-dihydropurine-2,6-dione | MW 362.35, colorless crystals: m.p. 273.5° C.; $^1$H NMR($CDCl_3$): 2.17(t, J = 2.6 Hz, 1 H), 3.59(s, 3 H), 4.05(s, 3 H), 4.78(d, J = 2.6 Hz, 2 H), 6.02(s, 2H, $O_2CH_2$), 6.81 (d, J = 8.2 Hz, 1 H), 7.00(d, J = 1.6 Hz, 1 H), 7.14(dd, J = 1.6 and 8.2) ppm. $^{13}$C NMR($CDCl_3$): 29.8, 30.5, 33.2, 70.5, 75.2, 78.5, 97.7, 101.8 ($O_2CH_2$), 107.7, 108.8, 111.7, 113.4, 127.6, 136.4, 147.7, 148.3, 149.7, 150.7, 153.7 ppm. |

TABLE 1-continued

| $R^1$ | $R^2$ | $R^3$ | $R^4$ | Name | MW/m.p./NMR |
|---|---|---|---|---|---|
| 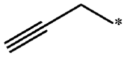 | 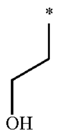 | —$CH_3$ | 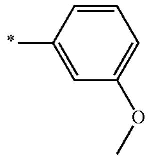 | 3-(2-Hydroxyethyl)-8-(3-methoxyphenylethynyl)-7-methyl-1-prop-2-ynyl-3,7-dihydropurine-2,6-dione | MW 378.39, colorless crystals, m.p. 212.8° C. $^1$H NMR($CDCl_3$): 2.18(t, J = 2.5 Hz, 1 H), 2.79(t, J = 5.4 Hz, 1H, OH), 3.81(s, 3H, $OCH_3$), 3.98(m, 2H, $CH_2$), 4.07(s, 3H, $N7CH_3$), 4.37(m, 2H, $CH_2$), 4.78(d, J = 2.5 Hz, 2 H), 6.98-7.00 (m, 1 H), 7.09-7.10(m, 1 H), 7.17-7.19(m, 1 H), 7.28-7.31(m, 1 H) ppm. $^{13}$C NMR($CDCl_3$): 30.7, 33.3, 46.2, 55.4, 61.5, 70.7, 76.4, 78.3, 97.6, 107.9, 116.8, 117.0, 121.2, 124.7, 129.8, 136.0, 148.0, 151.2, 153.6, 159.5 ppm. |
| 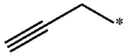 | 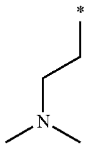 | —$CH_3$ | 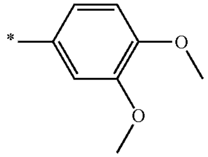 | 8-(3,4-Dimethoxyphenylethynyl)-3-(2-dimethylaminoethyl)-7-methyl-1-prop-2-ynyl-3,7-dihydropurine-2,6-dione | MW 435.5, colorless crystals, m.p. 201.1° C. $^1$H NMR($CDCl_3$): 2.16 (t, J = 2.2 Hz, 1 H), 2.30(s, 6H, $N(CH_3)2$), 2.70(t, J = 6.6 Hz, 2H, $CH_2$), 3.89(s, 3H, $OCH_3$), 3.91(s, 3H, $OCH_3$), 4.05(s, 3H, $N7CH_3$), 4.23(t, J = 6.6 Hz, 2H, $CH_2$), 4.77 (d, J = 2.2 Hz, 2 H), 6.85(d, J = 8.5 Hz, 1 H), 7.07(d, J = 2.2 Hz, 1 H), 7.22(dd, J = 2.2/8.5 Hz, 1 H) ppm. $^{13}$C NMR($CDCl_3$): 30.5, 33.2, 41.4, 45.7, 55.99, 56.0, 56.8, 70.5, 75.9, 78.6, 97.7, 107.8, 111.1, 112.3, 114.4, 126.1, 136.4, 148.1, 148.9, 150.5, 151.1, 153.9 ppm. |
| 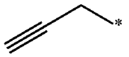 | —$CH_3$ | —$CH_3$ | 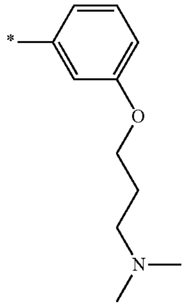 | 8-[3-(3-Dimethylaminopropoxy)phenylethynyl]-3,7-dimethyl-1-prop-2-ynyl-3,7dihydropurine-2,6-dione | MW 419.5, colorless crystals, m.p. 135.9° C. $^1$H NMR($CDCl_3$): 1.95 (dt, J = 7 Hz, 2H, $CH_2$), 2.17(t, J = 2.6 Hz, 1 H), 2.24(s, 6H, $N(CH_3)_2$), 2.44(t, J = 7 Hz, 2H, $CH_2$), 3.59(s, 3H, $N3CH_3$), 4.01(t, J = 7 Hz, 2H, $CH_2$), 4.07(s, 3H, $N7CH_3$), 4.78(d, J = 2.6 Hz, 2 H $CH_2$), 6.97-6.99(m, 1 H), 7.11(m, 1 H), 7.16-7.18(m, 1 H), 7.26-7.28(m, 1 H) ppm. $^{13}$C NMR($CDCl_3$): 27.4, 29.9, 30.6, 33.3, 45.5, 56.2, 66.4, 70.6, 76.5, 78.5, 97.5, 107.8, 117.4, 117.5, 121.2, 124.5, 129.8, 136.2 148.2, 150.7, 153.8, 158.9 ppm. |

TABLE 1-continued

| R[1] | R[2] | R[3] | R[4] | Name | MW/m.p./NMR |
|---|---|---|---|---|---|
| 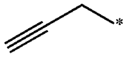 | —$CH_3$ | —$CH_3$ | 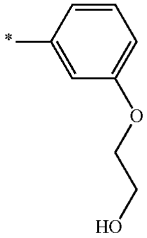 | 8-[3-(2-Hydroxyethoxy)phenylethynyl]-3,7-dimethyl-1-prop-2-ynyl-3,7dihydropurine-2,6-dione (JH06041): | MW 378.4, colorless crystals, m.p. 242.7° C. $^1$H NMR(DMSO-$d_6$): 3.09(t, J = 2.6 Hz, 1 H), 3.43(s, 3H, N3$CH_3$), 3.72(q, J = 5.1 Hz, 2H, $CH_2$), 4.00(s, 3H, N7$CH_3$), 4.04(t, J = 4.7 Hz, 2H, $CH_2$), 4.60 (d, J = 2.6 Hz, 2H, $CH_2$), 4.85(t, J = 5.4 Hz, 1H, OH), 7.09-7.12(m, 1 H), 7.26-7.27(m, 2 H), 7.37-7.40 (m, 1 H) ppm. $^{13}$C NMR(DMSO-$d_6$): 29.6, 30.3, 33.3, 59.6, 70.0, 73.1, 77.2, 79.5, 96.4, 107.5, 117.3, 117.7, 120.8, 124.4, 130.1, 135.1, 147.7, 150.2, 153.2, 158.9 ppm. |
| 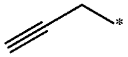 | —$CH_3$ | —$CH_3$ | 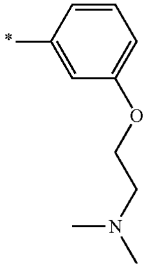 | 8-[3-(2-Dimethylaminoethoxy)phenyl ethynyl]-3,7-dimethyl-1-prop-2-ynyl-3,7dihydropurine-2,6-dione | MW 405.5, colorless crystals, m.p. 159.7° C. $^1$H NMR($CDCl_3$): 2.17 (t, J = 2.6 Hz, 1 H), 2.32(s, 6H, $N(CH_3)_2$), 2.73(t, J = 5.7 Hz, 2H, $CH_2$), 3.59(s, 3H, N3$CH_3$), 4.06(t, J = 5.7 Hz, 2H, $CH_2$), 4.07(s, 3H, N7$CH_3$), 4.78(d, J = 2.6 Hz, 2 H $CH_2$), 6.99-7.02(m, 1 H), 7.12-7.13 (m, 1 H), 7.17-7.19(m, 1 H), 7.26-7.30(m, 1 H) ppm. $^{13}$C NMR($CDCl_3$): 29.9, 30.6, 33.3, 45.9, 58.1, 66.2, 70.6, 76.5, 78.5, 97.4, 107.8, 117.48, 117.52, 121.2, 124.7, 129.8, 136.1, 148.2, 150.7, 153.8, 158.7 ppm. |
| 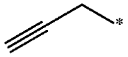 | —$CH_3$ | —$CH_3$ | 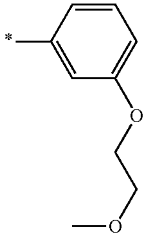 | 8-[3-(2-Methoxyethoxy)phenylethynyl]-3,7-dimethyl-1-prop-2-ynyl-3,7dihydropurine-2,6-dione | MW 392.4, colorless crystals, m.p. 200.8° C. $^1$H NMR($CDCl_3$): 2.17 (t, J = 2.6 Hz, 1 H), 3.44(s, 3H, $COCH_3$), 3.59(s, 3H, N3$CH_3$), 3.74(t, J = 4.8 Hz, 2H, $CH_2$), 4.07 (s, 3H, N7$CH_3$), 4.12(t, J = 4.8 Hz, 2H, $CH_2$), 4.78(d, J = 2.6 Hz, 2 H $CH_2$), 7.00-7.03(m, 1 H), 7.13(m, 1 H), 7.18-7.20(m, 1 H), 7.27-7.30 (m, 1 H) ppm. $^{13}$C NMR($CDCl_3$): 29.9, 30.6, 33.2, 59.3, 67.5, 70.6, 70.8, 76.5, 78.5, 97.4, 107.5, 117.5, 117.6, 121.2, 124.8, 129.8, 136.1, 148.2, 150.7, 153.8, 15.7 ppm. |

TABLE 1-continued

| $R^1$ | $R^2$ | $R^3$ | $R^4$ | Name | MW/m.p./NMR |
|---|---|---|---|---|---|
| 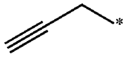 | 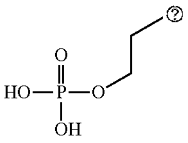 ⓘ indicates text missing or illegible when filed | —$CH_3$ | 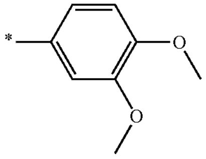 | (E)-Phosphoric Acid mono{3-[8-[(3,4-dimethoxyphenyl)ethynyl]-7-methyl-2,6-dioxo-1-prop-2-ynyl-1,2,6,7-tetrahydropurin-3-yl]propyl}ester | MW 502.4, pale yellow solid, m.p. 182.3° C. $^{1}H$ NMR(500 MHz, DMSO-$d_6$): δ = 1.95-2.02(m, 2 H), 3.09(t, J = 2.52 Hz, 1H, CC$\underline{H}$), 3.81(s, 3H, $OCH_3$), 3.82(s, 3H, $OCH_3$), 3.90(q, J = 6.62 Hz, 2 H), 4.00(s, 3H, $N7CH_3$), 4.06(t, J = 6.93 Hz, 2 H), 4.60(d, J = 2.52 Hz, 2H, C$\underline{H}_2$—CCH), 7.05(d, J = 8.20 Hz, 1H, 6'H), 7.27(d, J = 1.89 Hz, 1H, 2'H), 7.31(dd, J = 1.89 and 8.20 Hz, 1H, 5'H) ppm. $^{13}C$ NMR(125 MHz, DMSO-$d_6$): δ = 28.7(d, J = 7.23 Hz, $CH_2CH_2\underline{C}H_2O$), 30.3, 33.2, 40.6, 55.8(O$\underline{C}H_3$), 55.9(O$\underline{C}H_3$), 63.3(d, J = 4.98 Hz, $CH_2\underline{C}H_2CH_2O$), 73.1, 76.3, 79.6, 97.4, 107.5, 111.6, 112.1, 114.8, 126.0, 135.6, 147.4, 148.9, 149.9, 151.1, 153.2 ppm. $^{31}P$ NMR(202 MHz, DMSO-$d_6$): δ = −0.62(dd, J = 4.92 and 7.38 Hz) ppm. ESI +Q1 m/z 503(M + $H^+$). |
| 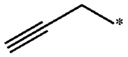 | 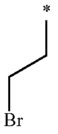 | —$CH_3$ | 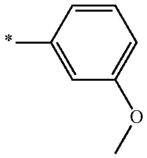 | 3-(2-Bromoethyl)-8-(3-methoxyphenylethynyl)-7-methyl-1-prop-2-ynyl-3,7-dihydropurine-2,6-dione | MW 441.3, colorless crystals, m.p. 162.6° C. $^{1}H$ NMR($CDCl_3$): 2.18 (t, J = 2.5 Hz, 1 H), 3.69(t, J = 7.0, 2H, $CH_2Br$), 3.82(s, 3H, $OCH_3$), 4.07(s, 3H, $N7CH_3$), 4.51(t, J = 7.0, 2H, $CH_2C\underline{H}_2N$), 4.77(d, J = 2.5 Hz, 2 H), 6.98-7.00(m, 1 H), 7.10-7.11(m, 1 H), 7.19-7.20(m, 1 H), 7.27-7.31(m, 1 H) ppm. $^{13}C$ NMR($CDCl_3$): 27.3, 30.6, 33.3, 44.3, 55.4, 70.7, 76.5, 78.3, 97.6, 107.8, 116.8, 117.0, 121.2, 124.7, 129.8, 131.2, 147.4, 150.2, 153.6, 159.5 ppm. |

TABLE 1-continued

| $R^1$ | $R^2$ | $R^3$ | $R^4$ | Name | MW/m.p./NMR |
|---|---|---|---|---|---|
| 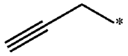 | 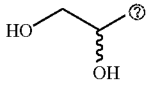 indicates text missing or illegible when filed | —$CH_3$ | 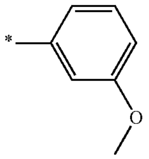 | (R/S)-3-(2,3-Dihydroxypropyl)-8-(3-methoxyphenylethynyl)-7-methyl-1-prop-2-ynyl-3,7-dihydropurine-2,6-dione | MW 408.4, colorless crystals, m.p. 176.1° C. $^1H$ NMR($CDCl_3$): 2.19 (t, J = 2.6 Hz, 1 H), 3.28(d, J = 5.7 Hz, 1 H), 3.40(t, J = 7.0 Hz), 3.58 (m, 2H, $CH_2$), 3.82(s, 3H, $OCH_3$), 4.07(s, 3H, $N7CH_3$), 4.08(m, 1 H), 4.33(ddd, J = 5.4, 14.5 and 35.6 Hz), 6.98-7.00(m, 1 H), 7.09-7.10 (m, 1 H), 7.17-7.19(m, 1 H), 7.28-7.32(m, 1 H) ppm. $^{13}C$ NMR($CDCl_3$): 30.8, 33.4, 45.6, 55.4, 62.9, 70.3, 70.9, 76.1, 78.1, 98.1, 107.8, 116.8, 117.1, 121.0, 124.7, 129.9, 136.1, 148.0, 151.7, 153.4, 159.5 ppm. |
| 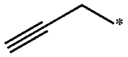 | 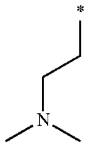 | —$CH_3$ | 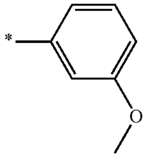 | 8-(3-Methoxyphenylethynyl)-3-(2-dimethylaminoethyl)-7-methyl-1-prop-2-ynyl-3,7-dihydropurine-2,6-dione | MW 405.5, colorless crystals, m.p. 162° C. $^1H$ NMR($CDCl_3$): 2.16(t, J = 2.5 Hz, 1 H), 2.30(s, 6H, $NCH_3$), 2.70(t, J = 6.7 Hz, 2H, $CH_2$), 3.82 (s, 3H, $OCH_3$), 4.06(s, 3H, $N7CH_3$), 4.23(t, J = 6.7 Hz, 2H, $CH_2$), 4.77(d, J = 2.5 Hz, 2 H), 6.97-6.99(m, 1 H), 7.11(m, 1 H), 7.18-7.20(m, 1 H), 7.28-7.31(m, 1 H) ppm. $^{13}C$ NMR($CDCl_3$): 30.5, 33.2, 41.4, 45.8, 55.4, 56.8, 70.5, 77.2, 78.6, 97.2, 108.0, 116.8, 116.9, 121.4, 124.7, 129.8, 136.0, 148.0, 150.5, 153.9, 159.5 ppm |
| 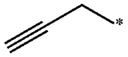 | 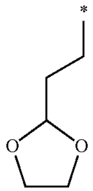 | —$CH_3$ | 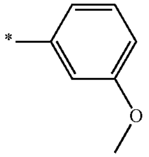 | 3-[2-(1,3-Dioxolan-2-yl)ethyl]-8-[(3-methoxyphenyl)ethynyl]-7-methyl-1-prop-2-ynyl-3,7-dihydropurine-2,6-dione | MW 434.5, colorless crystals, m.p. 133.9° C. $^1H$ NMR(500 MHz, $CDCl_3$): δ = 2.15(t, J = 2.52 Hz, 1H, CCH), 2.16-2.20(m, 2 H), 3.79-3.82(m, 2 H), 3.83(s, 3H, OCH), 3.92-3.96(m, 2 H), 4.07 (s, 3H, $N7CH_3$), 4.34(t, J = 6.94 Hz, 2 H), 4.79(d, J = 2.52 Hz, 2H, $\underline{CH_2}$—CCH), 5.01(t, J = 4.42 Hz, $\underline{1H}$, CH), 6.98(ddd, J = 1.26/2.52 and 8.43 Hz, 1H, 5'-H), 7.11(dd, J = 1.26 and 2.52 Hz, 1H, 2'H), 7.19 (d, J = 7.88 Hz, 1H, 6'H), 7.29(t, J = 7.88 Hz, 1H, 4'H) ppm. $^{13}C$ NMR(125 MHz, $CDCl_3$): δ = 30.3, 31.4, 33.3, 38.5, 55.6 ($OCH_3$), 64.5, 73.1, 77.3, 79.5, 96.4, 101.8, 107.7, 116.7, 117.3, 120.9, 124.5, 130.3, 135.1, 147.3, 149.8, 153.2, 159.4 ppm. |

TABLE 1-continued

| $R^1$ | $R^2$ | $R^3$ | $R^4$ | Name | MW/m.p./NMR |
|---|---|---|---|---|---|
| 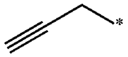 | 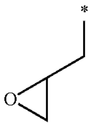 | —$CH_3$ | 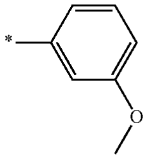 | 8-(3-Methoxyphenylethynyl)-7-methyl-3-(2-oxiran-2-ylmethyl)-1-prop-2-ynyl-3,7-dihydropurine-2,6-dione | MW 390.4, colorless crystals, m.p. 190.5° C. $^1H$ NMR($CDCl_3$): 2.18 (t, J = 2.6 Hz, 1 H), 2.76(dd, J = 2.6 and 5.0 Hz, 1 H), 2.81(dd, J = 3.8 and 5.0 Hz, 1 H), 3.39(m, 1 H), 3.82(s, 3H, $OCH_3$), 4.07(s, 3H, N7$CH_3$), 4.31(ddd, J = 5, 15 and 59 Hz, 2 H), 6.97-6.99(m, 1 H), 7.10-7.11(m, 1 H), 7.18-7.20(m, 1 H), 7.28-7.31(m, 1 H) ppm. $^{13}C$ NMR($CDCl_3$): 30.6, 33.3, 45.1, 46.3, 59.0, 55.4, 70.7, 76.6, 78.4, 97.5, 107.9, 116.8, 116.9, 121.2, 124.7, 129.8, 136.2, 147.8, 150.5, 153.7, 159.5 ppm. |
| 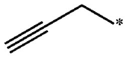 | 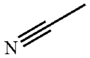 | —$CH_3$ | 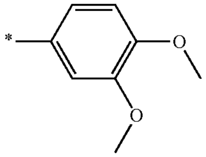 | {8-[(3,4-Dimethoxyphenyl)ethynyl]-7-methyl-2,6-dioxo-1-prop-2-ynyl-1,2,6,7-tetrahydropurin-3-yl}acetonitrile | MW 403.4, colorless crystals, m.p. 265.9° C. $^1H$ NMR(500 MHz, $CDCl_3$): δ = 2.20(t, J = 2.21 Hz, 1H, CCH), 3.90(s, 3H, $OCH_3$), 3.92(s, 3H, $OCH_3$), 4.08(s, 3 H), N7$CH_3$), 4.77(d, J = 2.21 Hz, 2H, $C\underline{H}_2$—CCH), 5.00(s, 2H, $CH_2CN$), 6.87(d, J = 8.51 Hz, 1H, 6'H), 7.07 (d, J = 1.89 Hz, 1H, 2'H), 7.23(dd, J = 1.89 and 8.20 Hz, 1H, 5'H) ppm. $^{13}C$ NMR(125 MHz, $CDCl_3$): δ = 30.5, 30.8, 33.4, 56.0($OCH_3$), 56.1 ($OCH_3$), 71.2, 75.4, 77.9, 98.8, 107.7, 111.2, 111.9, 113.8, 114.4, 126.2, 136.9, 146.0, 148.9, 149.6, 151.4, 153.1 ppm. |

TABLE 1-continued

| $R^1$ | $R^2$ | $R^3$ | $R^4$ | Name | MW/m.p./NMR |
|---|---|---|---|---|---|
| 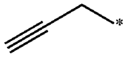 | 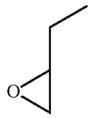 | $-CH_3$ | 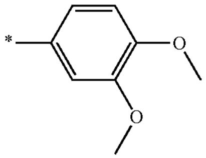 | 8-[(3,4-Dimethoxyphenyl)ethynyl]-7-methyl-3-(2-oxiran-2-ylethyl)-1-prop-2-ynyl-3,7-dihydropurine-2,6-dione | MW 434.5, colorless crystals, m.p. 197.4° C. $^1H$ NMR(500 MHz, $CDCl_3$): δ = 1.96-2.09(m, 2 H), 1.99(t, J = 2.52 Hz, 1H, CCH), 2.42(dd, J = 2.52 and 5.04 Hz, 1 H), 2.69(dd, J = 3.78 and 489 Hz, 1 H), 3.01-3.07(m, 1 H), 3.89 (s, 3H, $OCH_3$), 3.91(s, 3H, $OCH_3$), 4.06(s, 3H, $N7CH_3$), 4.25-4.32 (m, 1 H), 4.32-4.40(m, 1 H), 4.78 (d, J = 2.52 Hz, 2H, $\underline{CH_2}$—CCH), 6.86(d, J = 8.52 Hz, 1H, 6'H), 7.07 (d, J = 1.89 Hz, 1H, 2'H), 7.22(dd, J = 1.89 and 8.20 Hz, 1H, 5'H) ppm. $^{13}C$ NMR(125 MHz, $CDCl_3$): δ = 30.5, 31.2, 33.2, 40.8, 46.4, 50.0, 56.0($OCH_3$), 56.1($OCH_3$), 70.5, 75.8, 78.5, 98.0, 107.8, 111.1, 112.3, 114.4, 126.1, 136.5, 147.8, 148.9, 150.4, 151.4, 153.8 ppm. |
| 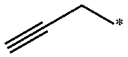 | 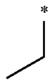 | 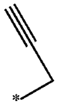 | 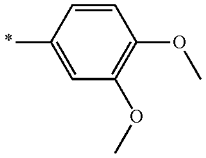 | 8-(3,4-Dimethoxyphenylethynyl)-3-ethyl-1,7-diprop-2-ynyl-3,7-dihydropurine-2,6-dione | MW 416.4, colorless crystals, m.p. 183.6° C. $^1H$ NMR($CDCl_3$): 1.36 (t, J = 7.3 Hz, 3H, CH3), 2.17(t, J = 2.5 Hz, 1 H), 2.43(t, J = 2.2 Hz, 1 H), 3.88(s, 3H, $OCH_3$), 3.91(s, 3H, $OCH_3$), 4.18(q, J = 7.3 Hz, 2 H), 4.78(d, J = 2.5 Hz, 2 H), 5.27 (d, J = 2.2 Hz, 2 H), 6.86(d, J = 8.6 Hz, 1 H), 7.10(d, J = 1.9 Hz, 1 H), 7.25(dd, J = 1.9/8.6 Hz, 1 H) ppm. $^{13}C$ NMR($CDCl_3$): 13.4, 30.5, 35.6, 38.9, 56.01, 56.04, 70.6, 74.0, 75.5, 76.4, 78.5, 98.9, 106.7, 111.2, 112.2, 114.5, 126.2, 136.2, 147.9, 148.9, 150.1, 151.3, 153.5 ppm. |

TABLE 1-continued

| $R^1$ | $R^2$ | $R^3$ | $R^4$ | Name | MW/m.p./NMR |
|---|---|---|---|---|---|
| 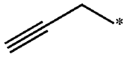 | 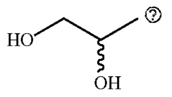 ⓘ indicates text missing or illegible when filed | —$CH_3$ | 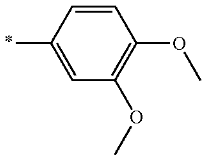 | (R/S)-3-(2,3-Dihydroxypropyl)-8-(3,4-dimethoxyphenylethynyl)-7-methyl-1-prop-2-ynyl-3,7-dihydropurine-2,6-dione | MW 438.4, colorless crystals, m.p. 204.6° C. $^1H$ NMR($CDCl_3$): 2.18(t, J = 2.5 Hz, 1 H), 3.58(m, 2H, $CH_2$), 3.90(s, 3H, $OCH_3$), 3.91(s, 3H, $OCH_3$), 4.07(s, 3H, N7$CH_3$), 4.08 (m, 1 H), 4.33(ddd, J = 5/15/36 Hz), 4.77(d, J = 2.5 Hz, 2 H), 6.86 (d, J = 9 Hz, 1 H), 7.06(d, J = 2 Hz, 1 H), 7.22(dd, J = 2/9 Hz, 1 H) ppm. $^{13}C$ NMR($CDCl_3$): 30.8, 33.4, 45.7, 56.0, 56.1, 62.8, 70.3, 70.9, 75.3, 78.1, 98.9, 107.6, 111.2, 111.9, 114.3, 126.2, 136.4, 148.0, 148.9, 151.4, 151.6, 153.4 ppm. |
| 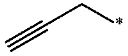 | 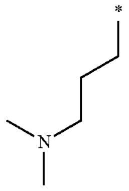 | —$CH_3$ | 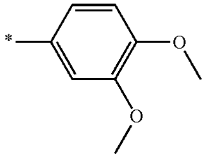 | 8-(3,4-Dimethoxyphenylethynyl)-3-(3-dimethylaminopropyl)-7-methyl-1-prop-2-ynyl-3,7-dihydropurine-2,6-dione | M = 449.5, colorless, crystals, m.p. 186.1° C. $^1H$ NMR($CDCl_3$): 2.01 (tt, J = 6.9/7.3, $CH_2$), 2.16(t, J = 2.6 Hz, 1 H), 2.30(s, 6H, $N(CH_3)_2$), 2.49(t, J = 6.9 Hz, 2H, $CH_2$), 3.89 (s, 3H, $OCH_3$), 3.91(s, 3H, $OCH_3$), 4.06(s, 3H, N7$CH_3$), 4.18(t, J = 7.3 Hz, 2H, $CH_2$), 4.77(d, J = 2.6 Hz, 2 H), 6.85(d, J = 8.5 Hz, 1 H), 7.07(d, J = 1.9 Hz, 1 H), 7.22(dd, J = 1.9/8.5 Hz, 1 H) ppm. $^{13}C$ NMR($CDCl_3$): 25.6, 30.5, 33.2, 41.8, 45.0, 56.0, 56.1, 56.6, 70.5, 75.8, 78.6, 97.9, 107.8, 111.1, 112.3, 114.4, 126.1, 136.5, 147.9, 148.9, 150.4, 151.1, 153.8 ppm. |
| 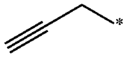 | 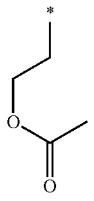 | —$CH_3$ | 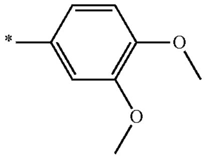 | 3-{8-[(3,4-Dimethoxyphenyl)ethynyl]-7-methyl-2,6-dioxo-1-prop-2-ynyl-1,2,6,7-tetrahydropurin-3-yl}ethyl acetate 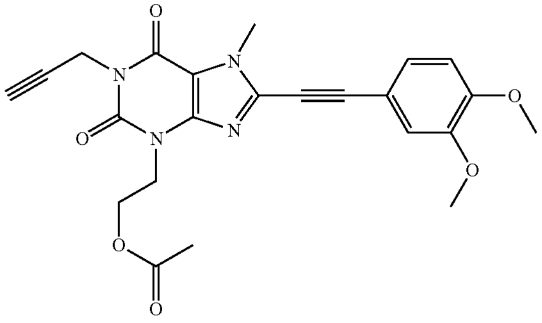 | MW 450.5, colorless crystals. $^1H$ NMR(500 MHz, $CDCl_3$): δ = 1.98 (s, 3H, $COCH_3$), 2.16(t, J = 2.5 Hz, 1H, CCH), 3.89(s, 3H, $OCH_3$), 3.91(s, 3H, $OCH_3$), 4.07(s, 3H, N7$CH_3$), 4.41(q, J = 3.8 Hz, 4H, $\underline{CH_2}\underline{CH_2}O$), 4.77(d, J = 2.5 Hz, 2H, $\underline{CH_2}CCH$), 6.86(d, J = 8.5 Hz, 1 H), 7.07(d, J = 1.6 Hz, 1 H), 7.22 (dd, J = 1.9 and 8.2 Hz, 1 H) ppm. $^{13}C$ NMR(125 MHz, $CDCl_3$): δ = 20.9, 30.6, 33.2, 42.3, 56.0 ($OCH_3$), 56.1($OCH_3$), 61.2, 70.5, 75.7, 78.5, 98.0, 107.7, 111.2, 112.2, 114.4, 126.1, 136.5, 147.8, 148.9, 150.5, 151.2, 153.7, 170.9 ppm. |

TABLE 1-continued

| $R^1$ | $R^2$ | $R^3$ | $R^4$ | Name | MW/m.p./NMR |
|---|---|---|---|---|---|
| 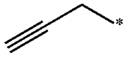 | 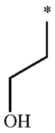 | $—CH_3$ | 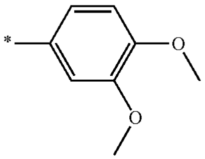 | 8-[(3,4-Dimethoxyphenyl)ethynyl]-3-(2-hydroxyethyl)-7-methyl-1-prop-2-ynyl-3,7-dihydropurine-2,6-dione 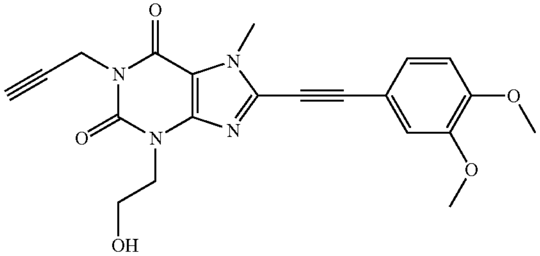 | MW 408.4, colorless crystals. $^1H$ NMR(500 MHz, $CDCl_3$): δ = 2.18 (t, J = 2.5 Hz, 1H, CCH), 2.85(t, J = 5.4 Hz, 1H, OH), 3.89(s, 3H, $OCH_3$), 3.91(s, 3H, $OCH_3$), 3.97 (q, J = 4.7 Hz, 2H, $C\underline{H}_2CH_2OH$), 4.07(s, 3H, $N7CH_3$), 4.37(t, J = 4.4 Hz, 2H, $CH_2C\underline{H}_2OH$), 4.78(d, J = 1.9 Hz, 2H, $C\underline{H}_2CCH$), 6.86(d, J = 8.5 Hz, 1 H), 7.07(d, J = 1.6 Hz, 1 H), 7.22(dd, J = 1.9 and 8.2 Hz, 1 H) ppm. $^{13}C$ NMR(125 MHz, $CDCl_3$): δ = 30.7, 33.3, 46.2, 56.0($OCH_3$), 56.1 ($OCH_3$), 61.6, 70.7, 75.6, 78.4, 98.3, 107.8, 111.2, 112.1, 114.4, 126.1, 136.4, 148.1, 148.9, 150.5, 151.2, 153.6 ppm. |
| 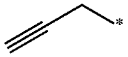 | 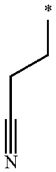 | $—CH_3$ | 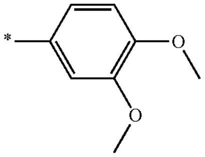 | 3-{8-[(3,4-Dimethoxyphenyl)ethynyl]-7-methyl-2,6-dioxo-1-prop-2-ynyl-1,2,6,7-tetrahydropurin-3-yl}propanenitrile 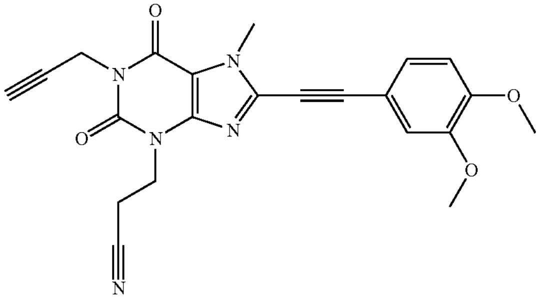 | MW 417.4, colorless crystals. $^1H$ NMR(500 MHz, $CDCl_3$): δ = 2.19 (t, J = 2.5 Hz, 1H, CCH), 2.91(t, J = 6.9 Hz, 2 H), 3.89(s, 3H, $OCH_3$), 3.91(s, 3H, $OCH_3$), 4.07(s, 3H, $N7CH_3$), 4.44(t, J = 6.9 Hz, 2 H), 4.77(d, J = 2.2 Hz, 2H, $C\underline{H}_2CCH$), 6.87(d, J = 8.2 Hz, 1 H), 7.08(d, J = 1.9 Hz, 1 H), 7.22(dd, J = 1.9 and 8.2 Hz, 1 H) ppm. $^{13}C$ NMR(125 MHz, $CDCl_3$): δ = 16.6, 30.6, 33.3, 38.9, 56.0 ($OCH_3$), 56.1($OCH_3$), 70.9, 75.5, 78.2, 98.4, 107.8, 111.2, 112.1, 114.4, 116.7(CN), 126.2, 136.7, 147.0, 148.9, 150.1, 151.3, 153.5 ppm. |

TABLE 1-continued

| R[1] | R[2] | R[3] | R[4] | Name | MW/m.p./NMR |
|---|---|---|---|---|---|
| 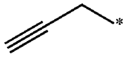 | 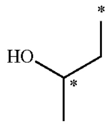 | —$CH_3$ | 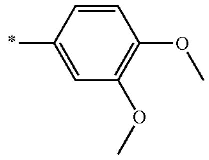 | (R/S)-8-[(3,4-Dimethoxyphenyl)ethynyl]-3-(2-hydroxypropyl)-7-methyl-1-prop-2-ynyl-3,7-dihydropurine-2,6-dione 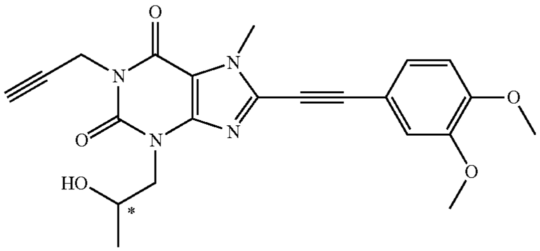 | MW 422.4, colorless crystals. $^1$H NMR(500 MHz, $CDCl_3$): δ = 1.28 (d, J = 5.7 Hz, 3H, CHOHC$\underline{H}_3$), 1.60(s, 1H, OH), 2.18(t, J = 2.2 Hz, 1H, CCH), 3.89(s, 3H, $OCH_3$), 3.91(s, 3H, $OCH_3$), 3.92(m, 1 H), 4.06(s, 3H, $N7CH_3$), 4.21(q, J = 6.6 Hz, 2 H), 4.78(d, J = 2.5 Hz, 2H, C$\underline{H}_2$CCH), 6.86(d, J = 8.5 Hz, 1 H), 7.06(d, J = 1.9 Hz, 1 H), 7.22 (dd, J = 1.9 and 8.4 Hz, 1 H) ppm. $^{13}$C NMR(125 MHz, $CDCl_3$): δ = 21.2(CHOH$\underline{C}H_3$), 30.7, 33.3, 50.7, 56.0($OCH_3$), 56.1($OCH_3$), 67.1, 70.7, 75.6, 78.4, 98.2, 107.7, 111.2, 112.2, 114.4, 126.1, 136.4, 148.3, 148.9, 151.2, 151.4, 153.6 ppm. ESI + Q1 m/z 423(M + H$^+$). |
| 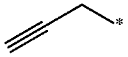 | 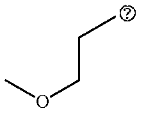 ⑦ indicates text missing or illegible when filed | —$CH_3$ | 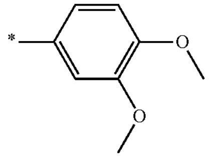 | 8-[(3,4-Dimethoxyphenyl)ethynyl]-3-(3-methoxypropyl)-7-methyl-1-prop-2-ynyl-3,7-dihydropurine-2,6-dione 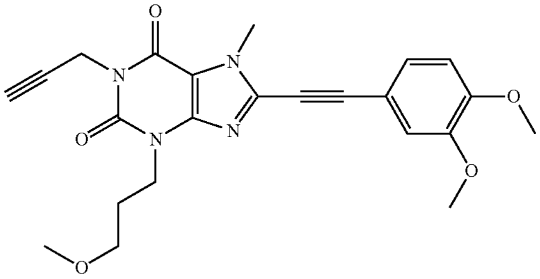 | MW 436.5, colorless crystals. $^1$H NMR(500 MHz, $CDCl_3$): δ = 2.05 (td, J = 6.3 and 6.9 Hz, 2 H), 2.16 (t, J = 2.5 Hz, 1H, CCH), 3.29(s, 3H, $CH_2CH_2CH_2OC\underline{H}_3$), 3.46(t, J = 6.0 Hz, 2 H), 3.89(s, 3H, $OCH_3$), 3.91(s, 3H, $OCH_3$), 4.06(s, 3H, $N7CH_3$), 4.22(t, J = 6.9 Hz, 2 H), 4.78(d, J = 2.5 Hz, 2H, C$\underline{H}_2$CCH), 6.86(d, J = 8.2 Hz, 1 H), 7.07(d, J = 1.9 Hz, 1 H), 7.22(dd, J = 1.9 and 8.2 Hz, 1 H) ppm. $^{13}$C NMR(125 MHz, $CDCl_3$): δ = 28.1, 30.5, 33.2, 41.3, 56.0 ($OCH_3$), 56.1($OCH_3$), 58.6, 70.2, 70.5, 75.9, 78.7, 97.8, 107.7, 111.1, 112.3, 114.4, 126.1, 136.5, 148.0, 148.9, 150.4, 151.1, 153.9 ppm. |

TABLE 1-continued

| $R^1$ | $R^2$ | $R^3$ | $R^4$ | Name | MW/m.p./NMR |
|---|---|---|---|---|---|
| 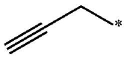 | 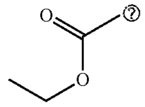<br>? indicates text missing or illegible when filed | —$CH_3$ | 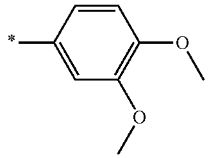 | {8-[(3,4-Dimethoxyphenyl)ethynyl]-7-methyl-1-prop-2-ynyl-1,2,6,7-tetrahydropurin-3-yl}acetic acid ethyl ester<br>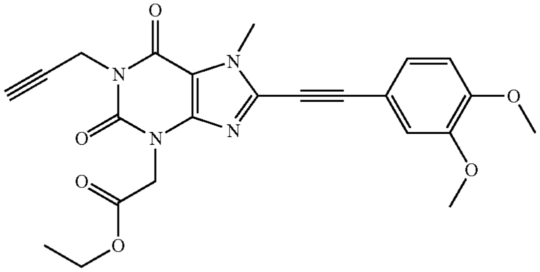 | MW 450.5, colorless, crystals. $^1H$ NMR(500 MHz, $CDCl_3$): $\delta$ = 1.27 (t, J = 7.3 Hz, 3H, $CO_2CH_2C\underline{H}_3$), 2.17(t, J = 2.2 Hz, 1H, CCH), 3.88 (s, 3H, $OCH_3$), 3.91(s, 3H, $OCH_3$), 4.06(s, 3H, $N7CH_3$), 4.22(q, J = 6.9 Hz, 2H, $CO_2C\underline{H}_2CH_3$), 4.77(d, J = 2.2 Hz, 2H, $C\underline{H}_2CCH$), 4.84(s, 2H, $C\underline{H}_2CO_2Et$), 6.85(d, J = 8.5 Hz, 1 H), 7.06(d, J = 1.9 Hz, 1 H), 7.21(dd, J = 1.9 and 8.5 Hz, 1 H) ppm.<br>$^{13}C$ NMR(125 MHz, $CDCl_3$): $\delta$ = 14.1, 30.6, 33.2, 43.9, 56.0 ($OCH_3$), 56.1($OCH_3$), 61.9, 70.7, 75.7, 78.3, 98.1, 107.6, 111.1, 112.2, 114.4, 126.1, 136.5, 147.5, 148.9, 150.4, 151.2, 153.7, 167.4 ($\underline{C}O_2Et$) ppm. |
| 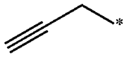 | 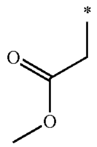 | —$CH_3$ | 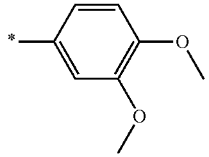 | {8-[(3,4-Dimethoxyphenyl)ethynyl]-7-methyl-1-prop-2-ynyl-1,2,6,7-tetrahydropurin-3-yl}acetic acid methyl ester<br>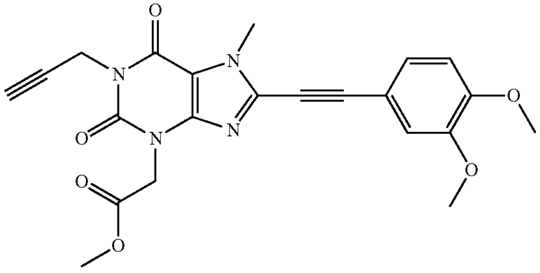 | MW 436.4, colorless crystals. $^1H$ NMR(500 MHz, $CDCl_3$): $\delta$ = 2.17 (t, J = 2.2 Hz, 1H, CCH), 3.76(s, 3H, $CO_2CH_3$), 3.88(s, 3H, $OCH_3$), 3.91(s, 3H, $OCH_3$), 4.06(s, 3H, $N7CH_3$), 4.77(d, J = 2.2 Hz, 2H, $C\underline{H}_2CCH$), 4.86(s, 2H, $C\underline{H}_2CO_2Me$), 6.87(d, J = 8.5 Hz, 1 H), 7.06(d, J = 1.9 Hz, 1 H), 7.21 (dd, J = 1.9 and 8.5 Hz, 1 H) ppm.<br>$^{13}C$ NMR(125 MHz, $CDCl_3$): $\delta$ = 30.6, 33.3, 43.8, 52.7($CO_2\underline{C}H_3$), 56.0($OCH_3$), 56.1($OCH_3$), 70.7, 75.6, 78.3, 98.2, 107.6, 111.1, 112.2, 114.4, 126.1, 136.5, 147.5, 148.9, 150.4, 151.2, 153.7, 167.9 ($\underline{C}O_2Et$) ppm. |

TABLE 1-continued

| $R^1$ | $R^2$ | $R^3$ | $R^4$ | Name | MW/m.p./NMR |
|---|---|---|---|---|---|
| 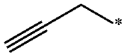 | 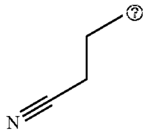<br>⑦ indicates text missing or illegible when filed | —$CH_3$ | 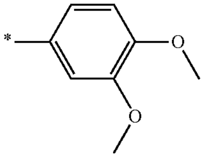 | 4-{8-[(3,4-Dimethoxyphenyl)ethynyl]-7-methyl-2,6-dioxo-1-prop-2-ynyl-1,2,6,7-tetrahydropurin-3-yl}butyronitrile<br>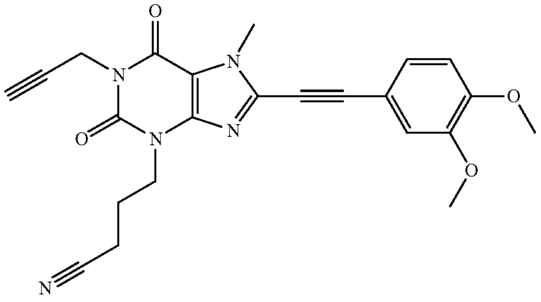 | MW 431.5, colorless crystals. $^1H$ NMR(500 MHz, $CDCl_3$): δ = 2.17 (t, J = 2.5 Hz, 1H, CCH), 2.20(q, J = 6.9 Hz, 2 H), 2.45(t, J = 7.6 Hz, 2 H), 3.89(s, 3H, $OCH_3$), 3.92(s, 3 H), $OCH_3$), 4.07(s, 3H, $N7CH_3$), 4.24(t, J = 6.9 Hz, 2 H), 4.77(d, J = 2.5 Hz, 2H, $C\underline{H_2}CCH$), 4.86(s, 2H, $C\underline{H_2}CO_2Me$), 6.86(d, J = 8.5 Hz, 1 H), 7.07(d, J = 1.9 Hz, 1 H), 7.21(dd, J = 1.9 and 8.5 Hz, 1 H) ppm.<br>$^{13}C$ NMR(125 MHz, $CDCl_3$): δ = 15.0, 24.3, 30.6, 33.3, 42.3, 56.0 ($OCH_3$), 56.1($OCH_3$), 70.7, 75.6, 78.4, 98.2, 107.8, 111.2, 112.2, 114.4, 118.9, 126.2, 136.6, 147.6, 148.9, 150.6, 151.2, 153.6 ppm. |
| 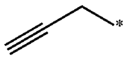 | 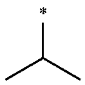 | —$CH_3$ | 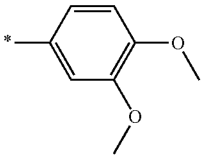 | 8-[(3,4-Dimethoxyphenyl)ethynyl]-3-isopropyl-7-methyl-1-prop-2-ynyl-3,7-dihydropurine-2,6-dione<br>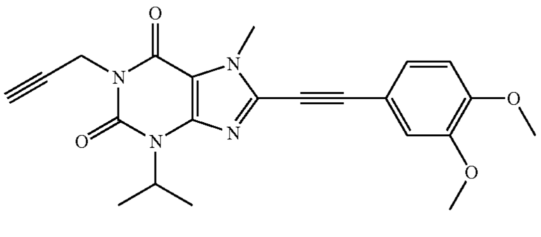 | MW 406.5, colorless crystals. $^1H$ NMR(500 MHz, $CDCl_3$): δ = 1.57 (s, 3 H), 1.59(s, 3 H), 2.16(t, J = 2.5 Hz, 1H, CCH), 3.89(s, 3H, $OCH_3$), 3.91(s, 3H, $OCH_3$), 4.06 (s, 3H, $N7CH_3$), 4.76(d, J = 2.5 Hz, 2H, $C\underline{H_2}CCH$), 5.18(m, 1 H), 6.86(d, J = 8.5 Hz, 1 H), 7.07(d, J = 1.9 Hz, 1 H), 7.22(dd, J = 1.9 and 8.5 Hz, 1 H) ppm.<br>$^{13}C$ NMR(125 MHz, $CDCl_3$): δ = 19.6 (2 × $CH_3$), 30.4, 33.1, 48.8, 56.0($OCH_3$), 56.1($OCH_3$), 70.4, 75.9, 78.7, 97.6, 108.1, 111.1, 112.4, 114.4, 126.1, 136.0, 147.8, 148.9, 149.9, 151.1, 153.9 ppm. |

TABLE 1-continued

| $R^1$ | $R^2$ | $R^3$ | $R^4$ | Name | MW/m.p./NMR |
|---|---|---|---|---|---|
| 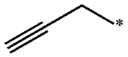 | 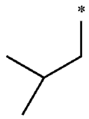 | —$CH_3$ | 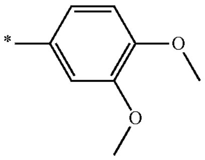 | 8-[(3,4-Dimethoxyphenyl)ethynyl]-3-isobutyl-7-methyl-1-prop-2-ynyl-3,7-dihydropurine-2,6-dione 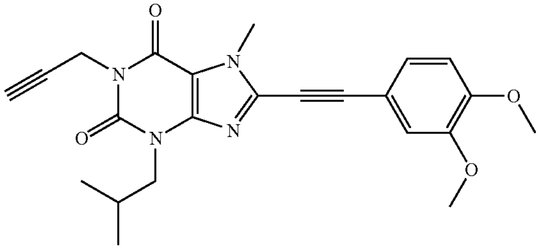 | MW 420.5, colorless crystals. $^1$H NMR(500 MHz, $CDCl_3$): δ = 0.93 (s, 3 H), 0.95(s, 3 H), 2.16(t, J = 2.5 Hz, 1H, CCH), 2.31(m, 1 H), 3.89(s, 3H, $OCH_3$), 3.91(s, 3H, $OCH_3$), 3.95(d, J = 7.6 Hz, 2 H), 4.06(s, 3H, $N7CH_3$), 4.78(d, J = 1.9 Hz, 2H, $C\underline{H_2}CCH$), 6.86(d, J = 8.5 Hz, 1 H), 7.07(d, J = 1.6 Hz, 1 H), 7.22(dd, J = 1.6 and 8.5 Hz, 1 H) ppm. $^{13}$C NMR(125 MHz, $CDCl_3$): δ = 19.9(2 × $CH_3$), 27.2, 30.5, 33.2, 50.5, 56.0($OCH_3$), 56.1($OCH_3$), 70.4, 75.9, 78.6, 97.8, 107.6, 111.1, 112.4, 114.4, 126.1, 136.4, 148.4, 148.9, 150.6, 151.1, 153.9 ppm. |
| 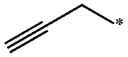 | 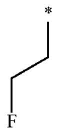 | —$CH_3$ | 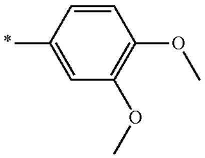 | 8-[(3,4-Dimethoxyphenyl)ethynyl]-7-methyl-3-(2-fluoroethyl)-1-prop-2-ynyl-3,7-dihydropurine-2,6-dione 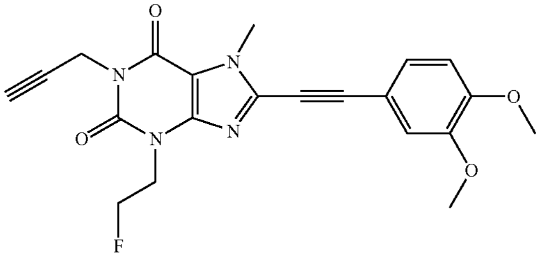 | MW 410.4, colorless crystals. $^1$H NMR(500 MHz, $CDCl_3$): δ = 2.17 (t, J = 2.5 Hz, 1H, CCH), 3.88(s, 3H, $OCH_3$), 3.91(s, 3H, $OCH_3$), 4.07(s, 3H, $N7CH_3$), 4.46(dt, J = 23.6 and 4.7 Hz, 2 H), 4.71(t, J = 4.7 Hz, 1 H), 4.77(d, J = 2.5 Hz, 2H, $C\underline{H_2}CCH$), 4.81(t, J = 4.4 Hz, 1 H), 6.85(d, J = 8.2 Hz, 1 H), 7.51 (d, J = 1.9 Hz, 1 H), 7.21(dd, J = 1.9 and 8.2 Hz, 1 H) ppm. $^{13}$C NMR(125 MHz, $CDCl_3$): δ = 30.6, 33.2, 43.4 and 43.6(d, $\underline{C}H_2F$), 56.0($OCH_3$), 56.1($OCH_3$), 70.7, 75.7, 78.4, 79.7, 81.0, 98.1, 107.7, 111.1, 112.1, 114.4, 126.1, 136.5, 147.9, 148.9, 150.4, 151.2, 153.7 ppm. |

TABLE 1-continued

| R¹ | R² | R³ | R⁴ | Name | MW/m.p./NMR |
|---|---|---|---|---|---|
| 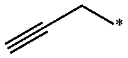 | 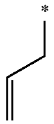 | —$CH_3$ | 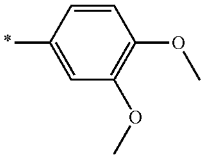 | 3-Allyl-8-[(3,4-Dimethoxyphenyl)ethynyl]-7-methyl-1-prop-2-ynyl-3,7-dihydropurine-2,6-dione 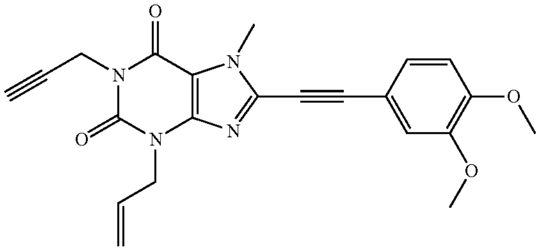 | MW 404.4, colorless crystals. $^1H$ NMR(500 MHz, $CDCl_3$): δ = 2.17 (t, J = 2.5 Hz, 1H, CCH), 3.89(s, 3H, $OCH_3$), 3.91(s, 3H, $OCH_3$), 4.07(s, 3H, $N7CH_3$), 4.72(dt, J = 1.3 and 5.7 Hz, 2H, $C\underline{H}_2CHCH_2$), 4.78(d, J = 2.5 Hz, 2H, $C\underline{H}_2CCH$), 5.21(dd, J = 0.9 and 10.4 Hz, 1H, $CH_2CHC\underline{H}_2$), 5.29(dd, J = 1.3 and 17.0 Hz, 1H, $CH_2CHC\underline{H}_2$), 5.98(m, 1H, $CH_2C\underline{H}CH_2$), 6.85(d, J = 8.2 Hz, 1 H), 7.07(d, J = 1.9 Hz, 1 H), 7.22(dd, J = 1.9 and 8.2 Hz, 1 H) ppm. $^{13}C$ NMR(125 MHz, $CDCl_3$): δ = 30.5, 33.2, 45.4, 56.0($OCH_3$), 56.1 ($OCH_3$), 70.6, 75.8, 78.5, 98.0, 107.7, 111.1, 112.3, 114.4, 118.3, 126.1, 131.6, 136.6, 147.8, 148.9, 150.2, 151.2, 153.8 ppm. |
| 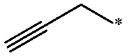 | 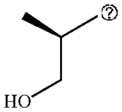 ⑦ indicates text missing or illegible when filed | —$CH_3$ | 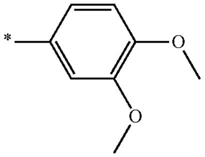 | (R)-8-[(3,4-Dimethoxyphenyl)ethynyl]-3-(3-hydroxy-2-methylpropyl)-7-methyl-1-prop-2-ynyl-3,7-dihydropurine-2,6-dione 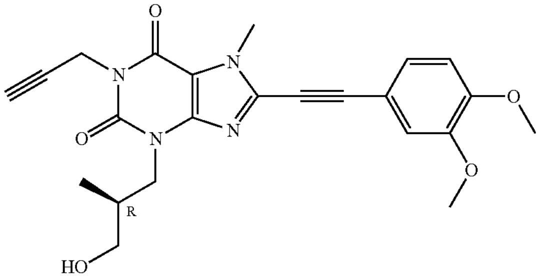 | MW 436.5, colorless crystals. $^1H$ NMR(500 MHz, $CDCl_3$): δ = 1.06 (d, J = 7.3 Hz, 3 H), 1.58(s, 1H, OH), 2.13(s, 1 H), 2.17(t, J = 2.5 Hz, 1H, CCH), 3.35(m, 1 H), 3.46 (m, 1 H), 3.85(dd, J = 6.3 and 8.5 Hz, 1 H), 3.89(s, 3H, $OCH_3$), 3.91 (s, 3H, $OCH_3$), 4.06(s, 3H, $N7CH_3$), 4.10(m, 1 H), 4.78(d, J = 2.2 Hz, 2H, $C\underline{H}_2CCH$), 6.86(d, J = 8.5 Hz, 1 h), 7.06(d, J = 1.6 Hz, 1 H), 7.21(dd, J = 1.6 and 8.5 Hz, 1 H) ppm. $^{13}C$ NMR(125 MHz, $CDCl_3$): δ = 14.7, 30.7, 33.3, 35.2, 45.3, 56.0 ($OCH_3$), 56.1($OCH_3$), 63.1, 70.7, 75.5, 78.4, 98.5, 107.5, 111.1, 112.1, 114.4, 126.2, 136.4, 148.3, 148.9, 151.1, 151.3, 153.6 ppm. $[\alpha]_D^{24}$ = +2.63° |

TABLE 1-continued

| $R^1$ | $R^2$ | $R^3$ | $R^4$ | Name | MW/m.p./NMR |
|---|---|---|---|---|---|
| 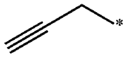 | 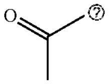 ⑦ indicates text missing or illegible when filed | —$CH_3$ | 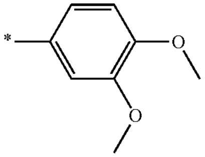 | 8-[(3,4-Dimethoxyphenyl)ethynyl]-7-methyl-3-(1-methyl-2-oxopropyl)-1-prop-2-ynyl-3,7-dihydropurine-2,6-dione 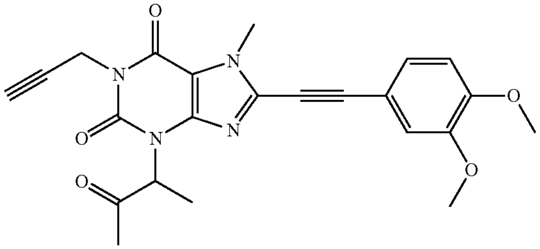 | MW 434.5, colorless crystals. $^1$H NMR(500 MHz, $CDCl_3$): δ = 1.69 (d, J = 6.9 Hz, 3 H), 2.16(t, J = 2.5 Hz, 1H, CCH), 2.17(s, 3 H), 3.89 (s, 3H, $OCH_3$), 3.91(s, 3H, $OCH_3$), 4.08(s, 3H, $N7CH_3$), 4.75(d, J = 2.2 Hz, 2H, $CH_2CCH$), 5.27(q, J = 6.9 Hz, 1 H), 6.86(d, J = 8.2 Hz, 1 H), 7.06(d, J = 1.9 Hz, 1 H), 7.21 (dd, J = 1.9 and 8.2 Hz, 1 H), ppm. $^{13}$C NMR(125 MHz, $CDCl_3$): δ = 14.0, 26.4, 30.5, 33.3, 56.0 ($OCH_3$), 56.1($OCH_3$), 59.4, 70.7, 75.6, 78.3, 98.2, 107.8, 111.1, 112.2, 114.4, 126.1, 136.4, 147.3, 148.9, 149.9, 151.2, 153.6, 202.9 ppm. |
| 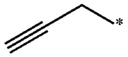 | 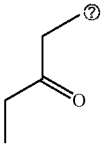 ⑦ indicates text missing or illegible when filed | —$CH_3$ | 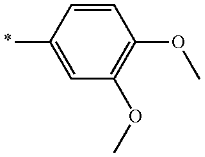 | 8-[(3,4-Dimethoxyphenyl)ethynyl]-7-methyl-3-(3-oxopentyl)-1-prop-2-ynyl-3,7-dihydropurine-2,6-dione 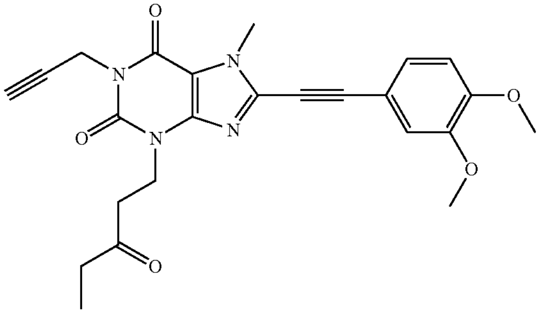 | MW 448.5, colorless crystals. $^1$H NMR(500 MHz, $CDCl_3$): δ = 1.04 (t, J = 7.3 Hz, 3 H), 2.17(t, J = 2.5 Hz, 1H, CCH), 2.45(q, J = 7.3 Hz, 2 H), 2.93(t, J = 7.6 Hz, 2 H), 3.89 (s, 3H, $OCH_3$), 3.91(s, 3H, $OCH_3$), 4.06(s, 3H, $N7CH_3$), 4.39(q, J = 7.3 Hz, 2 H), 4.76(d, J = 2.5 Hz, 2H, $CH_2CCH$), 6.86(d, J = 8.5 Hz, 1 H), 7.07(d, J = 1.9 Hz, 1 H), 7.22 (dd, J = 1.9 and 8.5 Hz, 1 H) ppm. $^{13}$C NMR(125 MHz, $CDCl_3$): δ = 29.7, 30.5, 33.2, 36.0, 38.9, 40.0, 56.0($OCH_3$), 56.1($OCH_3$), 70.6, 75.7, 78.5, 98.0, 107.8, 111.1, 112.2, 114.4, 126.1, 136.6, 147.7, 148.9, 150.2, 151.2, 153.7, 208.7 ppm. ESI + Q1 m/z 449(M + $H^+$). |

TABLE 1-continued

| $R^1$ | $R^2$ | $R^3$ | $R^4$ | Name | MW/m.p./NMR |
|---|---|---|---|---|---|
| 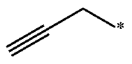 | 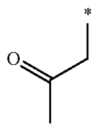 | —$CH_3$ | 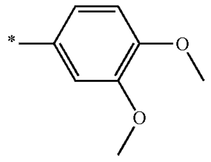 | 8-[(3,4-Dimethoxyphenyl)ethynyl]-7-methyl-3-(2-oxopropyl)-1-prop-2-ynyl-3,7-dihydropurine-2,6-dione 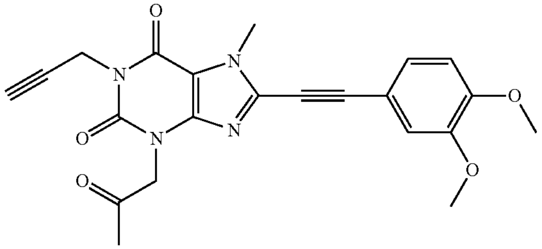 | MW 420.4, colorless crystals. $^1H$ NMR(500 MHz, $CDCl_3$): δ = 2.16 (t, J = 2.2 Hz, 1H, CCH), 2.26(s, 3 H), 3.88(s, 3H, $OCH_3$), 3.90(s, 3H, $OCH_3$), 4.06(s, 3H, $N7CH_3$), 4.76(d, J = 2.5 Hz, 2H, $C\underline{H}_2CCH$), 4.90(s, 2 H), 6.85(d, J = 8.2 Hz, 1 H), 7.04(d, J = 1.9 Hz, 1 H), 7.20 (dd, J = 1.9 and 8.2 Hz, 1 H) ppm. $^{13}C$ NMR(125 MHz, $CDCl_3$): δ = 27.1, 30.6, 33.2, 51.7, 56.0 ($OCH_3$), 56.1($OCH_3$), 70.7, 75.6, 78.3, 98.1, 107.5, 111.1, 112.2, 114.4, 126.1, 136.5, 147.5, 148.9, 150.4, 151.2, 153.7, 200.0 ppm. |
| 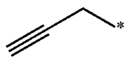 | 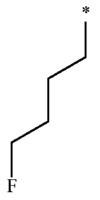 | —$CH_3$ | 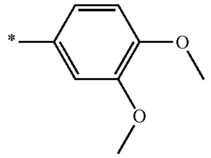 | 8-[(3,4-Dimethoxyphenyl)ethynyl]-3-(4-fluorobutyl)-7-methyl-1-prop-2-ynyl-3,7-dihydropurine-2,6-dione 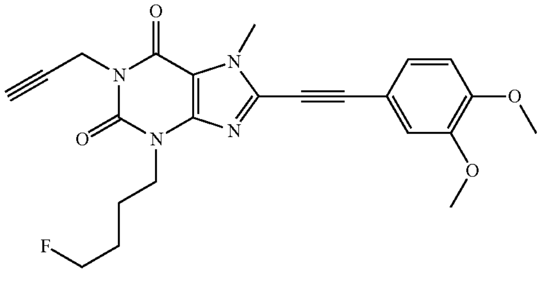 | MW 438.5, colorless crystals. $^1H$ NMR(500 MHz, $CDCl_3$): δ = 1.77 (m, 2 H), 1.91(t, J = 7.3 Hz, 2 H), 2.17(t, J = 2.2 Hz, 1H, CCH), 3.89 (s, 3H, $OCH_3$), 3.91(s, 3H, $OCH_3$), 4.07(s, 3H, $N7CH_3$), 4.17(t, J = 7.3 Hz, 2 H), 4.42(t, J = 6.0 Hz, 1 H), 4.51(t, J = 6.0 Hz, 1 H), 4.78 (d, J = 2.2 Hz, 2H, $C\underline{H}_2CCH$), 6.85 (d, J = 8.2 Hz, 1 H), 7.07(d, J = 1.6 Hz, 1 H), 7.22(dd, J = 1.6 and 8.2 Hz, 1 H) ppm. $^{13}C$ NMR(125 MHz, $CDCl_3$): δ = 23.9 and 24.0 (d, $\underline{C}H_2CH_2CH_2F$), 27.5 and 27.7(d, $CH_2\underline{C}H_2CH_2F$), 30.5, 32.2, 43.1, 56.0($OCH_3$), 56.1 ($OCH_3$), 70.5, 75.8, 78.5, 82.9 and 84.2(d, $CH_2CH_2\underline{C}H_2F$), 98.0, 107.7, 111.1, 112.3, 114.4, 126.1, 136.5, 147.9, 148.9, 150.4, 151.2, 153.8 ppm. |

TABLE 1-continued

| $R^1$ | $R^2$ | $R^3$ | $R^4$ | Name | MW/m.p./NMR |
|---|---|---|---|---|---|
| 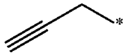 | 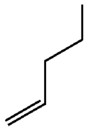 | —$CH_3$ | 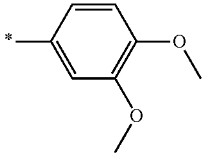 | 3-But-3-enyl-8-[(3,4-dimethoxyphenyl)ethynyl]-7-methyl-1-prop-2-ynyl-3,7-dihydropurine-2,6-dione 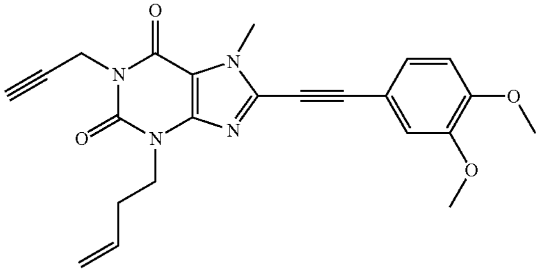 | MW 418.5, colorless crystals. $^1H$ NMR(500 MHz, $CDCl_3$): δ = 2.16 (t, J = 2.5 Hz, 1H, CCH), 2.54(q, J = 7.3 Hz, 2 H), 3.89(s, 3H, $OCH_3$), 3.91(s, 3H, $OCH_3$), 4.07(s, 3H, $N7CH_3$), 4.19(t, J = 7.3 Hz, 2 H), 4.77(d, J = 2.5 Hz, 2H, $\underline{CH_2}CCH$), 5.01(dd, J = 1.6 and 10.1 Hz, 1 H), 5.07(dd, J = 1.9 and 17.0 Hz, 1 H), 5.82(m, 1 H), 6.86(d, J = 8.5 Hz, 1 H), 7.08(d, J = 1.9 Hz, 1 H), 7.22 (dd, J = 1.9 and 8.5 Hz, 1 H) ppm. $^{13}C$ NMR(125 MHz, $CDCl_3$): δ = 30.5, 32.2, 33.2, 42.8, 56.0 ($OCH_3$), 56.1($OCH_3$), 70.5, 75.8, 78.6, 97.9, 107.7, 111.1, 112.3, 114.4, 117.5, 126.1, 134.3, 136.5, 147.9, 148.9, 150.3, 151.1, 153.8 ppm. |
| 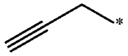 | 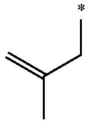 | —$CH_3$ | 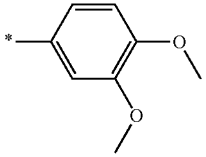 | 8-[(3,4-Dimethoxyphenyl)ethynyl]-7-methyl-3-(2-methylallyl)-1-prop-2-ynyl-3,7-dihydropurine-2,6-dione 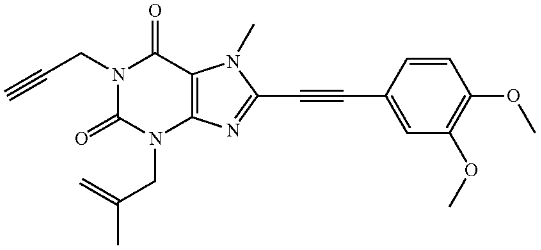 | MW 418.5, colorless crystals. $^1H$ NMR(500 MHz, $CDCl_3$): δ = 1.80 (s, 3 H), 2.16(t, J = 2.5 Hz, 1H, CCH), 3.88(s, 3H, $OCH_3$), 3.91(s, 3H, $OCH_3$), 4.07(s, 3H, $N7CH_3$), 4.64(s, 2 H), 4.71(s, 1 H), 4.79(d, J = 2.5 Hz, 2H, $\underline{CH_2}CCH$), 4.89(t, J = 1.3 Hz, 1 H), 6.85(d, J = 8.2 Hz, 1 H), 7.06(d, J = 1.9 Hz, 1 H), 7.22(dd, J = 1.9 and 8.2 Hz, 1 H) ppm. $^{13}C$ NMR(125 MHz, $CDCl_3$): δ = 20.4, 30.6, 33.2, 48.2, 56.0 ($OCH_3$), 56.1($OCH_3$), 70.5, 75.9, 78.5, 97.9, 107.6, 111.1, 111.4, 112.3, 114.4, 126.1, 136.6, 139.0, 148.1, 148.9, 150.3, 151.1, 153.8 ppm. |

TABLE 1-continued

| $R^1$ | $R^2$ | $R^3$ | $R^4$ | Name | MW/m.p./NMR |
|---|---|---|---|---|---|
| 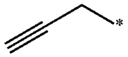 | 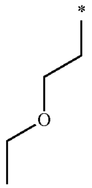 | $-CH_3$ | 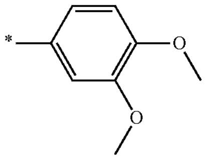 | 8-[(3,4-Dimethoxyphenyl)ethynyl]-3-(2-ethoxyethyl)-7-methyl-1-prop-2-ynyl-3,7-dihydropurine-2,6-dione 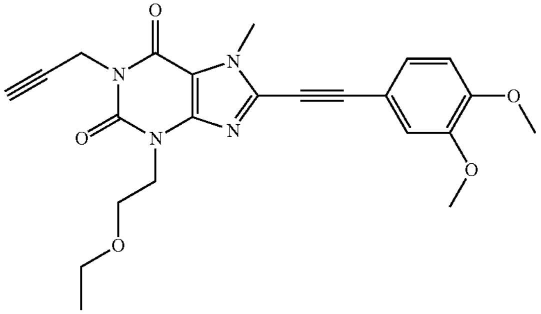 | MW 436.5, colorless crystals. $^1H$ NMR(500 MHz, $CDCl_3$): δ = 1.12 (t, J = 7.3 Hz, 3 H), 2.16(t, J = 2.2 Hz, 1H, CCH), 3.52(q, J = 6.9 Hz, 2 H), 3.78(t, J = 6.0 Hz, 2 H), 3.89 (s, 3H, $OCH_3$), 3.91(s, 3H, $OCH_3$), 4.06(s, 3H, $N7CH_3$), 4.32(t, J = 6.0 Hz, 2 H), 4.77(d, J = 2.5 Hz, 2H, $\underline{CH_2}CCH$), 4.89(t, J = 1.3 Hz, 1 H), 6.85(d, J = 8.2 Hz, 1 H), 7.07 (d, J = 1.9 Hz, 1 H), 7.21(dd, J = 1.9 and 8.2 Hz, 1 H) ppm. $^{13}C$ NMR(125 MHz, $CDCl_3$): δ = 15.1, 30.5, 33.2, 42.6, 56.0 ($OCH_3$), 56.1($OCH_3$), 66.2, 66.8, 70.5, 75.9, 78.6, 97.8, 107.7, 111.1, 112.3, 114.4, 126.1, 136.4, 148.1, 148.9, 150.5, 151.1, 153.9 ppm. |
| 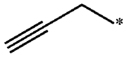 | 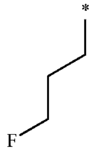 | $-CH_3$ | 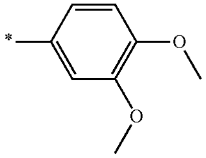 | 8-[(3,4-Dimethoxyphenyl)ethynyl]-3-(3-fluoropropyl)-7-methyl-1-prop-2-ynyl-3,7-dihydropurine-2,6-dione 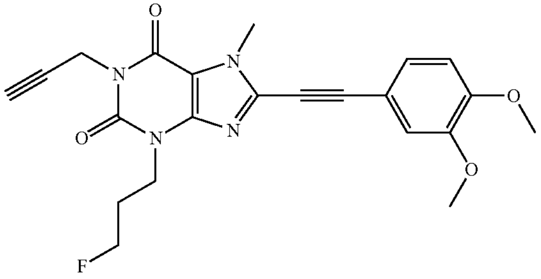 | MW 424.5, colorless crystals. $^1H$ NMR(500 MHz, $CDCl_3$): δ = 2.16 (q, J = 6.9 Hz, 2 H), 2.22(t, J = 2.5 Hz, 1H, CCH), 3.89(s, 3H, $OCH_3$), 3.91(s, 3H, $OCH_3$), 4.06(s, 3H, $N7CH_3$), 4.28(t, J = 6.6 Hz, 2 H), 4.50(t, J = 5.7 Hz, 1H, $\underline{CH_2}F$), 4.59(t, J = 5.7 Hz, 1H, $\underline{CH_2}F$), 4.78(d, J = 1.6 Hz, 2H, $\underline{CH_2}CCH$), 6.86(d, J = 8.2 Hz, 1 H), 7.07(d, J = 1.6 Hz, 1 H), 7.22(dd, J = 1.6 and 8.2 Hz, 1 H) ppm. $^{13}C$ NMR(125 MHz, $CDCl_3$): δ = 28.9 and 29.1(d, $\underline{C}H_2CH_2CH_2F$), 30.5, 33.2, 40.3 and 40.4(d, $CH_2\underline{C}H_2CH_2F$), 56.0($OCH_3$), 56.1 ($OCH_3$), 70.6, 75.8, 78.5, 81.1 and 82.4(d, $CH_2CH_2\underline{C}H_2F$), 98.0, 107.8, 111.1, 112.3, 114.4, 126.1, 136.6, 147.8, 148.9, 150.4, 151.2, 153.8 ppm. |

TABLE 1-continued

| $R^1$ | $R^2$ | $R^3$ | $R^4$ | Name | MW/m.p./NMR |
|---|---|---|---|---|---|
| 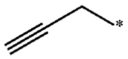 | 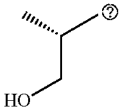 ⓘ indicates text missing or illegible when filed | —$CH_3$ | 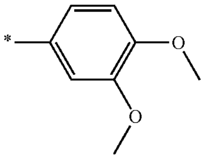 | (S)-8-[(3,4-Dimethoxyphenyl)ethynyl]-3-(3-hydroxy-2-methylpropyl)-7-methyl-1-prop-2-ynyl-3,7-dihydropurine-2,6-dione 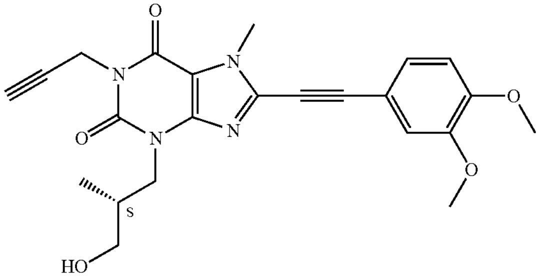 | MW 436.5, colorless crystals. $^1H$ NMR(500 MHz, $CDCl_3$): δ = 1.05 (d, J = 7.3 Hz, 3 H), 2.13(s, 1 H), 2.17(t, J = 2.5 Hz, 1H, CCH), 3.35 (m, 1 H), 3.46(m, 1 H), 3.85(dd, J = 6.0 and 8.8 Hz, 1 H), 3.89(s, 3H, $OCH_3$), 3.91(s, 3H, $OCH_3$), 4.06 (s, 3H, N7$CH_3$), 4.09(m, 1 H), 4.78 (d, J = 2.2 Hz, 2H, $\underline{CH_2}$CCH), 6.86 (d, J = 8.5 Hz, 1 H), 7.05(d, J = 1.9 Hz, 1 H), 7.21(dd, J = 1.9 and 8.5 Hz, 1 H) ppm. $^{13}C$ NMR(125 MHz, $CDCl_3$): δ = 14.7, 30.7, 33.3, 35.1, 45.3, 56.0 ($OCH_3$), 56.1($OCH_3$), 63.1, 70.7, 75.5, 78.3, 98.5, 107.5, 111.1, 112.1, 114.4, 126.2, 136.4, 148.3, 148.9, 151.1, 151.3, 153.6 ppm. $[\alpha]_D^{24}$ = +2.53° |
| 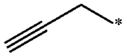 | 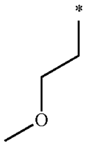 | —$CH_3$ | 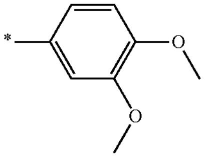 | 8-(3,4-Dimethoxyphenylethynyl)-3-(2-methoxyethyl)-7-methyl-1-prop-2-ynyl-3,7-dihydropurine-2,6-dione 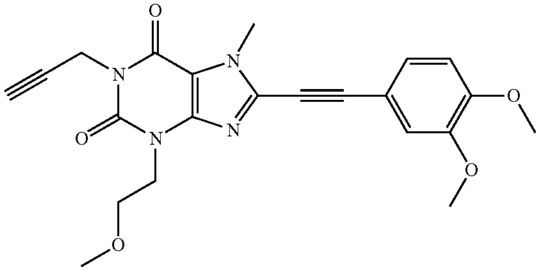 | MW 422.4, colorless crystals. $^1H$ NMR(500 MHz, $CDCl_3$): δ = 2.17 (t, J = 2.5 Hz, 1H, CCH), 3.34(s, 3H, $OCH_3$), 3.75(t, J = 5.65 Hz, 2 H), 3.89(s, 3H, $OCH_3$), 3.91(s, 3H, $OCH_3$), 4.06(s, 3H, N7$CH_3$), 4.33(t, J = 5.65 Hz, 2 H), 4.78(d, J = 2.5 Hz, 2H, $\underline{CH_2}$CCH), 6.85(d, J = 8.5 Hz, 1 H), 7.07(d, J = 1.6 Hz, 1 H), 7.21(dd, J = 1.6 and 8.5 Hz, 1 H) ppm. $^{13}C$ NMR(125 MHz, $CDCl_3$): δ = 30.5, 33.2, 42.7, 55.9, 56.0, 58.8, 69.1, 70.5, 75.9, 78.6, 97.8, 107.7, 111.1, 112.3, 114.4, 126.0 136.4, 148.1, 148.9, 150.5, 151.1, 153.8 ppm. |

TABLE 1-continued

| $R^1$ | $R^2$ | $R^3$ | $R^4$ | Name | MW/m.p./NMR |
|---|---|---|---|---|---|
| 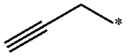 | $—CH_3$ | $—CH_3$ | 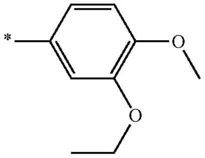 | 8-(3,4-Diethoxyphenylethynyl)-3,7-dimethyl-1-prop-2-ynyl-3,7-dihydropurine-2,6-dione 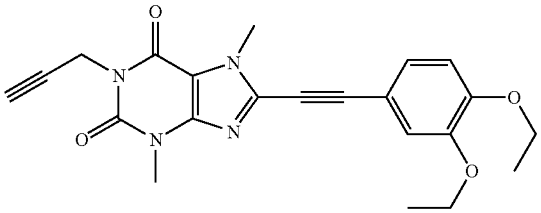 | MW 406.5, colorless crystals. $^1$H-NMR($CDCl_3$, 500 MHz): δ 1.45(m, 6H, 2 × $CH_2CH_3$), 2.17(t, J = 2.5 Hz, 1H, CCH), 3.59(s, 3 H $N3CH_3$), 4.06(s, 3H, $N7CH_3$), 4.07-4.12(m, 4H, 2 × $CH_2CH_3$), 4.78(d, J = 2.5 Hz, 2H, $CH_2CCH$), 6.84(d, J = 8.5 Hz, 1 H), 7.07(d, J = 2.0 Hz, 1 H), 7.18(dd, J = 2.0/8.5 Hz, 1 H) ppm. $^{13}$C-NMR: δ 14.6, 14.7, 29.8, 30.5, 33.2, 64.5, 64.7, 70.5, 75.6, 78.6, 98.3, 107.6, 112.0, 112.7, 116.3, 126.0, 136.6, 148.3, 148.4, 150.7, 151.0, 153.8 ppm. |
| 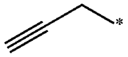 | $—CH_3$ | 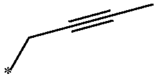 | 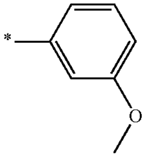 | 7-But-2-ynyl-8-(3-methoxyphenylethynyl)-3-methyl-1-prop-2-ynyl-3,7-dihydropurine-2,6-dione 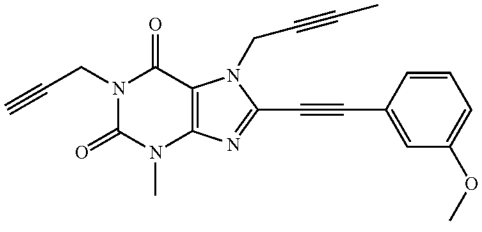 | MW 386.4, colorless crystals. $^1$H-NMR($CDCl_3$, 500 MHz): δ 1.79(t, J = 2.5 Hz, 3H, $CCCH_3$), 2.17(t, J = 2.5 Hz, 1H, CCH), 3.59(s, 3H, $N3CH_3$), 3.82(s, 3H, $OCH_3$), 4.79 (d, J = 2.5 Hz, 2H, $N1CH_2CC$), 5.21(q, J = 2.5 Hz, 2H, $N7CH_2CC$), 6.98-7.00(m, 1 H), 7.13-7.14(m, 1 H), 7.20-7.22(m, 1 H), 7.29-7.22(m, 1 H) ppm. $^{13}$C-NMR: δ 3.6, 29.9, 30.6, 36.3, 55.4, 70.6, 71.8, 76.5, 78.5, 82.2, 98.0, 106.8, 116.8, 116.9, 121.3, 124.7, 129.8, 135.7, 148.2, 150.6, 153.4, 159.4 ppm. |
| 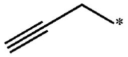 | $—C_2H_5$ | $—CH_3$ | 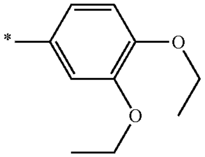 | 8-(3,4-Diethoxyphenylethynyl)-3-ethyl-7-methyl-1-prop-2-ynyl-3,7-dihydropurine-2,6-dione 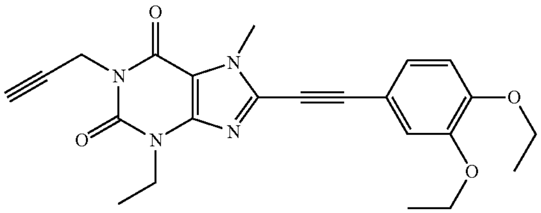 | MW 420.5, colorless crystals. $^1$H-NMR($CDCl_3$, 500 MHz): δ 1.35(t, J = 6.9 Hz, 3H, $NCH_2CH_3$) 1.45(t, J = 6.9 Hz, 3H, $OCH_2CH_3$), 1.46(t, J = 6.95 Hz, 3H, $OCH_2CH_3$), 2.17 (t, J = 2.2 Hz, 1H, CCH), 4.06(s, 3 H $N7CH_3$), 4.08(q, J = 6.9 Hz, 2H, $OCH_2CH_3$), 4.12(q, J = 6.95 Hz, 2H, $OCH_2CH_3$), 4.18(q, J = 6.95 Hz, 2H, $N3CH_2CH_3$), 4.78(d, J = 2.2 Hz, 2H, $CH_2CCH$), 6.84(d, J = 8.5 Hz, 1 H), 7.07(d, J = 1.9 Hz, 1 H), 7.18(dd, J = 1.9/8.5 Hz, 1 H) ppm. $^{13}$C-NMR: δ 13.4, 14.6, 14.7, 31.9, 33.2, 38.8, 64.5, 64.7, 70.5, 75.6, 78.7, 98.2, 107.8, 112.1, 112.7, 116.4, 126.0, 136.6, 147.8, 148.4, 150.2, 150.9, 153.9 ppm. |

TABLE 1-continued

| $R^1$ | $R^2$ | $R^3$ | $R^4$ | Name | MW/m.p./NMR |
|---|---|---|---|---|---|
| 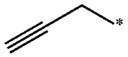 | —$CH_3$ | 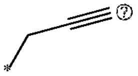 ⑦ indicates text missing or illegible when filed | 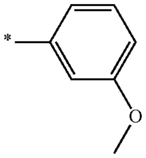 | 7-Cyanomethyl-8-(3-methoxyphenylethynyl)-3-methyl-1-prop-2-ynyl-3,7-dihydropurine-2,6-dione 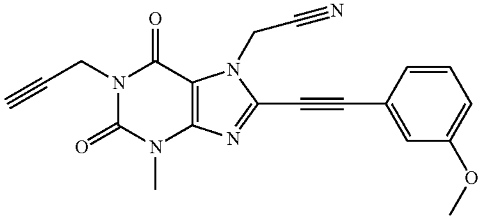 | MW 373.4, colorless crystals. $^1$H-NMR($CDCl_3$, 500 MHz): δ 2.19(t, J = 2.5 Hz, 1H, CCH), 3.61(s, 3H, N3$CH_3$), 3.83(s, 3H, $OCH_3$), 4.79 (d, J = 2.5 Hz, 2H, N1$CH_2$CC), 5.45(s, 2H, N7$CH_2$CN), 7.02-7.04 (m, 1 H), 7.15-7.16(m, 1 H), 7.24-7.26(m, 1 H), 7.31-7.34(m, 1 H) ppm. $^{13}$C-NMR: δ 30.0, 30.7, 33.2, 55.5, 71.0, 75.2, 78.0, 100.1, 106.4, 112.7, 116.9, 117.7, 120.4, 124.9, 130.0, 136.1, 148.5, 150.4, 153.5, 159.5 ppm. |
| 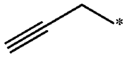 | 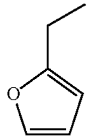 | —$CH_3$ | 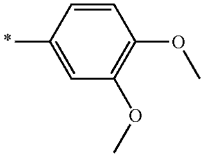 | 3-Furan-2-ylmethyl-8-(3,4-dimethoxyphenylethynyl)-7-methyl-1-prop-2-ynyl-3,7-dihydropurine-2,6-dione 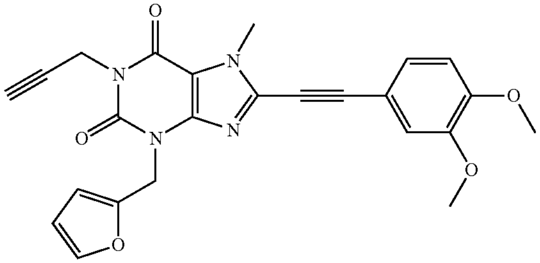 | MW 444.5, colorless crystals. $^1$H-NMR($CDCl_3$, 500 MHz): δ 2.16(t, J = 2.2 Hz, 1H, CCH), 3.89(s, 3H, $OCH_3$), 3.91(s, 3H, $OCH_3$), 4.06 (s, 3H, N7$CH_3$), 4.76(d, J = 2.2 Hz, 2H, N1$CH_2$CC), 5.29(s, 2H, N3$CH_2$), 6.28-6.29(m, 1 H), 6.44-6.45(m, 1 H), 6.85-6.86(m, 1 H), 7.07-7.08(m, 1 H), 7.21-7.24(m, 1 H), 7.32-7.33(m, 1 H) ppm. $^{13}$C-NMR: δ 30.6, 33.2, 39.5, 55.9, 56.0, 70.6, 75.9, 78.5, 98.0, 107.7, 109.7, 110.4, 111.1, 112.3, 114.4, 126.1, 136.5, 142.5, 147.6, 148.9, 149.2, 150.2, 151.1, 153.7 ppm. |
| 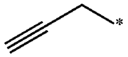 | —$C_2H_5$ | —$CH_3$ | 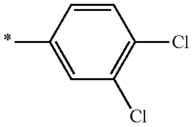 | 8-(3,4-Dichlorophenylethynyl)-3-ethyl-7-methyl-1-prop-2-ynyl-3,7-dihydropurine-2,6-dione 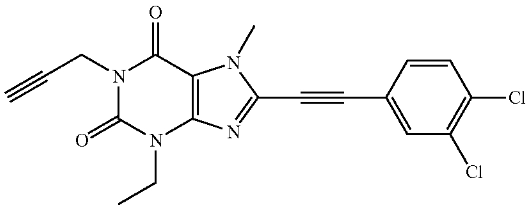 | MW 401.3, colorless crystals. $^1$H-NMR($CDCl_3$, 500 MHz): δ 1.35(t, J = 7.25 Hz, 3H, $NCH_2CH_3$), 2.17 (t, J = 2.2 Hz, 1H, CCH), 4.07(s, 3H, N7$CH_3$), 4.17(q, J = 7.25 Hz, 2H, N3$CH_2CH_3$), 4.78(d, J = 2.2 Hz, 2H, $CH_2$CCH), 7.42(dd, J = 1.9/8.5 Hz, 1 H), 7.47(d, J = 8.5 Hz, 1 H), 7.68(d, J = 1.9 Hz, 1 H) ppm. $^{13}$C-NMR: δ 13.3, 30.5, 33.3, 38.9, 70.6, 78.5, 78.6, 94.5, 108.2, 120.3, 130.8, 131.0, 133.2, 133.6, 135.0, 135.4, 147.7, 150.1, 153.9 ppm. |

TABLE 1-continued

| R[1] | R[2] | R[3] | R[4] | Name | MW/m.p./NMR |
|---|---|---|---|---|---|
| 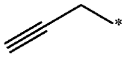 | —$CH_3$ | —$CH_3$ | 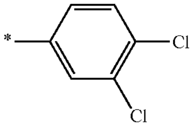 | 8-(3,4-dichlorophenylethynyl)-3,7-dimethyl-1-prop-2-ynyl-3,7-dihydropurine-2,6-dione 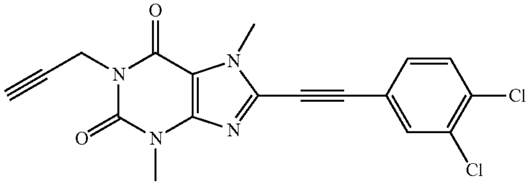 | MW 387.2, colorless crystals. $^1H$-NMR($CDCl_3$, 500 MHz): δ 2.17(t, J = 2.2 Hz, 1H, CCH), 3.59(s, 3H, N3$CH_3$), 4.07(s, 3H, N7$CH_3$), 4.78 (d, J = 2.2 Hz, 2H, $CH_2$CCH), 7.42 (dd, J = 1.9/8.2 Hz, 1 H), 7.47(d, J = 8.2 Hz, 1 H), 7.68(d, J = 1.9 Hz, 1 H) ppm. $^{13}C$-NMR: δ 29.9, 30.6, 33.3, 70.6, 78.4, 78.5, 94.7, 108.1, 120.2, 130.9, 131.0, 133.2, 133.6, 135.0, 135.4, 148.2, 150.6, 153.8 ppm. |
| 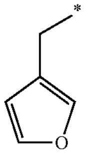 | —$C_2H_5$ | —$CH_3$ | 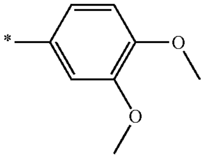 | 1-Furan-3-ylmethyl-8-(3,4-dimethoxyphenylethynyl)-3-ethyl-7-methyl-3,7-dihydropurine-2,6-dione 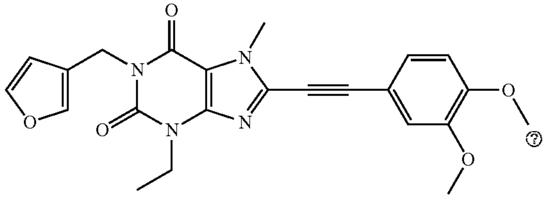 ⓘ indicates text missing or illegible when filed | MW 434.5, colorless crystals. $^1H$-NMR($CDCl_3$, 500 MHz): δ 1.33(t, J = 7 Hz, 3H, $CH_2CH_3$), 3.88(s, 3H, $OCH_3$), 3.91(s, 3H, $OCH_3$), 4.06(s, 3H, N7$CH_3$), 4.16(q, J = 7 Hz, 2H, N3$CH_2CH_3$), 5.01(s, 2H, N1$CH_2$), 6.51-6.52(m, 1 H), 6.85(d, J = 8.2 Hz, 1 H), 7.07(d, J = 1.9 Hz, 1 H), 7.22(dd, J = 1.9/8.2 Hz, 1 H), 7.30-7.31(m, 1 H), 7.54-7.55 (m, 1 H) ppm. $^{13}C$-NMR: δ 13.4, 33.2, 35.4, 38.7, 55.9, 56.0, 75.9, 97.7, 108.0, 111.1, 111.5, 112.4, 114.4, 120.8, 126.0, 136.2, 142.1, 142.6, 147.6, 148.9, 150.7, 151.1, 154.5 ppm. |
| 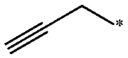 | 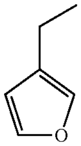 | —$CH_3$ | 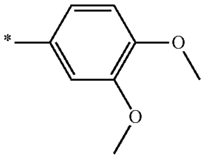 | 3-Furan-3-ylmethyl-8-(3,4-dimethoxyphenylethynyl)-7-methyl-1-prop-2-ynyl-3,7-dihydropurine-2,6-dione 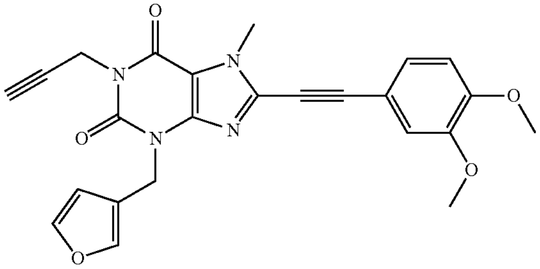 | MW 444.5, colorless crystals. $^1H$-NMR($CDCl_3$, 500 MHz): δ 2.16(t, J = 2.5 Hz, 1H, CCH), 3.90(s, 3H, $OCH_3$), 3.92(s, 3H, $OCH_3$), 4.05 (s, 3H, N7$CH_3$), 4.76(d, J = 2.5 Hz, 2H, N1$CH_2$CC), 5.12(s, 2H, N3$CH_2$), 6.55-6.56(m, 1 H), 6.86-6.87(m, 1 H), 7.08-7.09(m, 1 H), 7.22-7.24(m, 1 H), 7.30-7.31(m, 1 H), 7.60-7.61(m, 1 H) ppm. $^{13}C$-NMR: δ 30.5, 33.2, 37.6, 56.0, 56.1, 70.6, 75.8, 78.5, 97.9, 107.8, 111.1, 111.2, 112.3, 114.4, 119.9, 126.1, 136.5, 142.2, 142.9, 147.6, 148.9, 150.2, 151.2, 153.7 ppm. |

TABLE 1-continued

| $R^1$ | $R^2$ | $R^3$ | $R^4$ | Name | MW/m.p./NMR |
|---|---|---|---|---|---|
| 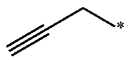 | —$CH_3$ | —$CH_3$ | 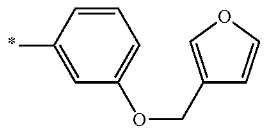 | 8-[3-(Furan-3-ylmethoxy)phenylethynyl]-3,7-dimethyl-1-prop-2-ynyl-3,7-dihydropurine-2,6-dione 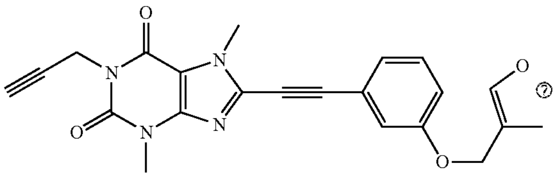 ⑦ indicates text missing or illegible when filed | MW 414.4, colorless crystals. $^1$H-NMR($CDCl_3$, 500 MHz): δ 2.17(t, J = 2.5 Hz, 1H, CCH), 3.59(s, 3H, N3$CH_3$), 4.07(s, 3H, N7$CH_3$), 4.78 (d, J = 2.5 Hz, 2H, N1$CH_2$CC), 4.94(s, 2H, $OCH_2$), 6.46-6.47(m, 1 H), 7.03-7.05(m, 1 H), 7.16-7.17 (m, 1 H), 7.20-7.22(m, 1 H), 7.29-7.31(m, 1 H), 7.42-7.43(m, 1 H), 7.49-7.50(m, 1 H) ppm. $^{13}$C-NMR: δ 29.9, 30.6, 33.3, 62.1, 70.6, 76.6, 78.5, 97.3, 107.9, 110.0, 117.7, 117.8, 120.8, 121.3, 125.0, 129.9, 136.1, 140.9, 143.7, 148.2, 150.7, 153.8, 158.4 ppm. |
| 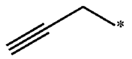 | —$CH_3$ | —$CH_3$ | 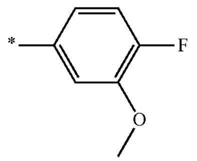 | 8-(4-Fluoro-3-methoxyphenylethynyl)-3,7-dimethyl-1-prop-2-ynyl-3,7-dihydropurine-2,6-dione 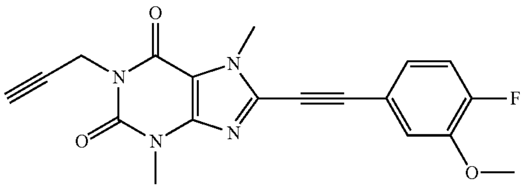 | MW 366.4, colorless crystals, m.p. ° C. $^1$H NMR(500 MHz, $CDCl_3$): δ = 2.17(t, J = 2.2 Hz, 1H, CCH), 3.59(s, 3H, N3$CH_3$) 3.89(s, 3H, $OCH_3$), 4.08(s, 3H, N7$CH_3$), 4.78 (d, J = 2.2 Hz, 2H, C$\underline{H}_2$CC), 7.06-7.19(m, 3 H) ppm. $^{13}$C NMR(125 MHz, $CDCl_3$): δ = 29.9, 30.6, 33.3, 56.3($OCH_3$), 70.6, 76.3, 78.5, 96.6(d, J = 1 Hz), 107.8, 116.5-116.8(m), 125.5(d, J = 7 Hz), 136.0, 147.9(d, J = 11 Hz), 148.2, 150.7, 152.7, 153.8, 154.8 ppm. |
| 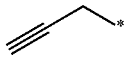 | —$C_2H_5$ | —$CH_3$ | 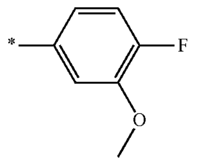 | 3-Ethyl-8-(4-fluoro-3-methoxyphenylethynyl)-7-methyl-1-prop-2-ynyl-3,7-dihydropurine-2,6-dione 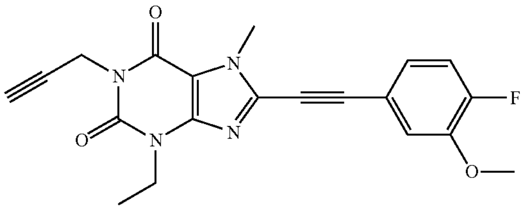 | MW 380.4, colorless crystals, m.p. ° C. $^1$H NMR(500 MHz, $CDCl_3$): δ = 1.35(t, J = 7.25 Hz, 3H, $CH_2$C$\underline{H}_3$), 2.17(t, J = 2.2 Hz, 1H, CCH), 3.89(s, 3H, $OCH_3$), 4.07(s, 3H, N7$CH_3$), 4.18(q, J = 7.25 Hz, 2H, C$\underline{H}_2$$CH_3$), 4.78(d, J = 2.2 Hz, 2H, C$\underline{H}_2$CC), 7.06-7.19(m, 3 H) ppm. $^{13}$C NMR(125 MHz, $CDCl_3$): δ = 13.4, 30.5, 33.3, 38.8, 56.3 ($OCH_3$), 70.5, 76.4, 78.6, 96.5(d, J = 1 Hz), 108.0, 116.6-116.8(m), 125.5(d, J = 7 Hz), 136.0, 147.8, 147.9(d, J = 12 Hz), 150.1, 152.7, 153.9, 154.7 ppm. |

TABLE 1-continued

| $R^1$ | $R^2$ | $R^3$ | $R^4$ | Name | MW/m.p./NMR |
|---|---|---|---|---|---|
| 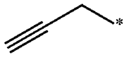 | 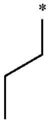 | —$CH_3$ | 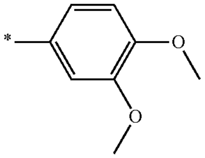 | 8-(3,4-Dimethoxyphenylethynyl)-7-methyl-3-propyl-1-prop-2-ynyl-3,7-dihydropurine-2,6-dione 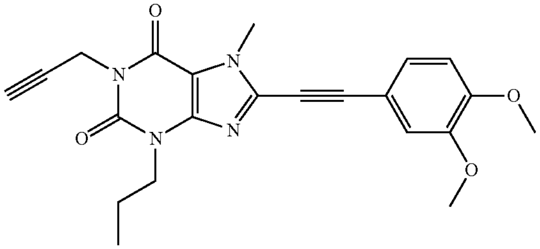 | MW 406.5, colorless crystals. $^1$H-NMR($CDCl_3$, 500 MHz): δ 0.96(t, J = 7.25 Hz, 3H, $CH_2CH_2CH_3$), 1.80(m, 2H, $CH_2CH_2CH_3$) 2.16(t, J = 2.5 Hz, 1H, CCH), 3.89(s, 3H, $OCH_3$), 3.91(s, 3H, $OCH_3$), 4.06 (s, 3H, $N7CH_3$), 4.07(m, 2H, $N3CH_2CH_2CH_3$), 4.78(d, J = 2.5 Hz, 2H, $N1CH_2CC$), 6.85(d, J = 8 Hz, 1 H), 7.07(d, J = 1.9 Hz, 1 H), 7.22(dd, J = 1.9/8 Hz, 1 H) ppm. $^{13}$C-NMR: δ 11.1, 21.3, 30.5, 33.2, 45.1, 56.0, 56.1, 70.4, 75.8, 78.6, 97.8, 107.7, 111.1, 112.3, 114.4, 126.1, 136.5, 148.1, 148.9, 150.4, 151.1, 153.9, ppm. |
| 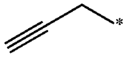 | 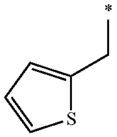 | —$CH_3$ | 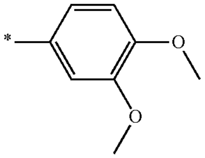 | 8-(3,4-Dimethoxyphenylethynyl)-7-methyl-1-prop-2-ynyl-3-thiophen-2-ylmethyl-3,7-dihydropurine-2,6-dione 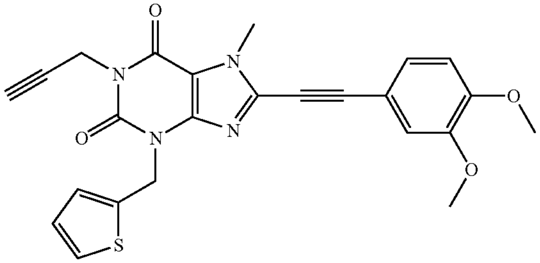 | MW 460.5, colorless crystals. $^1$H-NMR($CDCl_3$, 500 MHz): δ 2.16(t, J = 2.2 Hz, 1H, CCH), 3.90(s, 3H, $OCH_3$), 3.92(s, 3H, $OCH_3$), 4.05 (s, 3H, $N7CH_3$), 4.76(d, J = 2.2 Hz, 2H, $N1CH_2CC$), 5.44(s, 2H, $N3CH_2$), 6.86(d, J = 8 Hz, 1H, $H_{phenyl}$), 6.92(dd, J = 3/5 Hz, 1H, $H_{thiophen}$) 7.05(d, J = 2 Hz, 1H, $H_{phenyl}$), 7.20(dd, J = 1/5 Hz, 1H, $H_{thiophen}$), 7.23(dd, J = 2/8 Hz, 1H, $H_{phenyl}$), 7.27(dd, J = 1/3 Hz, 1H, $H_{thiophen}$) ppm. $^{13}$C-NMR: δ 30.5, 33.2, 41.0, 56.0, 56.1, 70.6, 75.9, 78.4, 98.0, 107.8, 111.1, 112.3, 114.4, 126.1, 126.2, 126.6, 136.5, 137.4, 147.4, 148.9, 150.1, 151.2, 153.7 ppm. |
| 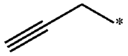 | 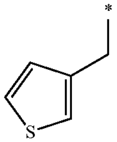 | —$CH_3$ | 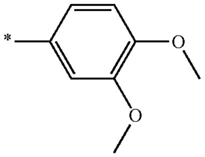 | 8-(3,4-Dimethoxyphenylethynyl)-7-methyl-1-prop-2-ynyl-3-thiophen-3-ylmethyl-3,7-dihydropurine-2,6-dione 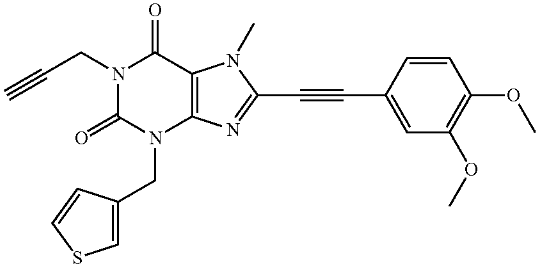 | MW 460.5, colorless crystals. $^1$H-NMR($CDCl_3$, 500 MHz): δ 2.16(t, J = 2.5 Hz, 1H, CCH), 3.90(s, 3H, $OCH_3$), 3.91(s, 3H, $OCH_3$), 4.05 (s, 3H, $N7CH_3$), 4.76(d, J = 2.5 Hz, 2H, $N1CH_2CC$), 5.27(s, 2H, $N3CH_2$), 6.86(d, J = 8 Hz, 1H, $H_{phenyl}$), 7.08(d, J = 2 Hz, 1H, $H_{phenyl}$), 7.08(d, J = 2 Hz, 1H, $H_{phenyl}$), 7.21-7.27(m, 3 H), 7.45-7.46(m, 1H, $H_{thiophen}$) ppm. $^{13}$C-NMR: δ 30.5, 33.2, 41.4, 56.0, 56.1, 70.6, 75.9, 78.5, 97.9, 107.8, 111.1, 112.3, 114.4, 125.1, 125.7, 126.1, 128.6, 136.3, 136.5, 147.7, 148.9, 150.3, 151.2, 153.7 ppm. |

TABLE 1-continued

| R$^1$ | R$^2$ | R$^3$ | R$^4$ | Name | MW/m.p./NMR |
|---|---|---|---|---|---|
| 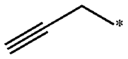 | 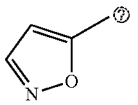 (?) indicates text missing or illegible when filed | —$CH_3$ | 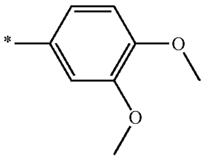 | 8-(3,4-Dimethoxyphenylethynyl)-3-isoxazol-5-ylmethyl-7-methyl-1-prop-2-ynyl-3,7-dihydropurine-2,6-dione 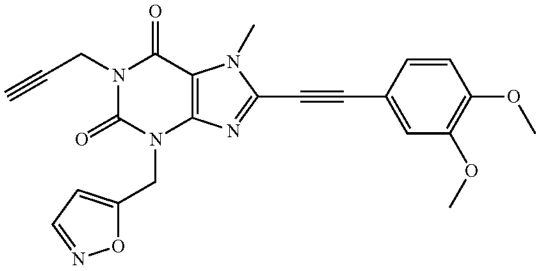 | MW 445.4, colorless crystals. $^1$H-NMR($CDCl_3$, 500 MHz): δ 2.17(t, J = 2.55 Hz, 1H, CCH), 3.89(s, 3H, $OCH_3$), 3.91(s, 3H, $OCH_3$), 4.07(s, 3H, N7$CH_3$), 4.76(d, J = 2.55 Hz, 2H, N1$CH_2$CC), 5.44(s, 2H, N3$CH_2$), 6.31(d, J = 1.6 Hz, 1H, $H_{isoxazol}$), 6.85(d, J = 8 Hz, 1H, $H_{phenyl}$), 7.07(d, J = 1.9 Hz, 1H, $H_{phenyl}$), 7.22(dd, J = 1.9/8 Hz, 1H, $H_{phenyl}$), 8.17(d, J = 1.6 Hz, 1H, $H_{isoxazol}$) ppm. $^{13}$C-NMR: δ 30.7, 33.3, 38.1, 56.0, 56.1, 70.8, 75.6, 78.2, 98.3, 102.9, 107.7, 111.1, 112.1, 114.1, 126.1, 136.7, 147.2, 148.9, 150.1, 150.3, 151.2, 153.5, 165.8 ppm. |
| 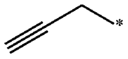 | 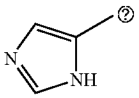 (?) indicates text missing or illegible when filed | —$CH_3$ | 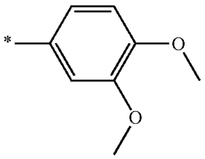 | 8-(3,4-Dimethoxyphenylethynyl)-3-(3H-imidazol-4-ylmethyl)-7-methyl-1-prop-2-ynyl-3,7-dihydropurine-2,6-dione 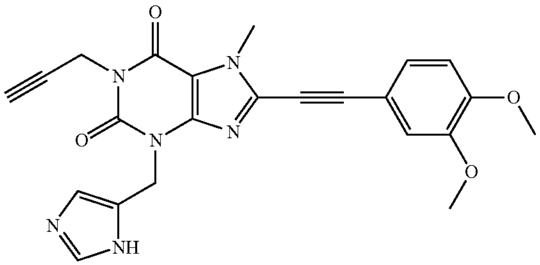 | MW 444.5, colorless crystals. $^1$H-NMR(DMSO-$D_6$, 500 MHz): δ 3.08 (t, J = 2.5 Hz, 1H, CCH), 3.80(s, 3H, $OCH_3$), 3.81(s, 3H, $OCH_3$), 3.99(s, 3H, N7$CH_3$), 4.60(d, J = 2.5 Hz, 2H, N1$CH_2$CC), 5.07(s, 2H, N3$CH_2$), 6.94(s, 1H, $H_{imidazol}$), 7.04(d, J = 8 Hz, 1H, $H_{phenyl}$), 7.26 (d, J = 1.9 Hz, 1H, $H_{phenyl}$), 7.29 (dd, J = 1.9/8 Hz, 1H, $H_{phenyl}$), 7.50 (s, 1H, $H_{imidazol}$), 11.90(s, 1H, NH) ppm. $^{13}$C-NMR: δ 30.3, 33.1, 41.0, 55.8, 55.9, 73.1, 76.3, 79.6, 97.2, 107.7, 111.6, 112.1, 113.9, 114.8, 125.9, 134.9, 135.6, 136.0, 147.6, 148.9, 149.8, 151.1, 153.2 ppm. |

TABLE 1-continued

| $R^1$ | $R^2$ | $R^3$ | $R^4$ | Name | MW/m.p./NMR |
|---|---|---|---|---|---|
| 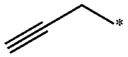 | 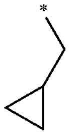 | —$CH_3$ | 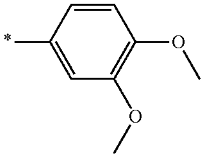 | 3-Cyclopropylmethyl-8-(3,4-dimethoxyphenylethynyl)-7-methyl-1-prop-2-ynyl-3,7-dihydropurine-2,6-dione 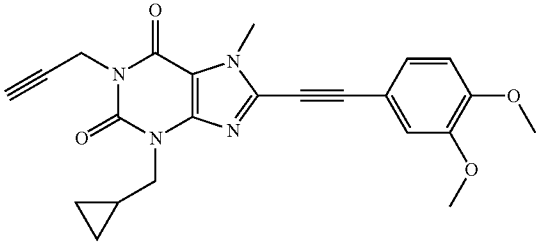 | MW 418.4, colorless crystals. $^1$H-NMR($CDCl_3$, 500 MHz): δ 0.49(m, 4H, $H_{cyclopropyl}$), 1.37(m, 1H, $H_{cyclopropyl}$), 2.17(t, J = 2.55 Hz, 1H, CH), 3.88(s, 3H, $OCH_3$), 3.90(s, 3H, $OCH_3$), 4.00(d, J = 7.25 Hz, 2H, N3$CH_2$), 4.07(s, 3H, N7$CH_3$), 4.79(d, J = 2.55 Hz, 2H, N1C$\underline{H}_2$CC), 6.85(d, J = 8.6 Hz, 1 H), 7.07(d, J = 1.9 Hz, 1 H), 7.22 (dd, J = 1.9/8.6 Hz, 1 H) ppm. $^{13}$C-NMR: δ 3.9, 10.0, 30.5, 33.2, 48.1, 55.9, 56.0, 70.6, 76.9, 78.7, 97.8, 107.8, 111.1, 112.3, 114.4, 126.1, 136.4, 148.2, 148.9, 150.1, 151.1, 153.9 ppm. |
| 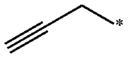 | 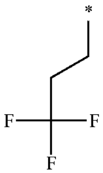 | —$CH_3$ | 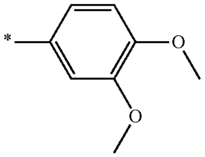 | 8-(3,4-Dimethoxyphenylethynyl)-7-methyl-1-prop-2-ynyl-3-(3,3,3-trifluoropropyl)-3,7-dihydropurine-2,6-dione 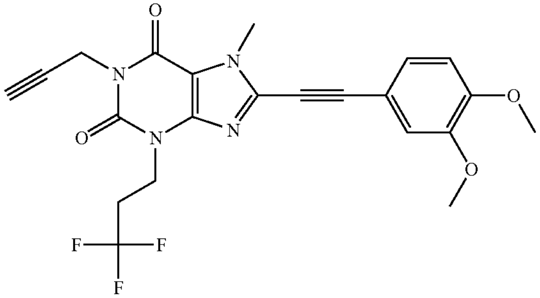 | MW 460.4, colorless crystals. $^1$H-NMR($CDCl_3$, 500 MHz): δ 2.18(t, J = 2.5 Hz, 1H, CCH), 2.65(m, 2H, $CH_2$), 3.89(s, 3H, $OCH_3$), 3.91(s, 3H, $OCH_3$), 4.07(s, 3H, N7$CH_3$), 4.39(m, 2H, $CH_2$), 4.77(d, J = 2.5 Hz, 2H, N1C$\underline{H}_2$CC), 6.86(d, J = 8.6 Hz, 1 H), 7.08(d, J = 1.9 Hz, 1 H), 7.23(dd, J = 1.9/8.6 Hz, 1 H) ppm. $^{13}$C-NMR: δ 30.6, 31.9(q, J = 29 Hz), 33.3, 36.87(q, J = 4 Hz), 56.0, 56.1, 70.7, 75.6, 78.3, 98.2, 107.8, 111.1, 112.2, 114.4, 125.7 (q, J = 277 Hz), 126.1, 136.7 147.3, 148.9, 150.1, 151.2, 153.6 ppm. |
| 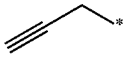 | —$C_2H_5$ | —$CH_3$ | 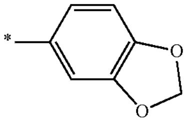 | 3-Ethyl-7-methyl-8-(3,4-methylenedioxyphenylethynyl)-1-prop-2-ynyl-3,7-dihydropurine-2,6-dione 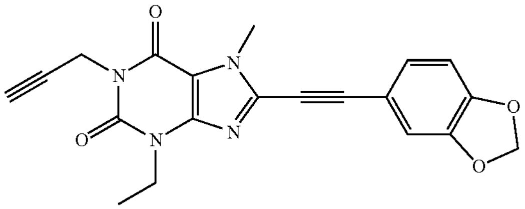 | MW 362.35, colorless crystals. $^1$H NMR($CDCl_3$): 1.34(t, J = 7.25 Hz, 3H, $CH_2C\underline{H}_3$), 2.17(t, J = 2.5 Hz, 1 H), 4.05(s, 3H, N7$CH_3$), 4.17(q, J = 7.25 Hz, $C\underline{H}_2CH_3$), 4.77(d, J = 2.5 Hz, 2H, N1$CH_2$CC), 6.01(s, 2H, $O_2CH_2$), 6.81(d, J = 7.9 Hz, 1 H), 7.00(d, J = 1.6 Hz, 1 H), 7.14 (dd, J = 1.6 and 7.9) ppm. $^{13}$C NMR($CDCl_3$): 13.3, 30.5, 33.2, 38.8, 70.5, 75.6, 78.6, 97.6, 101.7($O_2CH_2$), 107.8, 108.8, 111.7, 113.4, 127.6, 136.4, 147.7, 147.8, 149.6, 150.1, 153.8 ppm. |

TABLE 1-continued

| $R^1$ | $R^2$ | $R^3$ | $R^4$ | Name | MW/m.p./NMR |
|---|---|---|---|---|---|
| 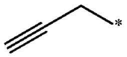 | 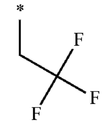 | —$CH_3$ | 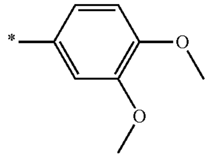 | 8-(3,4-Dimethoxyphenylethynyl)-7-methyl-1-prop-2-ynyl-3-(2,2,2-trifluoroethyl)-3,7-dihydropurine-2,6-dione 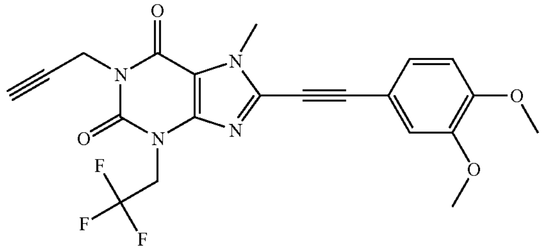 | MW 446.4, colorless crystals. $^1$H-NMR($CDCl_3$, 500 MHz): δ 2.19(t, J = 2.5 Hz, 1H, CCH), 3.89(s, 3H, $OCH_3$), 3.91(s, 3H, $OCH_3$), 4.07 (s, 3H, $N7CH_3$), 4.76(m, 2H, $N3CH_2$), 4.78(d, J = 2.5 Hz, 2H, $N1C\underline{H}_2CC$), 6.86(d, J = 8.55 Hz, 1 H), 7.07(d, J = 1.9 Hz, 1 H), 7.23 (dd, J = 1.9/8.55 Hz, 1 H) ppm. $^{13}$C-NMR: δ 30.9, 33.3, 43.6(q, J = 36 Hz), 56.0, 56.1, 70.9, 75.5, 78.1, 98.4, 107.7, 111.1, 112.1, 114.4, 123.5(q, J = 281 Hz), 126.2, 136.6, 147.1, 148.9, 150.2, 151.3, 153.4 ppm. |
| 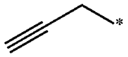 | —$C_2H_5$ | —$CH_3$ | 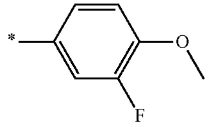 | 3-Ethyl-8-(3-fluoro-4-methoxyphenylethynyl)-7-methyl-1-prop-2-ynyl-3,7-dihydropurine-2,6-dione 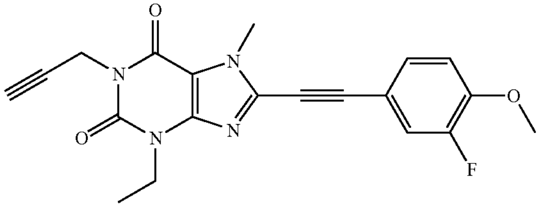 | MW 380.4, colorless crystals, m.p. ° C. $^1$H NMR(500 MHz, $CDCl_3$): δ = 1.35(t, J = 7.25 Hz, 3H, $CH_2C\underline{H}_3$), 2.17(t, J = 2.5 Hz, 1H, CCH), 3.92(s, 3H, $OCH_3$), 4.06(s, 3H, $N7CH_3$), 4.18(q, J = 7.25 Hz, 2H, $C\underline{H}_2CH_3$), 4.78(d, J = 2.5 Hz, 2H, $C\underline{H}_2CC$), 6.95(t, J = 8.5 Hz, 1 H), 7.31(dd, J = 2/11 Hz, 1 H), 7.36(ddd, J = 1.3/2/8.5 Hz, 1 H) ppm. $^{13}$C NMR(125 MHz, $CDCl_3$): δ = 13.3, 30.5, 33.2, 38.8, 56.2 ($OCH_3$), 70.5, 76.4, 78.6, 96.25(d, J = 2.5 Hz), 107.9, 112.5(d, J = 8.5 Hz), 113.28(d, J = 2 Hz), 119.5(d, J = 20 Hz), 129.2(d, J = 3 Hz), 136.1, 147.7, 149.8(d, J = 11 Hz), 150.1, 151.7, 153.8, ppm. |

TABLE 1-continued

| $R^1$ | $R^2$ | $R^3$ | $R^4$ | Name | MW/m.p./NMR |
|---|---|---|---|---|---|
| 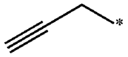 | —$CH_3$ | —$CH_3$ | 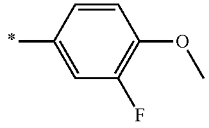 | 8-(3-Fluoro-4-methoxphenylethynyl)-3,7-dimethyl-1-prop-2-ynyl-3,7-dihydropurine-2,6-dione 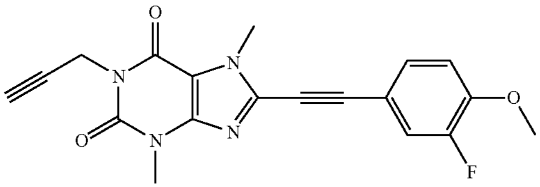 | MW 366.4, colorless crystals. $^1H$ NMR(500 MHz, $CDCl_3$): δ = 2.17 (t, J = 2.5 Hz, 1H, CCH), 3.58(s, 3H, $N3CH_3$), 3.92(s, 3H, $OCH_3$), 4.06(s, 3H, $N7CH_3$), 4.78(d, J = 2.5 Hz, 2H, $C\underline{H}_2CC$), 6.95(t, J = 8.5 Hz, 1 H), 7.29(dd, J = 2/11 Hz, 1 H), 7.32(ddd, J = 1.3/2/8.5 Hz, 1 H) ppm. $^{13}C$ NMR(125 MHz, $CDCl_3$): δ = 29.9, 30.6, 33.2, 56.3($OCH_3$), 70.6, 76.3, 78.5, 96.4(d, J = 2.5 Hz), 107.9, 112.5(d, J = 8 Hz), 113.3(d, J = 2 Hz), 119.5(d, J = 20 Hz), 129.2(d, J = 3 Hz), 136.1 148.2, 149.8(d, J = 11 Hz), 150.1, 151.0, 152.7, 153.8, ppm. |
| 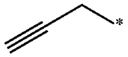 | —$C_2H_5$ | —$CH_3$ | 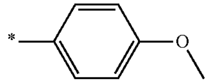 | 3-Ethyl-8-(4-methoxphenylethynyl)-7-methyl-1-prop-2-ynyl-3,7-dihydropurine-2,6-dione 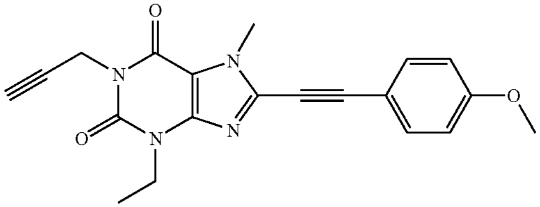 | MW 362.4, colorless crystals. $^1H$-NMR($CDCl_3$, 500 MHz): δ 1.35(t, J = 7.25 Hz, 3H, $NCH_2C\underline{H}_3$), 2.16 (t, J = 2.2 Hz, 1H, CCH), 3.83(s, 3H, $OCH_3$), 4.05(s, 3H, $N7CH_3$), 4.19(q, J = 7.25 Hz, 2H, $N3C\underline{H}_2CH_3$), 4.78(d, J = 2.2 Hz, 2H, $C\underline{H}_2CCH$), 6.90(m, J = 5/9 Hz, 2 H), 7.54(m, J = 5/9 Hz, 2 H) ppm. $^{13}C$-NMR: δ 13.4, 30.4, 33.2, 38.8, 55.4, 70.5, 76.0, 78.7, 97.8, 107.8, 112.3, 114.4, 133.8, 136.6, 147.8, 150.2, 153.9, 161.1 ppm. |
| 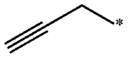 | —H | —CH3 | 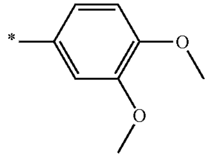 | 8-[(3,4-Dimethoxyphenyl)ethynyl]-7-methyl-1-prop-2-ynyl-3,7-dihydropurine-2,6-dione | MW 364.4, colorless solid, m.p. 279.7° C. 1H NMR(500 MHz, DMSO-d6): δ = 3.07(t, J = 2.2 Hz, 1H, CCH), 3.80(s, 3H, OCH3), 3.81(s, 3H, OCH3), 3.96(s, 3H, N7CH3), 4.55(d, J = 2.2 Hz, 2H, CH2—CCH), 7.05(d, J = 8.5 Hz, 1H, 6'H), 7.24(d, J = 1.9 Hz, 1H, 2'H), 7.28(dd, J = 1.9 and 8.2 Hz, 1H, 5'H) ppm. $^{13}C$ NMR): (125 MHz, DMSO-d6): δ = 29.4, 33.0 55.8(OCH3), 55.9 (OCH3), 72.9, 76.4, 79.7, 96.9, 107.2, 111.7, 112.1, 114.8, 125.9, 135.7, 147.0, 148.9, 150.2, 151.1, 153.9 ppm. |

TABLE 1-continued

| $R^1$ | $R^2$ | $R^3$ | $R^4$ | Name | MW/m.p./NMR |
|---|---|---|---|---|---|
| 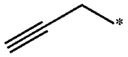 | —H | —$CH_3$ | 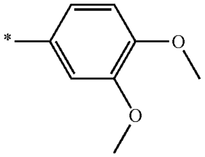 | 8-[(3,4-Dimethoxyphenyl)ethynyl]-7-methyl-1-prop-2-ynyl-3,7-dihydro-1H-purine-2,6-dione 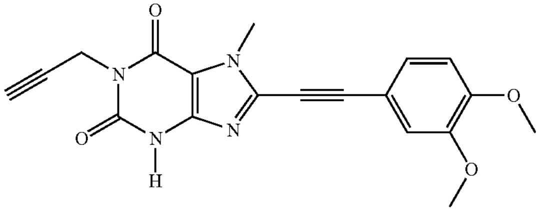 | MW 364.6, colorless solid, m.p. 279.7° C. $^1H$ NMR(500 MHz, DMSO-$d_6$): δ = 3.07(t, J = 2.2 Hz, 1H, CCH), 3.80(s, 3H, $OCH_3$), 3.81(s, 3H, $OCH_3$), 3.96(s, 3H, N7$CH_3$), 4.55(d, J = 2.2 Hz, 2H, $CH_2$—CCH), 7.05(d, J = 8.5 Hz, 1H, 6'H), 7.24(d, J = 1.9 Hz, 1H, 2'H), 7.28(dd, J = 1.9 and 8.2 Hz, 1H, 5'H) ppm. $^{13}C$ NMR(125 MHz, DMSO-$d_6$): δ = 29.4, 33.0, 55.8($OCH_3$), 55.9 ($OCH_3$), 72.9, 76.4, 79.7, 96.9, 107.2, 111.7, 112.1, 114.8, 125.9, 135.7, 147.0, 148.9, 150.2, 151.1, 153.9 ppm. |
| 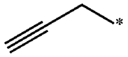 | 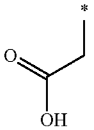 | —$CH_3$ | 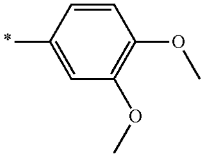 | 4-[8-(3,4-Dimethoxyphenylethynyl)-7-methyl-2,6-dioxo-1-prop-2-ynyl-1,2,6,7-tetrahydropurin-3-yl]acetic acid 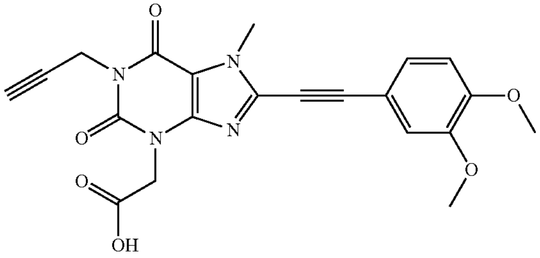 | MW 422.4, colorless crystals. $^1H$ NMR(500 MHz, DMSO-$d_6$): δ = 3.06(t, J = 2.2 Hz, 1H, CCH), 3.80(s, 3H, $OCH_3$), 3.81(s, 3H, $OCH_3$), 3.99(s, 3H, N7$CH_3$), 4.14 (s, 2H, $CH_2CO_2Me$), 4.60(d, J = 1.3 Hz, 2H, $CH_2CCH$), 7.04(d, J = 8.2 Hz, 1 H), 7.27(d, J = 1.9 Hz, 1 H), 7.29(dd, J = 1.9 and 8.2 Hz, 1 H), 10.43(s, 1H, OH) ppm. $^{13}C$ NMR(125 MHz, DMSO-$d_6$): δ = 30.1, 33.1, 47.1, 55.8($OCH_3$), 55.9($OCH_3$), 72.9, 76.4, 79.8, 97.0, 106.9, 111.8, 112.1, 114.9, 125.9, 135.4, 148.6, 148.9, 150.2, 151.1, 153.4, 167.6($CO_2H$) ppm. ESI +Q1 m/z 423(M + $H^+$). |
| 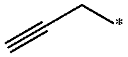 | 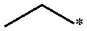 | —$CH_3$ | 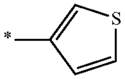 | 3-Ethyl-7-methyl-1-prop-2-ynyl-8-thiophen-3-ylethynyl-3,7-dihydropurine-2,6-dione 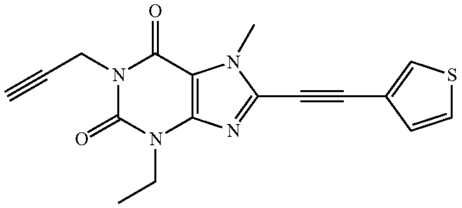 | MW 338.4, colorless crystals. $^1H$-NMR($CDCl_3$, 500 MHz): 1.34(t, J = 7.25 Hz, 3H, $CH_2CH_3$), 2.17(t, J = 2.2 Hz, 1H, CCH), 4.06(s, 3H, N7$CH_3$), 4.18(q, J = 7.25 Hz, 2H, $CH_2CH_3$), 4.78(d, J = 2.2 Hz, 2H, N1$CH_2$CC), 7.25(dd, J = 1.3/5.0 Hz, 1 H), 7.35(dd, J = 3.0/5.0 Hz, 1 H), 7.72(dd, J = 1.3/3.0 Hz, 1 H) ppm. |

TABLE 1-continued

| $R^1$ | $R^2$ | $R^3$ | $R^4$ | Name | MW/m.p./NMR |
|---|---|---|---|---|---|
| 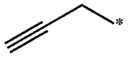 | 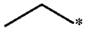 | —$CH_3$ | 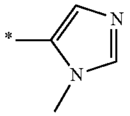 | 3-Ethyl-7-methyl-8-(3-methyl-3H-imidazol-4-ylethynyl)-1-prop-2-ynyl-3,7-dihydropurine-2,6-dione 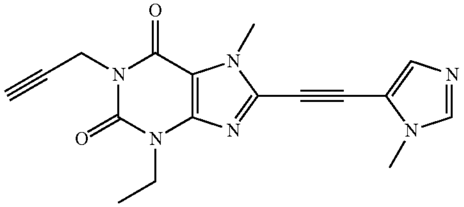 | MW 336.4, colorless crystals. $^1$H-NMR($CDCl_3$, 500 MHz): δ 1.34(t, J = 7.25 Hz, 3H, $CH_2C\underline{H}_3$), 2.17(t, J = 2.5 Hz, 1H, CCH), 3.77(s, 3H, $N_{imidazol}CH_3$), 4.09(s, 3H, $N7CH_3$), 4.17(q, J = 7.25 Hz, 2H, $C\underline{H}_2CH_3$), 4.78(d, J = 2.5 Hz, 2H, $N1C\underline{H}_2CC$), 7.51(br s, 1 H), 7.55 (br s, 1 H) ppm. $^{13}$C-NMR: δ 13.3, 30.5, 32.5, 33.3, 38.9, 70.6, 78.5, 84.4, 85.4, 108.1, 114.1, 135.6, 137.9, 139.8, 147.8, 150.1, 153.9 ppm. |
| 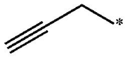 | 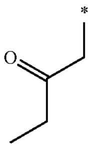 | —$CH_3$ | 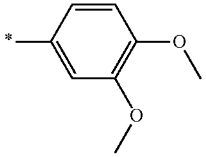 | 8-[(3,4-Dimethoxyphenyl)ethynyl]-7-methyl-3-(2-oxobutyl)-1-prop-2-ynyl-3,7-dihydropurine-2,6-dione 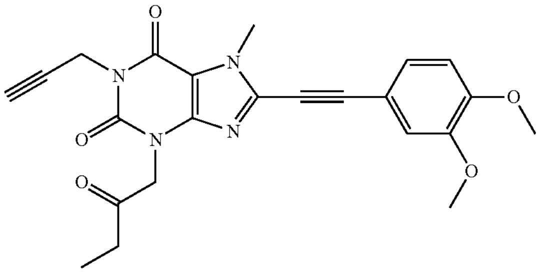 | MW 434.5, colorless crystals. $^1$H NMR(500 MHz, $CDCl_3$): δ = 1.12 (t, J = 7.3 Hz, 3H, $COCH_2CH_3$), 2.17(t, J = 2.5 Hz, 1H, CCH), 2.56(q, J = 7.3 Hz, 2H, $COCH_2CH_3$), 3.87(s, 3H, $OCH_3$), 3.91(s, 3H, $OCH_3$), 4.06(s, 3H, $N7CH_3$), 4.76(d, J = 2.5 Hz, 2H, $CH_2CCH$), 4.89(s, 2H, $CH_2CO$), 6.85(d, J = 8.5 Hz, 1 H), 7.05(d, J = 1.6 Hz, 1 H), 7.20(dd, J = 1.6 and 8.5 Hz, 1 H) ppm. $^{13}$C NMR(125 MHz, $CDCl_3$): δ = 7.3, 30.6, 33.2, 33.3, 50.9, 56.0 ($OCH_3$), 56.1($OCH_3$), 70.7, 75.6, 78.4, 98.0, 107.6, 111.1, 112.2, 114.4, 126.1, 136.5, 147.7, 148.9, 150.4, 151.2, 153.7, 202.9 ppm. |
| 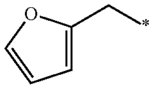 | 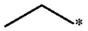 | —$CH_3$ | 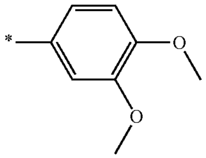 | 1-Furan-2-ylmethyl-8-(3,4-dimethoxyphenylethynyl)-3-ethyl-7-methyl-3,7-dihydropurine-2,6-dione 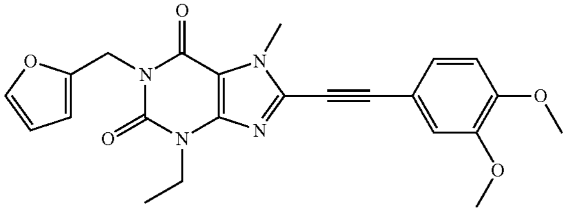 | MW 434.5, colorless crystals. $^1$H-NMR($CDCl_3$, 500 MHz): δ 1.33(t, J = 7 Hz, 3H, $CH_2C\underline{H}_3$), 3.88(s, 3H, $OCH_3$), 3.90(s, 3H, $OCH_3$), 4.07(s, 3H, $N7CH_3$), 4.16(q, J = 7 Hz, 2H, $N3C\underline{H}_2CH_3$), 5.20(s, 2H, $N1CH_2$), 6.28-6.29(m, 1 H), 6.38-6.39(m, 1 H), 6.85(d, J = 8.2 Hz, 1 H), 7.07(d, J = 1.9 Hz, 1 H), 7.22(dd, J = 1.9/8.2 Hz, 1 H), 7.32-7.33(m, 1 H) ppm. $^{13}$C-NMR(125 MHz, $CDCl_3$): δ = 13.3, 33.2, 37.2, 38.7, 55.9, 56.0, 75.9, 97.7, 107.9, 109.2, 110.3, 111.1, 112.4, 114.4, 126.0, 136.3, 142.1, 147.6, 148.9, 150.4, 150.6, 151.1, 154.4 ppm. |

TABLE 1-continued

| $R^1$ | $R^2$ | $R^3$ | $R^4$ | Name | MW/m.p./NMR |
|---|---|---|---|---|---|
| 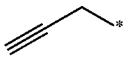 | 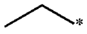 | —$CH_3$ | 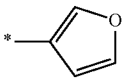 | 3-Ethyl-8-furan-3-ylethynyl-7-methyl-1-prop-2-ynyl-3,7-dihydropurine-2,6-dione 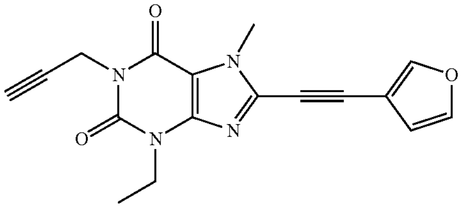 | MW 322.3, colorless crystals. $^1$H-NMR($CDCl_3$, 500 MHz): δ 1.34(t, J = 7.1 Hz, 3H, $CH_2CH_3$), 2.17(t, J = 2.5 Hz, 1H, CCH), 4.04(s, 3H, N7$CH_3$), 4.17(q, J = 7.1 Hz, 2H, $CH_2CH_3$), 4.78(d, J = 2.5 Hz, 2H, N1$CH_2$CC), 6.57(dd, J = 0.8/1.9 Hz, 1 H), 7.44(t, J = 1.7 Hz, 1 H), 7.81(dd, J = 0.8/1.6 Hz, 1 H) ppm. |
| 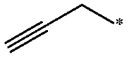 | 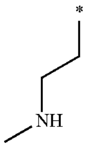 | —$CH_3$ | 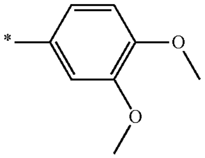 | -[(3,4-Dimethoxyphenyl)ethynyl]-7-methyl-3-[2-(methylamino)ethyl]-1-prop-2-ynyl-3,7-dihydropurine-2,6-dione 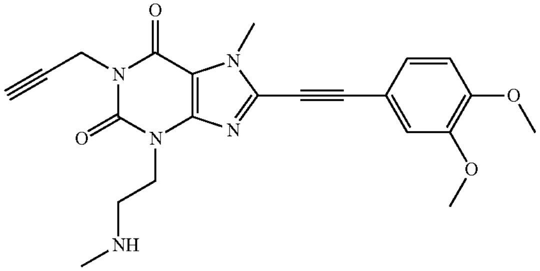 | MW 421.5, colorless crystals. $^1$H NMR(500 MHz, $CDCl_3$): δ = 1.23 (s, 1H, N$H$CH_3$), 1.94(t, J = 3.5 Hz, 3H, NH$CH_3$), 2.17(t, J = 2.2 Hz, 1H, CCH), 3.44(t, J = 6.0 Hz, 2 H), 3.89(s, 3H, $OCH_3$), 3.91(s, 3H, $OCH_3$), 4.07(s, 3H, N7$CH_3$), 4.16(t, J = 6.3 Hz, 2 H), 4.78(d, J = 2.5 Hz, 2H, $CH_2$CCH), 6.86(d, J = 8.5 Hz, 1 H), 7.08(d, J = 1.9 Hz, 1 H), 7.22(dd, J = 1.9 and 8.5 Hz, 1 H) ppm. $^{13}$C NMR(125 MHz, $CDCl_3$): δ = 26.8, 29.8, 30.5, 33.2, 42.6, 56.0 ($OCH_3$), 56.1($OCH_3$), 70.6, 75.8, 78.5, 98.0, 107.7, 111.1, 112.3, 114.4, 126.1, 136.5, 147.9, 148.9, 150.4, 151.2, 153.8 ppm. ESI +Q1 m/z 422(M + $H^+$). |

TABLE 2a
| Structure | Rat $A_1$ AR rat cortex [$^3$H] CCPA $K_i$ [nM] | Rat $A_{2A}$ AR rat striatum [$^3$H] MSX-2 $K_i$ [nM] |
|---|---|---|
| Comparative Example 1 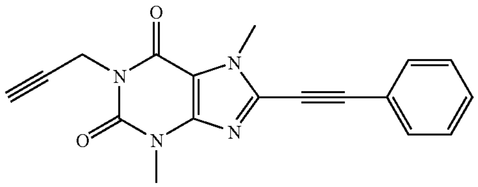 | >1000 | 186 ± 60<br>300 ± 7* |
| Comparative Example 2 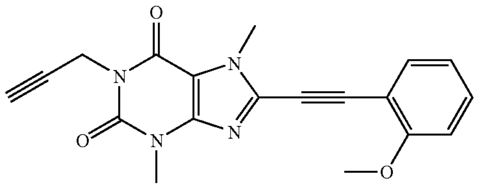 | >10000 | >10000 |
| Comparative Example 3 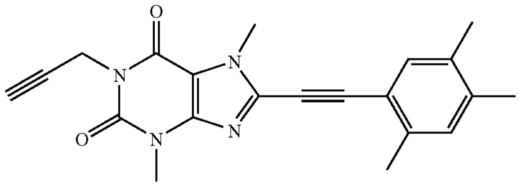 | >10000 | 4340 ± 840 |
| 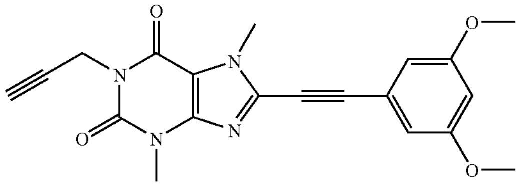 | >10000 | 190 ± 50 |
| 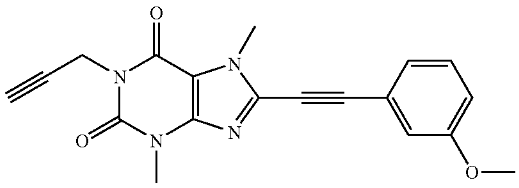 | >10000 | 30.9 ± 8.0 |
| 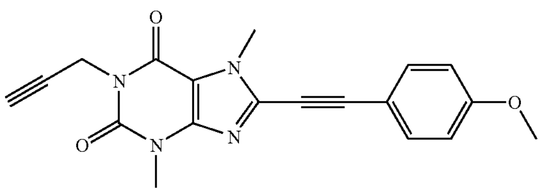 | >10000 | 123 ± 38 |
| 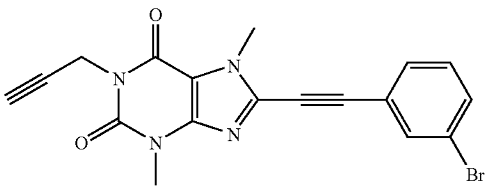 | ≧10000 | 151 ± 19 |

TABLE 2a-continued
| Structure | Rat $A_1$ AR rat cortex [$^3$H] CCPA $K_i$ [nM] | Rat $A_{2A}$ AR rat striatum [$^3$H] MSX-2 $K_i$ [nM] |
|---|---|---|
| 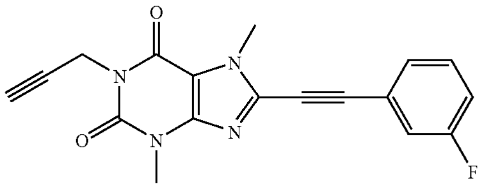 | >10000 | 466 ± 36 |
| 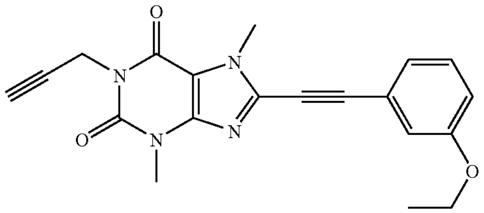 | ca. 10000 | 174 ± 42 |
| 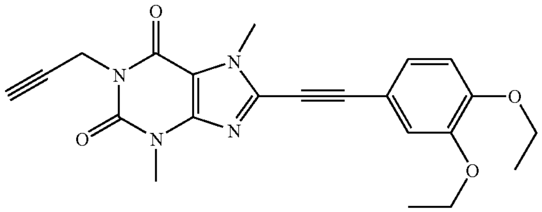 | >1000 | 951 ± 224 |
| 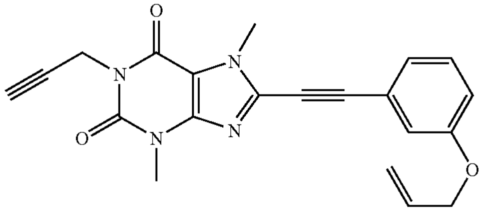 | ≧10000 | 152 ± 63 |
| 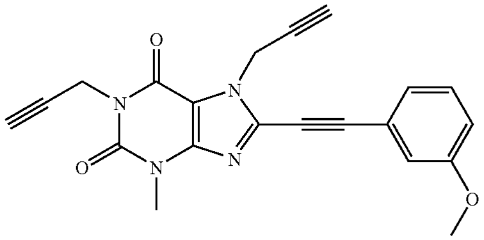 | ≧10000 | 90.0 ± 35.7 |
| 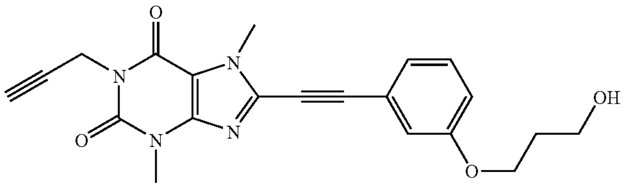 | ≧10000 | 211 ± 46 |
| 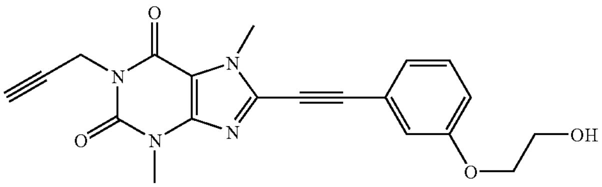 | ≧10000 | 117 ± 25 |

TABLE 2a-continued
| Structure | Rat $A_1$ AR rat cortex [$^3$H] CCPA $K_i$ [nM] | Rat $A_{2A}$ AR rat striatum [$^3$H] MSX-2 $K_i$ [nM] |
| --- | --- | --- |
| 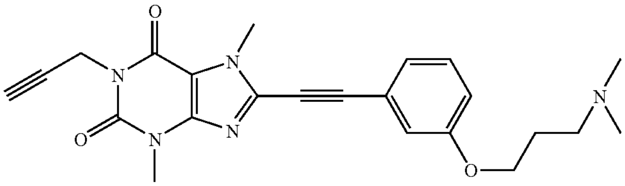 | 186 ± 3 | 40 ± 1 |
| 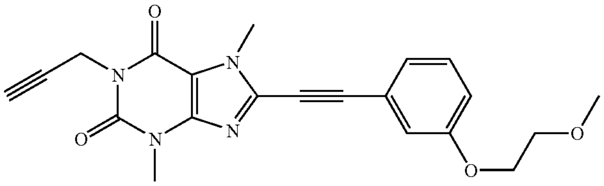 | ≧10000 | 219 ± 52 |
| 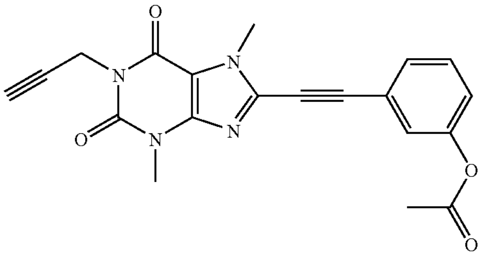 | 1170 ± 731 | 140 ± 12 |
| 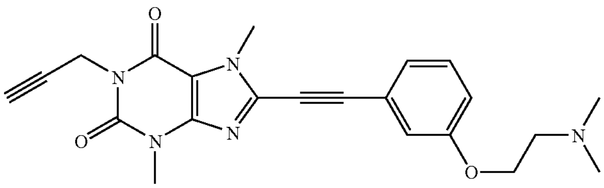 | 194 ± 33 | 49 ± 5 |
| 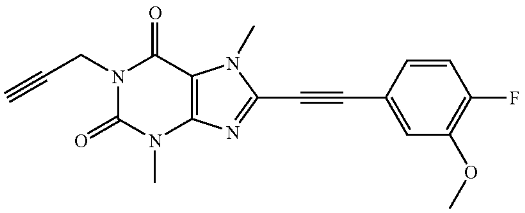 | >1000 | 70.3 ± 5.39 |
| 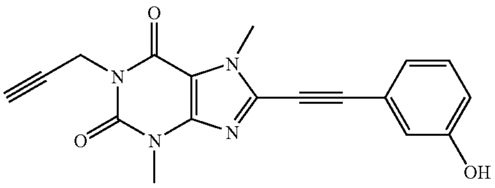 | 425 ± 99 | 173 ± 35 |
| 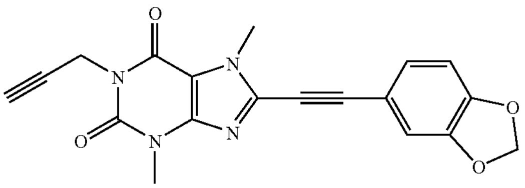 | >10000 | 166 ± 34 |

TABLE 2a-continued
| Structure | Rat $A_1$ AR rat cortex [$^3$H] CCPA $K_i$ [nM] | Rat $A_{2A}$ AR rat striatum [$^3$H] MSX-2 $K_i$ [nM] |
|---|---|---|
| 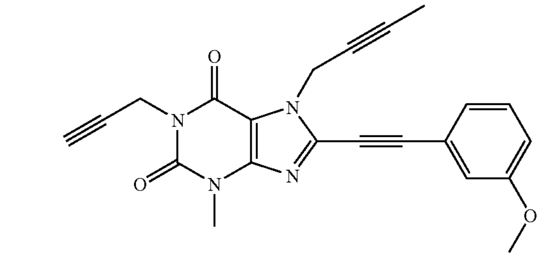 | 96.0 ± 16.4 | 36.2 ± 4.5 |
| 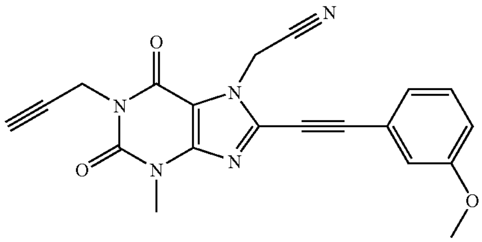 | >1000 | 56.2 ± 12.9 |
| 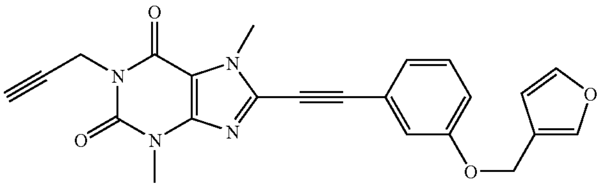 | >1000 | 66.4 ± 19.0 |
| 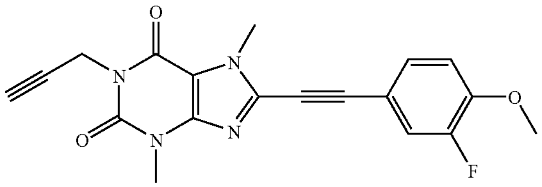 | >1000 | 194 ± 39 |
| 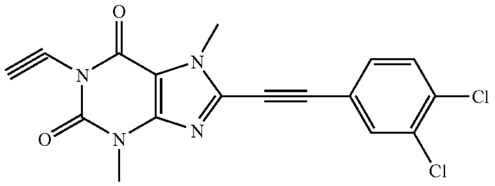 | >1000 | >1000 |
| 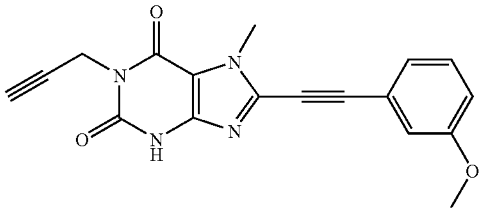 | >1000 | 135 ± 28 |
| 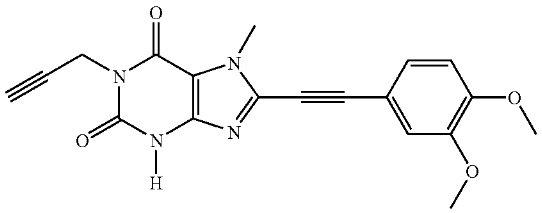 | ≧10000 | 15 ± 2 |

TABLE 2a-continued
| Structure | Rat $A_1$ AR rat cortex [$^3$H] CCPA $K_i$ [nM] | Rat $A_{2A}$ AR rat striatum [$^3$H] MSX-2 $K_i$ [nM] |
|---|---|---|
| 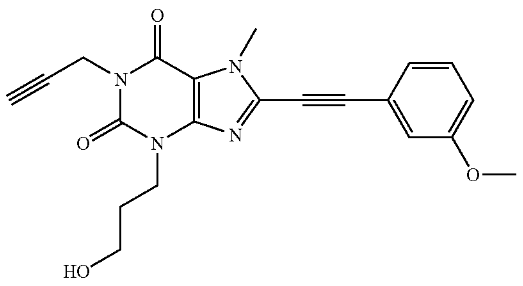 | 142 ± 8 | 11.8 ± 1.6 |
| 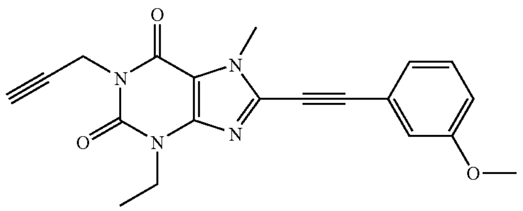 | >10000 | 49.9 ± 9.7 |
| 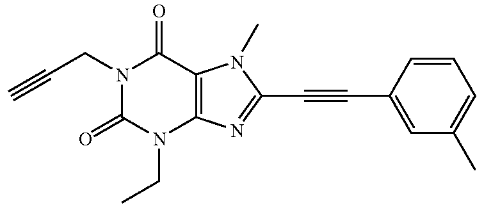 | >10000 | 76.3 ± 17.1 |
| 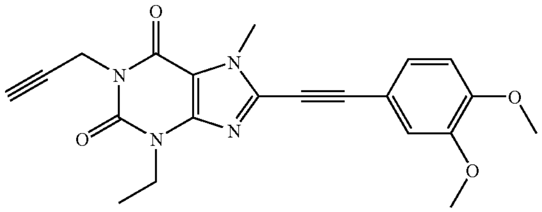 | >>3000 | 47.2 ± 7.3 |
| 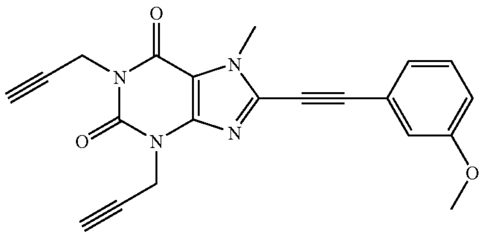 | >10000 | 80.7 ± 21.1 |
| 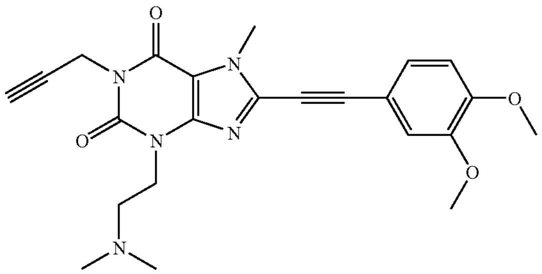 | 810 ± 145 | 54 ± 5 |

TABLE 2a-continued
| Structure | Rat $A_1$ AR rat cortex [$^3$H] CCPA $K_i$ [nM] | Rat $A_{2A}$ AR rat striatum [$^3$H] MSX-2 $K_i$ [nM] |
|---|---|---|
| 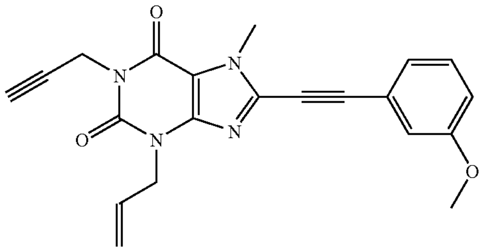 | >1000 | 41.8 ± 4.3 |
| 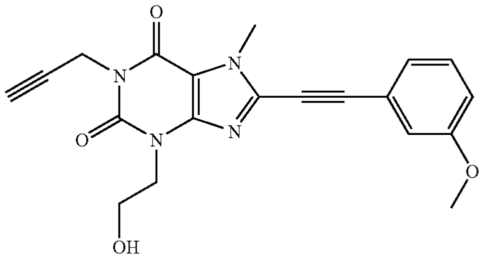 | >1000 | 103 ± 15 |
| 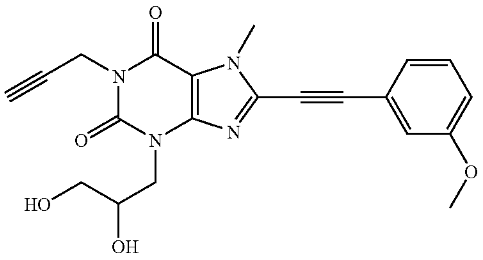 | >1000 | 69.8 ± 17.1 |
| 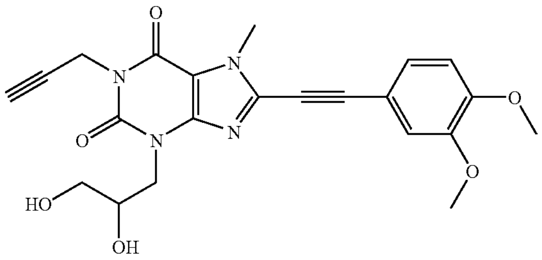 | ≧1000 | 42.3 ± 5.7 |
| 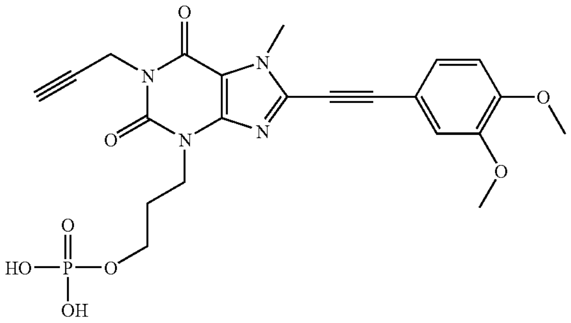 | 136 ± 19 | 37 ± 11 |

TABLE 2a-continued
| Structure | Rat $A_1$ AR rat cortex [$^3$H] CCPA $K_i$ [nM] | Rat $A_{2A}$ AR rat striatum [$^3$H] MSX-2 $K_i$ [nM] |
|---|---|---|
| 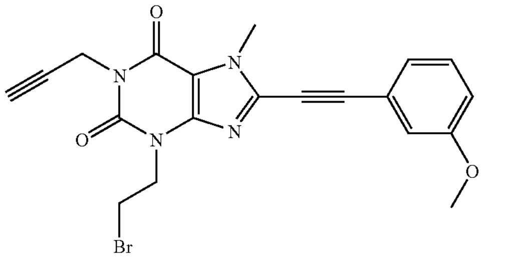 | >1000 | 90 ± 25 |
| 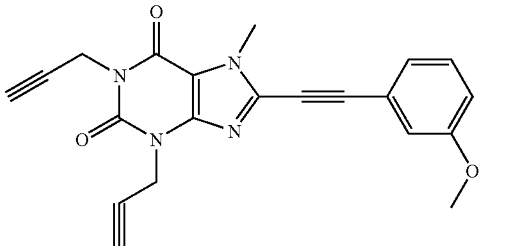 | >10000 | 80.7 ± 21.1 |
| 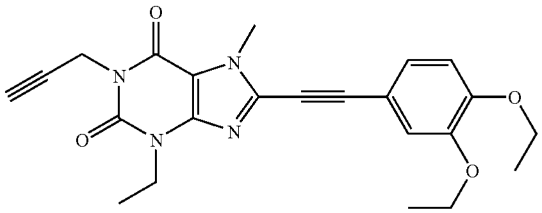 | >1000 | 166 ± 50 |
| 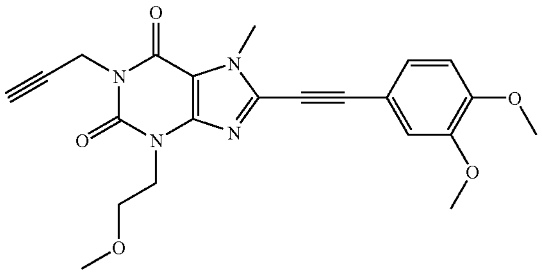 | >1000 | 45.9 ± 13.5 |
| 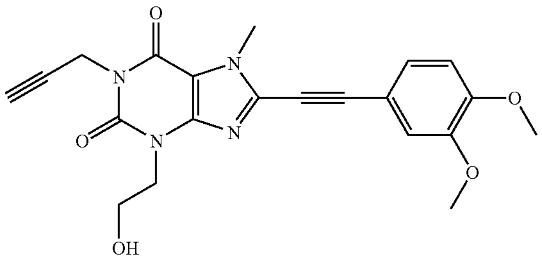 | >1000 | 45.5 ± 10.4 |

TABLE 2a-continued
| Structure | Rat $A_1$ AR rat cortex [$^3$H] CCPA $K_i$ [nM] | Rat $A_{2A}$ AR rat striatum [$^3$H] MSX-2 $K_i$ [nM] |
|---|---|---|
| 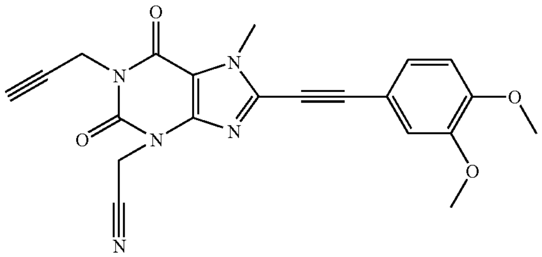 | >1000 | 40 ± 0.6 |
| 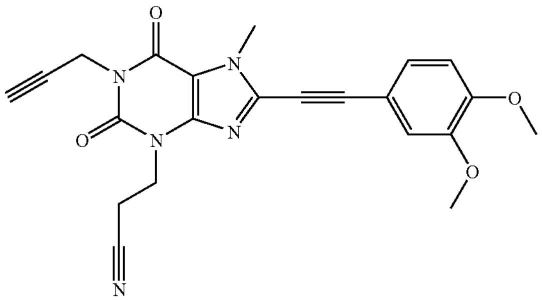 | >1000 | 76.4 ± 32.9 |
| 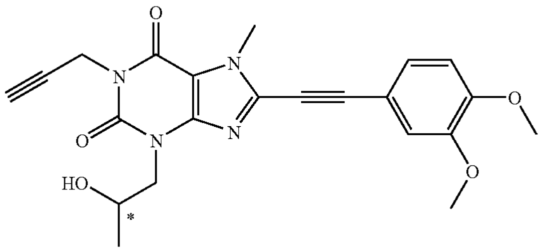 | 189 ± 33 | 13.3 ± 1.4 |
| 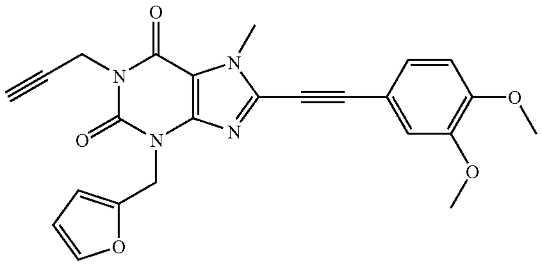 | 76.8 ± 22.9 | 6.74 ± 1.00 |
| 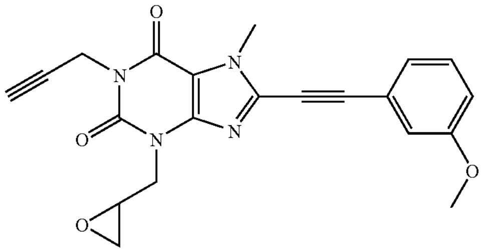 | >1000 | 38.2 ± 12.0 |

TABLE 2a-continued
| Structure | Rat $A_1$ AR rat cortex [$^3$H] CCPA $K_i$ [nM] | Rat $A_{2A}$ AR rat striatum [$^3$H] MSX-2 $K_i$ [nM] |
|---|---|---|
| 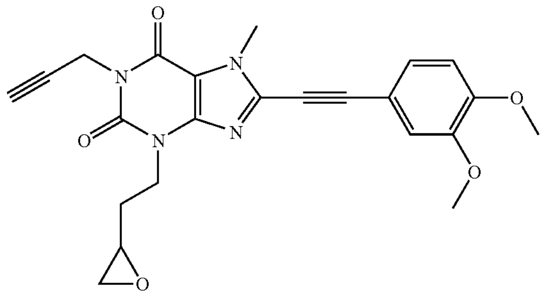 | 64 ± 5.4 | 19.2 ± 1.4 |
| 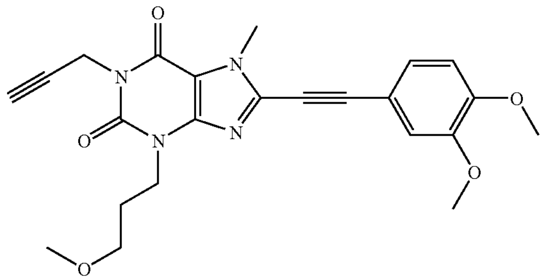 | >1000 | 44.0 ± 6.2 |
| 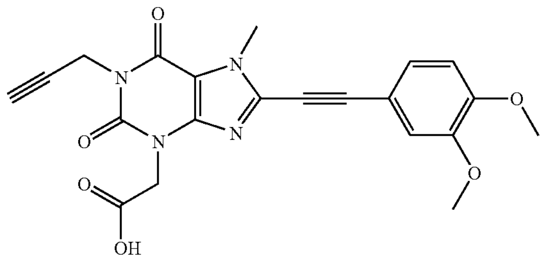 | >1000 (n = 1) | 272 ± 57 (n = 2) |
| 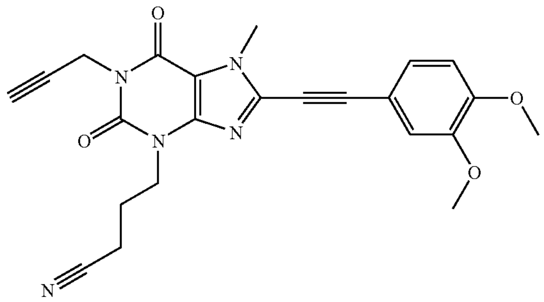 | >1000 | 22.9 ± 7.6 |
| 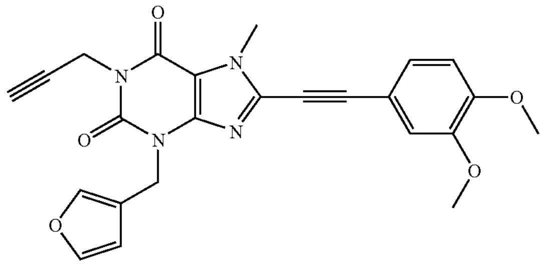 | >1000 | 5.16 ± 1.91 |

TABLE 2a-continued
| Structure | Rat $A_1$ AR rat cortex [$^3$H] CCPA $K_i$ [nM] | Rat $A_{2A}$ AR rat striatum [$^3$H] MSX-2 $K_i$ [nM] |
|---|---|---|
| 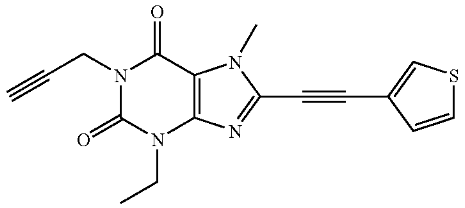 | >1000 | 108 ± 31 |
| 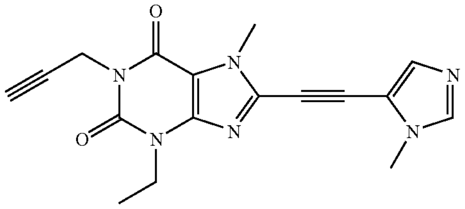 | 460 ± 61 | 119 ± 26 |
| 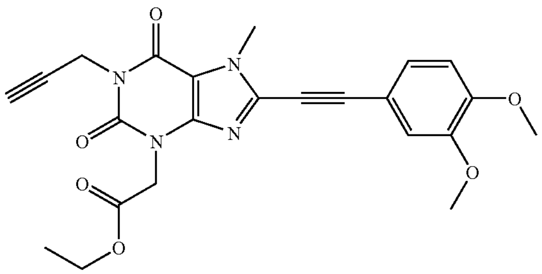 | ≧1000 | 167 ± 82 |
| 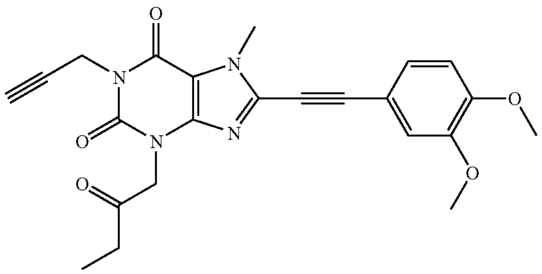 | >1000 | 91.7 ± 38.3 |
| 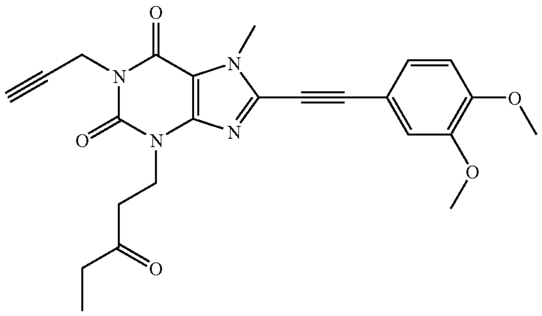 | 111 ± 26 | 103 ± 15 |
| 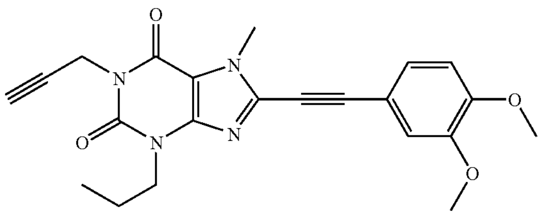 | ≧1000 | 13.4 ± 6.5 |

TABLE 2a-continued
| Structure | Rat $A_1$ AR rat cortex [$^3$H] CCPA $K_i$ [nM] | Rat $A_{2A}$ AR rat striatum [$^3$H] MSX-2 $K_i$ [nM] |
|---|---|---|
| 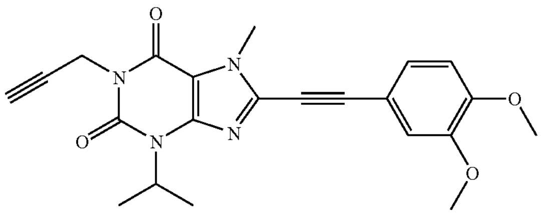 | ≧1000 | 118 ± 19 |
| 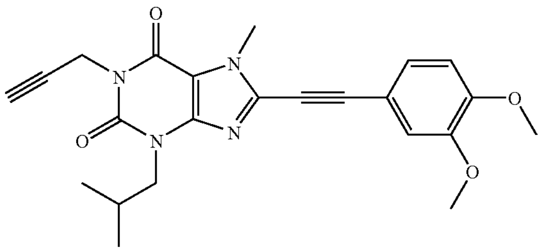 | ≧1000 | 5.54 ± 1.30 |
| 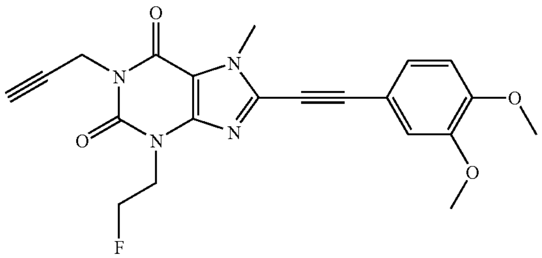 | ≧1000 | 9.99 ± 0.70 |
| 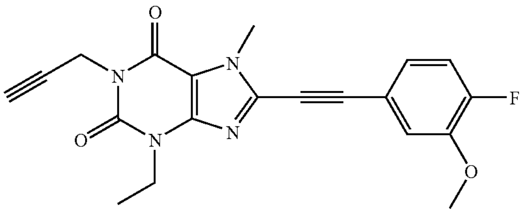 | >1000 | 43.1 ± 13.2 |
| 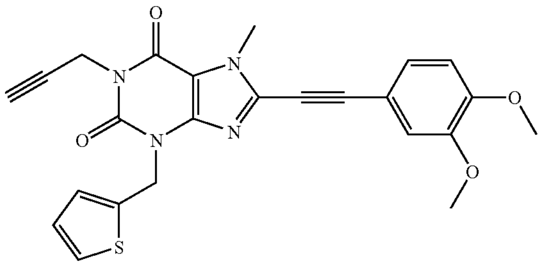 | >1000 | 103 ± 21 |
| 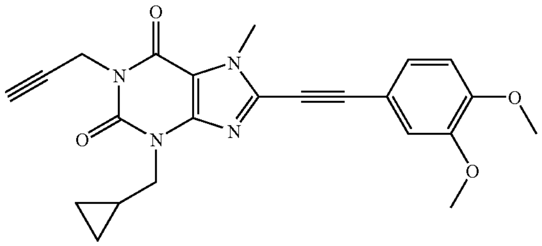 | >1000 | 10.2 ± 4.2 |

TABLE 2a-continued
| Structure | Rat $A_1$ AR rat cortex [$^3$H] CCPA $K_i$ [nM] | Rat $A_{2A}$ AR rat striatum [$^3$H] MSX-2 $K_i$ [nM] |
|---|---|---|
| 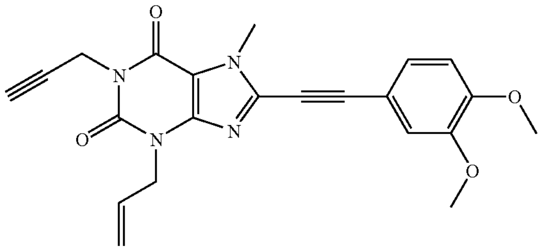 | >1000 | 9.5 ± 1.6 |
| 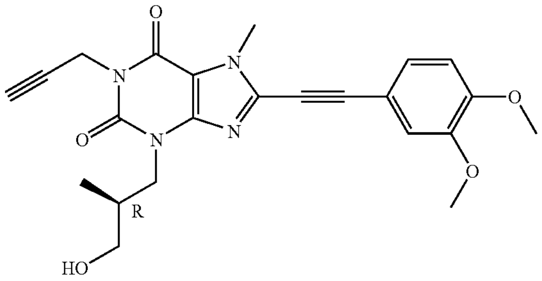 | 146 ± 46 | 1.83 ± 0.38 |
| 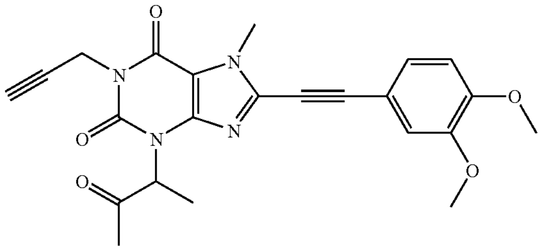 | 157 ± 12 | 16 ± 6 |
| 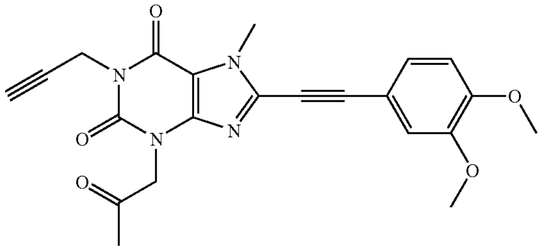 | >1000 | 18.5 ± 5 |
| 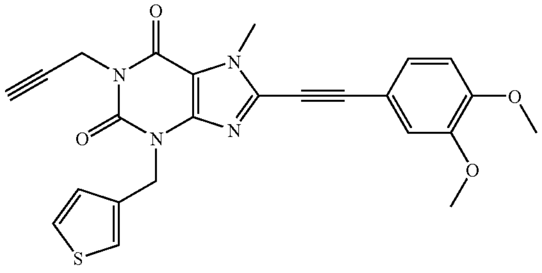 | >1000 | 28.0 ± 4.2 |

TABLE 2a-continued
| Structure | Rat $A_1$ AR rat cortex [$^3$H] CCPA $K_i$ [nM] | Rat $A_{2A}$ AR rat striatum [$^3$H] MSX-2 $K_i$ [nM] |
|---|---|---|
| 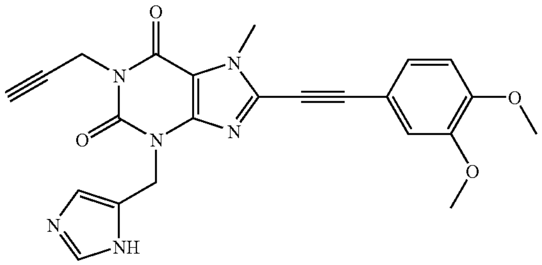 | >1000 | 28.8 ± 4.1 |
| 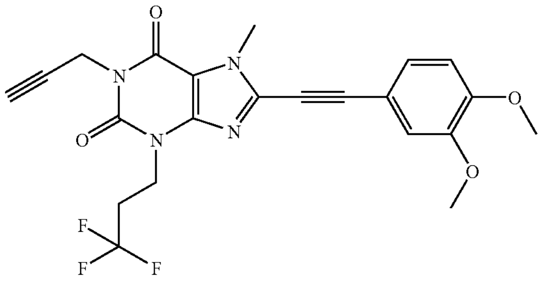 | 234 ± 47 | 24.2 ± 3.8 |
| 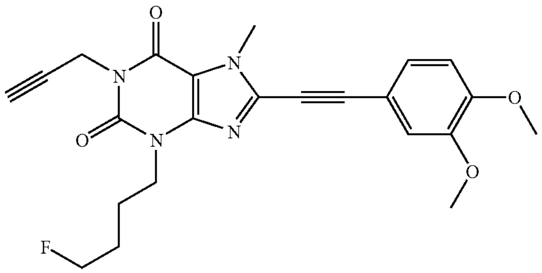 | 209 ± 42 | 11.7 ± 1.7 |
| 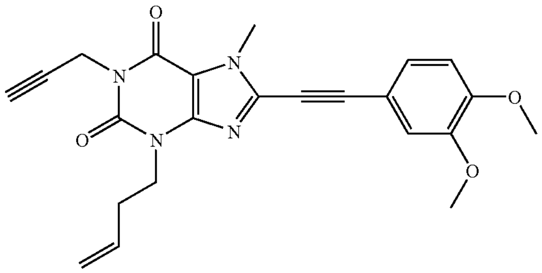 | 176 ± 59 | 34.9 ± 6.9 |
| 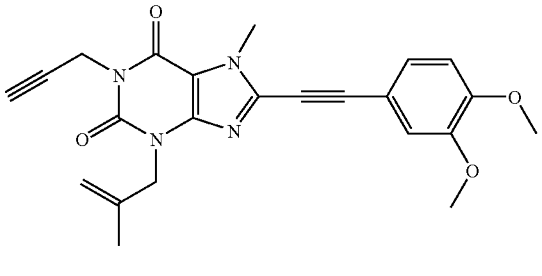 | >1000 | 28.6 ± 9.7 |

TABLE 2a-continued
| Structure | Rat $A_1$ AR rat cortex [$^3$H] CCPA $K_i$ [nM] | Rat $A_{2A}$ AR rat striatum [$^3$H] MSX-2 $K_i$ [nM] |
|---|---|---|
| 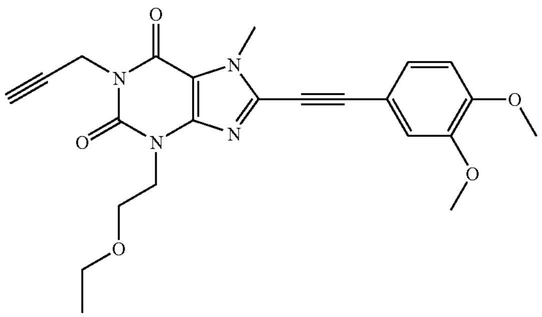 | >1000 | 35.6 ± 14.1 |
| 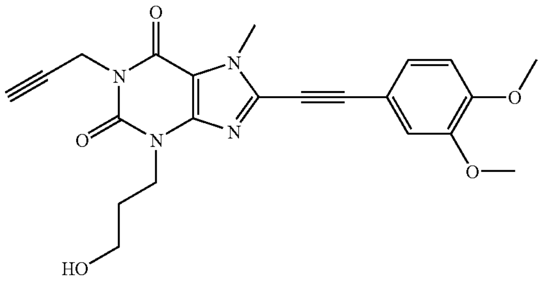 | 337 ± 67 | 30.1 ± 5.4 |
| 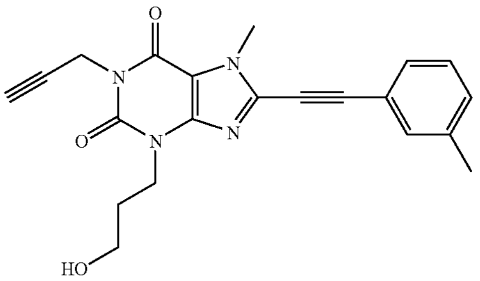 | 467 ± 6 | 47 ± 2 |
| 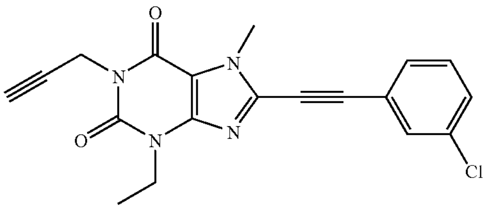 | 488 ± 253 | 141 ± 28 |
| 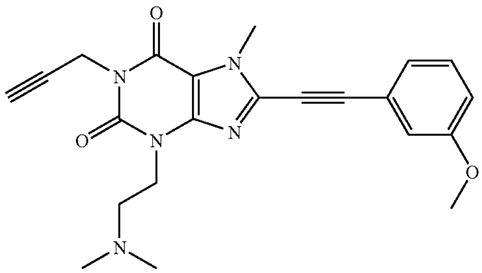 | >1000 | 161 ± 35 |

TABLE 2a-continued
| Structure | Rat $A_1$ AR rat cortex [$^3$H] CCPA $K_i$ [nM] | Rat $A_{2A}$ AR rat striatum [$^3$H] MSX-2 $K_i$ [nM] |
|---|---|---|
| 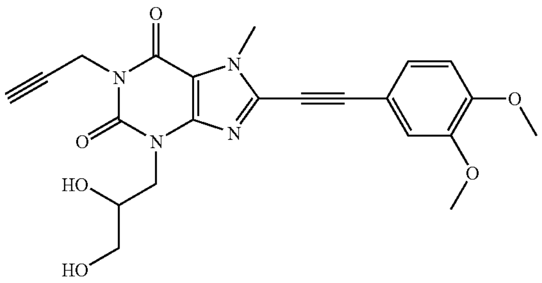 | >1000 | 42.3 ± 5.7 |
| 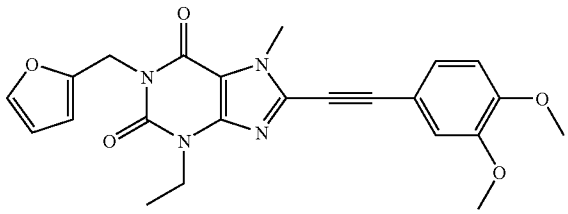 | 208 ± 54 | 90.9 ± 7.0 |
| 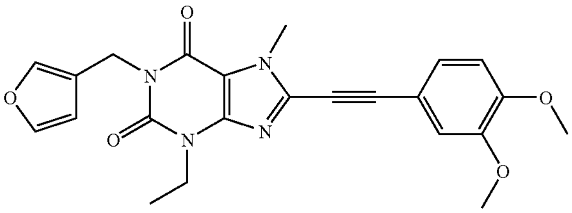 | 1252 ± 106 | 90.7 ± 11.2 |
| 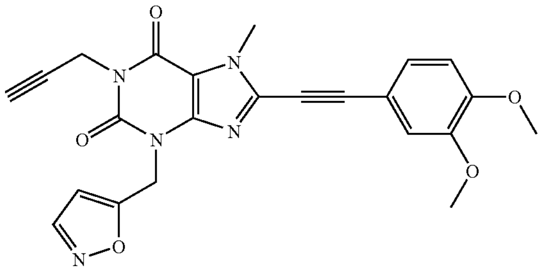 | >1000 | 17.9 ± 5.5 |
| 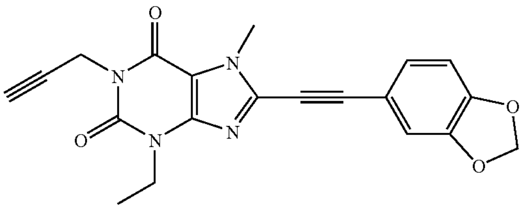 | >1000 | 29.6 ± 6.1 |
| 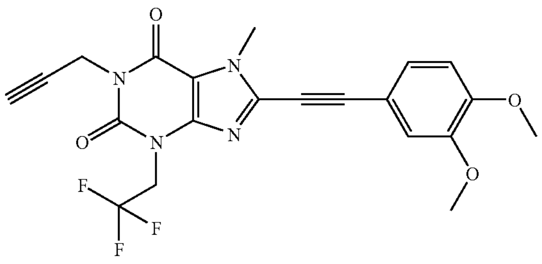 | ≧1000 | 12.7 ± 2.8 |

TABLE 2a-continued
| Structure | Rat $A_1$ AR rat cortex [$^3$H] CCPA $K_i$ [nM] | Rat $A_{2A}$ AR rat striatum [$^3$H] MSX-2 $K_i$ [nM] |
|---|---|---|
| 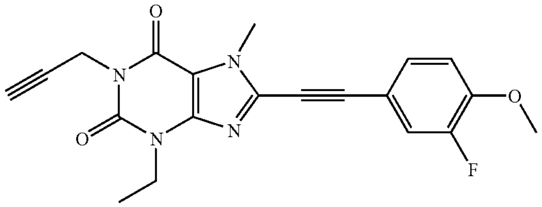 | ≧1000 | 52.6 ± 19.5 |
| 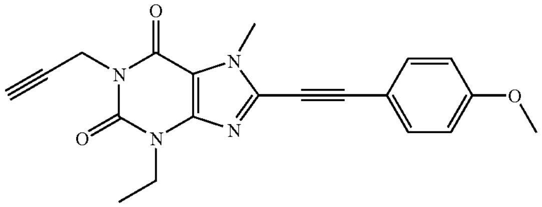 | >1000 | 28.6 ± 13.3 |
| 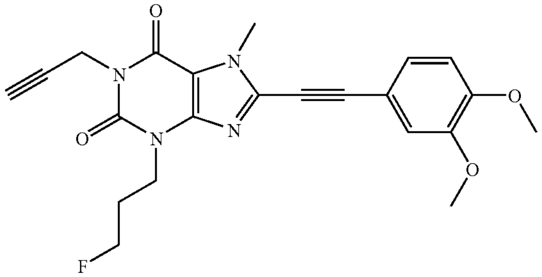 | ≧1000 | 16.3 ± 2.8 |
| 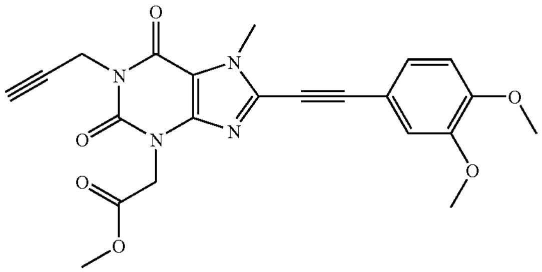 | 286 ± 11 | 36.5 ± 6.1 |
| 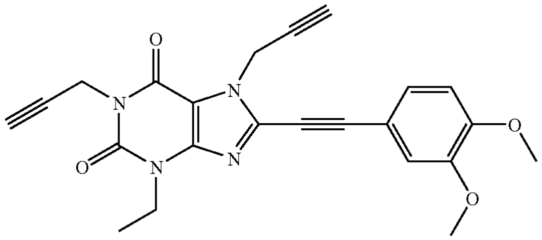 | >1000 | 132 ± 60 |
| 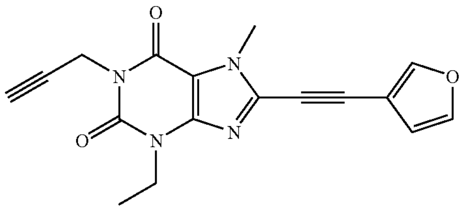 | >1000 | 220 ± 21 |

TABLE 2a-continued
| Structure | Rat $A_1$ AR rat cortex [$^3$H] CCPA $K_i$ [nM] | Rat $A_{2A}$ AR rat striatum [$^3$H] MSX-2 $K_i$ [nM] |
|---|---|---|
| 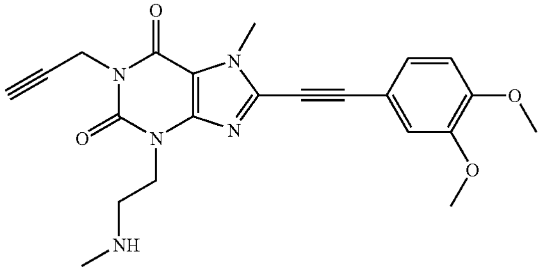 | ≧1000 | 134 ± 16 |
| 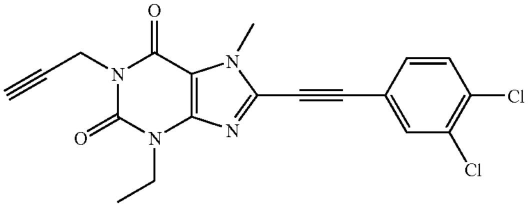 | >1000 | 132 ± 96 |
| 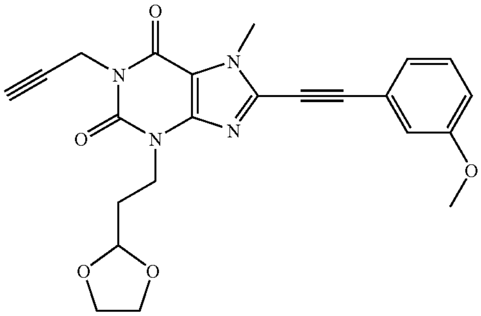 | ≧1000 | 120 ± 18 |
*Müller C.E. et al., Eur. J. Med. Chem. 1997, 32, 709-719.
TABLE 2b
| Structure | $A_1$ - ADENOSINE RECEPTOR HUMAN RECOMBINANT [$^3$H] CCPA $K_{i-}$ [nM] | $A_{2A}$ - ADENOSINE RECEPTOR HUMAN RECOMBINANT [$^3$H] MSX-2 $K_{i-}$ [nM] |
|---|---|---|
| Comparative Example 1 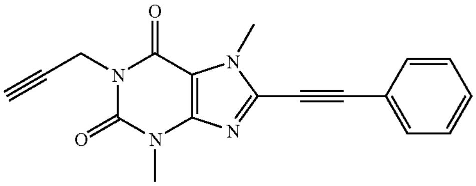 | — | 314 ± 71* |
| 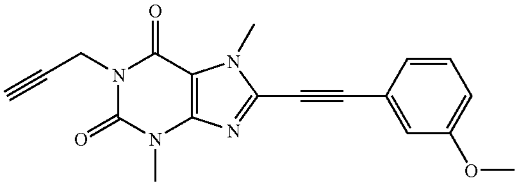 | >10000 | 608 ± 111 |

TABLE 2b-continued
| Structure | $A_1$ - ADENOSINE RECEPTOR HUMAN RECOMBINANT [$^3$H] CCPA $K_i$ [nM] | $A_{2A}$ - ADENOSINE RECEPTOR HUMAN RECOMBINANT [$^3$H] MSX-2 $K_i$ [nM] |
|---|---|---|
| 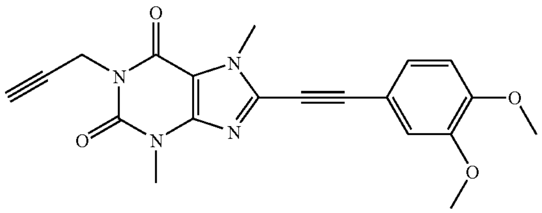 | >3000 | 36.4 ± 0.6 |
| 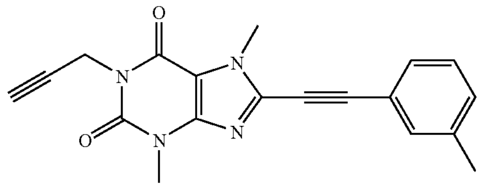 | >10000 | 225 ± 52 |
| 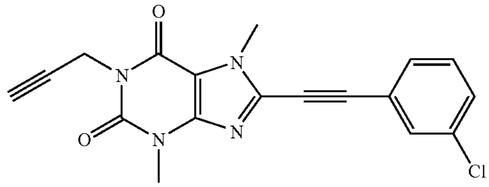 | >10000 | 423 ± 28 |
| 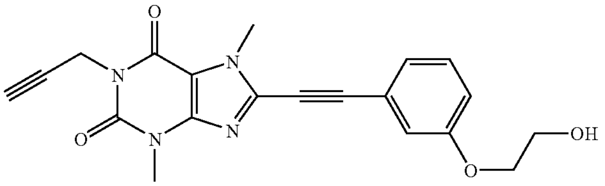 | >1000 | 226 ± 62 |
| 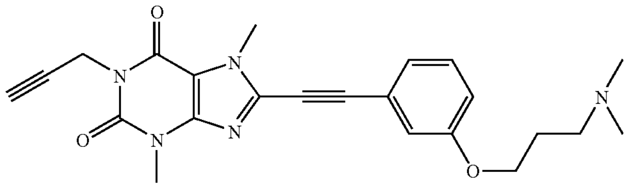 | 1743 ± 546 | 11.6 ± 2.1 |
| 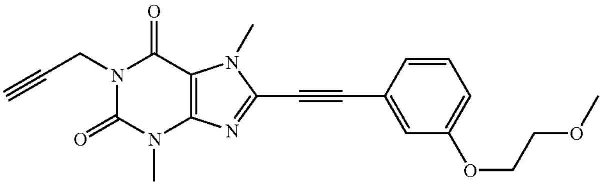 | >1000 | 28.9 ± 1.3 |
| 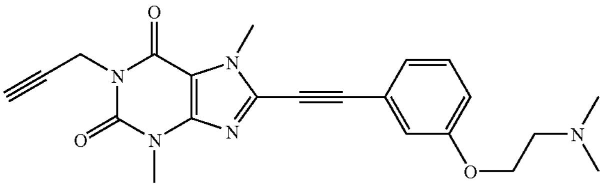 | >1000 | 90.3 ± 13.7 |

TABLE 2b-continued
| Structure | $A_1$ - ADENOSINE RECEPTOR HUMAN RECOMBINANT [$^3$H] CCPA $K_i$ [nM] | $A_{2A}$ - ADENOSINE RECEPTOR HUMAN RECOMBINANT [$^3$H] MSX-2 $K_i$ [nM] |
|---|---|---|
| 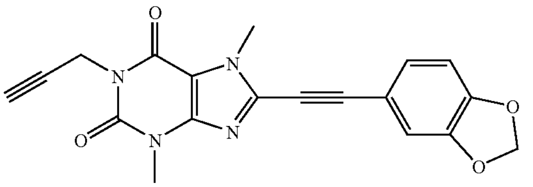 | nd | 52.3 ± 13.4 |
| 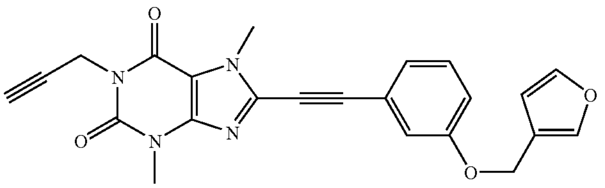 | >1000 | <10 |
| 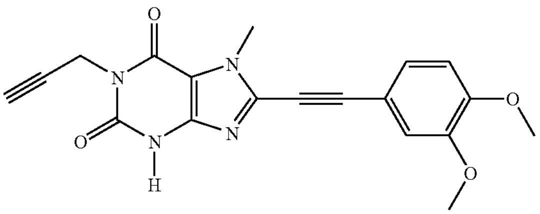 | >1000 | 18.4 ± 3.0 |
| 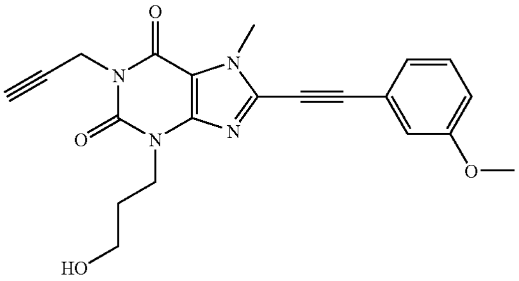 | >3000 | 5.5 ± 1.4 |
| 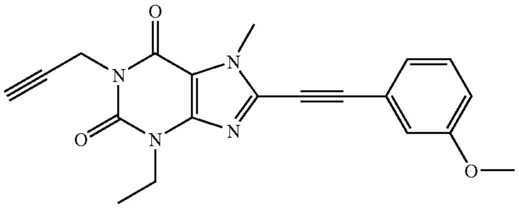 | >3000 | 64.8 ± 12.0 |
| 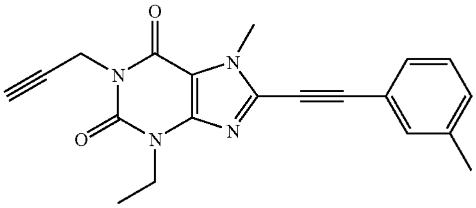 | >3000 | 89.7 ± 16.1 |

TABLE 2b-continued
| Structure | $A_1$ - ADENOSINE RECEPTOR HUMAN RECOMBINANT [$^3$H] CCPA $K_i$- [nM] | $A_{2A}$ - ADENOSINE RECEPTOR HUMAN RECOMBINANT [$^3$H] MSX-2 $K_i$- [nM] |
|---|---|---|
| 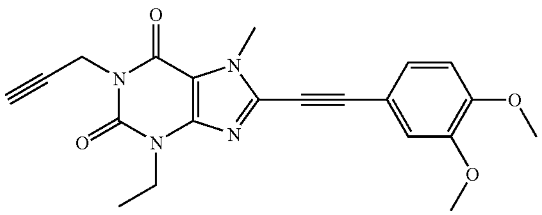 | >1000 | 17.7 ± 0.7 |
| 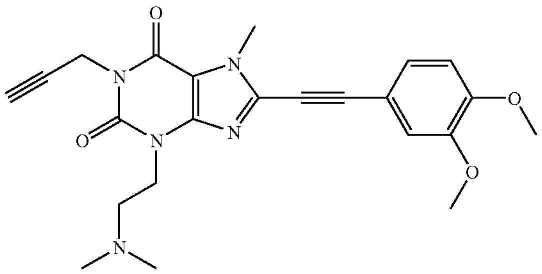 | >20000 | 51.7 ± 8.7 |
| 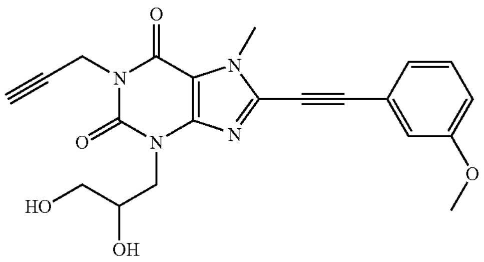 | >3000 | 175 ± 44 |
| 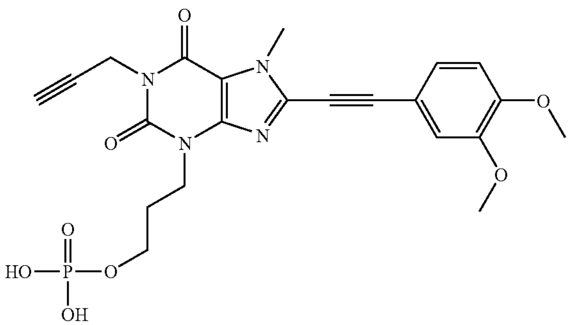 | nd | 50.7 ± 21.2 |
| 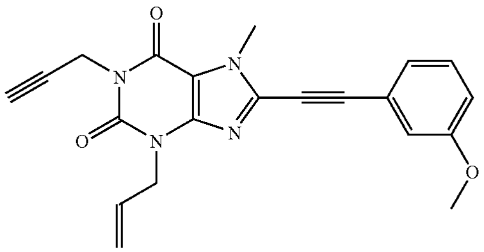 | nd | 35.6 ± 10.9 |

TABLE 2b-continued
| Structure | $A_1$ - ADENOSINE RECEPTOR HUMAN RECOMBINANT [$^3$H] CCPA $K_i$ [nM] | $A_{2A}$ - ADENOSINE RECEPTOR HUMAN RECOMBINANT [$^3$H] MSX-2 $K_i$ [nM] |
|---|---|---|
| 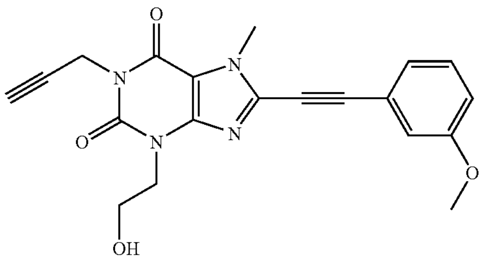 | nd | 165 ± 14 |
| 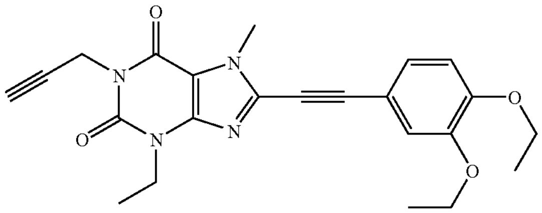 | >1000 | 83.4 ± 26.5 |
| 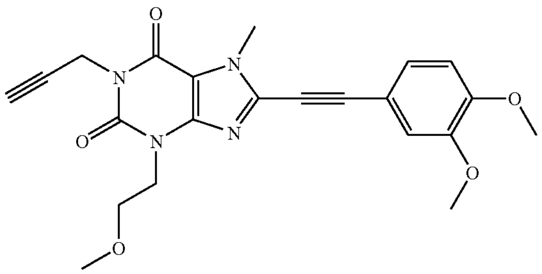 | >1000 | 55.3 ± 4.3 |
| 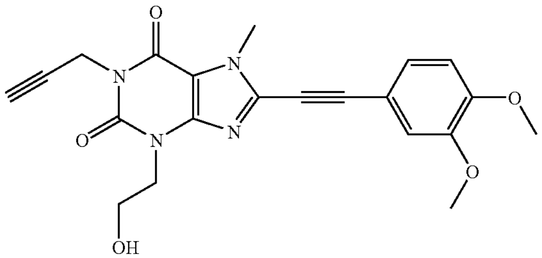 | >1000 | 59.8 ± 35.7 |
| 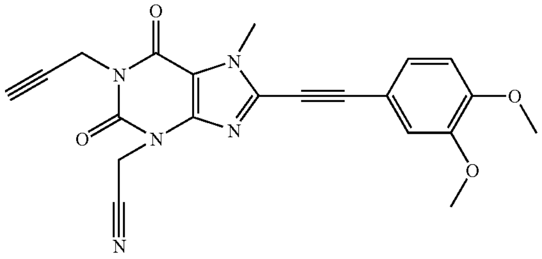 | >1000 | 32.2 ± 20.5 |

TABLE 2b-continued
| Structure | $A_1$ - ADENOSINE RECEPTOR HUMAN RECOMBINANT [$^3$H] CCPA $K_i$- [nM] | $A_{2A}$ - ADENOSINE RECEPTOR HUMAN RECOMBINANT [$^3$H] MSX-2 $K_i$- [nM] |
|---|---|---|
| 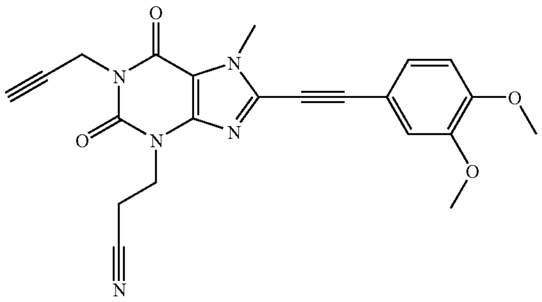 | >1000 | 84.3 ± 31.0 |
| 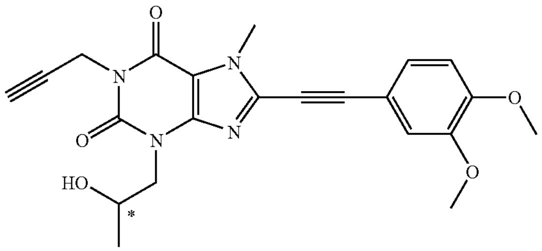 | >1000 | 14.0 ± 4.1 |
| 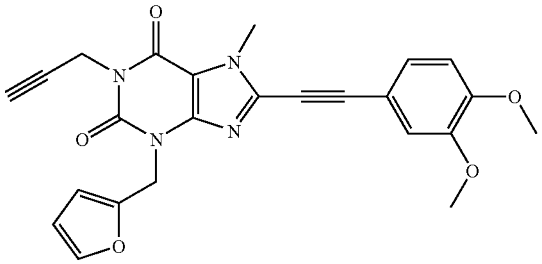 | >1000 | 13.9 ± 0.8 |
| 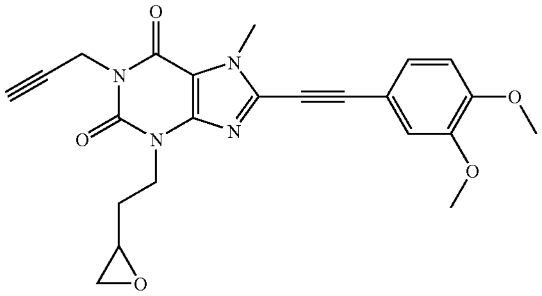 | nd | 96.3 ± 3.1 |
| 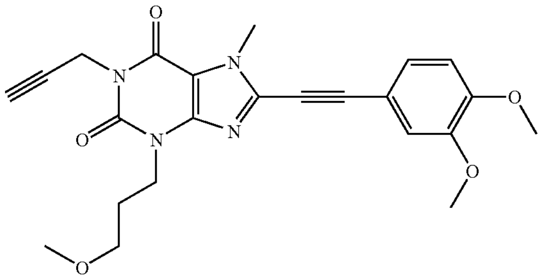 | >1000 | 123 ± 62 |

TABLE 2b-continued
| Structure | $A_1$- ADENOSINE RECEPTOR HUMAN RECOMBINANT [$^3$H] CCPA $K_i$- [nM] | $A_{2A}$- ADENOSINE RECEPTOR HUMAN RECOMBINANT [$^3$H] MSX-2 $K_i$- [nM] |
|---|---|---|
| 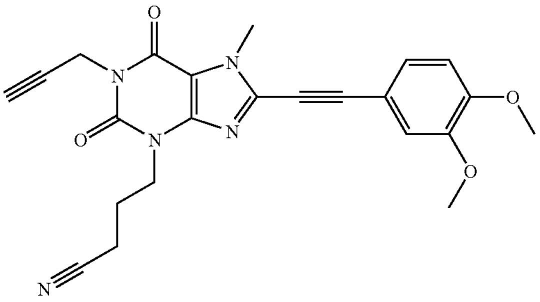 | >1000 | 58.0 ± 13.3 |
| 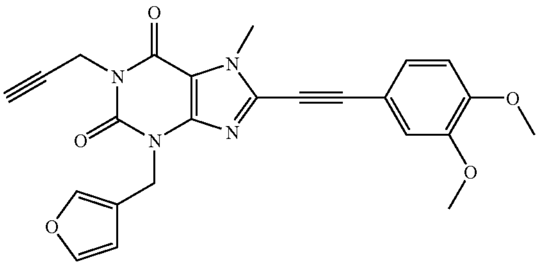 | >1000 | 8.4 ± 6.7 |
| 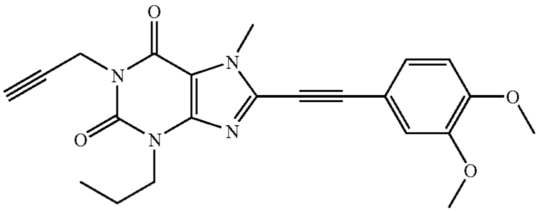 | >1000 | 36.6 ± 8.7 |
| 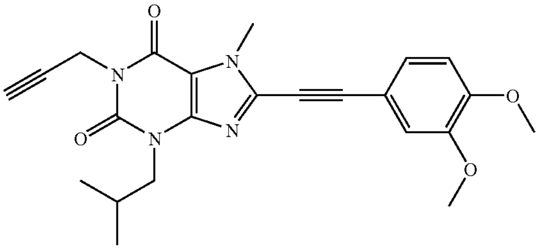 | ≧1000 | 200 ± 99 |
| 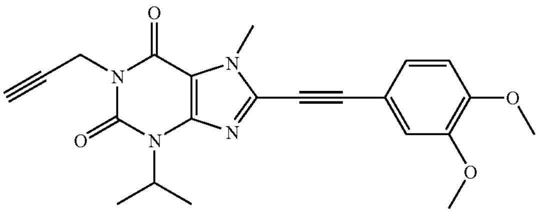 | >1000 | 127 ± 19 |

TABLE 2b-continued
| Structure | $A_1$ - ADENOSINE RECEPTOR HUMAN RECOMBINANT [$^3$H] CCPA $K_i$ [nM] | $A_{2A}$ - ADENOSINE RECEPTOR HUMAN RECOMBINANT [$^3$H] MSX-2 $K_i$ [nM] |
|---|---|---|
| 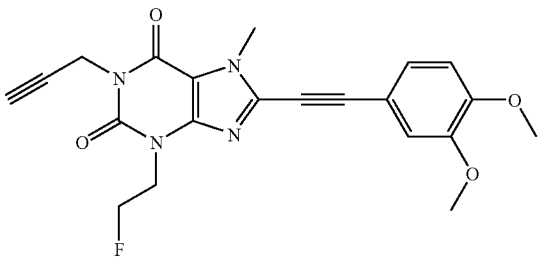 | >1000 | 30.8 ± 4.9 |
| 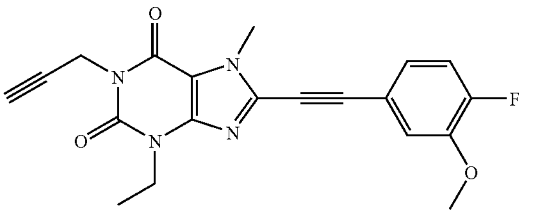 | >1000 | 100 ± 28 |
| 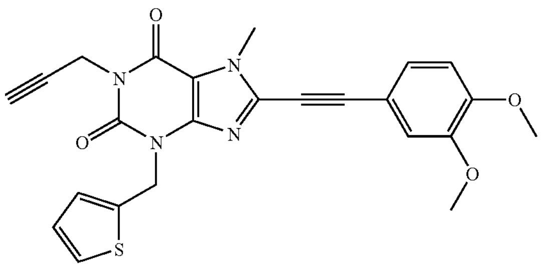 | >1000 | 416 ± 44 (n = 2) |
| 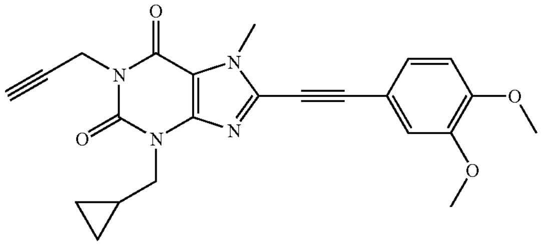 | >1000 | 56.3 ± 26.4 (n = 2) |
| 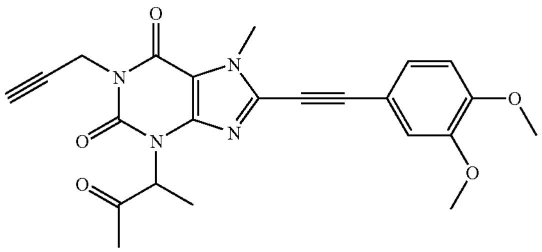 | nd | 54 (n = 1) |

TABLE 2b-continued
| Structure | $A_1$ - ADENOSINE RECEPTOR HUMAN RECOMBINANT [$^3$H] CCPA $K_i$- [nM] | $A_{2A}$ - ADENOSINE RECEPTOR HUMAN RECOMBINANT [$^3$H] MSX-2 $K_i$- [nM] |
|---|---|---|
| 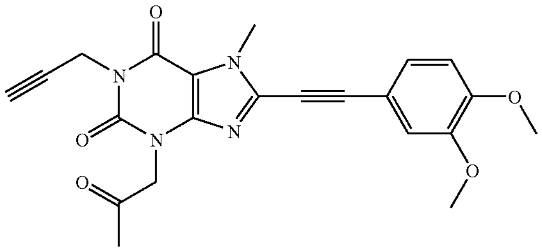 | nd | 273 (n = 1) |
| 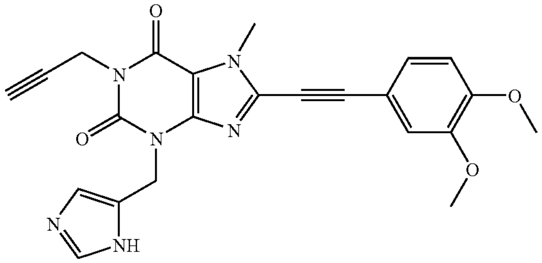 | >1000 | 103 (n = 1) |
| 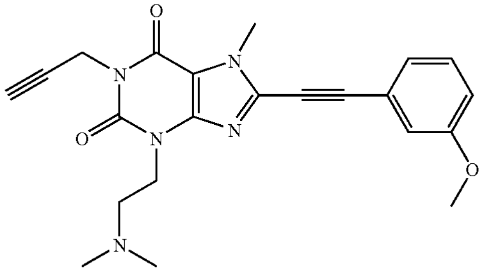 | nd | 569 ± 10.7 |
| 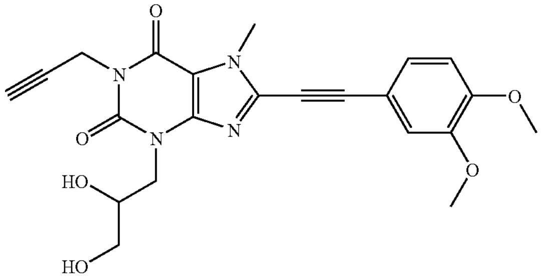 | >1000 | 62.7 ± 10.7 |
| 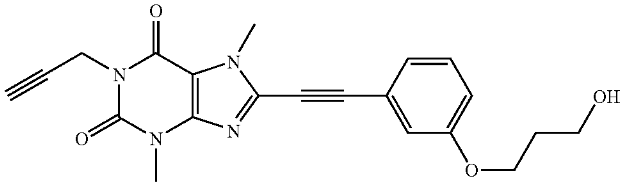 | nd | 299 ± 72 |

TABLE 2b-continued

| Structure | $A_1$ - ADENOSINE RECEPTOR HUMAN RECOMBINANT [$^3$H] CCPA $K_i$- [nM] | $A_{2A}$ - ADENOSINE RECEPTOR HUMAN RECOMBINANT [$^3$H] MSX-2 $K_i$- [nM] |
|---|---|---|
| 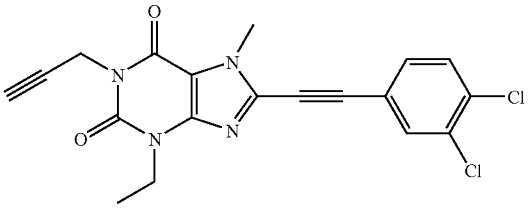 | >1000 | 738 ± 146 |
| 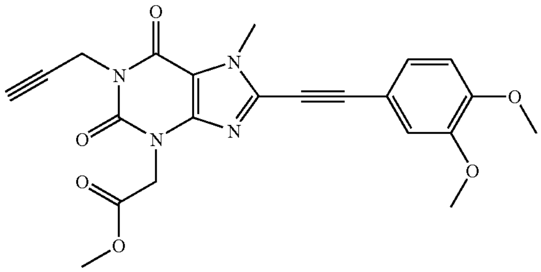 | >1000 | 38.2 ± 8.5 |
| 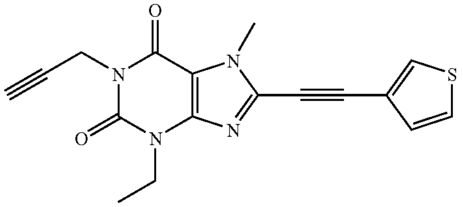 | nd | 82.5 (n = 1) |
| 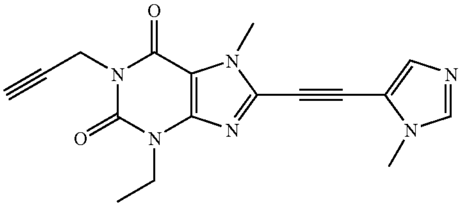 | nd | 82.1 ± 26.0 (n = 2) |

*calculated by extrapolation. A full inhibition curve was not possible due to limited water-solubility of the compound.

TABLE 3a

| N3-ethyl vs N3-methyl and human $A_{2A}$R binding | | | |
|---|---|---|---|
| Structure R2 = methyl | $A_{2A}$- ADENOSINE RECEPTOR HUMAN RECOMBINANT [$^3$H] MSX-2 $K_i$- [nM] | Structure R2 = ethyl | $A_{2A}$- ADENOSINE RECEPTOR HUMAN RECOMBINANT [$^3$H] MSX-2 $K_i$- [nM] |
| 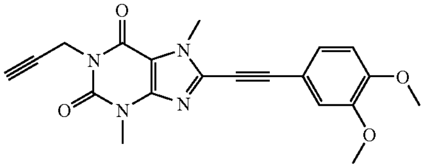 | 89.7 ± 16.1 | 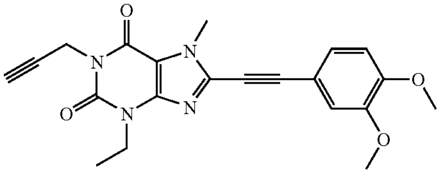 | 17.7 ± 0.7 |

TABLE 3a-continued
| N3-ethyl vs N3-methyl and human $A_{2A}$R binding | | | |
|---|---|---|---|
| Structure R2 = methyl | $A_{2A}$- ADENOSINE RECEPTOR HUMAN RECOMBINANT [$^3$H] MSX-2 $K_i$- [nM] | Structure R2 = ethyl | $A_{2A}$- ADENOSINE RECEPTOR HUMAN RECOMBINANT [$^3$H] MSX-2 $K_i$- [nM] |
| 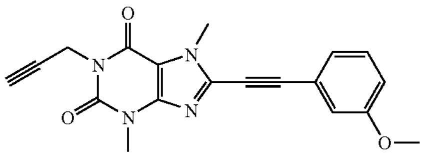 | 608 ± 111 | 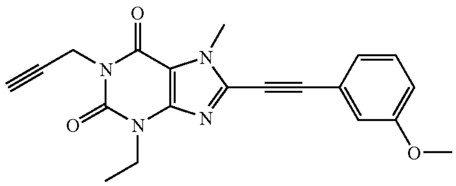 | 64.8 ± 12.0 |
| 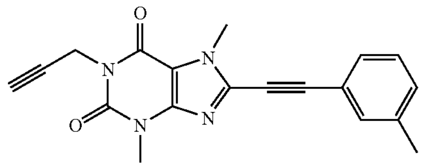 | 225 ± 52 | 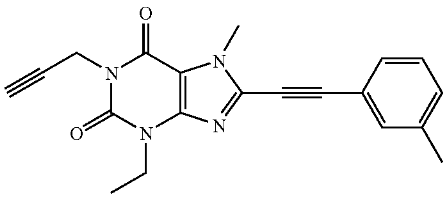 | 89.7 ± 16.1 |
TABLE 4
| Structure | $A_1$ AR | $A_{2A}$ AR | $A_{2B}$ AR | $A_3$ AR |
|---|---|---|---|---|
| 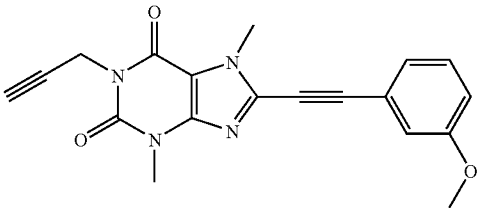 | 5 | 81 | 19 | 24 |
| 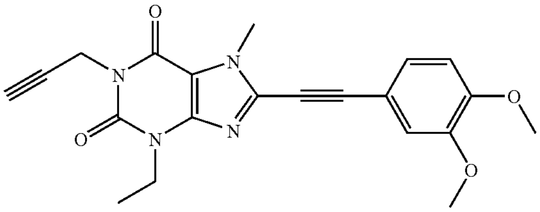 | 4 | 95 | 14 | 38 |
| 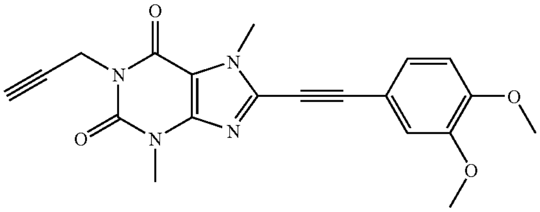 | 10 | 85 | 19 | 16 |
| 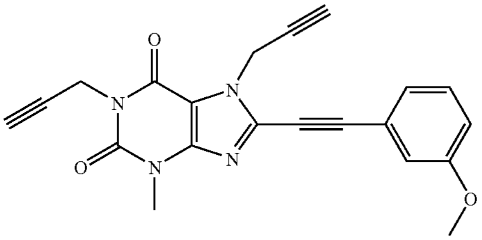 | 24 | 86 | 22 | 37 |

TABLE 4-continued
| Structure | $A_1$ AR | $A_{2A}$ AR | $A_{2B}$ AR | $A_3$ AR |
|---|---|---|---|---|
| 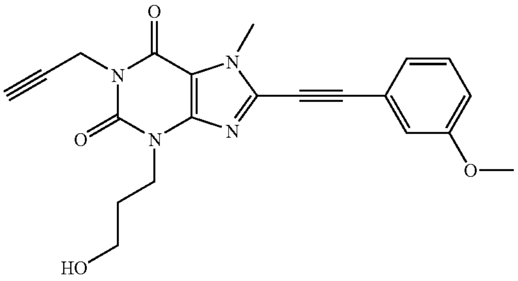 | 41 | 93 | 6 | 37 |
| 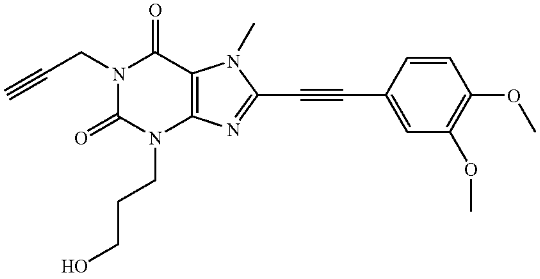 | 34 | 97 | 14 | 36 |
| 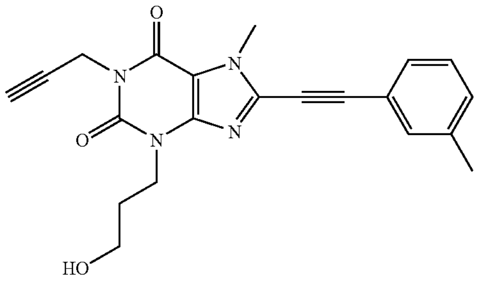 | 43 | 92 | 17 | 54 |
TABLE 5
| Structure | $K_i$ [nM] $rA_{2A}$ rat striatum [$^3$H] MSX-2 (n = 3) | $K_i$ [nM] (+100 mM NaCl) rA2A rat striatum [$^3$H] MSX-2 (n = 3) | Sodium Chloride-Shift $K_i$ (+NaCl)/$K_i$ (−NaCl) |
|---|---|---|---|
| 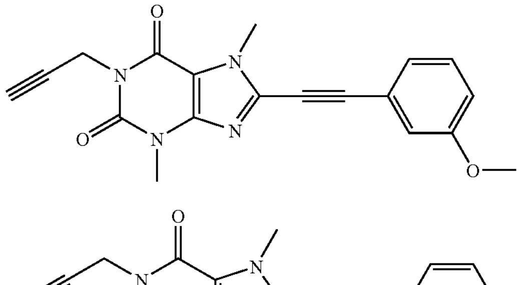 | 30.9 ± 8.0 | 33.2 ± 9.9 | 0.97 ± 0.03 |
| 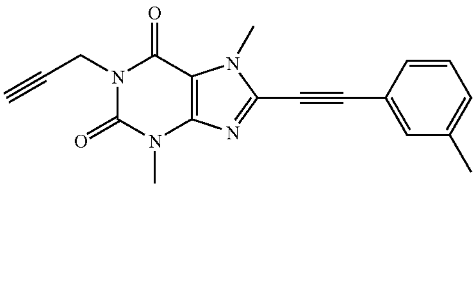 | 43.4 ± 11.6 | 53.1 ± 5.9 | 1.19 ± 0.16 |

TABLE 5-continued

| Structure | $K_i$ [nM] $rA_{2A}$ rat striatum [$^3$H] MSX-2 (n = 3) | $K_i$ [nM] (+100 mM NaCl) rA2A rat striatum [$^3$H] MSX-2 (n = 3) | Sodium Chloride-Shift $K_i$ (+NaCl)/ $K_i$ (−NaCl) |
|---|---|---|---|
| 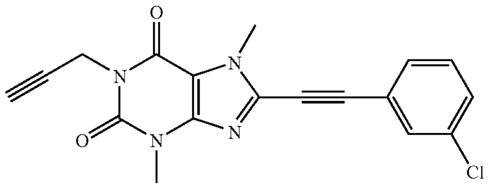 | 46.0 ± 9.0 | 39.5 ± 13.1 | 0.82 ± 0.13 |

TABLE 6

| Structure | $A_1$ AR $IC_{50}$ μM | $A_1$ AR Imax % | $A_1$ AR $K_i$ [μM] | $A_{2A}$ AR $IC_{50}$ μM | $A_{2A}$ AR Imax % | $A_{2A}$ AR $K_i$ [μM] |
|---|---|---|---|---|---|---|
| 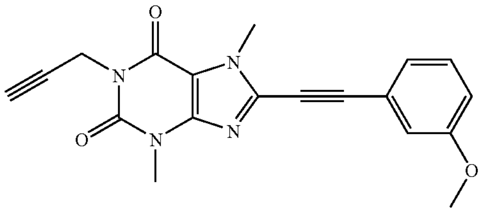 | No significant activity detected | No significant activity detected | No significant activity detected | 1.9 | 90 | 0.178 |
| 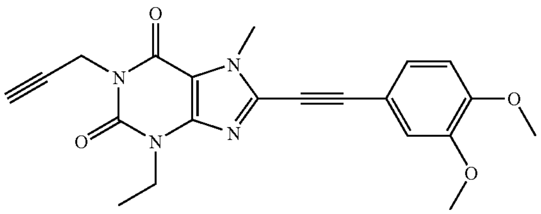 | 3.9 | 49 | 0.854 | 0.2 | 97 | 0.023 |
| 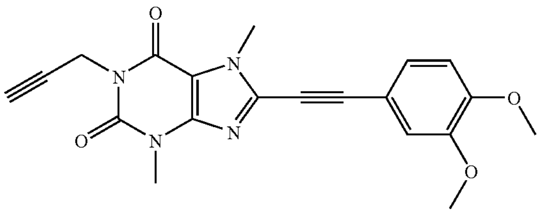 | No significant activity detected | No significant activity detected | No significant activity detected | 0.6 | 95 | 0.058 |
| 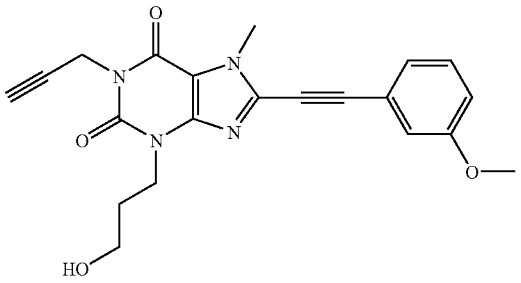 | 1.7 | 90 | 0.370 | 0.9 | 117 | 0.082 |

TABLE 6-continued

| Structure | $A_1$ AR $IC_{50}$ μM | $A_1$ AR Imax % | $A_1$ AR $K_i$ [μM] | $A_{2A}$ AR $IC_{50}$ μM | $A_{2A}$ AR Imax % | $A_{2A}$ AR $K_i$ [μM] |
|---|---|---|---|---|---|---|
| 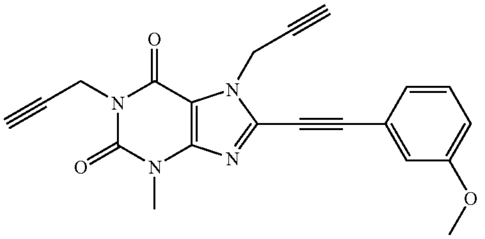 | 2.3 | 55 | 0.501 | 0.5 | 86 | 0.047 |
| 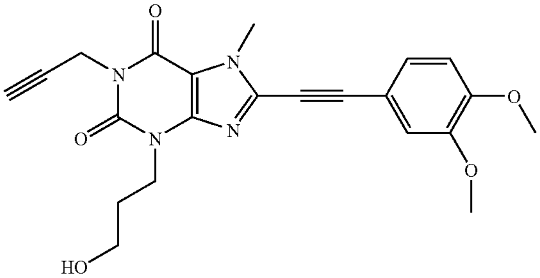 | 1.8 | 92 | 0.401 | 0.3 | 117 | 0.026 |
| 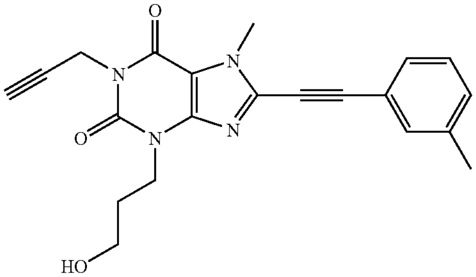 | 1.3 | 102 | 0.289 | 0.4 | 109 | 0.040 |
| CPX ($A_1$ receptor antagonist) 5-Amino-7-(β-phenylethyl)-2-(8-furyl)pyrazolo(4.3-e)-1.2.4-triazolo(1.5-c)pyrimidine ($A_{2A}$ receptor antagonist) | 14 nM | 100 | 3.1 | 6.7nM | 100 | 0.6 |

TABLE 7

| FOB Method | Parameter | Recorded as | |
|---|---|---|---|
| Home cage | Body posture | Score | Normal<br>Sleeping<br>Hunchback. relieving posture<br>Lying on side<br>Flat body posture |
| Handling reaction | Handling reaction | Score | Easy<br>Difficult<br>Freezing |
| Body temperature | Rectal temperature | Temperature | ° C. |
| Viewing jar | Palpebral closure | Score | Open<br>Half/¾ shut<br>Shut |
| | Lacrimation | Score | none<br>moisture around eyes<br>moisture flows from eyes |
| | Salivation | Score | None<br>Moisture around mouth |

TABLE 7-continued

| FOB Method | Parameter | | Recorded as |
|---|---|---|---|
| | | | Moisture flows from mouth |
| | Rearing | Number | N |
| | Scratching (non-stereotype) | Number | N |
| | Jumps | Number | N |
| | Touch reactivity | Score | Normal (head turning or no interest)<br>Retreat. twitch<br>Freezing<br>Biting. attack |
| | Fear reaction | Score | Approach<br>None<br>Retreat. twitch<br>Freezing<br>Biting. attack |
| | Startle response | Score | Twitch<br>Jump<br>None |
| Walking alley | Crossings | Number | N |
| | Akinesia | Occurrence | No/yes |
| | Gait characterization | Score | Normal<br>Staggering<br>Atactic<br>Retraction of hindlimbs<br>Sneaking<br>n/a |
| Inclined Plane | Righting reflex | Direction | Upstairs<br>Downstairs<br>None |
| | Leaving | Time | s |
| Bar test | Catalepsy | Time | s |
| Hand-held tests | Muscle tone | Score | Normal<br>Soft<br>Hard |
| | Lid closing reflex (right/left eye) | Occurrence | Yes/no |
| | Struggle | Occurrence | Yes/no |
| Tail flick test | Analgesia | Time | s |
| Grip-strength test | Grip-strength - fore paws | Score | Grasp and pull<br>Grasp without pull<br>No grasp |
| | Grip-strength - hind paws | Score | Grasp and pull<br>Grasp without pull<br>no grasp |
| Throughout the test | Piloerection | Occurrence | No/yes |
| | Stereotypies<br>Licking<br>Scanning<br>Scratching<br>Chewing | Occurrence | No/yes |
| | Tremor | Occurrence | No/yes |
| | Convulsion | Occurrence | No/yes |
| | Head twitches/<br>Wet dog shakes | Occurrence | No/yes |
| | Fore paw treading | Occurrence | No/yes |
| | Flat body posture | Occurrence | No/yes |
| | Diarrhoea | Occurrence | No/yes |
| | Vocalization<br>Spontaneously<br>During touching | Occurrence | No/yes |
| | Trembling | Occurrence | No/yes |
| | Hind leg abduction | Occurrence | No/yes |
| | Straub tail | Occurrence | No/yes |
| | Sneezing | Occurrence | No/yes |
| | Coughing | Occurrence | No/yes |
| | Death | Occurrence | No/yes |
| | Respiration | Score | Normal<br>Slow<br>Slow and flat<br>Slow and intermittent<br>Fast<br>Fast and flat |
| | Remarkable miscellaneous behaviour | | Type. number and situation |

TABLE 8

| SAC Method | Parameter | | Recorded as |
|---|---|---|---|
| Home cage | Body posture | Score | Normal<br>Sleeping<br>Hunchback. relieving posture<br>Lying on side<br>Flat body posture |
| Throughout the test | Piloerection | Occurrence | No/yes |
| | Stereotypies | Occurrence | No/yes |
| | Licking | | |
| | Scanning | | |
| | Scratching | | |
| | Chewing | | |
| | Tremor | Occurrence | No/yes |
| | Convulsion | Occurrence | No/yes |
| | Head twitches/<br>Wet dog shakes | Occurrence | No/yes |
| | Fore paw treading | Occurrence | No/yes |
| | Flat body posture | Occurrence | No/yes |
| | Diarrhoea | Occurrence | No/yes |
| | Vocalization | Occurrence | No/yes |
| | Spontaneously | | |
| | During touching | | |
| | Trembling | Occurrence | No/yes |
| | Hind leg abduction | Occurrence | No/yes |
| | Straub tail | Occurrence | No/yes |
| | Sneezing | Occurrence | No/yes |
| | Coughing | Occurrence | No/yes |
| | Death | Occurrence | No/yes |
| | Remarkable miscellaneous behaviour | Type. number and situation | |
| Bar test | Catalepsy | Time | s |

TABLE 9

| FU Method | Parameter | | Recorded as |
|---|---|---|---|
| Home cage | Body posture | Score | Normal<br>Sleeping<br>Hunchback. relieving posture<br>Lying on side<br>Flat body posture |
| Handling reaction | Handling reaction | Score | Easy<br>Difficult<br>Freezing |
| Bar test | Catalepsy | Time | s |
| Body weight | Body weight | Weight | g |
| Body temperature | Rectal temperature | Temperature | ° C. |
| Throughout the test | Piloerection | Occurrence | No/yes |
| | Stereotypies | Occurrence | No/yes |
| | Licking | | |
| | Scanning | | |
| | Scratching | | |
| | Chewing | | |
| | Tremor | Occurrence | No/yes |
| | Convulsion | Occurrence | No/yes |
| | Head twitches/<br>Wet dog shakes | Occurrence | No/yes |
| | Fore paw treading | Occurrence | No/yes |
| | Flat body posture | Occurrence | No/yes |
| | Diarrhoea | Occurrence | No/yes |
| | Vocalization | Occurrence | No/yes |
| | Spontaneously | | |
| | During touching | | |
| | Trembling | Occurrence | No/yes |
| | Hind leg abduction | Occurrence | No/yes |
| | Straub tail | Occurrence | No/yes |
| | Sneezing | Occurrence | No/yes |
| | Coughing | Occurrence | No/yes |
| | Death | Occurrence | No/yes |
| | Respiration | Score | Normal<br>Slow<br>Slow and flat |

TABLE 9-continued

| FU Method | Parameter | | Recorded as |
|---|---|---|---|
| | | | Slow and intermittent |
| | | | Fast |
| | | | Fast and flat |
| | Remarkable miscellaneous behaviour | Type. number and situation | |

TABLE 10

| | Structure | |
|---|---|---|
| | 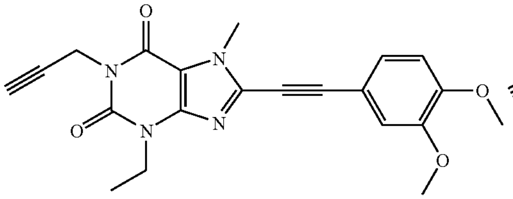 | 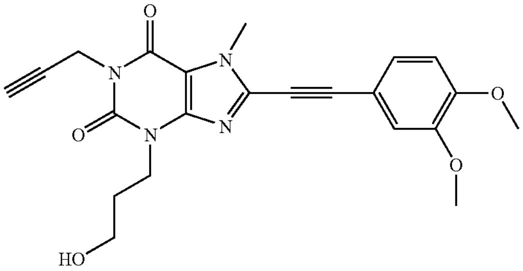 |
| Patterns Activity | +++ | ++ |
| Motor Coordination | 0 | – |
| Catalepsy | 0 | 0 |
| Hypersensitivity | ++ | 0 |
| Temperature | + | – |
| Respiration | +++ | +++ |
| Tremor | 0 | + |
| Stereotypies | ++ | + |

| | |
|---|---|
| | 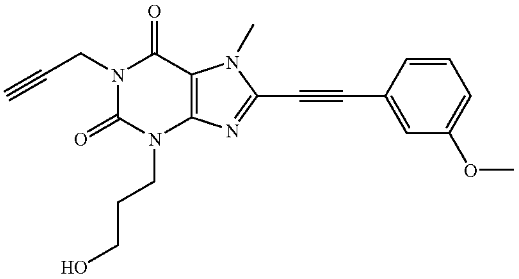 |
| Patterns Activity | + |
| Motor Coordination | 0 |
| Catalepsy | 0 |
| Hypersensitivity | + |
| Temperature | 0 |
| Respiration | ++ |
| Tremor | 0 |
| Stereotypies | 0 |

+++ = very strong effect.
++ = strong effect.
+ = average effect.
0 = no effect.
– = negative effect.

The invention claimed is:

1. A compound corresponding in structure to formula (Ia)

formula (Ia)

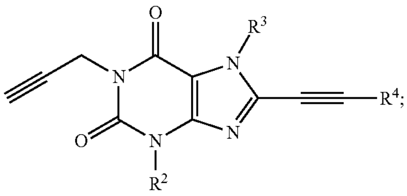

or a pharmaceutically acceptable salt, diastereomer or enantiomer thereof wherein, $R^2$ is hydrogen or methyl;

$R^3$ is methyl, propargyl, butynyl, or cyanomethyl;

$R^4$ is imidazol-2-yl or thien-3-yl optionally substituted with one or more substituents selected from halogen, methyl, or methoxy;

or $R^4$ is phenyl which is substituted in meta position to its attachment position to the triple bond with a residue selected from the group consisting of amino, —$OR^5$ and methyl; and which in para position is unsubstituted or substituted with methoxy, methyl, or fluoro;

or $R^4$ is phenyl that is annelated in 3- and 4-position to a second heterocyclic 5 or 6-membered ring which contains one or more oxygen atoms thus forming a bicyclic ring system, which can be substituted with a methyl, methoxy or hydroxyl group;

$R^5$ is hydrogen or methyl;

or $R^5$ is ($C_1$-$C_4$)-alkyl substituted in one or more places, in the same way or differently, with methoxy, carboxy, hydroxyl or a phosphate ester thereof, or with —$NR^6R^7$, and $R^6$ and $R^7$ are independently hydrogen, or ($C_1$-$C_3$)-alkyl; or $R^6$ and $R^7$ together with the nitrogen atom to which they are attached form a five or six membered ring which may contain one or two additional ring forming heteroatoms selected from N and O, and the five or six membered ring may be unsubstituted or substituted with one or more residues selected from the group consisting of ($C_1$-$C_3$)-alkyl; hydroxyl($C_1$-$C_3$)-alkyl; amino($C_1$-$C_3$)-alkyl; ($C_1$-$C_3$)-alkoxy($C_1$-$C_3$)-alkyl; halo($C_1$-$C_3$)-alkyl; mono($C_1$-$C_2$)-alkylamino($C_1$-$C_3$)-alkyl; and di($C_1$-$C_2$)-alkylamino($C_1$-$C_3$)-alkyl.

2. A compound corresponding in structure to formula (Ia)

formula (Ia)

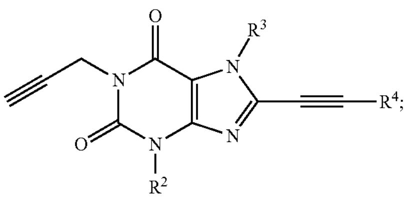

or a pharmaceutically acceptable salt, diastereomer or enantiomer thereof wherein, $R^2$ is hydrogen, methyl, $NR^6R^7$; or $R^2$ is ($C_2$-$C_4$)-alkyl, ($C_2$-$C_4$)-alkenyl, ($C_2$-$C_4$)-alkynyl; or $R^2$ is methyl which is substituted with a residue selected from the group consisting of cyano, carboxy, ($C_3$-$C_5$)-cycloalkyl, ($C_1$-$C_2$)-alkoxycarbonyl, ($C_1$-$C_2$)-alkylcarbonyl, mono($C_1$-$C_2$)-alkylamino, di($C_1$-$C_2$)-alkylamino, a 3 to 5-membered heterocyclyl ring and a 5 to 6-membered heteroaryl ring; or $R^2$ is ethyl, which is substituted in one or more places, in the same way or differently, with a substituent selected from the group consisting of fluoro; chloro; bromo; cyano; carboxy; methylcarbonyl; methoxycarbonyl; mono($C_1$-$C_2$)-alkylamino; di($C_1$-$C_2$)-alkylamino; —$OR^8$; a 3 to 5-membered oxygen-containing heterocyclyl; hydroxyl; a phosphate ester or a substituted or unsubstituted naturally occurring amino acid ester of said hydroxyl group; or $R^2$ is propyl or butyl, which is substituted in one or more places, in the same way or differently, with a substituent selected from the group consisting of fluoro; chloro; bromo; cyano; carboxy; —$OR^8$; hydroxyl or a phosphate ester or an ester of a substituted or unsubstituted naturally occurring amino acid of said hydroxyl group;

$R^3$ is methyl, propargyl, butynyl, or cyanomethyl;

$R^4$ is phenyl which is substituted in meta and/or in para position to its attachment to the triple bond with chloro, methyl, or a group —$OR^5$; or $R^4$ is thien-3-yl, furan-3-yl or a imidazol-2-yl, each of which is optionally substituted at one of its ring forming carbon atoms with one or more substituents selected from the group consisting of halogen, methyl, and methoxy; and wherein the imidazol-2-yl residue is optionally substituted in its N1 position by a methyl group;

$R^5$ is methyl, ethyl, or ($C_1$-$C_4$)-alkyl which is substituted with OH, a phosphate ester thereof or —$NR^6R^7$;

$R^6$ and $R^7$ are independently hydrogen, methyl or ethyl; and $R^8$ is ($C_1$-$C_3$)-alkyl or ($C_1$-$C_3$)-alkoxy-($C_1$-$C_3$)-alkyl.

3. A compound corresponding in structure to formula (IIIa)

formula (IIIa)

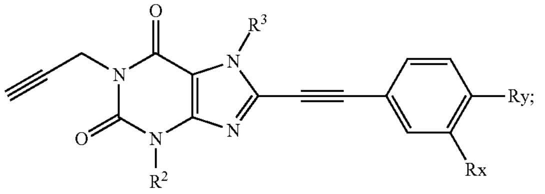

or a pharmaceutically acceptable salt, diastereomer or enantiomer thereof wherein, $R^2$ is ($C_2$-$C_4$)-alkyl, ($C_2$-$C_4$)-alkenyl, ($C_2$-$C_4$)-alkinyl, or $R^2$ is methyl, which is substituted with a residue selected from cyano, carboxy, methylcarbonyl, ($C_3$-$C_5$)-cycloalkyl, methoxycarbonyl, monomethylamino, dimethylamino, furanyl, thienyl, imidazolyl, oxazolyl, isoxazolyl, or a heterocyclyl with 3 to 5 ring atoms, or $R^2$ is ethyl, which is substituted in one or more places, in the same way or differently, with fluoro, chloro, bromo, cyano, methylcarbonyl, monomethylamino, dimethylamino, —$OR^8$, oxiran-2-yl, hydroxyl or a phosphate ester or an ester of an amino acid of said hydroxyl group, $R^2$ is propyl or butyl, which is substituted in one or more places, in the same way or differently, with fluoro, chloro, bromo, cyano, methoxy, hydroxyl or a phosphate ester or an ester of an amino acid of said hydroxyl group;

$R^3$ is methyl, propargyl, butynyl, or cyanomethyl;

Rx is selected from the group consisting of halogen, amino, methyl, and —$OR^5$;

Ry is selected from the group consisting of hydrogen, fluoro, chloro, bromo, methyl and methoxy; or Rx and Ry together with the carbon atoms to which they are attached form a second heterocyclic 5 or 6-membered ring which contains one or more oxygen atoms thus forming a bicyclic ring system, which can be substituted with one or two residues selected from methoxy, methyl and hydroxyl;

$R^5$ is methyl or furanylmethyl, or $R^5$ is ($C_1$-$C_4$)-alkyl substituted in one or more places, in the same way or differently, with carboxy, hydroxyl or a phosphate ester thereof, or —$NR^6R^7$;

$R^6$ and $R^7$ are independently hydrogen, ($C_1$-$C_3$)-alkyl, or form together with the nitrogen atom to which they are attached a five or six membered ring which may contain one or two additional ring forming heteroatoms selected from N and O, and which five or six membered ring may be unsubstituted or may be substituted at the second ring forming nitrogen, if present, with one or more residues selected from ($C_1$-$C_3$)-alkyl; hydroxyl($C_1$-$C_3$)-alkyl; amino($C_1$-$C_3$)-alkyl; ($C_1$-$C_3$)-alkoxy($C_1$-$C_3$)-alkyl; halo($C_1$-$C_3$)-alkyl; mono($C_1$-$C_2$)-alkylamino($C_1$-$C_3$)-alkyl; and di($C_1$-$C_2$)-alkylamino($C_1$-$C_3$)-alkyl; and $R^8$ is methyl.

4. A compound corresponding in structure to formula (IIIa)

formula (IIIa)

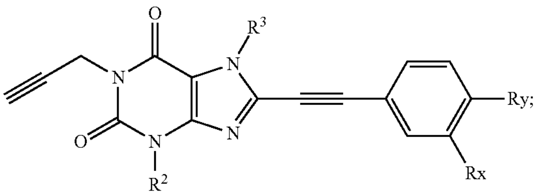

or a pharmaceutically acceptable salt, diastereomer or enantiomer thereof wherein, $R^2$ is ($C_2$-$C_4$)-alkyl, ($C_2$-$C_4$)-alkenyl, ($C_2$-$C_4$)-alkinyl, or $R^2$ is methyl, which is substituted with cyano, carboxy, oxiran-2-yl, furan-2-yl, furan-3-yl, thien-2-yl, thien-3-yl, isoxazol-5-yl, imidazol-4-yl, cyclopropyl or methoxycarbonyl; or $R^2$ is ethyl, which is substituted in one or more places, in the same way or differently, with fluoro, chloro, bromo, cyano, oxiran-2-yl, mono($C_1$-$C_2$)alkyl amino, di($C_1$-$C_2$) alkyl amino, hydroxyl or a phosphate ester thereof or $R^2$ is propyl, which is substituted in one or more places, in the same way or differently with fluoro, chloro, bromo, cyano, hydroxyl or a phosphate ester thereof $R^2$ is butyl, which is substituted in one or more places with hydroxyl or a phosphate ester of said hydroxyl group;

$R^3$ is methyl, propargyl, butynyl, or cyanomethyl;

Rx is selected from the group consisting of fluoro, chloro, bromo, methyl, methoxy, ethoxy, allyloxy, methoxyethoxy, hydroxyethoxy, mono($C_1$-$C_2$)-alkylaminopropoxy, mono($C_1$-$C_2$)-alkylaminoethyloxy, di($C_1$-$C_2$)-alkylaminopropoxy, di($C_1$-$C_2$)-alkylaminoethyloxy, furanylmethyloxy, and carboxymethyloxy;

Ry is selected from the group consisting of hydrogen, methoxy, ethoxy, fluoro, and chloro, or Rx and Ry together with the carbon atoms to which they are attached form a second heterocyclic five membered ring which contains one or two ring forming heteroatoms selected among O and N thus forming together with the phenyl ring a bicyclic ring system.

5. A compound according to claim 2, wherein $R^2$ is ethyl, propyl, butyl, allyl, butenyl, propargyl or butynyl, or $R^2$ is methyl, which is substituted with a residue selected from cyano, carboxy, methylcarbonyl, methoxycarbonyl, cyclopropyl, furanyl, thienyl, imidazolyl, oxazolyl, isoxazolyl, or oxiranyl, or $R^2$ is ethyl, which is substituted in one or two places with fluoro, chloro, bromo, cyano, methylcarbonyl, monomethylamino, dimethylamino, methoxy, ethoxy, hydroxyl or a phosphate ester of said hydroxyl group, $R^2$ is propyl, which is substituted in one or two places with fluoro, chloro, bromo, cyano, methoxy, hydroxyl or a phosphate ester of said hydroxyl group, or $R^2$ is butyl, which is substituted in one or more places with hydroxyl or is substituted with a phosphate ester of a hydroxyl group.

6. A compound according to claim 3 wherein $R^2$ is $C_2$-$C_4$ alkyl, $C_3$-$C_4$ alkenyl, $C_3$-$C_4$-alkynyl, or $R^2$ is methyl, which is substituted with cyano, oxiran-2-yl, furan-2-yl, furan-3-yl, thien-2-yl, thien-3-yl, cyclopropyl, methylcarbonyl, methoxycarbonyl, or $R^2$ is ethyl which is substituted with halogen, cyano, methylcarbonyl, or oxiran-2-yl, or $R^2$ is propyl or butyl, which is substituted with halogen or cyano; and Rx is amino or $OR^5$, and Ry is selected from the group consisting of hydrogen, methoxy, and fluoro, $R^5$ is $C_1$-$C_5$-alkyl which is substituted with a hydroxyl group, a phosphate ester of a hydroxyl group, or with $NR^6R^7$;

$R^6$ and $R^7$ are independently hydrogen, ($C_1$-$C_2$)-alkyl, or form together with the nitrogen atom to which they are attached a five membered ring which may contain one additional ring forming nitrogen atom which nitrogen atom may be further substituted with a residue selected from ($C_1$-$C_2$)-alkyl; hydroxyl($C_1$-$C_3$)-alkyl; amino($C_1$-$C_3$)-alkyl; ($C_1$-$C_2$)-alkoxy($C_1$-$C_2$)-alkyl; halo($C_1$-$C_2$)-alkyl; mono($C_1$-$C_2$)-alkylamino($C_1$-$C_2$)-alkyl; and di($C_1$-$C_2$)-alkylamino($C_1$-$C_2$)-alkyl.

7. A compound according to anyone any one of claims 3-6, wherein $R^2$ is methyl, which is substituted with (i) methylamino, or (ii) di($C_1$-$C_2$)alkylamino; or $R^2$ is ethyl, which is substituted with (iii) one or more —OH groups, (iv) a phosphate ester of a OH group (v) methylamino, or (vi) di($C_1$-$C_2$)alkylamino; or $R^2$ is propyl or butyl, each of which is substituted with (i) one or more —OH groups or (ii) a phosphate ester of a OH group.

8. A compound according to one of claims 3-6, wherein $R_2$ is ethyl, propyl, butyl; allyl, butenyl, propargyl, methylcarbonylmethyl, methylcarbonylethyl, methoxycarbonylmethyl, carboxy, cyanomethyl, 2-cyanoethyl, 3-cyanopropyl, 2,3-dihydroxypropyl and the phosphate esters thereof, furan-2-ylmethyl, furan-3-ylmethyl, thien-2-ylmethyl, thien-3-ylmethyl, isoxazol-5-ylm-ethyl, imidazol-4-ylmethyl, oxiran-2-yl-methyl, 2-methoxyethyl, 2-hydroxyethyl and the phosphate ester thereof, oxiran-2-yl-ethyl, 3-hydroxypropyl and the phosphate ester thereof, 2-hydroxypropyl and the phosphate ester thereof, 3-hydroxy-2-methylpropyl and the phosphate ester thereof, 2,2,2-trifluoroethyl, 3,3,3-trifluoropropyl, cyclopropylmethyl, 2-ethoxyethyl, 2-methoxyethyl, 2-fluoroethyl, 2-bromoethyl, 3-fluoro-propyl, 4-fluorobutyl, 3-methoxypropyl, methylamino-ethyl, or N,N-dimethylaminoethyl.

9. A compound according to any one of claims 2, 3, or 6, wherein $R^2$ is ethyl, n-propyl or fluoro($C_2$-$C_4$)-alkyl.

10. A compound according to any one of claims 3-6, wherein Rx and Ry are both methoxy.

* * * * *

UNITED STATES PATENT AND TRADEMARK OFFICE
CERTIFICATE OF CORRECTION

PATENT NO. : 8,044,061 B2
APPLICATION NO. : 11/963477
DATED : October 25, 2011
INVENTOR(S) : Christa Müller et al.

It is certified that error appears in the above-identified patent and that said Letters Patent is hereby corrected as shown below:

In the Specifications

Column 2, line 54, replace “8-(phenylethynyl)-DPMX” with --8-(phenylethynyl)-DMPX--.

Column 4, line 67, replace “lengthhs” with --lengths--.

Column 12, line 47, replace “term(s)” with --term(s))--.

Column 19, line 18, replace

“ 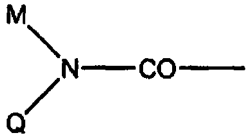 and 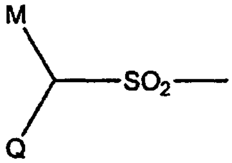 ” with

-- 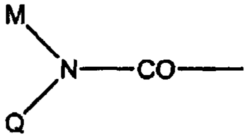 and 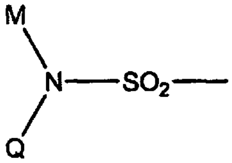 --.

Column 35, line 5, replace “(93 yield” with --(93% yield--.

Column 38, line 1, replace “addid” with --adding--.

Signed and Sealed this
Twelfth Day of November, 2013

Teresa Stanek Rea
*Deputy Director of the United States Patent and Trademark Office*

Column 41, line 30, replace
“ 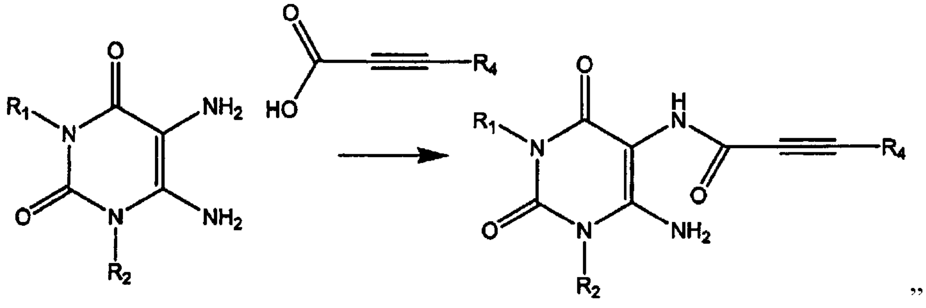 ” with
-- 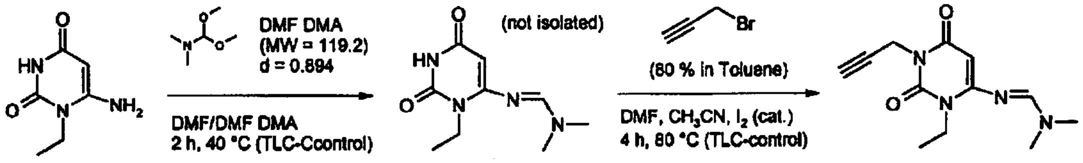
--.
Column 50, line 35, replace “dried al” with --dried at--.
Column 65, line 23, replace
“ 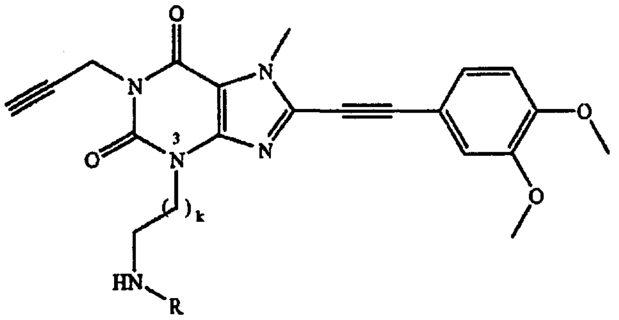 ” with
-- 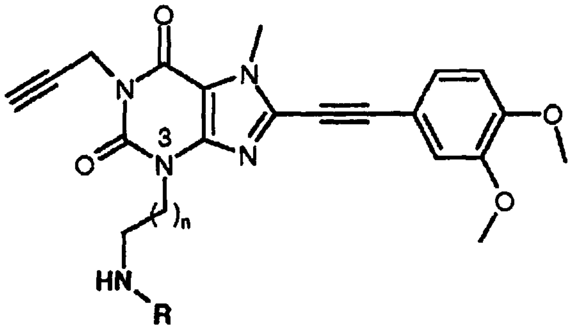 --.
Column 72, line 14, replace “$EC_{50}$” with --$EC_{80}$--.
Column 83, table 1, column MW/m.p.,/NMR, line 20 replace “9.85(d, 1H, OH)” with --9.85(s, 1H, OH)--.
Column 90, table 1, column Name, line 35, replace “7-dihydropueine-2” with --7-dihydropurine-2--.

Column 99, table 1, column $R^2$, line 1, replace
" 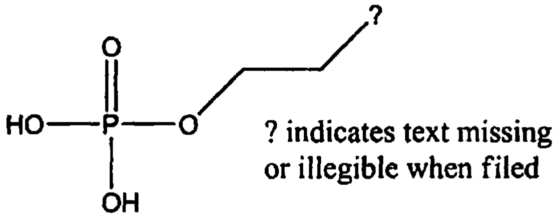
" with -- 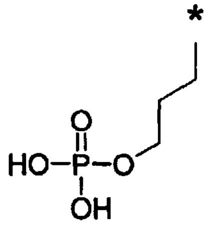 --.
Column 101, table 1, column $R^2$, line 1 replace
" 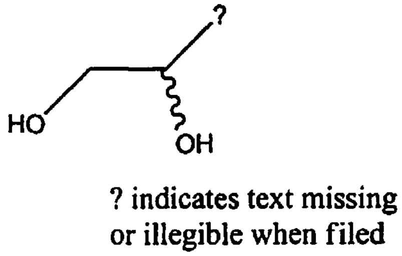
" with -- 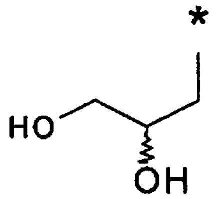 --.
Column 103, table 1, column $R^2$, line 18, replace " 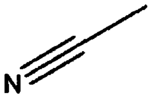 " with -- 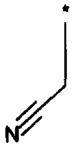 --.
Column 105, table 1, column $R^2$, line 1, replace " 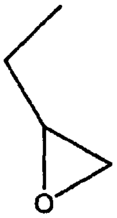 " with -- 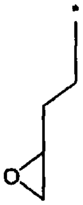 --.
Column 107, table 1, column $R^2$, line 1, replace " 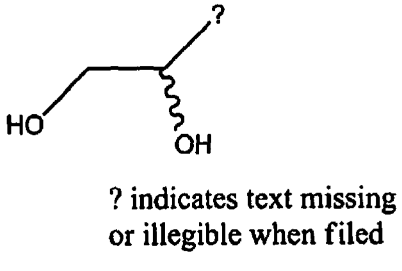
" with
-- 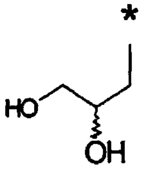 --.

Column 112, table 1, column $R^2$, line 21, replace " 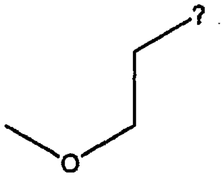 ? indicates text missing or illegible when filed " with -- 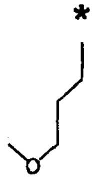 --.

Column 113, table 1, column $R^2$, line 1, replace " 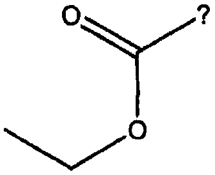 ? indicates text missing or illegible when filed " with -- 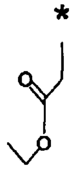 --.

Column 115, table 1, column $R^2$, line 1, replace " 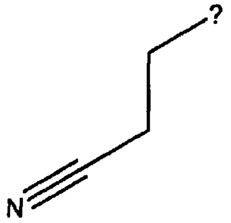 ? indicates text missing or illegible when filed " with -- 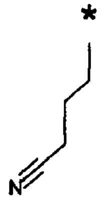 --.

Column 120, table 1, column $R^2$, line 22, replace " 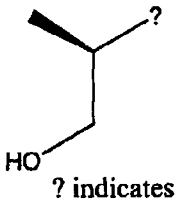 ? indicates text missing or illegible when filed " with -- 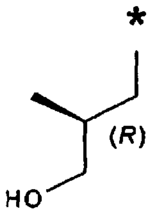 --.

Column 121, table 1, column $R^2$, line 1, replace " 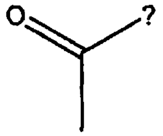 ? indicates text missing or illegible when filed " with -- 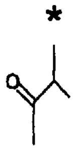 --.
Column 122, table 1, column $R^2$, line 1, replace " 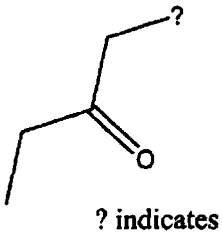 ? indicates text missing or illegible when filed " with
-- 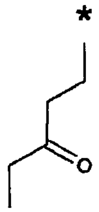 --.
Column 129, table 1, column $R^2$, line 1, replace " 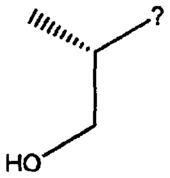 ? indicates text missing or illegible when filed '" with
-- 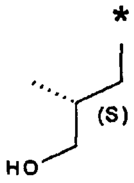 --.
Column 131, table 1, column $R^4$, line 1, replace " 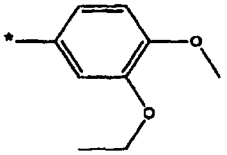 " with -- 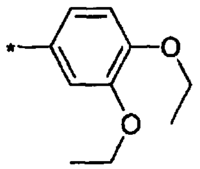 --.

Column 133, table 1, Column $R^3$, line 1, replace " 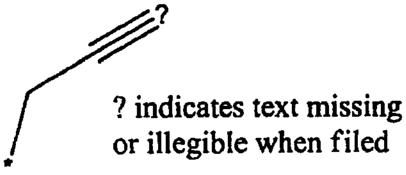
," with -- 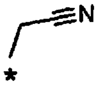 --.
Column 133, table 1, Column $R^2$, line 16, replace " 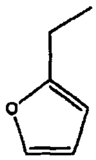 ," with -- 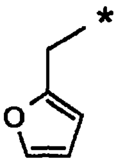 --.
Column 135, table 1, Column Name, line 22, replace
" 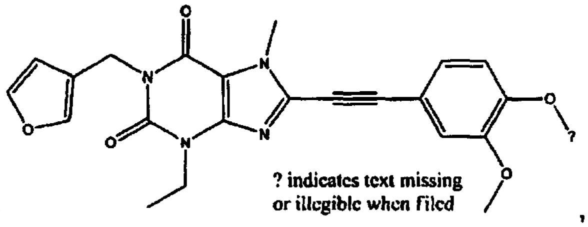
," with
-- 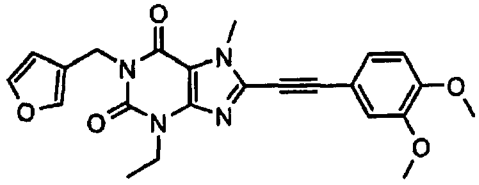 --.
Column 136, table 1, column $R^2$, line 31, replace " 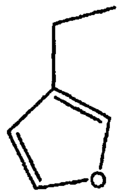 ," with -- 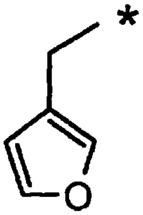 --.
Column 137, table 1, column Name, line 1, replace
" 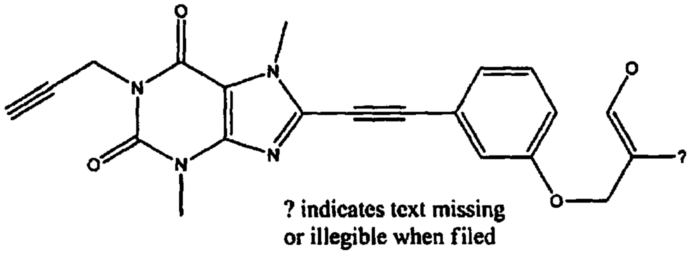
" with -- 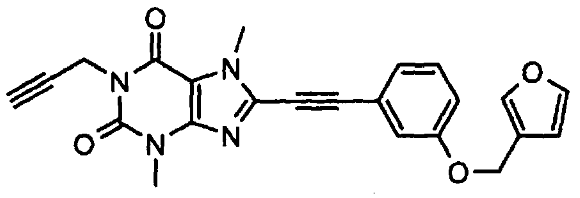 --.

Column 140, table 1, column MW/m.p.,/NMR, line 33, replace "126.6, 136.5" with --126.6, 128.6, 136.5--.

Column 140, table 1, column MW/m.p.,/NMR, line 41-44, replace "6.86 (d, J = 8 Hz, 1H, $H_{phenyl}$), 7.08 (d, J = 2 Hz, 1H, $H_{phenyl}$), 7.08 (d, J = 2 Hz, 1H, $H_{phenyl}$), 7.21-7.27 (m, 3H)" with --6.86 (d, J = 8 Hz, 1H, $H_{phenyl}$), 7.08 (d, J = 2 Hz, 1H, $H_{phenyl}$), 7.21-7.27 (m, 3H)--.

Column 141, Table 1, Column $R^2$, line 1, replace " 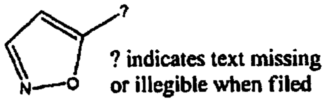

" with

-- 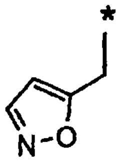 --.

Column 142, table 1, Column $R^2$, line 19, replace " 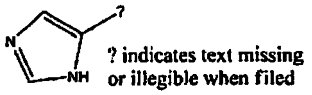

" with

-- 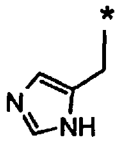 --.

Column 143, table 1, column MW/m.p.,/NMR, line 1, replace "MW 418.4, colorless" with --MW 418.5, colorless--.

Column 143, table 1, MW/m.p.,/NMR, line 5, replace "1H, CH), 3.88 (s, 3H, $OCH_3$), 3.90" with --1H, CCH), 3.88 (s, 3H, $OCH_3$), 3.90--.

Column 143, table 1; MW/m.p.,/NMR, line 13 replace "56.0, 70.6, 76.9, 78.7" with --56.0, 70.5, 75.9, 78.7--.

Column 149, table 1, MW/m.p.,/NMR, line 1 replace "MW 364.6, colorless solid, m.p.," with --MW 364.4, colorless solid, m.p.--.

In the Claims

Column 224, lines 29-30, replace “thien-3-yl, cyclopropyl, methylcarbonyl” with --thien-3-yl, isozazol-5-yl, imidazole-4-yl, cyclopropyl, methylcarbonyl--.